US010646463B2

(12) United States Patent
Shanahan et al.

(10) Patent No.: US 10,646,463 B2
(45) Date of Patent: May 12, 2020

(54) TREATMENT FOR TUMORS DRIVEN BY METABOLIC DYSFUNCTION

(71) Applicant: SynDevRx, Inc., Cambridge, MA (US)

(72) Inventors: James Shanahan, Cambridge, MA (US); Peter Cornelius, Old Lyme, CT (US)

(73) Assignee: SynDevRx, Inc., Cambridge, MA (US)

( * ) Notice: Subject to any disclaimer, the term of this patent is extended or adjusted under 35 U.S.C. 154(b) by 0 days.

(21) Appl. No.: 15/403,675

(22) Filed: Jan. 11, 2017

(65) Prior Publication Data
US 2017/0196830 A1    Jul. 13, 2017

Related U.S. Application Data

(60) Provisional application No. 62/277,293, filed on Jan. 11, 2016, provisional application No. 62/393,929, filed on Sep. 13, 2016, provisional application No. 62/395,446, filed on Sep. 16, 2016.

(51) Int. Cl.
*A61K 31/336* (2006.01)
*A61K 47/65* (2017.01)
*A61K 47/58* (2017.01)

(52) U.S. Cl.
CPC ............ *A61K 31/336* (2013.01); *A61K 47/58* (2017.08); *A61K 47/65* (2017.08)

(58) Field of Classification Search
CPC ....... A61K 47/65; A61K 31/336; A61K 47/58
See application file for complete search history.

(56) References Cited

U.S. PATENT DOCUMENTS

| | | | |
|---|---|---|---|
| 4,997,878 A | 3/1991 | Bock et al. | |
| 5,037,883 A | 8/1991 | Kopecek et al. | |
| 5,037,957 A | 8/1991 | Grubb et al. | |
| 5,166,172 A | 11/1992 | Kishimoto et al. | |
| 5,258,453 A | 11/1993 | Kopecek et al. | |
| 5,773,522 A | 6/1998 | Angelucci et al. | |
| 6,063,812 A | 5/2000 | Hong et al. | |
| 6,291,671 B1 | 9/2001 | Inoue et al. | |
| 6,306,819 B1 | 10/2001 | Rubnick et al. | |
| 6,436,912 B1 | 8/2002 | Inoue et al. | |
| 6,464,850 B1 | 10/2002 | Zhang et al. | |
| 6,548,477 B1 | 4/2003 | Olson et al. | |
| 6,759,509 B1 | 7/2004 | King et al. | |
| 6,803,438 B1 | 10/2004 | Brocchini et al. | |
| 6,811,788 B2 | 11/2004 | Yu | |
| 6,811,996 B1 | 11/2004 | Inoue et al. | |
| 6,835,807 B1 | 12/2004 | Susaki et al. | |
| 6,949,584 B2 | 9/2005 | Folkman et al. | |
| 7,041,818 B2 | 5/2006 | Susaki et al. | |
| 7,091,186 B2 | 8/2006 | Senter et al. | |
| 7,223,837 B2 | 5/2007 | De Groot et al. | |
| 7,332,523 B2 | 2/2008 | Folkman et al. | |
| 7,553,816 B2 | 6/2009 | Senter et al. | |
| 7,700,280 B2 * | 4/2010 | Al-Murrani ......... | C12N 15/113 435/6.12 |
| 7,943,569 B2 | 5/2011 | Gemeinhart et al. | |
| 8,349,891 B2 | 1/2013 | Crawford et al. | |
| 8,367,721 B2 | 2/2013 | Hughes et al. | |
| 8,399,512 B2 | 3/2013 | Akullian et al. | |
| 9,173,956 B2 | 11/2015 | Petersen et al. | |
| 9,320,805 B2 | 4/2016 | Petersen | |
| 9,433,600 B2 | 9/2016 | Petersen et al. | |
| 9,585,909 B2 | 3/2017 | Petersen | |
| 9,730,955 B2 | 8/2017 | Petersen | |
| 9,750,737 B2 | 9/2017 | Petersen et al. | |
| 9,757,373 B2 | 9/2017 | Petersen et al. | |
| 9,969,722 B2 | 5/2018 | Petersen et al. | |
| 10,010,544 B2 | 7/2018 | Petersen et al. | |
| 10,159,692 B2 | 12/2018 | Petersen | |
| 10,287,277 B2 | 5/2019 | Petersen | |
| 2002/0076442 A1 | 6/2002 | Burke et al. | |
| 2004/0001801 A1 | 1/2004 | Madison et al. | |
| 2004/0116348 A1 | 6/2004 | Chau et al. | |
| 2004/0229945 A1 | 11/2004 | Satchi-Fainaro et al. | |
| 2005/0036948 A1 | 2/2005 | Kasina et al. | |
| 2006/0206948 A1 | 9/2006 | Zhao | |
| 2006/0276512 A1 | 12/2006 | Han et al. | |
| 2007/0142302 A1 | 6/2007 | Mitra et al. | |
| 2007/0287680 A1 | 12/2007 | Cuchelkar et al. | |
| 2008/0112919 A1 | 5/2008 | Satchi-Fainaro et al. | |
| 2008/0248030 A1 | 10/2008 | Folkman et al. | |
| 2009/0093014 A1 | 4/2009 | Burnet et al. | |
| 2010/0111894 A1 | 5/2010 | Benny-Ratsaby et al. | |
| 2011/0263561 A1 | 10/2011 | Heinrich et al. | |

(Continued)

FOREIGN PATENT DOCUMENTS

| | | |
|---|---|---|
| CA | 1305053 | 7/1992 |
| EP | 0673258 | 5/2003 |

(Continued)

OTHER PUBLICATIONS

Goktas et al., Urology, 2005, 65: 1168-1172. (Year: 2005).*
Bae et al., "Obesity and glycemic control in pateints with *diabetes mellitus*: Analysis of physician electronic health records in the US from 2009-2011" *J. Diabetes and its Complications*, (2016) v. 30, pp. 212-220.
Brakenhielm et al. "Angiogenesis Inhibitor, TNP-470, Prevents Diet-Induced and Genetic Obesity in Mice", *Circulation Research*, 2004, vol. 94, p. 1579-1588.
Kim et al. "Assessment of the anti-obesity effects of the TNP-470 analog, CKD-732", *Journal of Molecular Endocrinology*, 2007, vol. 38, p. 455-465.

(Continued)

*Primary Examiner* — James H Alstrum-Acevedo
*Assistant Examiner* — Kaipeen E Yang
(74) *Attorney, Agent, or Firm* — Cooley LLP; Ivor R. Elrifi; Matthew Pavao

(57) ABSTRACT

The present disclosure relates to modified or polymer conjugated MetAP2 inhibitors. The present disclosure also relates to methods of treating metabolically-driven diseases and disorders, such as certain cancers.

38 Claims, 34 Drawing Sheets

(56) References Cited

U.S. PATENT DOCUMENTS

| | | |
|---|---|---|
| 2011/0294952 A1 | 12/2011 | Petersen |
| 2013/0064832 A1 | 3/2013 | Aikawa et al. |
| 2013/0137831 A1 | 5/2013 | Petersen |
| 2013/0216494 A1 | 8/2013 | Petersen |
| 2014/0308235 A1 | 10/2014 | Petersen et al. |
| 2015/0141580 A1 | 5/2015 | Petersen et al. |
| 2015/0374657 A1 | 12/2015 | Petersen et al. |
| 2016/0184345 A1 | 6/2016 | Petersen |
| 2016/0256483 A1 | 9/2016 | Petersen |
| 2016/0346244 A1 | 12/2016 | Petersen et al. |
| 2017/0028014 A1 | 2/2017 | Petersen et al. |
| 2017/0258925 A1 | 9/2017 | Petersen |
| 2018/0271856 A1 | 9/2018 | Petersen |

FOREIGN PATENT DOCUMENTS

| | | |
|---|---|---|
| WO | WO 2003/086382 | 10/2003 |
| WO | WO 2004/110358 | 12/2004 |
| WO | WO 2009/141826 | 11/2006 |
| WO | WO 2008/011114 A2 | 1/2008 |
| WO | WO 2009/036108 | 3/2009 |
| WO | WO 2009/051706 | 4/2009 |
| WO | WO 2009/073445 A2 | 6/2009 |
| WO | WO 2010/003475 | 1/2010 |
| WO | WO 2010/065877 | 6/2010 |
| WO | WO 2010/096603 | 8/2010 |
| WO | WO 2011/127304 | 10/2011 |
| WO | WO 2011/150022 | 12/2011 |
| WO | WO 2011/150088 | 12/2011 |
| WO | WO 2012/122264 | 9/2012 |
| WO | WO 2017/100553 A1 | 6/2017 |
| WO | WO 2017/123603 A1 | 7/2017 |

OTHER PUBLICATIONS

Lijnen et al. "Fumagillin Reduces Adipose Tissue Formation in Murine Models of Nutritionally Induced Obesity", Obesity, 2010, vol. 18, No. 12, p. 2241-2246.

Arico-Muendel, C.C. et al., "Carbamate Analogues of Fumagillin as Potent, Targeted Inhibitors of Methionine Aminopeptidase-2", J. Med. Chem., 52:8047-8056 (2009).

Bernier, S.G. et al., "Fumagillin class inhibitors of methionine aminopeptidase-2", Drugs of the Future, 30(5):497-508 (2005).

Blencowe, C.A. et al., "Self-immolative linkers in polymeric delivery systems", Polym. Chem., 2:773-790 (2011).

Chau, Y. et al., "Antitumor efficacy of a novel polymer-peptide-drug conjugate in human tumor xenograft models", Int. J. Cancer, 118:1519-1526 (2006).

D'Souza, A.J.M. et al., "Release from Polymeric Prodrugs: Linkages and Their Degradation", J. Pharm. Sci., 93(8):1962-1979 (2004).

Ducry, L. and Stump, B., "Antibody-Drug Conjugates: Linking Cytotoxic Payloads to Monoclonal Antibodies", Bioconj. Chem., 21:5-13 (2010).

Esposito et al. "The metabolic syndrome and inflammation: association or causation?" Nutr. Metab. Cardiovasc. Dis. 14(5):228-232 (2004).

Han, C.K. et al., "Design and synthesis of highly potent fumagillin analogues from homology modeling for a human MetAP-2", Biorg. Med. Chem. Lett., 10:39-43 (2000).

Herbst, R.S. et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", Journal of Clinical Oncology, 20(22):4440-4447 (2002).

Hughes, T. "ZGN-201 (ZGN), a Methionine Aminopeptidase 2 (MetAP2) Inhibitor, Durably Eliminates Excess Body Fat in Obese Mice through Regulation of Fat Metabolism and Food Intake", American Diabetes Association, Sep. 20, 2010; Retrieved from the internet: https://professional.diabetes.org/abstract/zgn-201-zgn-methionine-aminopeptidase-2-metap2-inhibitor-durably-eliminates-excess-body-fat.

Jeong, B-S. et al., "Total synthesis and antiangiogenic activity of cyclopentane analogues of fumagillol", Bioorganic and Medicinal Chemistry Letters, 15:3580-3583 (2005).

Joharapurkar et al. "Inhibition of the methionine aminopeptidase 2 enzyme for the treatment of obesity", Diabetes, Metabolic Syndrome and Obesity: Targets and Therapy. 2014:7; pp. 73-84 (2014).

Kahn et al. "Mechanisms linking obesity to insulin resistance and type 2 diabetes." Nature, vol. 444, 2006, p. 840-846.

Kim et al, "5-Demethoxyfumagillol, a Potent Angiogenesis Inhibitor Isolated from Aspergillus fumigatus", Chem. Pharm. Bull., 52(4): 447-450 (2004).

Law and Tung, "Proteolysis: A Biological Process Adapted in Drug Delivery, Therapy, and Imaging", Bioconjugate Chem., 20:1683-1695 (2009).

Lee, H.W. et al., "Design, Synthesis, and Antiangiogenic Effects of a Series of Potent Novel Fumagillin Analogues", Chem. Pharm. Bull., 55(7):1024-1029 (2007).

Mann-Steinberg and Satchi-Fainaro, "TNP-470: The Resurrection of the First Synthetic Angiogenesis Inhibitor", Folkman and Figg, Angiogenesis: An Integrative Approach from Science to Medicine, 35:395-414 (2008).

Mason, S. D. and Joyce, J. A. "Proteolytic networks in cancer", Trends in Cell Biology v. 21, No. 4, (2011) pp. 228-237.

Satchi-Fainaro, R. et al. "Targeting angiogenesis with a conjugate of HPMA copolymer and TNP-470", Nature Med., 10(3): 255-261 (2004).

Segal, E. et al., "Design and development of polymer conjugates as anti-angiogenic agents", Adv. Drug. Deliv. Reviews, 61(13):1159-1176 (2009).

Shiose, Y. et al., "Relationship between Drug Release of DE-310, Macromolecular Prodrug of DX-8951f, and Cathepsins Activity in Several Tumors", Biol. Pharm. Bull., 30(12):2365-2370 (2007).

Shiose, Y. et al., "Systematic Research of Peptide Spacers Controlling Drug Release from Macromolecular Prodrug System, Carboxymethyldextran Polyalcohol—Peptide—Drug Conjugates", Bioconjugate Chem., 20(1):60-70 (2009).

Subr, V. et al., "Poly[M-)2-hydroxypropyl)methacrylamide] Conjugates of Methotrexate Synthesis and in vitro Drug Release", J Controlled Release, 49:123-132 (1997).

Sutherland, J. et al. "The Metabolic Syndrome and Inflammation" Metabolic Syndrome and Related Disorders 2(2):82-104 (2004).

Golub et al. Science v. 286, (1999) pp. 531-537.

Klok et al., Obesity Reviews (2007) vol. 8, pp. 21-34.

Anderson, "The Process of Structure-Baed Drug Design", Chemistry & Biology, 2003, vol. 10, p. 787-797.

Berge et al. "Pharmaceutical Salts" Journal of Pharmaceutical Sciences, 1977, vol. 66, No. 1, p. 1-19.

Chang, "Common Therapeutic Target for Both Cancer and Obesity", World Journal of Biological Chemistry, 2017, vol. 8, No. 2, p. 102-107.

Martyn et al. "Obesity-Induced Insulin Resistance and Hyperglycemia: Etiological Factors and Molecular Mechanisms", Anesthesiology, 2008, vol. 109, No. 1, p. 137-148.

Thiel, "Structure-aided drug design's next generation", Nature Biotechnology, 2004, vol. 22, No. 5, p. 513-519.

Xavier et al. "One-week intervention period led to improvements in glycemic control and reduction in DNA damage levels in patients with type 2 diabetes mellitus", Diabetes Research and Clinical Practice, 2014, vol. 105, p. 356-363.

* cited by examiner

TREATMENT FOR TUMORS DRIVEN BY METABOLIC DYSFUNCTION

CROSS-REFERENCE TO RELATED APPLICATIONS

This application claims priority to, and the benefit of, U.S. Ser. No. 62/277,293, filed on Jan. 11, 2016, U.S. Ser. No. 62/393,929, filed on Sep. 13, 2016 and U.S. Ser. No. 62/395,446, filed on Sep. 16, 2016. The contents of each application are incorporated herein by reference in its entirety.

FIELD OF THE DISCLOSURE

The present disclosure provides compounds, pharmaceutical compositions and methods for treating patients with a proliferation disorder, such as cancer, complicated by metabolic dysfunction. The disclosure relates to the fields of biomedicine, pharmacology, and molecular biology.

BACKGROUND OF THE DISCLOSURE

It is well established that obesity and metabolic dysfunction are risk factors for a person to develop cancer. However, there is no specific treatment regimen for metabolically dysfunctional people once they are diagnosed with cancer or proliferation related disorders. Recent discoveries in cancer research have revealed complex interactions between certain cancer patient's endocrine health and the progression of their cancer that center on metabolic factors, adipose tissue-derived hormones and the chronic inflammation that accompanies excess visceral adiposity. In select cancers, these adipose tissue-derived hormones stimulate specific oncogenic pathways, thereby increasing cancer cell proliferation, invasiveness and ultimately, killing the patient faster than cancer patients with normal physiologic levels of these metabolic factors. Other visceral adipose tissue-derived hormones play a protective role in cancer, and are often suppressed with excess visceral adiposity. Despite the fact that this cancer/metabolic nexus is reported to result directly in over 80,000 deaths annually in the U.S. alone, there are no treatments specifically designed for this disease nexus and patient population.

Accordingly, new compounds, pharmaceutical compositions and methods for treating patients with proliferation disorder, such as cancer, complicated by metabolic dysfunction are needed. The present disclosure addresses these needs.

SUMMARY OF THE DISCLOSURE

The present disclosure provides methods of treating, or ameliorating at least one symptom of, a proliferation disorder, such as cancer, in a subject in need thereof, comprising administering at least one compound of the present disclosure in a therapeutically effective amount to the subject to treat the proliferation disorder, wherein the subject has a metabolic dysfunction.

The present disclosure also provides methods of treating a metabolically-sensitive tumor in a subject in need thereof comprising administering at least one compound of the present disclosure in a therapeutically effective amount to the subject to treat the metabolically-sensitive tumor, wherein the subject has a metabolic dysfunction.

In one aspect, the present disclosure provides a method for treating, or ameliorating at least one symptom of, cancer or treating a metabolically-sensitive tumor in a subject in need thereof comprising administering at therapeutically effective amount of at least one compound of the Formula

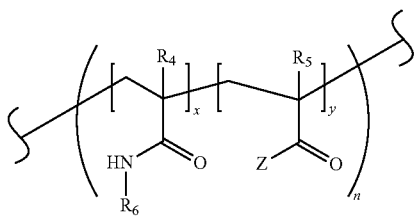

wherein, independently for each occurrence,
$R_4$ is H or $C_1$-$C_6$ alkyl;
$R_5$ is H or $C_1$-$C_6$ alkyl;
$R_6$ is $C_2$-$C_6$ hydroxyalkyl;
Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W;
$AA_1$ is glycine, alanine, or $H_2N(CH_2)_mCO_2H$, wherein m is 2, 3, 4 or 5;
$AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;
$AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;
$AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;
$AA_5$ is a bond, or glycine, valine, tyrosine, tryptophan, phenylalanine, methionine, leucine, isoleucine, or asparagine;
$AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5;
L is —OH, —O-succinimide, —O-sulfosuccinimide, alkoxy, aryloxy, acyloxy, aroyloxy, alkoxycarbonyloxy, aryloxycarbonyloxy, —$NH_2$, —NH($C_2$-$C_6$ hydroxyalkyl), halide or perfluoroalkyloxy;
Q is NR, O, or S;
X is M-$(C(R)_2)_p$-M-J-M-$(C(R)_2)_p$-M-V;
M is a bond, or C(O);
J is a bond, or $((CH_2)_qQ)_r$, $C_5$-$C_8$ cycloalkyl, aryl, heteroaryl, NR, O, or S;
Y is NR, O, or S;
R is H or alkyl;
V is a bond or

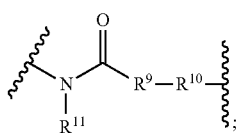

R⁹ is alkyl, aryl, aralkyl, or a bond; or R⁹ taken together with Y forms a heterocyclic ring;

R¹⁰ is amido or a bond;

R¹¹ is H or alkyl;

W is a MetAP2 inhibitor moiety or alkyl;

x is in the range of 1 to about 450;

y is in the range of 1 to about 30;

n is in the range of 1 to about 100;

p is 0 to 20;

q is 2 or 3;

r is 1, 2, 3, 4, 5, or 6;

or a pharmaceutically acceptable salt, prodrug, metabolite, analog or derivative thereof, wherein the subject has a metabolic dysfunction, and wherein the cancer is treated.

In one aspect, the present disclosure least one compound, or a pharmaceutically acceptable salt, prodrug, metabolite, analog or derivative thereof, has the Formula:

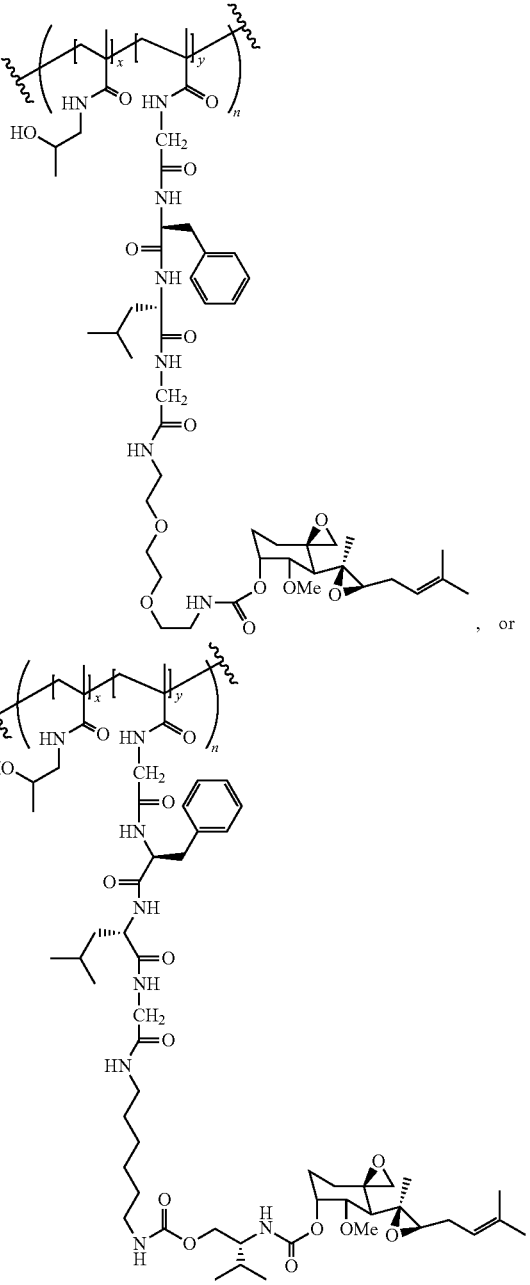

The present disclosure also provides a method for treating, or ameliorating at least one symptom of, cancer or treating a metabolically-sensitive tumor in a subject in need thereof comprising administering a therapeutically effective amount of at least one compound, or a pharmaceutically acceptable salt, prodrug, metabolite, analog or derivative thereof, represented by: Z-Q-X—Y—C(O)—W wherein, independently for each occurrence, Z is —H, —H₂N-AA₃-AA₄-AA₅-AA₆-C(O)— or Z is H₂N-AA₅-AA₆-C(O);

AA₃ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

AA₄ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

$AA_5$ is a bond, or glycine, valine, tyrosine, tryptophan, phenylalanine, methionine, leucine, isoleucine, or asparagine;

$AA_6$ is alanine, asparagine, citrulline, glutamine, glycine, leucine, methionine, phenylalanine, serine, threonine, tryptophan, tyrosine, valine or $H_2N(CH_2)mCO_2H$, wherein m is 2, 3, 4 or 5;

Q is NR, O, or S;

X is $M-(C(R)_2)_p-M-J-M-(C(R)_2)_p-M-V$;

M is a bond, or C(O);

J is a bond, or $((CH_2)_qQ)_r$, $C_5$-$C_8$ cycloalkyl, aryl, heteroaryl, NR, O, or S;

Y is NR, O, or S;

R is H or alkyl;

V is a bond or

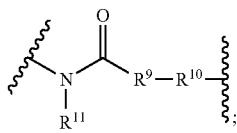

$R^9$ is alkyl, aryl, aralkyl, or a bond; or $R^9$ taken together with Y forms a heterocyclic ring;

$R^{10}$ is amido or a bond;

$R^{11}$ is H or alkyl;

W is a MetAP2 inhibitor moiety;

p is 0 to 20;

q is 2 or 3; and r is 1, 2, 3, 4, 5, or 6.

wherein the subject has a metabolic dysfunction, and wherein the cancer is treated.

The cancer can be post-menopausal HR+/Her2– breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof.

The metabolic dysfunction can be excessive visceral adiposity, elevated leptin levels, depressed adiponectin levels, high leptin-to-adiponectin ratio, elevated fasting insulin levels accompanied by chronic inflammation, or combinations thereof.

The methods of the present disclosure can further including treating, or ameliorating at least one symptom of, the metabolic dysfunction in said subject. The methods of the present disclosure can further including increasing adiponectin, decreasing leptin, decreasing fasting insulin, or combinations thereof in said subject.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference in their entirety for all purposes. The references cited herein are not admitted to be prior art to the claimed disclosure. In the case of conflict, the present specification, including definitions, will control. In addition, the materials, methods and examples are illustrative only and are not intended to be limiting.

Other features and advantages of the disclosure will be apparent from the following detailed description and claims.

DETAILED DESCRIPTION OF THE DISCLOSURE

Methods of Use

Figure 1A:
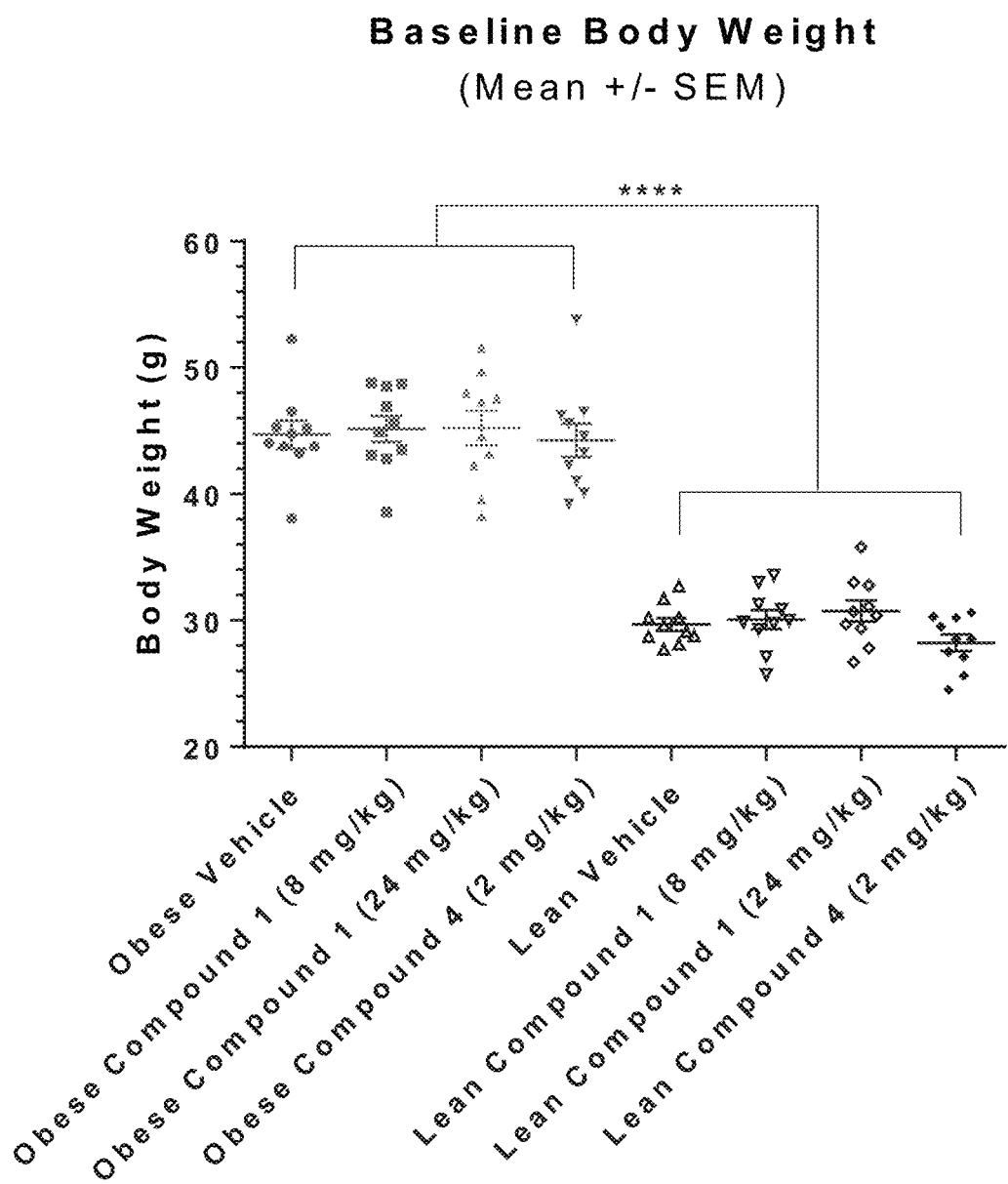
FIG. 1A is a graph baseline body weight in mice on a high-fat diet compared to a low-fat diet.

The present disclosure provides methods of treating, or ameliorating at least one symptom of, a proliferation disorder in a subject in need thereof, comprising administering at least one MetAP2 inhibitor in a therapeutically effective amount to the subject to treat the proliferation disorder, wherein the subject has a metabolic dysfunction. In a preferred aspect, the proliferation disorder is cancer. The cancer can be post-menopausal HR+/Her2− breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof. The metabolic dysfunction can include excessive visceral adiposity, elevated leptin levels, depressed adiponectin levels, high leptin-to-adiponectin ratio, elevated fasting insulin levels accompanied by chronic inflammation, or combinations thereof. Preferably, the metabolic dysfunction is low adiponectin, elevated leptin, elevated fasting insulin, or combinations thereof. The methods of the present disclosure can also include treating, or ameliorating at least one symptom of, the metabolic dysfunction in addition to treating, or ameliorating at least one symptom of, the proliferation disorder.

The present disclosure also provides methods of treating, or ameliorating at least one symptom of, a proliferation disorder in a subject in need thereof, comprising administering at least one fumagillin analog or derivative in a therapeutically effective amount to the subject to treat the proliferation disorder, wherein the subject has a metabolic dysfunction. In a preferred aspect, the proliferation disorder is cancer. The cancer can be post-menopausal HR+/Her2− breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof. The metabolic dysfunction can include excessive visceral adiposity, elevated leptin levels, depressed adiponectin levels, high leptin-to-adiponectin ratio, elevated fasting insulin levels accompanied by chronic inflammation, or combinations thereof. Preferably, the metabolic dysfunction is low adiponectin, elevated leptin, elevated fasting insulin, or combinations thereof. The methods of the present disclosure can also include treating, or ameliorating at least one symptom of, the metabolic dysfunction in addition to treating, or ameliorating at least one symptom of, the proliferation disorder.

The present disclosure also provides methods of treating, or ameliorating at least one symptom of, a proliferation disorder in a subject in need thereof, comprising administering at least one compound of the present disclosure in a therapeutically effective amount to the subject to treat the proliferation disorder, wherein the subject has a metabolic dysfunction. In a preferred aspect, the proliferation disorder is cancer. The cancer can be post-menopausal HR+/Her2− breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof. The metabolic dysfunction can include excessive visceral adiposity, elevated leptin levels, depressed adiponectin levels, high leptin-to-adiponectin ratio, elevated fasting insulin levels accompanied by chronic inflammation, or combinations thereof. Preferably, the metabolic dysfunction is low adiponectin, elevated leptin, elevated fasting insulin, or combinations thereof. The methods of the present disclosure can also include treating, or ameliorating at least one symptom of, the metabolic dysfunction in addition to treating, or ameliorating at least one symptom of, the proliferation disorder.

The present disclosure also provides methods of treating a metabolically-sensitive tumor in a subject in need thereof comprising administering at least one MetAP2 inhibitor in a therapeutically effective amount to the subject to treat the metabolically-sensitive tumors, wherein the subject has a metabolic dysfunction. The metabolically-sensitive tumor can be the result of post-menopausal HR+/Her2− breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof. The metabolic dysfunction can include excessive visceral adiposity, elevated leptin levels, depressed adiponectin levels, high leptin-to-adiponectin ratio, elevated fasting insulin levels accompanied by chronic inflammation, or combinations thereof. Preferably, the metabolic dysfunction is low adiponectin, elevated leptin, elevated fasting insulin, or combinations thereof. The methods of the present disclosure can also include treating, or ameliorating at least one symptom of, the metabolic dysfunction in addition to treating the metabolically-sensitive tumor.

The present disclosure also provides methods of treating a metabolically-sensitive tumor in a subject in need thereof comprising administering at least one fumagillin analog or derivative in a therapeutically effective amount to the subject to treat the metabolically-sensitive tumor, wherein the subject has a metabolic dysfunction. The metabolically-sensitive tumor can be the result of post-menopausal HR+/Her2− breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof. The metabolic dysfunction can include excessive visceral adiposity, elevated leptin levels, depressed adiponectin levels, high leptin-to-adiponectin ratio, elevated fasting insulin levels accompanied by chronic inflammation, or combinations thereof. Preferably, the metabolic dysfunction is low adiponectin, elevated leptin, elevated fasting insulin, or combinations thereof. The methods of the present disclosure can also include treating, or ameliorating at least one symptom of, the metabolic dysfunction in addition to treating the metabolically-sensitive tumor.

The present disclosure also provides methods of treating a metabolically-sensitive tumor in a subject in need thereof comprising administering at least one compound of the present disclosure in a therapeutically effective amount to the subject to treat the metabolically-sensitive tumor, wherein the subject has a metabolic dysfunction. The metabolically-sensitive tumor can be the result of post-menopausal HR+/Her2− breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof. The metabolic dysfunction can include excessive visceral adiposity, elevated leptin levels, depressed adiponectin levels, high leptin-to-adiponectin ratio, elevated fasting insulin levels accompanied by chronic inflammation, or combinations thereof. Preferably, the metabolic dysfunction is low adiponectin, elevated leptin, elevated fasting insulin, or combinations thereof. The methods of the present disclosure can also include treating, or ameliorating at least one symptom of, the metabolic dysfunction in addition to treating the metabolically-sensitive tumor.

Obesity has been identified as a risk factor for postmenopausal breast cancer and excess visceral adipose tissue is associated with a worse response to chemotherapy and reduced progression and/or disease-free survival (Schaffler, A., et al. (2007) Nat Clin Pract Endocrinol Metab 3:345-54; Vona-Davis, L. Rose, D P. (2007) Endocr Relat Cancer 14:189-206). Adipose tissue-derived factors (e.g. leptin, adiponectin, aromatase, IL-6) have been proposed as possible mediators of the obesity-breast cancer link, and recent data draw attention specifically to the adipokines leptin and adiponectin (Cleary, M P., et al. (2009) Front Biosci (School Ed) 1:329-57; Cleary, M P., et al. (2010) Vet Pathol 47:202-13). The molecular basis for underlying the role of leptin, adiponectin and other hormones, such as insulin and insulin-life growth factors have recently been described. Circulating adiponectin levels are inversely correlated with body mass index (BMI); in contrast, serum leptin positively correlates with BMI (Ryan, A S., et al. (2003) Diabetes Care 26:2383-8; Wauters, M., et al. (2000) Eur J Endocrinol 143:293-311). In obese individuals, especially in those with high visceral fat content, adiponectin levels are depressed (Brochu-Gaudreau K, et al. Endocrine 2010, 37(1):11-32). Adiponectin is found in human serum at concentrations of 2-20 µg/ml (Grossmann, M E., et al. (2008) Br J Cancer 98:370-9). The mechanism underlying adiponectin signaling and cancer prevention is thought to involve the activation of intracellular signals AMPK and inhibition of growth and survival pathways (Brochu-Gaudreau K, et al. Endocrine 2010, 37(1):11-32, Pfeiler G et al., Maturitas 2009, 63(3):253-256). Further, adiponectin may exert its biological activity indirectly, through selective sequestration of different growth factors (e.g., basic fibroblast growth factor, platelet-derived growth factor BB, heparin-binding epidermal growth factor) and inhibition of their normal receptor binding. These interactions involve specific oligomeric forms of adiponectin. Barb, D., Williams, C J., Neuwirth, A K., Mantzoros, C S. (2007) Am J Clin Nutr 86:s858-66. Wang et al. (2005) J Biol Chem 280:18341-7).

Several epidemiological studies found an inverse relation between adiponectin levels and breast cancer risk (Barb, et al. (2007) Am J Clin Nutr 86:s858-66; Miyoshi, et al. (2003) Clin Cancer Res 9:5699-704. Mantzoros, et al. (2004) J Clin Endocrinol Metab 89:1102-7; Chen, D C., et al. (2006) Cancer Lett 237:109-14). In breast cancer patients, the adiponectin levels and the adiponectin-to-leptin ratio tend to be reduced relative to that found in lean women (Cleary M P., et al., (2009) Front Biosci (Schol Ed) 1:329-57; Cleary, M P., et al. (2006) Cancer Lett 237:109-14). Breast cancer patients with low adiponectin levels are reported to have more aggressive tumors and higher frequency of lymph node metastasis (Schaffler, A., et al. (2007) Nat Clin Pract Endocrinol Metab 3:345-54; Hou, W K., et al. (2007) Chin Med J (Engl) 120:1592-6).

In one aspect, the present disclosure provides methods of utilizing at least one MetAP2 inhibitor, at least one fumagillin analog or derivative and/or at least one compound of the present disclosure to treat specific tumor types that are exacerbated by metabolic dysfunction, including post-menopausal HR+/Her2− breast cancer, castration resistant prostate cancer, esophageal carcinoma, colorectal adenocarcinoma, cervical cancer, endometrial cancer, ovarian cancer, pancreatic adenocarcinoma, gall bladder cancer, liver cancer, clear-cell renal cancer, melanoma, multiple myeloma, or combinations thereof. In preferred aspects, the present methods disclose subcutaneous administration of an MetAP2 inhibitor in cancer patients with metabolic dysfunction. The metabolic dysfunction can include excessive visceral adiposity, elevated leptin levels, depressed adiponectin levels, high leptin-to-adiponectin ratio, elevated fasting insulin levels accompanied by chronic inflammation, or combinations thereof. The present methods can restore the patient to a more metabolically neutral and stable state and slow or reverse the progression of the patient's cancer.

Described herein are methods to improve the underlying metabolic dysfunction in patients with metabolically-sensitive tumors. The methods of treating the metabolically-sensitive tumors include increasing the levels of adiponectin, lowering the levels of leptin, improving the leptin-to-adiponectin ratio, or combinations thereof. Subcutaneous administration of the MetAP2 inhibitors described herein have demonstrated the ability to improve these levels and ratios in cancer patients, and thus, can be used for the treatment of metabolically sensitive tumors which can benefit from an adiponectin upregulation along with improved leptin sensitivity. Accordingly, in certain aspects, the MetAP2 inhibitors described herein can treat cancers including post-menopausal hormone-receptor positive (HR+) breast cancer, castration resistant prostate cancer, esophageal adenocarcinoma, colorectal adenocarcinoma, cervical cancer, endometrial cancer, ovarian cancer, pancreatic adenocarcinoma, gall bladder, hepatocellular carcinoma, clear-cell renal cancer, melanoma, multiple myeloma, or combinations thereof. The aforementioned cancers can be related to, at least in part, to adiponectin deficiency and/or adiponectin resistance.

The present disclosure also provides methods of treating cancer in a subject in need thereof, said method comprising the steps of (i) identifying the patient as having post-menopausal hormone-receptor positive (HR+) breast cancer, castration resistant prostate cancer, esophageal adenocarcinoma, colorectal adenocarcinoma, cervical, cancer endometrial cancer, ovarian cancer, pancreatic adenocarcinoma, gall bladder cancer, hepatocellular carcinoma, clear-cell renal cancer, melanoma, multiple myeloma, or a combination thereof; (ii) determining whether the cancer patient has metabolic dysfunction, and (iii) if the subject is identified as having one of the cancers in step (i) and metabolic dysfunction in step (ii), administering a therapeutically effective amount of at least one MetAP2 inhibitor, at least one fumagillin analog or derivative, or at least one compound of the present disclosure. Preferably, the subject is administered a compound of the present disclosure. Preferably, the compound is administered subcutaneously. The metabolic dysfunction can include excessive visceral adiposity, elevated leptin levels, depressed adiponectin levels, high leptin-to-adiponectin ratio, elevated fasting insulin levels accompanied by chronic inflammation, or combinations thereof. Preferably, the metabolic dysfunction is low adiponectin, elevated leptin, elevated fasting insulin, or combinations thereof. The methods of the present disclosure can also include treating, or ameliorating at least one symptom of, the metabolic dysfunction in addition to treating the cancer.

In another aspect, the present disclosure provides a method of determining whether a tumor is metabolically sensitive and comprising: (1) measuring the level of fasting insulin and glucose to determine the HOMA score (insulin sensitivity level) for the patient, (2) comparing the HOMA score to that of lean patients, and (3) determining that, if the level of the HOMA score is larger than the metabolically normal level, the cancer is susceptible to treatment with at least one MetAP2 inhibitor, at least one fumagillin analog or derivative, or at least one compound of the present disclosure.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. Preferably, the subject having a cell proliferative disorder also has metabolic dysfunction.

A "subject" includes a mammal. The mammal can be e.g., any mammal, e.g., a human, primate, bird, mouse, rat, fowl, dog, cat, cow, horse, goat, rabbit, camel, sheep or a pig. Preferably, the mammal is a human. The term "subject" and "patient" are used interchangeably herein.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the disclosure encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. A cell proliferative disorder includes a non-cancer condition or disorder. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; skin-related hyperproliferative disorders, psoriasis; eczema; atopic dermatitis; hyperpigmentation disorders, eye-related hyperproliferative disorders, age-related macular degeneration, ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis;

graft-versus-host reaction; fibroadipose hyperplasia; spinocerebullar ataxia type 1; CLOVES syndrome; Harlequin ichthyosis; macrodactyly syndrome; Proteus syndrome (Wiedemann syndrome); LEOPARD syndrome; systemic sclerosis; Multiple Sclerosis; lupus; fibromyalgia; AIDS and other viral diseases such as Herpes Zoster, Herpes Simplex I or II, influenza virus and cytomegalovirus; diabetes mellitus; hemihyperplasia-multiple lipomatosis syndrome; megalencephaly; rare hypoglycemia, Klippel-Trenaunay syndrome; harmatoma; Cowden syndrome; or overgrowth-hyperglycemia.

Exemplary cancers include, but are not limited to, adrenocortical carcinoma, AIDS-related cancers, AIDS-related lymphoma, anal cancer, anorectal cancer, cancer of the anal canal, anal squamous cell carcinoma, angiosarcoma, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, head and neck squamous cell carcinoma, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, T-cell lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, lung squamous cell carcinoma, AIDS-related lymphoma, non-Hodgkin lymphoma, primary central nervous system lymphoma, B-cell lymphoma, primary effusion lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, pancreatic endocrine tumor, paranasal sinus and nasal cavity cancer, parathyroid cancer, cholangiocarcinoma, penile cancer, pharyngeal cancer, pheochromocytoma, pineoblastoma and supratentorial primitive neuroectodermal tumors, pituitary tumor, pituitary adenoma, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present disclosure can be used to treat a cancer selected from the group consisting of a hematologic cancer of the present disclosure or a hematologic cell proliferative disorder of the present disclosure. A hematologic cancer of the present disclosure can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PNO (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter of the present disclosure is in direct contact with a cell, or is close enough to induce a desired biological effect in a cell.

In addition to treating or alleviating at least one symptom of one or more proliferation disorders, the compounds of the present disclosure can also treat or alleviate a variety of related disorders.

In particular, addition to treating or alleviating at least one symptom of one or more proliferation disorders, the compounds of the present disclosure can also treat or alleviate at least one metabolic dysfunction selected from the group consisting of excessive visceral adiposity, elevated leptin levels, depressed adiponectin levels, high leptin-to-adiponectin ratio, elevated fasting insulin levels accompanied by chronic inflammation, or combinations thereof. Preferably, the metabolic dysfunction that is treated or ameliorated is low adiponectin, elevated leptin, elevated fasting insulin, or combinations thereof.

In addition to treating or alleviating at least one symptom of one or more proliferation disorders, the compounds of the present disclosure can also treat or alleviate at least one symptom of obesity.

In addition to treating or alleviating at least one symptom of one or more proliferation disorders, the compounds of the present disclosure can also decrease body weight. In certain aspects, the subject is overweight or obese. In certain aspects, the subject is in need of reducing excess adipose tissue.

Obesity and being overweight refer to an excess of fat in a subject in proportion to lean body mass. Excess fat accumulation is associated with an increase in size (hypertrophy or steatosis) as well as number (hyperplasia) of adipose tissue cells. Obesity can be due to any cause, whether genetic (e.g. Prader-Willi Syndrome) or environmental. Obesity is variously measured in terms of absolute weight, weight:height ratio, degree of excess body fat, distribution of visceral or subcutaneous fat, and societal and esthetic norms. A common measure of body fat is Body Mass Index (BMI). The BMI refers to the ratio of body weight (expressed in kilograms) to the square of height (expressed in meters). Body mass index can be accurately calculated using the formulas: SI units: BMI=weight(kg)/(height$^2$(m$^2$), or US units: BMI=(weight(b)*703)/(height$^2$(in$^2$).

As described herein, "overweight" refers to a condition whereby an otherwise healthy adult that has a BMI of 25 kg/m$^2$ to 29.9 kg/m$^2$. As described herein, "obese" or "obesity" refers to a condition whereby an otherwise healthy adult that has a BMI of 30 kg/m$^2$ or greater. Obesity has several subcategories. An adult that has a BMI of 35 kg/m$^2$ or greater is referred to as "severely obese" or "severe obesity". An adult that has a BMI of ≥40-44.9 kg/m$^2$ or and adult that has a BMI of 35 kg/m$^2$ or greater and at least one obesity-related health condition is referred to as "morbidly obese" or "morbid obesity". An adult that has a BMI of 45 kg/m$^2$ or greater is referred to as "super obese" or "super obesity". For children, the definitions of overweight and obese take into account age and gender effects on body fat.

Different countries can define obesity and overweight with different BMI. The term "obesity" is meant to encompass definitions in all countries. For example, the increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25.0 kg/m$^2$. Ethnic South and Central Americans tend to be categorized more closely to Asians than Europeans or North Americans.

BMI does not account for the fact that excess adipose tissue can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass can involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Another method is fan-beam dual energy X-ray absorptiometry (DEXA). DEXA allows body composition, particularly total body fat and/or regional fat mass, to be determined non-invasively. MRI can also be used to determine composition non-invasively.

In addition to treating or alleviating at least one symptom of one or more proliferation disorders, the compounds of the present disclosure can also decrease adipocytes or adipose tissue. Decreasing adipocytes means decreasing the number or decreasing the size (fat content) of the adipocytes. In certain aspects, the compounds of the present disclosure shrink the adipocytes in the subject. The adipose tissue can be white adipose tissue or brown adipose tissue.

In addition to treating or alleviating at least one symptom of one or more proliferation disorders, the compounds of the present disclosure can also decrease food intake. A reduction in food intake means a decrease in daily food intake. A decrease in daily food intake can be about a 5% decrease to about a 50% decrease (e.g., about 5%, about 10%, about 20%, about 30%, about 40% or about 50%). Based on a 2000 kcal daily diet, the decrease is about 100 kcal to about 1000 kcal decrease per day (e.g., about 100 kcal, about 200 kcal, about 400 kcal, about 600 kcal, about 800 kcal or about 1000 kcal).

In addition to treating or alleviating at least one symptom of one or more proliferation disorders, the compounds of the present disclosure can also reduce a sense of hunger in a subject. The subject can also have a decrease in food intake. Sense of hunger can be assessed in a fasted state using a 10-point visual analog scale (VAS), which is well utilized in appetite research. See, Flint et al. *Int. J. Obes. Relat. Metab. Disord.* 24(1): 38-48, 2000. Specifically, subjects are asked to rate their overall sense of hunger for the previous 2 days on a scale of 1-10, where 10 was extremely hungry and 1 was not hungry at all.

In addition to treating or alleviating at least one symptom of one or more proliferation disorders, the compounds of the present disclosure can also decrease waist circumference. Waist circumference is assessed by using a tape measure placed around the abdomen 1 cm above the iliac crest. The subjects of the present disclosure can have a decrease in waist circumference from about 1 inch to about 20 inches (e.g., 1, 2, 3, 4, 5, 6, 7, 8, 9, 10, 11, 12, 13, 14, 15, 16, 17, 18, 19 or 20 inches).

In addition to treating or alleviating at least one symptom of one or more proliferation disorders, the compounds of the present disclosure can also decrease body fat and provide substantial maintenance of muscle mass in said patient. In certain aspects, upon administration, fat oxidation is enhanced in a patient as compared to a patient on a restricted food intake diet alone. Such a patient can retain substantially more muscle mass as compared to body fat reduction in a patient using an energy restricted diet alone.

In addition to treating or alleviating at least one symptom of one or more proliferation disorders, the compounds of the present disclosure can also lower insulin levels, leptin levels or both in the subject. In certain aspects, the subject is overweight or obese. In certain aspects, the subject is in need of reducing excess adipose tissue.

In addition to treating or alleviating at least one symptom of one or more proliferation disorders, the compounds of the present disclosure can also improve surgical outcome comprising administering, prior to surgery, at least one compound of the present disclosure in a therapeutically effective amount to the subject to improve surgical outcome. In certain aspects, administration reduces liver and/or abdominal fat in said patient and improves surgical outcome. In certain aspects, the surgery is non-acute surgery. Such surgeries can include bariatric surgery, cardiovascular surgery, abdominal surgery, or orthopedic surgery.

As used herein, "monotherapy" refers to the administration of a single active or therapeutic compound of the present disclosure to a subject in need thereof. For example, administering a cancer monotherapy with one of the compounds of the present disclosure, or a pharmaceutically acceptable salt, prodrug, metabolite, analog or derivative thereof, to a subject in need of treatment of cancer. Monotherapy can be contrasted with combination therapy, in which a combination of multiple active compounds is administered, as described below. In one aspect, monotherapy with a compound of the present disclosure, or a pharmaceutically acceptable salt, prodrug, metabolite, polymorph or solvate thereof, is more effective than combination therapy in inducing a desired biological effect.

As used herein, "combination therapy" or "co-therapy" includes the administration of at least two compounds of the present disclosure, or pharmaceutically acceptable salts, prodrugs, metabolites, polymorphs or solvates thereof, as part of a specific treatment regimen intended to provide the beneficial effect from the co-action of these at least two compounds of the present disclosure. The beneficial effect of the combination includes, but is not limited to, pharmacokinetic or pharmacodynamic co-action resulting from the combination of these at least two compounds of the present disclosure. Administration of these at least two compounds of the present disclosure in combination typically is carried out over a defined time period (usually minutes, hours, days or weeks depending upon the combination selected). "Combination therapy" can be, but generally is not, intended to encompass the administration of two or more of these compounds of the present disclosure as part of separate monotherapy regimens that incidentally and arbitrarily result in the combinations of the present disclosure.

"Combination therapy" also embraces the administration of the compounds of the present disclosure in further combination with a second active agent and/or non-drug therapy (e.g., surgery or radiation treatment). Where the combination therapy further comprises a non-drug treatment, the non-drug treatment can be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks. The second active agent can be conjugated to a polymer.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous manner as used herein is administration of the at least two therapeutic agents within 1 hour of each other. Substantially simultaneous administration can be accomplished, for example, by administering to the subject a single composition having a fixed ratio of each therapeutic agent or in separate capsules for each of the therapeutic agents. Sequential manner as used herein is administration of one of the at least two therapeutic agents more than one hour after the other of the at least two therapeutic agents. Preferably, for sequential administration, one of the at least two therapeutic agents is administered at least 12 hours, at least 24 hours, at least 48 hours, at least 96 hours or at least one week after administration of the other therapeutic agent. Sequential or substantially simultaneous administration of each therapeutic agent can be effected by any appropriate route including, but not limited to, oral routes, intravenous routes, subcutaneous routes, intramuscular routes, and direct absorption through mucous membrane tissues. The therapeutic agents can be administered by the same route or by different routes. For example, a first therapeutic agent of the combination selected can be administered by subcutaneous injection while the other therapeutic agents of the combination can be administered orally. Alternatively, for example, all therapeutic agents can be administered orally or all therapeutic agents can be administered by subcutaneous injection. The sequence in which the therapeutic agents are administered is not narrowly critical.

In a preferred aspect, the second active agent is a chemotherapeutic agent. The additional chemotherapeutic agent (also referred to as an anti-neoplastic agent or anti-proliferative agent) can be an alkylating agent; an antibiotic; an anti-metabolite; a detoxifying agent; an interferon; a polyclonal or monoclonal antibody; an EGFR inhibitor; an FGFR inhibitor, a HER2 inhibitor; a histone deacetylase inhibitor; a hormone; a mitotic inhibitor; an MTOR inhibitor; a multi-kinase inhibitor; a serine/threonine kinase inhibitor; a tyrosine kinase inhibitors; a VEGF/VEGFR inhibitor; a taxane or taxane derivative, an aromatase inhibitor, an anthracycline, a microtubule targeting drug, a topoisomerase poison drug, an inhibitor of a molecular target or enzyme (e.g., a kinase inhibitor), a cytidine analogue drug or any chemotherapeutic, anti-neoplastic or anti-proliferative agent listed in www.cancer.org/docroot/cdg/cdg_0.asp.

Exemplary alkylating agents include, but are not limited to, cyclophosphamide (Cytoxan; Neosar); chlorambucil (Leukeran); melphalan (Alkeran); carmustine (BiCNU); busulfan (Busulfex); lomustine (CeeNU); dacarbazine (DTIC-Dome); oxaliplatin (Eloxatin); carmustine (Gliadel); ifosfamide (Ifex); mechlorethamine (Mustargen); busulfan (Myleran); carboplatin (Paraplatin); cisplatin (CDDP; Platinol); temozolomide (Temodar); thiotepa (Thioplex); bendamustine (Treanda); or streptozocin (Zanosar).

Exemplary antibiotics include, but are not limited to, doxorubicin (Adriamycin); doxorubicin liposomal (Doxil); mitoxantrone (Novantrone); bleomycin (Blenoxane); daunorubicin (Cerubidine); daunorubicin liposomal (DaunoXome); dactinomycin (Cosmegen); epirubicin (Ellence); idarubicin (Idamycin); plicamycin (Mithracin); mitomycin (Mutamycin); pentostatin (Nipent); or valrubicin (Valstar).

Exemplary anti-metabolites include, but are not limited to, fluorouracil (Adrucil); capecitabine (Xeloda); hydroxyurea (Hydrea); mercaptopurine (Purinethol); pemetrexed (Alimta); fludarabine (Fludara); nelarabine (Arranon); cladribine (Cladribine Novaplus); clofarabine (Clolar); cytarabine (Cytosar-U); decitabine (Dacogen); cytarabine liposomal (DepoCyt); hydroxyurea (Droxia); pralatrexate (Folotyn); floxuridine (FUDR); gemcitabine (Gemzar); cladribine (Leustatin); fludarabine (Oforta); methotrexate (MTX; Rheumatrex); methotrexate (Trexall); thioguanine (Tabloid); TS-1 or cytarabine (Tarabine PFS).

Exemplary detoxifying agents include, but are not limited to, amifostine (Ethyol) or mesna (Mesnex).

Exemplary interferons include, but are not limited to, interferon alfa-2b (Intron A) or interferon alfa-2a (Roferon-A).

Exemplary polyclonal or monoclonal antibodies include, but are not limited to, trastuzumab (Herceptin); ofatumumab (Arzerra); bevacizumab (Avastin); rituximab (Rituxan); cetuximab (Erbitux); panitumumab (Vectibix); tositumomab/iodine[131] tositumomab (Bexxar); alemtuzumab (Campath); ibritumomab (Zevalin; In-111; Y-90 Zevalin); gemtuzumab (Mylotarg); eculizumab (Soliris) ordenosumab; nivolumab (Opdivo); pembrolizumab (Keytruda); ipilimumab (Yervoy); pidilizumab; atezolizumab.

Exemplary EGFR inhibitors include, but are not limited to, gefitinib (Iressa); lapatinib (Tykerb); cetuximab (Erbitux); erlotinib (Tarceva); panitumumab (Vectibix); PKI-166; canertinib (CI-1033); matuzumab (Emd7200) or EKB-569.

Exemplary HER2 inhibitors include, but are not limited to, trastuzumab (Herceptin); lapatinib (Tykerb) or AC-480.

Histone Deacetylase Inhibitors include, but are not limited to, vorinostat (Zolinza).

Exemplary hormones include, but are not limited to, tamoxifen (Soltamox; Nolvadex); raloxifene (Evista); megestrol (Megace); leuprolide (Lupron; Lupron Depot; Eligard; Viadur); fulvestrant (Faslodex); letrozole (Femara); triptorelin (Trelstar LA; Trelstar Depot); exemestane (Aromasin); goserelin (Zoladex); bicalutamide (Casodex); anastrozole (Arimidex); fluoxymesterone (Androxy; Halotestin); medroxyprogesterone (Provera; Depo-Provera); estramustine (Emcyt); flutamide (Eulexin); toremifene (Fareston); degarelix (Firmagon); nilutamide (Nilandron); abarelix (Plenaxis); or testolactone (Teslac).

Exemplary mitotic inhibitors include, but are not limited to, paclitaxel (Taxol; Onxol; Abraxane); docetaxel (Taxotere); vincristine (Oncovin; Vincasar PFS); vinblastine (Velban); etoposide (Toposar; Etopophos; VePesid); teniposide (Vumon); ixabepilone (Ixempra); nocodazole; epothilone; vinorelbine (Navelbine); camptothecin (CPT); irinotecan (Camptosar); topotecan (Hycamtin); amsacrine or lamellarin D (LAM-D).

Exemplary MTOR inhibitors include, but are not limited to, everolimus (Afinitor) or temsirolimus (Torisel); rapamune, ridaforolimus; or AP23573.

Exemplary multi-kinase inhibitors include, but are not limited to, sorafenib (Nexavar); sunitinib (Sutent); BIBW 2992; E7080; Zd6474; PKC-412; motesanib; or AP24534.

Exemplary serine/threonine kinase inhibitors include, but are not limited to, ruboxistaurin; eril/easudil hydrochloride; flavopiridol; seliciclib (CYC202; Roscovitrine); SNS-032 (BMS-387032); Pkc412; bryostatin; KAI-9803; SF1126; VX-680; Azd1152; Arry-142886 (AZD-6244); SCIO-469; GW681323; CC-401; CEP-1347 or PD 332991.

Exemplary tyrosine kinase inhibitors include, but are not limited to, erlotinib (Tarceva); gefitinib (Iressa); imatinib (Gleevec); sorafenib (Nexavar); sunitinib (Sutent); trastuzumab (Herceptin); bevacizumab (Avastin); rituximab (Rituxan); lapatinib (Tykerb); cetuximab (Erbitux); panitumumab (Vectibix); everolimus (Afinitor); alemtuzumab (Campath); gemtuzumab (Mylotarg); temsirolimus (Torisel); pazopanib (Votrient); dasatinib (Sprycel); nilotinib (Tasigna); vatalanib (Ptk787; ZK222584); CEP-701; SU5614; MLN518; XL999; VX-322; Azd0530; BMS-354825; SKI-606 CP-690; AG-490; WHI-P154; WHI-P131; AC-220; or AMG888.

Exemplary VEGF/VEGFR inhibitors include, but are not limited to, bevacizumab (Avastin); sorafenib (Nexavar); sunitinib (Sutent); ranibizumab; pegaptanib; or vandetinib.

Exemplary microtubule targeting drugs include, but are not limited to, paclitaxel, docetaxel, vincristin, vinblastin, nocodazole, epothilones and navelbine.

Exemplary topoisomerase poison drugs include, but are not limited to, teniposide, etoposide, adriamycin, camptothecin, daunorubicin, dactinomycin, mitoxantrone, amsacrine, epirubicin and idarubicin.

Exemplary taxanes or taxane derivatives include, but are not limited to, paclitaxel and docetaxol.

Exemplary general chemotherapeutic, anti-neoplastic, anti-proliferative agents include, but are not limited to, altretamine (Hexalen); isotretinoin (Accutane; Amnesteem; Claravis; Sotret); tretinoin (Vesanoid); azacitidine (Vidaza); bortezomib (Velcade) asparaginase (Elspar); levamisole (Ergamisol); mitotane (Lysodren); procarbazine (Matulane); pegaspargase (Oncaspar); denileukin diftitox (Ontak); porfimer (Photofrin); aldesleukin (Proleukin); lenalidomide (Revlimid); bexarotene (Targretin); thalidomide (Thalomid); temsirolimus (Torisel); arsenic trioxide (Trisenox); verteporfin (Visudyne); mimosine (Leucenol); (1M tegafur—0.4 M 5-chloro-2,4-dihydroxypyrimidine—1 M potassium oxonate) or lovastatin.

In another aspect, the additional chemotherapeutic agent can be a cytokine such as G-CSF (granulocyte colony stimulating factor). In another aspect, a compound of the present disclosure, or a pharmaceutically acceptable salt, prodrug, metabolite, analog or derivative thereof, may be administered in combination with radiation therapy. Radiation therapy can also be administered in combination with a compound of the present disclosure and another chemotherapeutic agent described herein as part of a multiple agent therapy. In yet another aspect, a compound of the present disclosure, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), rituximab, Xeloda (capecitabine), Cisplatin (CDDP), Carboplatin, TS-1 (tegafur, gimestat and otastat potassium at a molar ratio of 1:0.4:1), Camptothecin-11 (CPT-11, Irinotecan or Camptosar™) or CMFP (cyclophosphamide, methotrexate, 5-fluorouracil and prednisone).

In certain aspects, a compound of the present disclosure, or a pharmaceutically acceptable salt, prodrug, metabolite, polymorph or solvate thereof, may be administered with an inhibitor of an enzyme, such as a receptor or non-receptor kinase. Receptor and non-receptor kinases of the disclosure are, for example, tyrosine kinases or serine/threonine kinases. Kinase inhibitors of the disclosure are small molecules, polynucleic acids, polypeptides, or antibodies.

Exemplary kinase inhibitors include, but are not limited to, BIBW 2992 (targets EGFR and Erb2), Cetuximab/Erbitux (targets Erb1), Imatinib/Gleevic (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), sorafenib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HERS), and AP24534 (multiple targets including Flt3).

Exemplary serine/threonine kinase inhibitors include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCIO-469 (targets MAP/MEK), GW681323 (targets MAP/MEK), CC-401 (targets JNK), CEP-1347 (targets JNK), and PD 332991 (targets CDK).

Contemplated second active agents also include those administered to treat type 2 diabetes such as sulfonylureas (e.g., chlorpropamide, glipizide, glyburide, glimepiride); meglitinides (e.g., repaglinide and nateglinide); biguanides (e.g., metformin); thiazolidinediones (rosiglitazone, troglitazone, and pioglitazone); glucagon-like 1 peptide mimetics (e.g. exenatide and liraglutide); sodium-glucose cotransporter inhibitors (e.g., dapagliflozin), dipeptidyl peptidase 4 inhibitors (e.g. gliptins), sodium—glucose linked transporter inhibitors, renin inhibitors, and alpha-glucosidase inhibitors (e.g., acarbose and meglitol), and/or those administered to treat cardiac disorders and conditions, such as hypertension, dyslipidemia, ischemic heart disease, cardiomyopathy, cardiac infarction, stroke, venous thromboembolic disease and pulmonary hypertension, which have been linked to overweight or obesity, for example, chlorthalidone; hydrochlorothiazide; indapamide, metolazone; loop diuretics (e.g., bumetanide, ethacrynic acid, furosemide, lasix, torsemide); potassium-sparing agents (e.g., amiloride hydrochloride, spironolactone, and triamterene); peripheral agents (e.g., reserpine); central alpha-agonists (e.g., clonidine hydrochloride, guanabenz acetate, guanfacine hydrochloride, and methyldopa); alpha-blockers (e.g., doxazosin mesylate, prazosin hydrochloride, and terazosin hydrochloride); beta-blockers (e.g., acebutolol, atenolol, betaxolol, nisoprolol fumarate, carteolol hydrochloride, metoprolol tartrate, metoprolol succinate, Nadolol, penbutolol sulfate, pindolol, propranolol hydrochloride, and timolol maleate); combined alpha- and beta-blockers (e.g., carvedilol and labetalol hydrochloride); direct vasodilators (e.g., hydralazine hydrochloride and minoxidil); calcium antagonists (e.g., diltiazem hydrochloride and verapamil hydrochloride); dihydropyridines (e.g., amlodipine besylate, felodipine, isradipine, nicardipine, nifedipine, and nisoldipine); ACE inhibitors (benazepril hydrochloride, captopril, enalapril maleate, fosinopril sodium, lisinopril, moexipril, quinapril hydrochloride, ramipril, trandolapril); angiotensin II receptor blockers (e.g., losartan potassium, valsartan, and Irbesartan); and combinations thereof, as well as statins such as mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin., typically for treatment of dyslipidemia.

Other second active agents that may be co-administered (e.g. sequentially or simultaneously) include agents administered to treat ischemic heart disease including statins, nitrates (e.g., Isosorbide Dinitrate and Isosorbide Mononitrate), beta-blockers, and calcium channel antagonists, agents administered to treat cardiomyopathy including inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers, agents administered to treat cardiac infarction including ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase), agents administered to treat strokes including anti-platelet agents (e.g., Aspirin, Clopidogrel, Dipyridamole, and Ticlopidine), anticoagulant agents (e.g., Heparin), and thrombolytic agents, agents administered to treat venous thromboembolic disease including anti-platelet agents, anticoagulant agents, and thrombolytic agents, agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil, agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex, agents administered to treat sleep apnea include Modafinil and amphetamines, agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents, agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid, agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax), agents administered to treat polycystic ovary syndrome include insulin-sensitizers, combinations of synthetic estrogen and progesterone, Spironolactone, Eflornithine, and Clomiphene, agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone, agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta, agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic, agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate), agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers, and other weight loss agents, including serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, and topamax.

As used herein, "treating" or "treat" describes the management and care of a patient for the purpose of combating a disease, condition, or disorder and includes the administration of a compound of the present disclosure, or a pharmaceutically acceptable salt, prodrug, metabolite, polymorph or solvate thereof, to alleviate the symptoms or complications of a disease, condition or disorder, or to eliminate the disease, condition or disorder.

A compound of the present disclosure, or a pharmaceutically acceptable salt, prodrug, metabolite, polymorph or solvate thereof, can also be used to prevent a disease, condition or disorder. As used herein, "preventing" or "prevent" describes reducing or eliminating the onset of the symptoms or complications of the disease, condition or disorder.

As used herein, the terms "ameliorate" or "alleviate" are meant to describe a process by which the severity of a sign or symptom of a disorder is decreased. Importantly, a sign or symptom can be alleviated without being eliminated. In a preferred aspect, the administration of pharmaceutical compositions of the disclosure leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute). Furthermore, severity describes a nuclear grade, which refers to the size and shape of the nucleus in tumor cells and the percentage of tumor cells that are dividing (see, National Cancer Institute).

In another aspect of the disclosure, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness.

Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin, some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant disclosure.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present disclosure, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present disclosure, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present disclosure, or a pharmaceutically acceptable salt, prodrug, metabolite, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present disclosure, or a pharmaceutically acceptable salt, prodrug, metabolite, polymorph or solvate thereof, can induce or activate cell death selectively in cancer cells. Administering to a subject in need thereof a compound of the present disclosure, or a pharmaceutically acceptable salt, prodrug, metabolite, polymorph or solvate thereof, can induce or activate cell death selectively in cancer cells. Contacting a cell with a compound of the present disclosure, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present disclosure, or a pharmaceutically acceptable salt, prodrug, metabolite, polymorph or solvate thereof, induces cell death selectively in one or more cells affected by a cell proliferative disorder.

The present disclosure relates to a method of treating or preventing cancer by administering a compound of the present disclosure, or a pharmaceutically acceptable salt, prodrug, metabolite, polymorph or solvate thereof, to a subject in need thereof, where administration of the compound of the present disclosure, or a pharmaceutically acceptable salt, prodrug, metabolite, polymorph or solvate thereof, results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

A "therapeutically effective amount" of a compound, with respect to use in treatment, refers to an amount of a compound in a preparation which, when administered as part of a desired dosage regimen (to a mammal, preferably a human) alleviates a symptom, ameliorates a condition, or slows or prevents the onset of disease conditions according to clinically acceptable standards for the disorder or condition to be treated or the cosmetic purpose, e.g., at a reasonable benefit/risk ratio applicable to any medical treatment. A "therapeutically effective amount" is synonymous with "efficacious dose".

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing intensity, duration, or frequency of attack of the disease, and decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. For example, an effective amount of a compound of the present disclosure for treating a proliferation disorder is an amount sufficient to treat or ameliorate one or more symptoms associated with the proliferation disorder. An "effective amount" is an amount sufficient to result in one or more of the following (which can also correspond to various aspects of the disclosure): reducing tumor size, reducing tumor volume, reducing tumor number, decrease in metastatic lesions, increase in survival time, decrease in mortality rate, decrease in tumor growth rate, decrease in tumor regrowth, reduction in proportion of proliferating cells, or increasing the quality of life of those suffering from a proliferation disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. In providing a subject with one or more of the compounds described herein, the dosage of administered compound(s) will vary depending upon such factors as the subject's age, weight, height, sex, general medical condition, previous medical history, disease progression, route of administration, formulation and the like.

Dosages for a compound of the present disclosure may be determined empirically in individuals who have been given one or more administration(s). Individuals are given incremental dosages of a compound of the present disclosure. To assess efficacy of a compound of the present disclosure, markers of the disease state can be monitored. It will be apparent to one of skill in the art that the dosage will vary depending on the individual, the stage of the disease (e.g., tumor size, tumor grade, tumor number), and the past and concurrent treatments being used.

Toxicity and therapeutic efficacy of compounds of the present disclosure can be determined by standard pharmaceutical procedures in experimental animals. Toxic doses may be determined as the maximum tolerated dose (MTD) or alternatively the LD50 (the dose lethal to 50% of the population). Efficacious doses may be determined as the ED50 (the dose therapeutically effective in 50% of the population) or dose required to provide some average amount of change in an animal (e.g. the dose required to provide an average reduction in systolic blood pressure of 10 mm Hg in a group of subjects).

Ideally, the efficacious and toxic doses may be determined in the same species. However if they are determined in different species, allometric scaling may be used to translate the efficacious or toxic dose to another species. The dose ratio between toxic and therapeutic effects is the therapeutic index and it can be expressed as the ratio LD50/ED50. In comparing mice to rats, the commonly accepted scaling factor is 2; the rat dose is estimated to be one-half the dose in mice. Thus if the toxic dose in a rat is 100 mg/kg and the efficacious dose in a mouse is 1 mg/kg, the therapeutic index in the rat may be calculated as efficacious dose in rat equals 1 mg/kg/2 or 0.5 mg/kg and the therapeutic index is 200. FDA defines a drug as having a narrow therapeutic range if: (a) less than 2-fold difference between median lethal and median effective dose, or (b) less than 2-fold difference between minimum toxic and minimum effective concentrations in the blood.

Compounds of the present disclosure which exhibit large therapeutic indices are preferred. While compounds of the present disclosure that exhibit toxic side effects may be used, care should be taken to design a delivery system that targets such compounds of the present disclosure to the site of affected tissue in order to minimize potential damage to uninfected cells and, thereby, reduce side effects.

The data obtained from animal studies can be used in formulating a range of dosage for use in humans. The dosage of such compounds of the present disclosure lies preferably within a range of circulating concentrations that include the efficacious dose range with little or no toxicity. The dosage may vary within this range depending upon the dosage form employed and the route of administration utilized. For compounds of the present disclosure with a MW less than 1000, the therapeutically effective dose can be estimated initially from cell culture assays while animal models will provide a better estimation of dose for conjugates where the linker requires cleavage to release an active moiety. Such information can be used to more accurately determine useful doses in humans. It is well known in the art that polymer conjugation dilutes the activity of the active moiety (polymer is a diluent). This is exemplified in the mouse dosing model of the anti-cancer drugs shown in the following Table.

| Parent Drug | Drug Dose (mg/kg) | Conjugate | Conjugate Dose (mg/kg) |
| --- | --- | --- | --- |
| TNP-470 | 30 (qod) | XMT-1107 | 800 |
| Docetaxel | 12 (Q4d) | Opaxio | 480 |
| CPT-11 | 20 (q2d) | EZN-2208 | 145 (q2d) |
| Doxorubicin | 5 (q4d) | PK1 | 62 (q7d) |
| Carboplatin | 60 (Qd) | AP-5356 | 2200 |

The polymer conjugate and modified compounds of the present disclosure surprisingly provide superior efficacy and lower toxicity when compared to the unconjugated and or unmodified parent drug/active moiety.

For example, the fumagillol conjugates and modified fumagillol compounds of the present disclosure are surprisingly superior to fumagillol small molecules as they provide increased tumor reduction in DIO mice at equivalent molar doses. The compounds of the present disclosure may be used at lower molar doses and with less frequent dosing to provide equivalent tumor reduction. Lower molar doses and reduced dosing frequency reduce systemic drug exposure and systemic drug toxicity.

Traditional polymer conjugates dilute activity, increase doses by 5-20× and provide little change in therapeutic index (<2×). In contrast, the polymer conjugate compounds of the present disclosure surprisingly and unexpectedly provide an enhanced therapeutic index (order of magnitude improvement) and demonstrate increased activity at a reduced dose.

In the methods of the present disclosure, the polymer conjugate compounds of the present disclosure surprisingly demonstrate efficacy with less frequent dose administration (e.g., q4d, dosing every fourth day, q7d, dosing every seventh day, q8d, dosing every eighth day), doses which are decreased at least 84 mole % fumagillol equivalent, reduced AUC in non-target compartments while therapeutic index is increased (>10×).

In another aspect, provided herein are effective dosages of a compound of the present disclosure. For example, provided here are methods that include administering doses of a compound of the present disclosure that are effective for tumor reduction. For example, contemplated dosage of a compound of the present disclosure in the methods described herein may include administering a dose independent of body weight of about 200 mg/day, about 80 mg/day, about 40 mg/day, about 20 mg/day, about 10 mg/day, about 5 mg/day, about 3 mg/day, about 2 mg/day, about 1 mg/day, about 0.5 mg/day, about 0.2 mg/day, about 0.05 mg/day, about 0.01 mg/day, or about 0.001 mg/day.

An effective amount of the drug for tumor reduction in a patient may also be dosed based on body weight or surface area and be about 0.0001 mg/kg to about 5 mg/kg of body weight per day. For example, a contemplated dosage may be from about 0.001 to 5 mg/kg of body weight per day, about 0.001 mg/kg to 1 mg/kg of body weight per day, about 0.001 mg/kg to 0.1 mg/kg of body weight per day, about 0.001 to about 0.010 mg/kg of body weight a day or about 0.007 mg/kg of body weight a day in single, divided, or continuous doses. These doses may be adjusted for the patient's weight in kg, body surface area in $m^2$, and age in years. For example, a contemplated dosage may be about 1 $mg/m^2$ to about 50 $mg/m^2$, about 5 $mg/m^2$ to about 25 $mg/m^2$, about 5 $mg/m^2$ to about 50 $mg/m^2$, about 5 $mg/m^2$ to about 15 $mg/m^2$, or about 5 $mg/m^2$ to about 10 $mg/m^2$.

An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Administration of a compound of the present disclosure in accordance with the method in the present disclosure can be continuous or intermittent, depending, for example, upon the recipient's physiological condition, whether the purpose of the administration is therapeutic or prophylactic, and other factors known to skilled practitioners. The administration of a compound of the present disclosure may be essentially continuous over a preselected period of time or may be in a series of spaced doses.

For repeated administrations over several days or longer, depending on the condition, the treatment is sustained until a desired suppression of disease symptoms occurs or until sufficient therapeutic levels are achieved. For example, dosing from one to five times a week is contemplated. Other dosing regimens include a regimen of, 1 to 5 times per week, every three to four days, or less frequently. In certain aspects, a compound of the present disclosure is administered about every fourth day, about every seventh day, about ever tenth day or about every fourteenth day. In some aspects, a compound of the present disclosure is administered about once per week, once every two weeks, or about 1 to 4 times per month depending on the duration of the response to drug administration. Intermittent dosing regimen with staggered dosages spaced by 2 days up to 7 days or even 14 days may be used. In some aspects, treatment may start with a daily dosing and later change to weekly even monthly dosing. The progress of this therapy is easily monitored by conventional techniques and assays, or by measuring MetAP2 as described in U.S. Pat. No. 6,548,477.

Frequency of administration may be determined and adjusted over the course of therapy. For example, frequency of administration may be determined or adjusted based on the type and severity of the disease to be treated, whether the agent is administered for preventive or therapeutic purposes, previous therapy, the patient's clinical history and response to the agent, and the discretion of the attending physician. Typically the clinician will administer a compound of the present disclosure until a dosage is reached that achieves the desired result Treatment can be continued for as long or as short a period as desired. A suitable treatment period can be, for example, at least about one week, at least about four weeks, at least about one month, at least about six months, at least about 1 year, at least about 2 years, or indefinitely. A treatment period can terminate when a desired result, for example tumor reduction target, is achieved. For example, when loss of about 5% tumor size, about 10% tumor size, about 20% tumor size, about 30% tumor size or more has been achieved. A treatment regimen can include a corrective phase, during which a compound of the present disclosure is administered in dose, or dosing frequency, sufficient to provide reduction of tumor size is administered, followed by a maintenance phase, during which a lower compound dose, or decreased dosing frequency, sufficient to prevent tumor regrowth is administered.

Compounds and Pharmaceutical Compositions of the Present Disclosure

The present disclosure provides compositions and drug conjugate compositions including an active moiety modified, a conjugate moiety, and a cleavable linker, wherein cleavage of the linker occurs substantially in a target tissue to produce a modified active moiety having reduced efflux from target tissue compared to the unmodified active moiety. The present disclosure also provides compositions including a modified active moiety.

The conjugate moiety used depends on the physicochemical properties of both the conjugate moiety and the active moiety, in addition to biological requirements, e.g., pharmacokinetic and pharmacodynamic properties of the active moiety and knowledge of the disease state. One of skill in the art will be able to select an appropriate conjugate moiety based upon the above considerations. The conjugate moiety may be used to deliver small molecule active moieties or larger molecule active moieties, such as proteins, peptides, or oligonucleotides.

The conjugate moiety improves the delivery of an active moiety to target. The conjugate moiety is chosen to maximize bioavailability of the active moiety, optimize onset, duration, and rate of delivery of the active moiety, and maintain the concentration of an active moiety in a target tissue within a therapeutic range as long as required for effective treatment. The conjugate moiety may also assist in minimizing adverse side effects of an active moiety. Thus the conjugate moiety prolongs pharmacological activity of an active moiety, stabilizes labile active moieties from chemical and proteolytic degradation, minimizes side effects, increases solubility, and targets the active moiety to specific cells or tissues.

Other properties of the conjugate moiety to be considered are that the conjugate moiety is minimally or non-immunogenic and non-toxic. The molecular weight of the conjugate moiety should be sufficiently large to avoid rapid elimination via kidney ultrafiltration and low enough to prevent undesirable accumulation within the body. In certain aspects, the conjugate moiety is hydrophilic and is biodegradable. Conjugate moieties that are non-biodegradable are also suitable with compositions and methods of the disclosure. The conjugate moiety should be able to carry the required amount of active moiety and protect against premature metabolism of the active moiety in transit to the target tissue.

Exemplary conjugates include all forms of polymers, synthetic polymers as well as natural product related polymers including peptides, polysaccharides, polynucleic acids, antibodies and aptamers. In preferable aspects, the conjugate is a synthetic polymer. Exemplary polymers of the disclosure have been described in U.S. Pat. No. 4,997,878 to Bock et al, U.S. Pat. No. 5,037,883 to Kopecek et al. U.S. Pat. No. 5,258,453 to Kopecek et al., U.S. Pat. No. 6,464,850 to Zhang et al., U.S. Pat. No. 6,803,438 to Brocchini et al., each of which is incorporated by reference in its entirety. Additional exemplary polymers have been described in Subr et al., J Controlled Release, 18, 123-132 (1992). In some aspects, the method of synthesis of the polymer may lead to the coupling of two or more polymer chains and may increase the weight average molecular weight of the polymer conjugate. It is further recognized that if this coupling occurs, the linkages will be biodegradable.

The active moiety may be any compound or molecule that produces a therapeutic effect in a subject. In certain aspects, the compound or molecule has a molecular weight of 2000 Daltons or less, 1500 Daltons or less, 1000 Daltons or less, 500 Daltons or less, 250 Daltons or less, 100 Daltons or less, 75 Daltons or less, 50 Daltons or less, or 25 Daltons or less. In certain aspects, the compound or molecule is a methionine aminopeptidase-2 (MetAP2) inhibitor. In certain aspects, the compound or molecule is fumagillin, fumagillol, or an analog, derivative, salt or ester thereof. The compound or molecule chosen will depend on the condition or disease to be treated. In certain aspects, two or more active moieties may be used. In certain aspects an active moiety and an inactive "capping" moiety may be used. In compositions of the disclosure, the conjugate moiety is joined to the active moiety via a linker. Any linker structure known in the art may be used to join the modified active moiety to the conjugate moiety. The linker used will depend on the physiological conditions of the target tissue, the properties of the active moiety that are being optimized, and the cleavage mechanism. D'Souza et al. review various types of linkers including linkers that operate via proteolytic cleavage "Release from Polymeric Prodrugs: Linkages and Their Degradation" *J. Pharm. Sci.*, 93, 1962-1979 (2004). Blencoe et al. describe a variety of self-immolative linkers, "Self-immolative linkers in polymeric delivery systems" *Polym. Chem.* 2, 773-790 (2011). Ducry et al. review linkers in *Bioconj. Chem.* 21, 5-13 (2010) "Antibody-Drug Conjugates: Linking Cytotoxic Payloads to Monoclonal Antibodies". Peptide linkers suitable for cleavage by matrix metalloproteinases (MMPs) are described in Chau et al. "Antitumor efficacy of a novel polymer-peptide-drug conjugate in human tumor xenograft models" *Int. J. Cancer* 118, 1519-1526 (2006) and Chau et al. U.S. patent publication number 2004/0116348. Other linker chemistries suitable with compositions of the disclosure are shown in Shiose et al. *Biol. Pharm. Bull.* 30(12) 2365-2370 (2007); Shiose et al.

Bioconjugate Chem. 20(1) 60-70 (2009); Senter, U.S. Pat. No. 7,553,816; De Groot, U.S. Pat. No. 7,223,837; King, U.S. Pat. No. 6,759,509; Susaki, U.S. Pat. No. 6,835,807; Susaki U.S. Pat. No. 6,436,912; and Gemeinhart U.S. Pat. No. 7,943,569.

In certain aspects, the linker is a peptide linker. Exemplary peptide linkers are described in U.S. Pat. No. 6,835,807 to Susaki et al., U.S. Pat. No. 6,291,671 to Inoue et al., U.S. Pat. No. 6,811,996 to Inoue et al., U.S. Pat. No. 7,041,818 to Susaki et al., U.S. Pat. No. 7,091,186 to Senter et al., U.S. Pat. No. 7,553,816 to Senter et al. each of which is incorporated by reference in its entirety. Additional exemplary peptides and their cleavage have been described in Shiose et al. *Biol. Pharm. Bull.* 30(12) 2365-2370 (2007) and Shiose et al. Bioconjugate Chem. 20(1) 60-70 (2009). Peptide linkers suitable for cleavage by matrix metalloproteinases (MMPs) are described in Chau et al. "Antitumor efficacy of a novel polymer-peptide-drug conjugate in human tumor xenograft models" *Int. J. Cancer* 118, 1519-1526 (2006) and Chau et al. U.S. patent publication number 2004/0116348.

The linker may be cleaved by any mechanism known in the art. For example, the linkers may be designed for proteolytic cleavage or intracellular proteolytic cleavage. In certain aspects, the linker is designed such that there is no cleavage of the linker in plasma or there is a very low rate of cleavage in the plasma. Exemplary linker structures are described in further detail below.

In certain aspects, the linker has a structure such that it is to be preferentially cleaved in disease tissue. Since most hydrolases exist in both normal and diseased tissue, the linker should be cleaved by a hydrolase that is more active in disease tissue and/or more prevalent in disease tissue. For example, tumors have generally upregulated metabolic rates and in particular over express proteases including the cathepsins. The upregulation and role of proteases in cancer is described by Mason et al. *Trends in Cell Biology* 21, 228-237 (2011).

In certain aspects, the class of active moieties that are modified are moieties that irreversibly bind to their targets, i.e., after release from the conjugate the active moiety covalently binds to the biochemical target. Once bound, the active moiety cannot diffuse or be transported out of the cell. For targeting to occur in the case of irreversible binding, the rate of small molecule binding to target, $k_{rev1}$, should be significant relative to the rate of small molecule efflux, $k_{sm-1}$. If the rate of efflux is high relative to small molecule binding, small molecule equilibrium will be established between the plasma and the intracellular compartment and there will be no advantage to intracellular delivery relative to extracellular delivery.

In other aspects, the class of active moieties that are modified are moieties that reversibly bind to their targets. For targeting to occur in the case of reversible binding, the equilibrium constant for small molecule binding to target $K=k_{rev1}/k_{rev-1}$ should be large and the "on-rate", $k_{rev1}$, should be large relative to the rate of small molecule efflux, $k_{sm-1}$. If the rate of efflux is high relative to small molecule binding, small molecule equilibrium will be established between the plasma and the intracellular compartment and there will be no advantage to intracellular delivery relative to extracellular delivery. Such a relationship is described schematically below, where: [PC]=concentration of polymer conjugate; [SM]=concentration of released small molecule; plasma=plasma concentration; icell=intracellular concentration; icell-target=small molecule reversibly bound to intracellular target; and inactive=inactive metabolite of small molecule. In certain aspects, when $k_{rev-1}$=zero, the moiety irreversibly binds to its target.

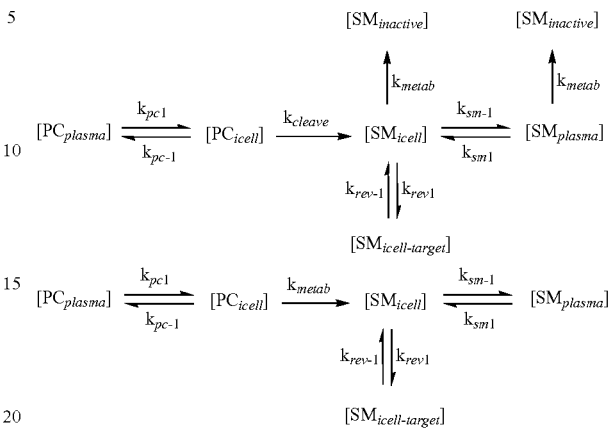

In other aspects, the class of active moieties that are modified are moieties that have very high equilibrium constants and high "on-rates" relative to efflux. In other aspects, the class of active moieties that are modified are moieties that undergo intracellular metabolism at a high rate relative to efflux.

In certain aspects, modifications to the active moiety are accomplished by using a linker having a structure such that upon cleavage, a fragment of the linker remains attached to the active moiety. That fragment may change any of the molecular weight, hydrophobicity, polar surface area, or charge of the active moiety, thereby producing a modified active moiety having reduced efflux from a target cell compared to the unmodified active moiety. For example, coupling MetAP2 inhibitory active moieties via the linkers described herein provide conjugates in which upon cleavage of the linker, produce an active moiety having a fragment of the linker attached thereto (modified active moiety). The modified active moieties described herein may have reduced efflux from a cell compared to the unmodified active moieties, resulting in modified active moieties with superior efficacy to the parent small molecules and superior efficacy to the parent small molecules and superior pharmacokinetic profiles.

The present disclosure provides conjugates with linkers having the structure:

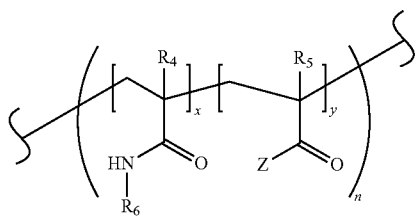

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X-Y-C(O)—W; $AA_1$ is glycine, alanine, or $H_2N(CH_2)mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —$NH_2$, —$NH(C_2-C_6$ hydroxyalkyl), halide or perfluoroalkyloxy; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

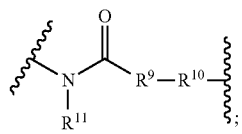

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 100; p is 0 to 20; q is 2 or 3; and r is 1, 2, 3, 4, 5, or 6. In some aspects, n is in the range of about 1 to about 90; about 1 to about 80; about 1 to about 70; about 1 to about 60; about 1 to about 55; or about 1 to about 50.

In certain aspects, $R_4$ is $C_1$-$C_6$ alkyl. In certain aspects, $R_4$ is methyl. In certain aspects, $R_5$ is $C_1$-$C_6$ alkyl. In certain aspects, $R_5$ is methyl. In certain aspects, $R_6$ is 2-hydroxyethyl, 2-hydroxypropyl or 3-hydroxypropyl. In certain aspects, $R_6$ is 2-hydroxypropyl.

In certain aspects, the compound has a molecular weight of greater than about 100 kDa. In certain aspects, the compound has a molecular weight of less than about 100 kDa. In other aspects, the molecular weight is less than about 95 kDa. In other aspects, the molecular weight is less than about 90 kDa. In other aspects, the molecular weight is less than about 80 kDa. In other aspects, the molecular weight is less than about 70 kDa. In other aspects, the molecular weight is less than about 65 kDa. In other aspects, the molecular weight is less than about 60 kDa. In other aspects, the molecular weight is less than about 45 kDa. In other aspects, the molecular weight is less than about 35 kDa.

In certain aspects, the ratio of x to y is in the range of about 100:1 to about 1:1. In certain aspects, the ratio of x to y is in the range of about 30:1 to about 3:1. In other aspects, the ratio of x to y is in the range of about 19:2 to about 7:2. In certain aspects, the ratio of x to y is in the range of about 9:1 to about 4:1. In certain aspects, the ratio of x to y is about 11:1. In certain aspects, the ratio of x to y is about 9:1. In certain aspects, the ratio of x to y is about 4:1. In certain aspects, the ratio of x to y is about 12:1. For example, in certain aspects, the ratio of x:y is about 3:1; the ratio of x:y is about 4:1; the ratio of x:y is about 5:1; the ratio of x:y is about 6:1; the ratio of x:y is about 7:1; the ratio of x:y is about 8:1; the ratio of x:y is about 9:1; the ratio of x:y is about 10:1; the ratio of x:y is about 11:1; the ratio of x:y is about 12:1; the ratio of x:y is about 13:1; the ratio of x:y is about 14:1; the ratio of x:y is about 15:1; the ratio of x:y is about 16:1; the ratio of x:y is about 17:1; the ratio of x:y is about 18:1; the ratio of x:y is about 19:1; the ratio of x:y is about 20:1; the ratio of x:y is about 21:1; the ratio of x:y is about 22:1; the ratio of x:y is about 23:1; the ratio of x:y is about 24:1; the ratio of x:y is about 25:1; the ratio of x:y is about 26:1; the ratio of x:y is about 27:1; the ratio of x:y is about 28:1; the ratio of x:y is about 29:1; or the ratio of x:y is about 30:1.

In certain aspects, Z is —NH-$AA_1$-$AA_2$-$AA_3$-$AA_4$-$AA_5$-$AA_6$-C(O)-L. In certain aspects, L is methoxy, ethoxy, pentafluorophenyloxy, phenyloxy, acetoxy, fluoride, chloride, methoxycarbonyloxy; ethoxycarbonyloxy, phenyloxycarbonyloxy, 4-nitrophenyloxy, trifluoromethoxy, pentafluoroethoxy, or trifluoroethoxy. In certain aspects, L is 4-nitrophenyloxy.

In certain aspects, Z is —NH-$AA_1$-$AA_2$-$AA_3$-$AA_4$-$AA_5$-$AA_6$-C(O)-Q-X—Y—C(O)—W. In certain aspects, $AA_1$ is glycine. In certain aspects, $AA_2$ is glycine. In certain aspects, $AA_3$ is glycine. In certain aspects, $AA_4$ is glycine or phenylalanine. In certain aspects, $AA_5$ is leucine, phenylalanine, valine or tyrosine. In certain aspects, $AA_6$ is asparagine, citrulline, glutamine, glycine, leucine, methionine, threonine or tyrosine. In certain aspects, $AA_5$-$AA_6$ is Leu-Cit, Leu-Gln, Leu-Gly, Leu-Leu, Leu-Met, Leu-Thr, Phe-Cit, Phe-Gln, Phe-Leu, Phe-Met, Phe-Thr, Val-Asn, Val-Cit, Val-Gln, Val-Leu, Val-Met, Val-Thr, Tyr-Cit, Tyr-Leu, or Tyr-Met. In certain aspects, $AA_1$, $AA_3$ and $AA_5$ are glycine, valine, tyrosine, tryptophan, phenylalanine, methionine, leucine, isoleucine, or asparagine. In certain aspects, $AA_2$, $AA_4$ and $AA_6$ are glycine, asparagine, citrulline, glutamine, glycine, leucine, methionine, phenylalanine, threonine or tyrosine. In certain aspects, $AA_2$ is a bond; and $AA_3$ is a bond. In certain aspects, $AA_1$ is glycine; $AA_4$ is phenylalanine; $AA_5$ is leucine; and $AA_6$ is glycine.

In certain aspects, W is

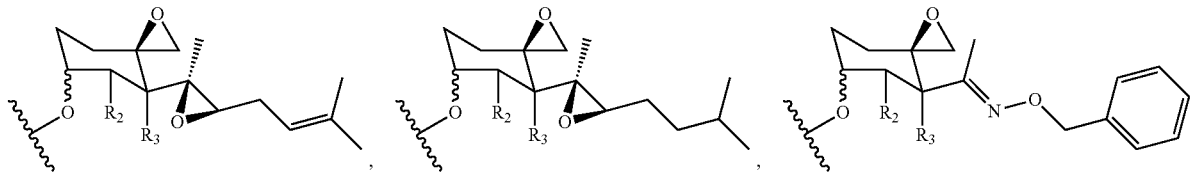

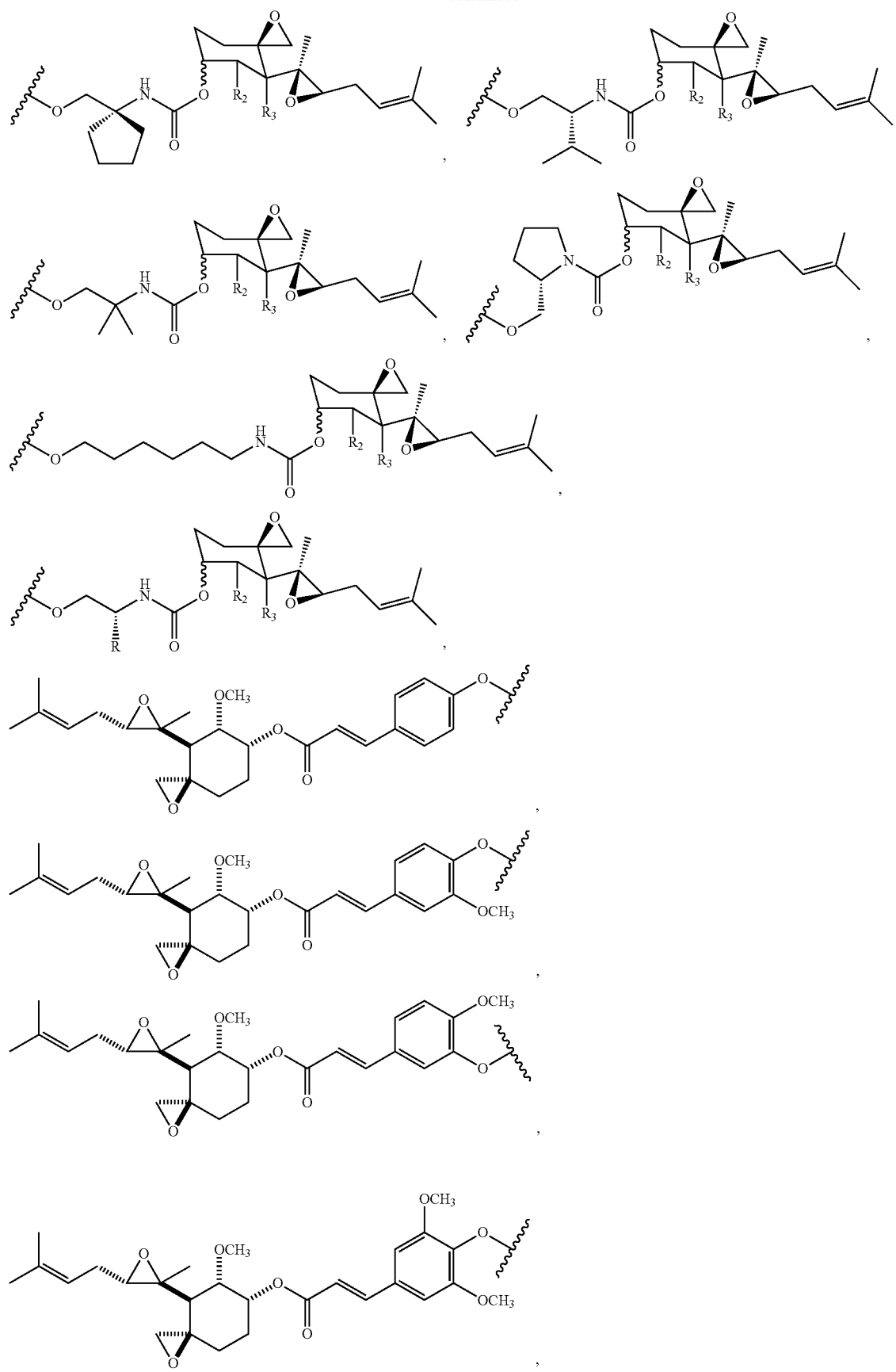

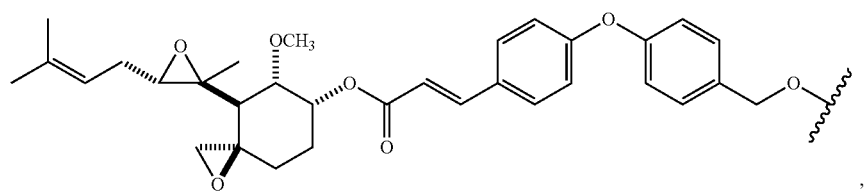,
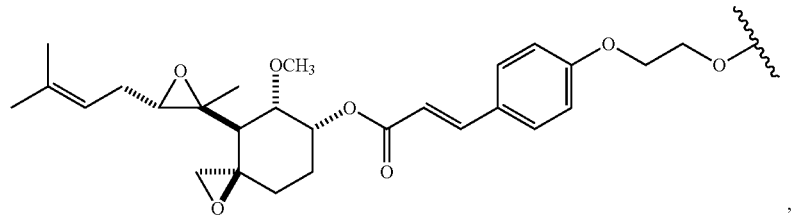,
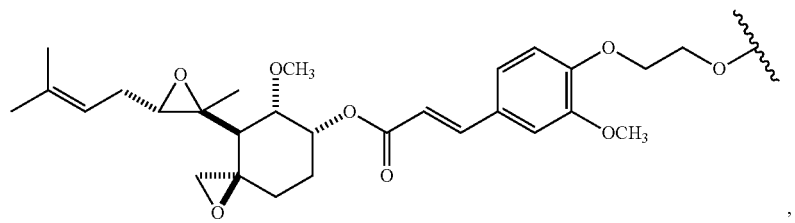,
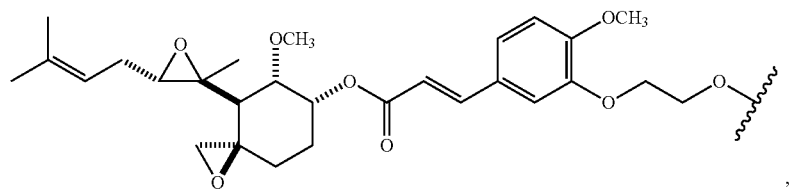,
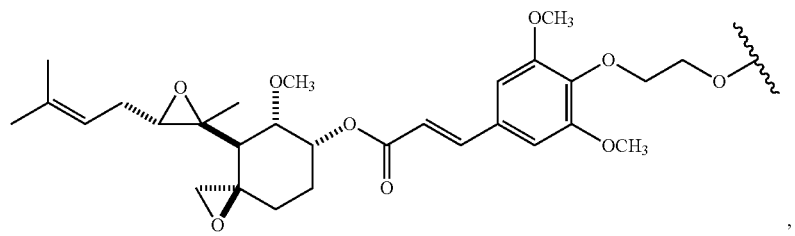,
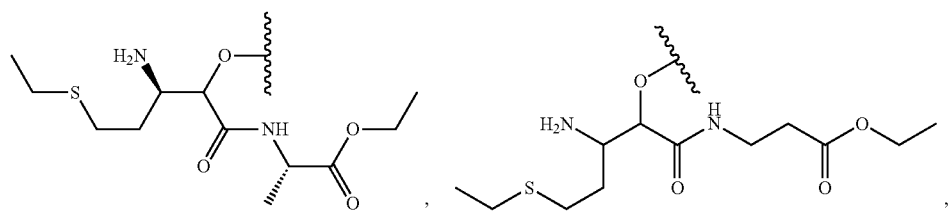,
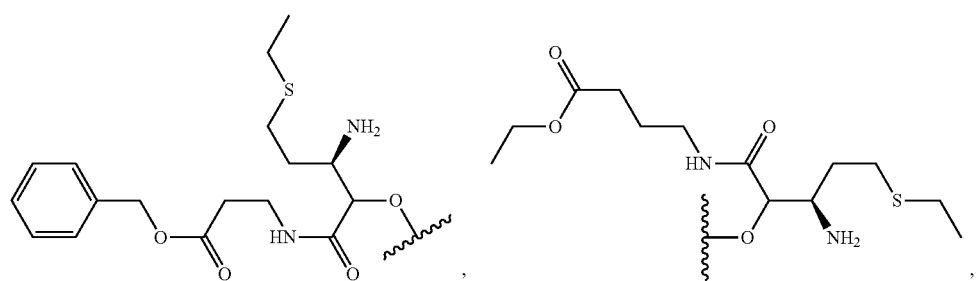, -continued
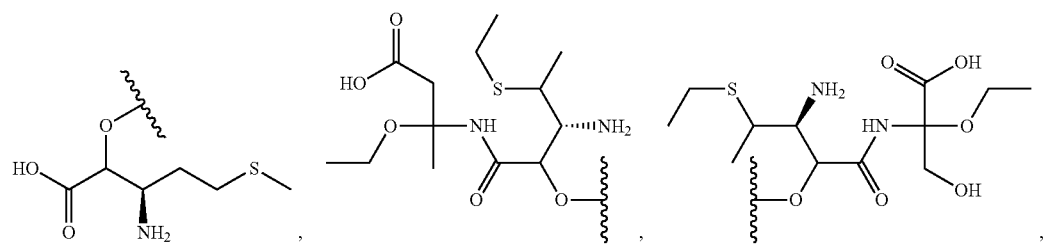
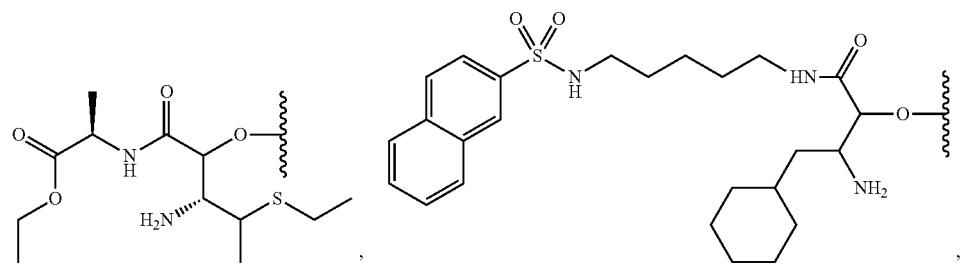
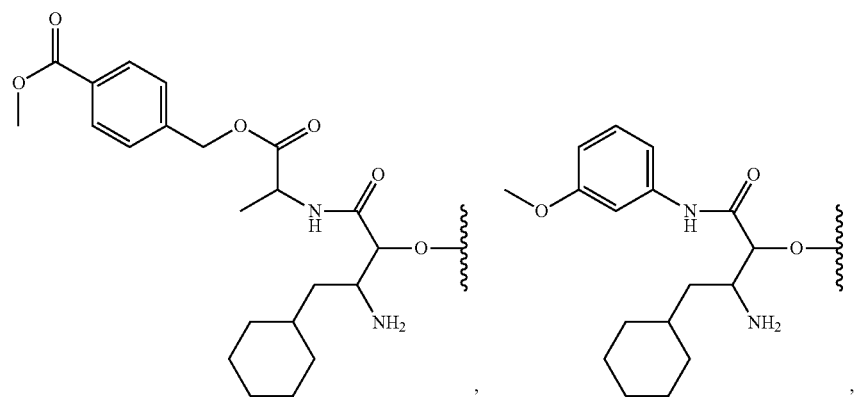
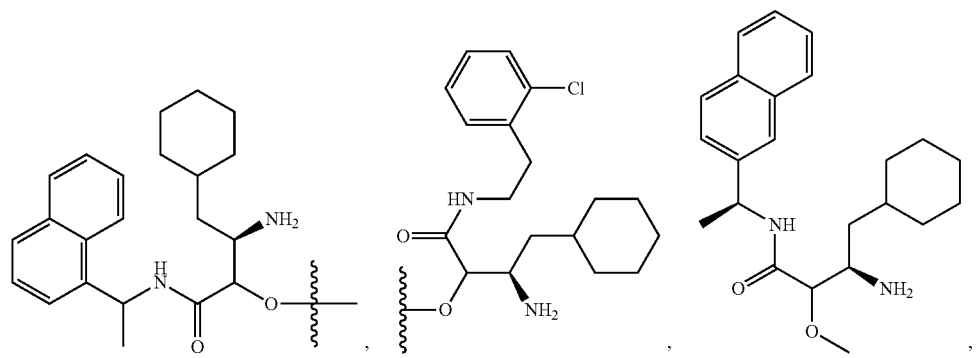
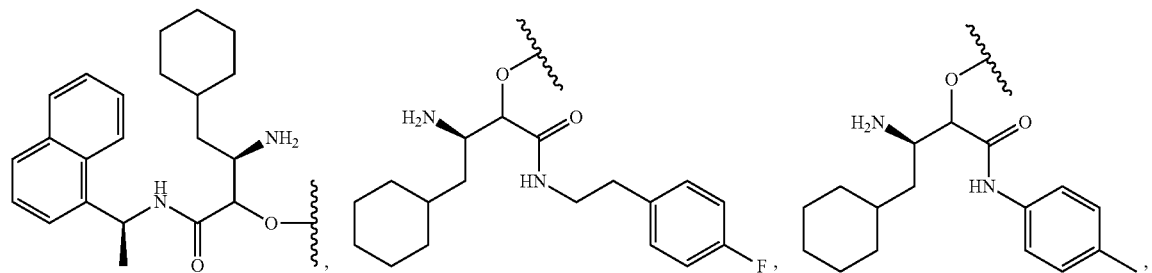

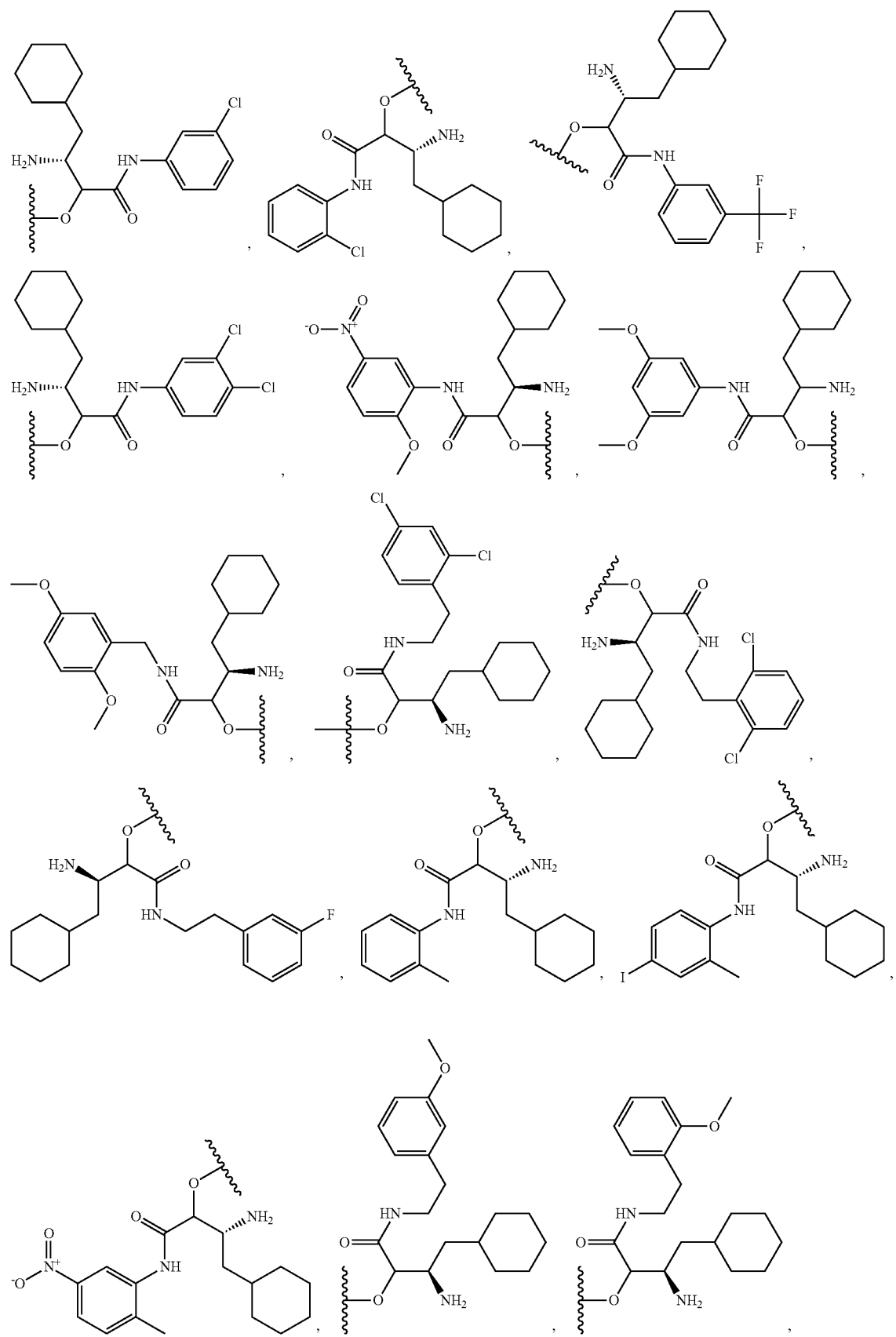

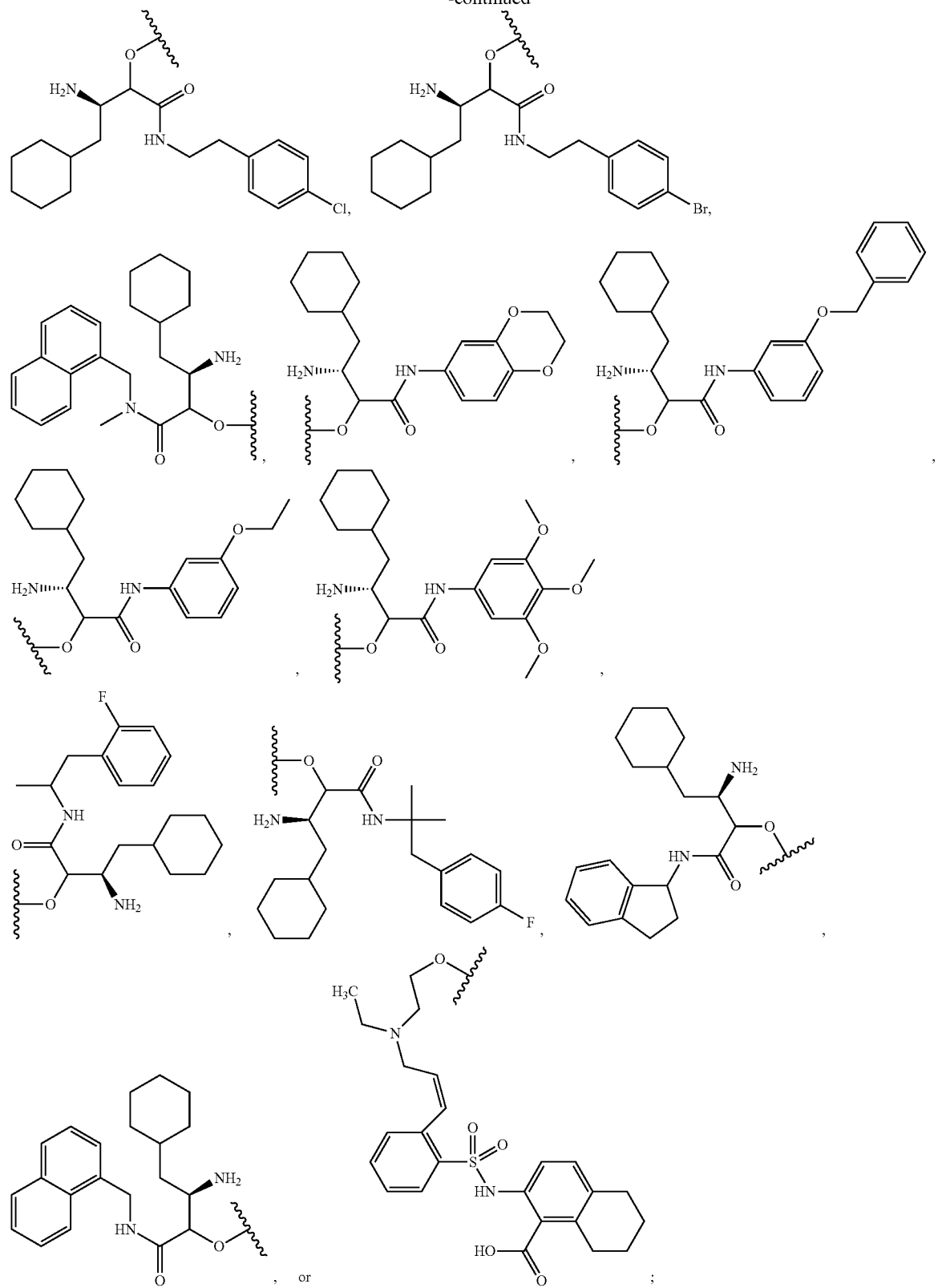
wherein R$_2$ is —OH or methoxy; and R$_3$ is H, —OH or methoxy.

In certain aspects, W is
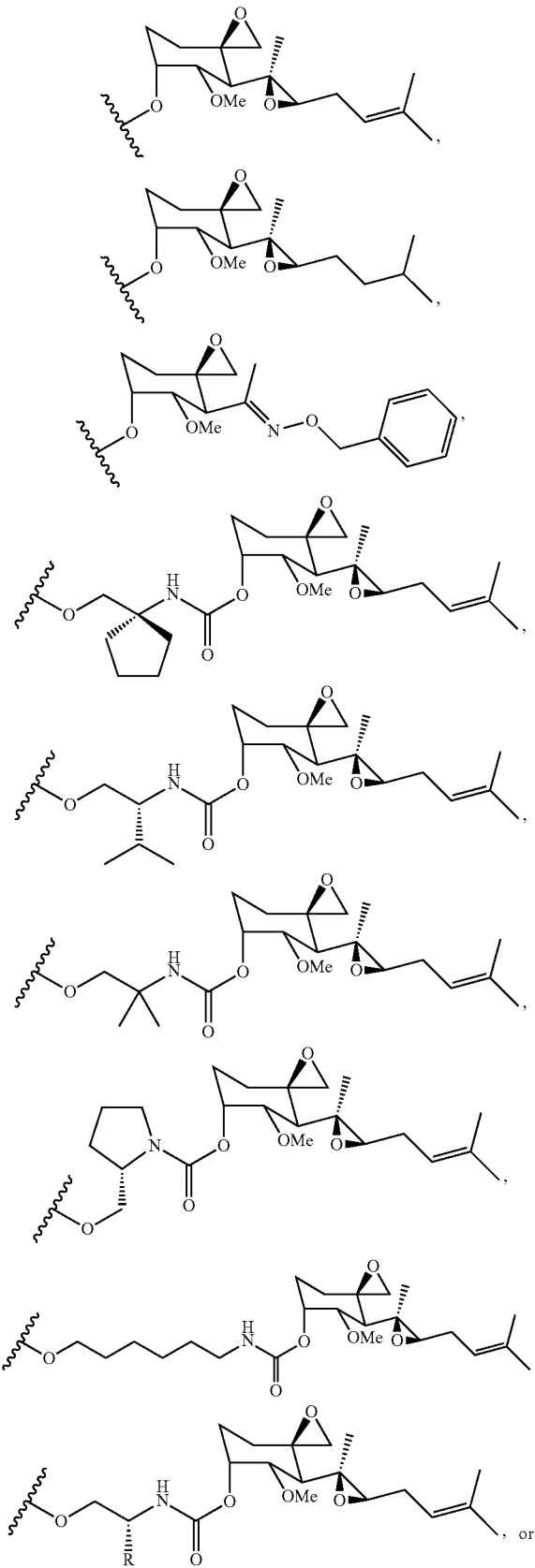
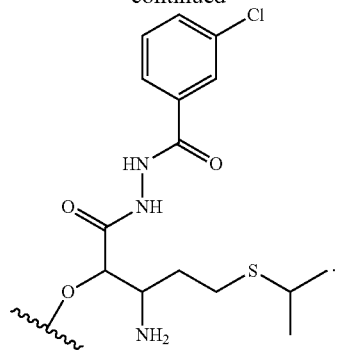
In certain aspects, W is
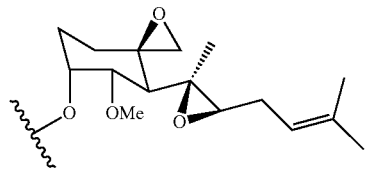
In certain aspects, Q is NR. In other aspects, Q is S.
In certain aspects, J is NR. In other aspects, J is $((CH_2)_qQ)_r$. In other aspects, J is $C_5$-$C_8$ cycloalkyl. In certain aspects, J is aryl.
In certain aspects, Y is NR. In other aspects, Y is S.
In certain aspects, -Q-X—Y— is
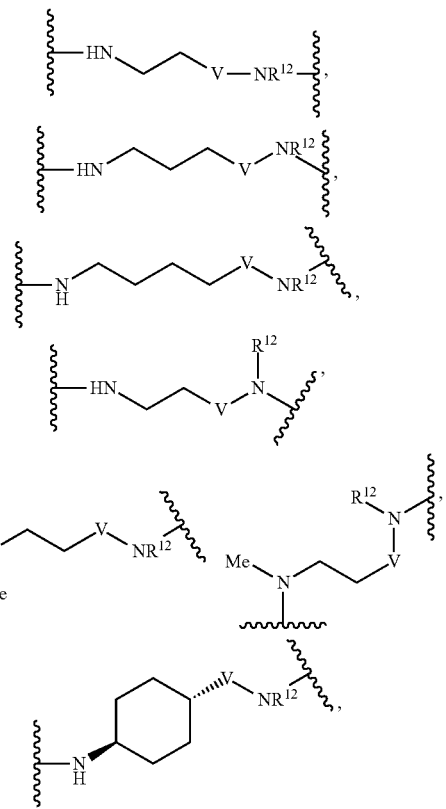

-continued
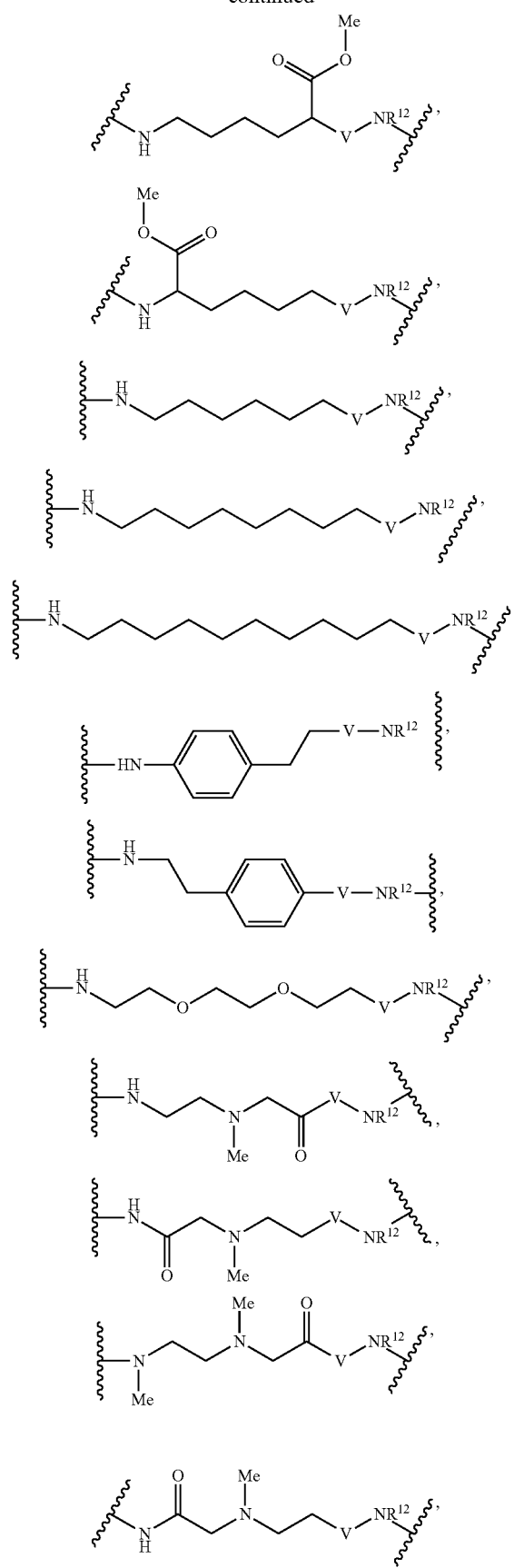
-continued
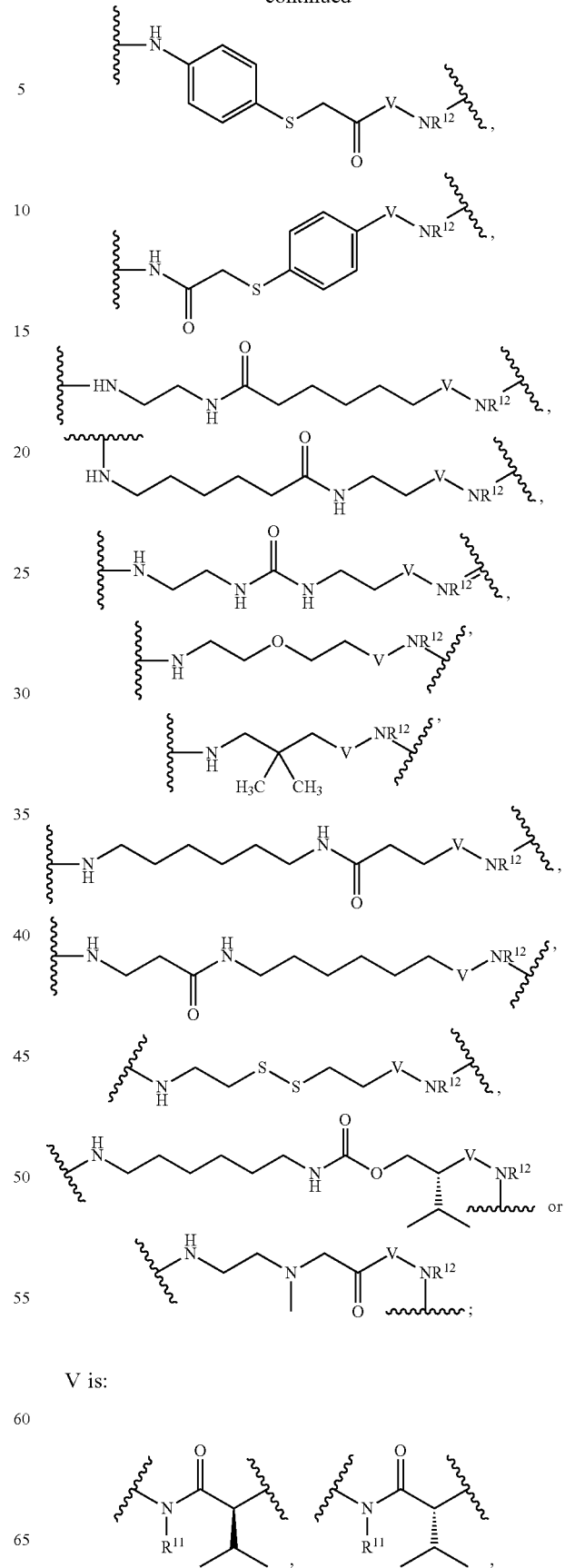
V is:

-continued

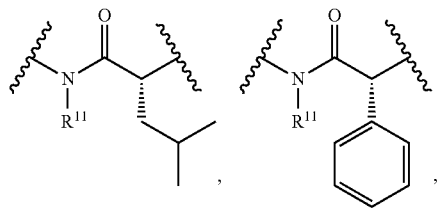

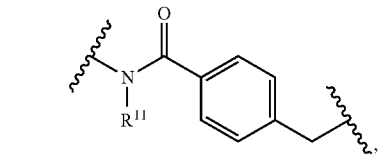

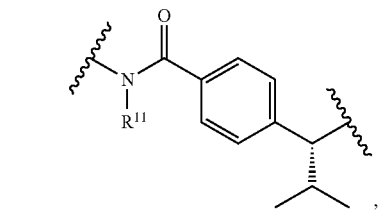

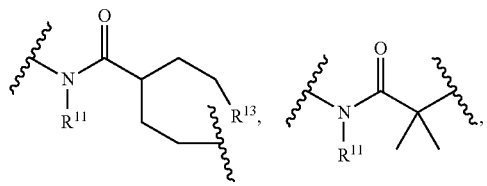

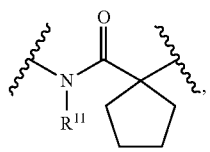

or a bond; $R^{12}$ is H or Me; or $R^{12}$ taken together with $R^{14}$ forms a piperidine ring; $R^{11}$ is H or Me; and $R^{13}$ taken together with $R^{12}$ forms a piperidine ring.

In certain aspects, -Q-X—Y— is

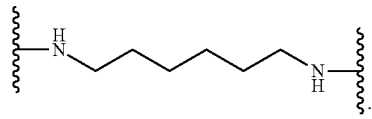 [SMILES: *NCCCCCCN*]

In certain aspects, -Q-X—Y— is

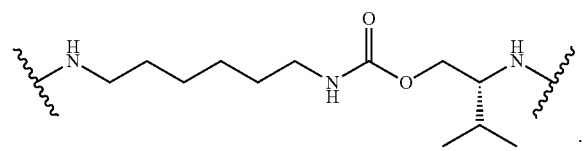 [SMILES: *NCCCCCCNC(=O)OC[C@H](N*)C(C)C]

In certain aspects, -Q-X—Y— is

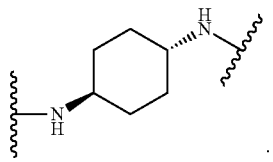 [SMILES: *N[C@H]1CC[C@H](N*)CC1]

In certain aspects, -QXY is

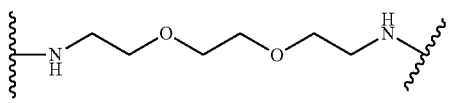

In certain aspects, -Q-X—Y— is

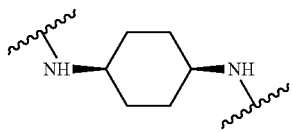 [SMILES: *N[C@H]1CC[C@@H](N*)CC1]

In certain aspects, -Q-X—Y— is

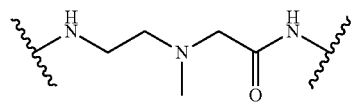

In certain aspects, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

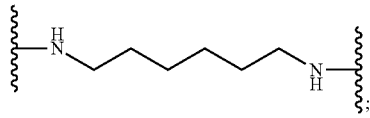 [SMILES: *NCCCCCCN*]

and W is

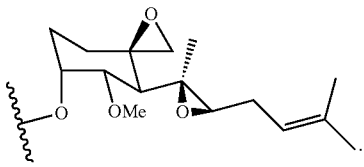

In certain aspects, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

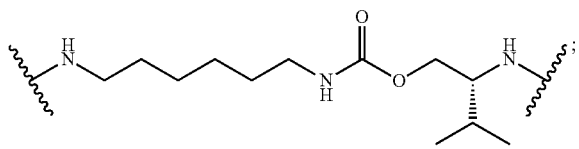 [SMILES: *NCCCCCCNC(=O)OC[C@H](N*)C(C)C]

and W is

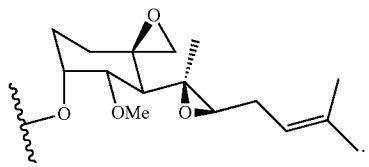

In certain aspects, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

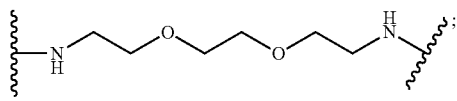 [SMILES: *NCCOCCOCCN*]

and W is

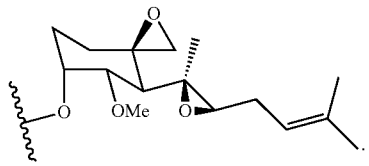

In certain aspects, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

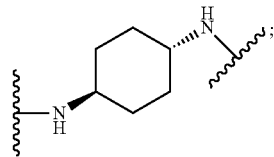 [SMILES: *N[C@H]1CC[C@H](N*)CC1]

and W is

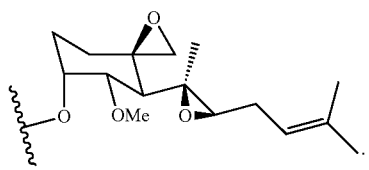

In certain aspects, -Q-X—Y— is a self-immolating linker that releases the MetAP2 inhibitor in the form of a carbamate derivative, as shown in the scheme below:

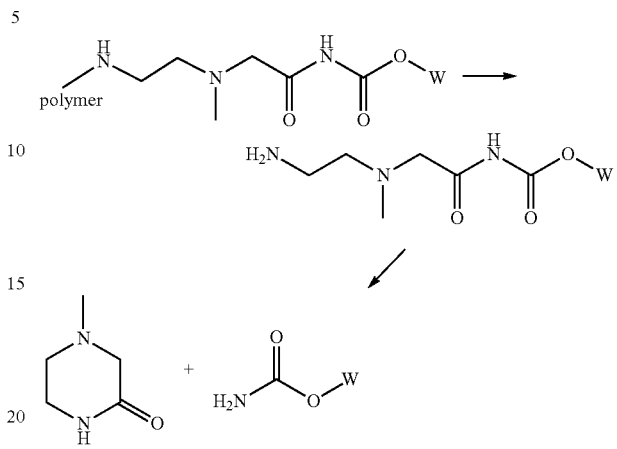

Another aspect of the present disclosure provides conjugates with linkers having the structure: Z-Q-X—Y—C(O)—W; wherein, independently for each occurrence, Z is $H_2N$-$AA_2$-$AA_3$-$AA_4$-$AA_5$-$AA_6$-C(O)— or H; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, alanine, cysteine, glycine, isoleucine, leucine, methionine, phenylalanine, valine, tryptophan, or; $AA_6$ is alanine, asparagine, citrulline, glutamine, glycine, leucine, methionine, phenylalanine, serine, threonine, tryptophan, tyrosine, valine or $H_2N(CH_2)mCO_2H$, wherein m is 2, 3, 4 or 5; Q is NR, O, or S; X is M-$(C(R)_2)_p$-M-J-M-$(C(R)_2)_p$-M-V; M is a bond, or C(O); J is a bond, or $((CH_2)_qQ)_r$, $C_5$-$C_8$ cycloalkyl, aryl, heteroaryl, NR, O, or S; Y is NR, O, or S; R is H or alkyl; V is a bond or

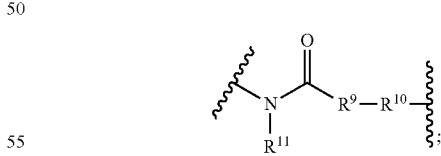

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety; p is 0 to 20; q is 2 or 3; and r is 1, 2, 3, 4, 5, or 6.

In certain aspects, Z is $H_2N$-$AA_5$-$AA_6$-C(O)—. In certain aspects, $AA_5$ is alanine, cysteine, glycine, isoleucine, leucine, methionine, phenylalanine, valine, tryptophan, or tyrosine and $AA_6$ is glycine. In certain aspects, $AA_5$ is leucine and $AA_6$ is glycine. In certain aspects, $AA_5$ is valine and $AA_6$ is glycine. In certain aspects, $AA_5$ is phenylalanine and $AA_6$ is glycine. In certain aspects, $AA_5$ is glycine and $AA_6$ is glycine. In certain aspects, $AA_5$ is not valine.

In other aspects, Z is $H_2N-AA_3-AA_4-AA_5-AA_6-C(O)-$. In certain aspects, $AA_5$ is alanine, cysteine, glycine, isoleucine, leucine, methionine, phenylalanine, valine, tryptophan, or tyrosine and each of $AA_3$, $AA_4$, or $AA_6$ is glycine. In certain aspects, $AA_5$ is leucine and each of $AA_3$, $AA_4$, or $AA_6$ is glycine. In certain aspects, $AA_5$ is valine and each of $AA_3$, $AA_4$, or $AA_6$ is glycine. In certain aspects, $AA_5$ is phenylalanine and each of $AA_3$, $AA_4$, or $AA_6$ is glycine. In certain aspects, $AA_3$ is glycine, $AA_4$ is phenylalanine, $AA_5$ is leucine and $AA_6$ is glycine. In certain aspects, each of $AA_3$, $AA_4$, $AA_5$ and $AA_6$ is glycine. In certain aspects, $AA_5$ is not valine.

In certain aspects, Z is H. In other aspects, Z is $H_2N-AA_6-C(O)-$. In certain aspects, $AA_6$ is glycine.

In certain aspects, Q is NR. In certain aspects, M is a bond. In certain aspects, J is a bond. In certain aspects, Y is NR.

In certain aspects, W is:

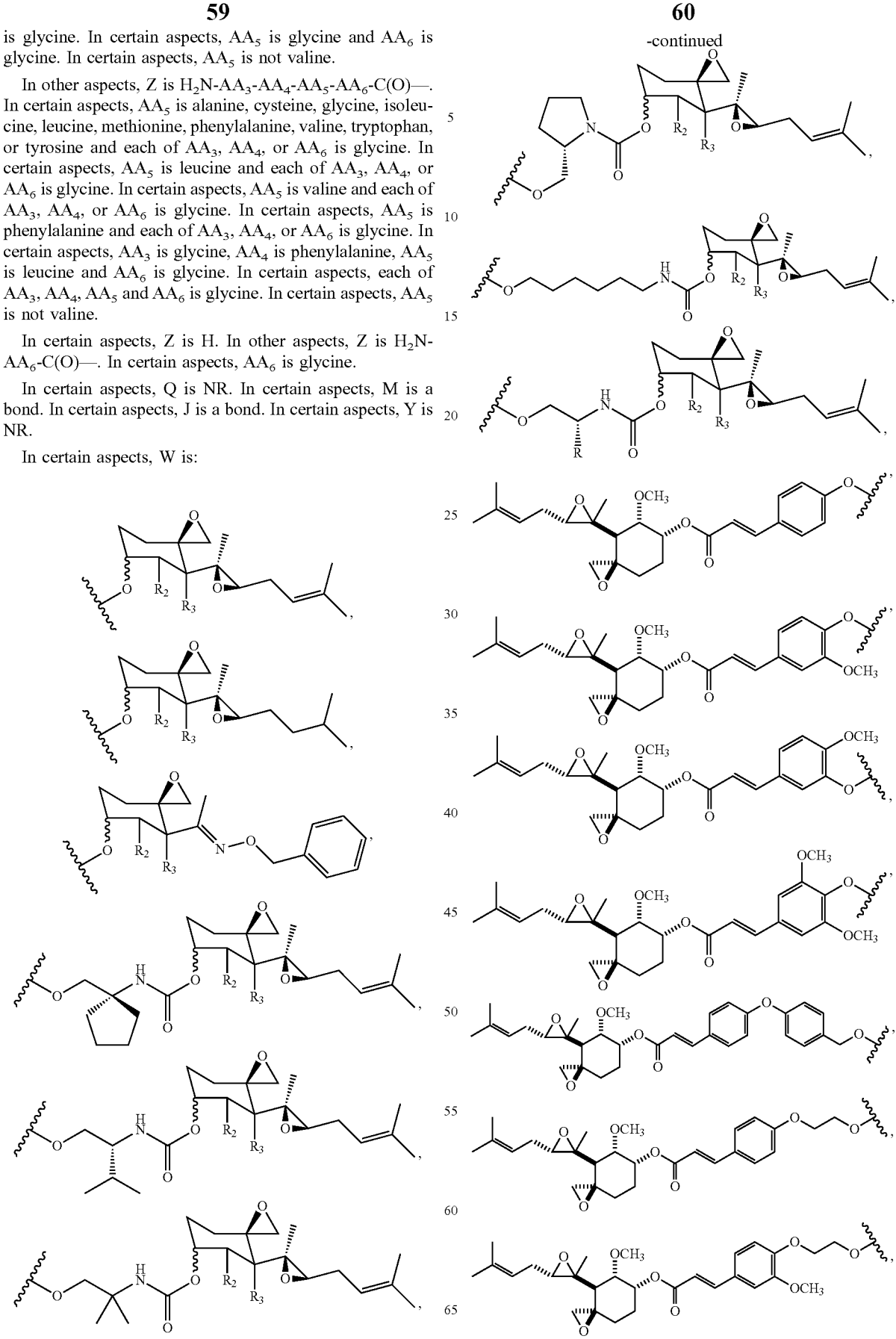

61
-continued
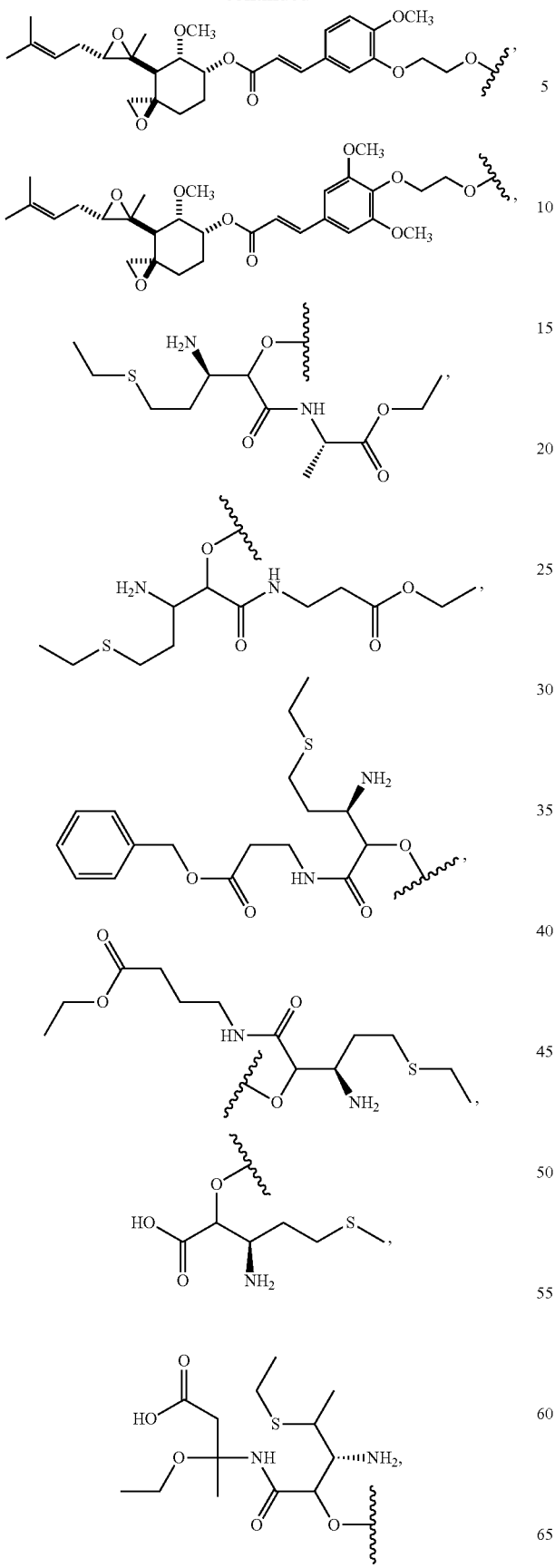
62
-continued
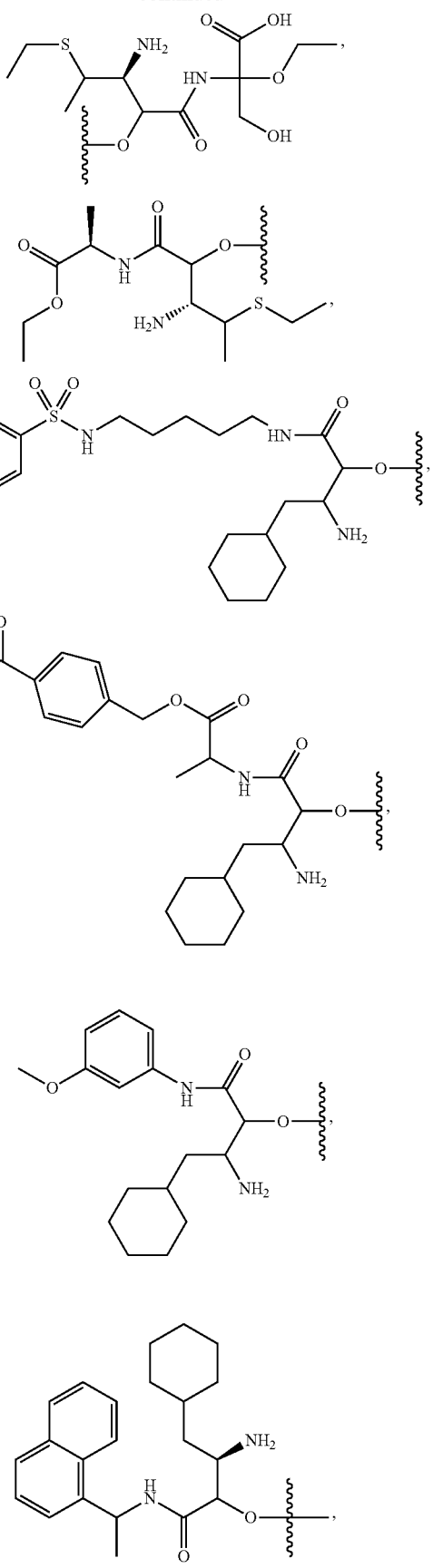

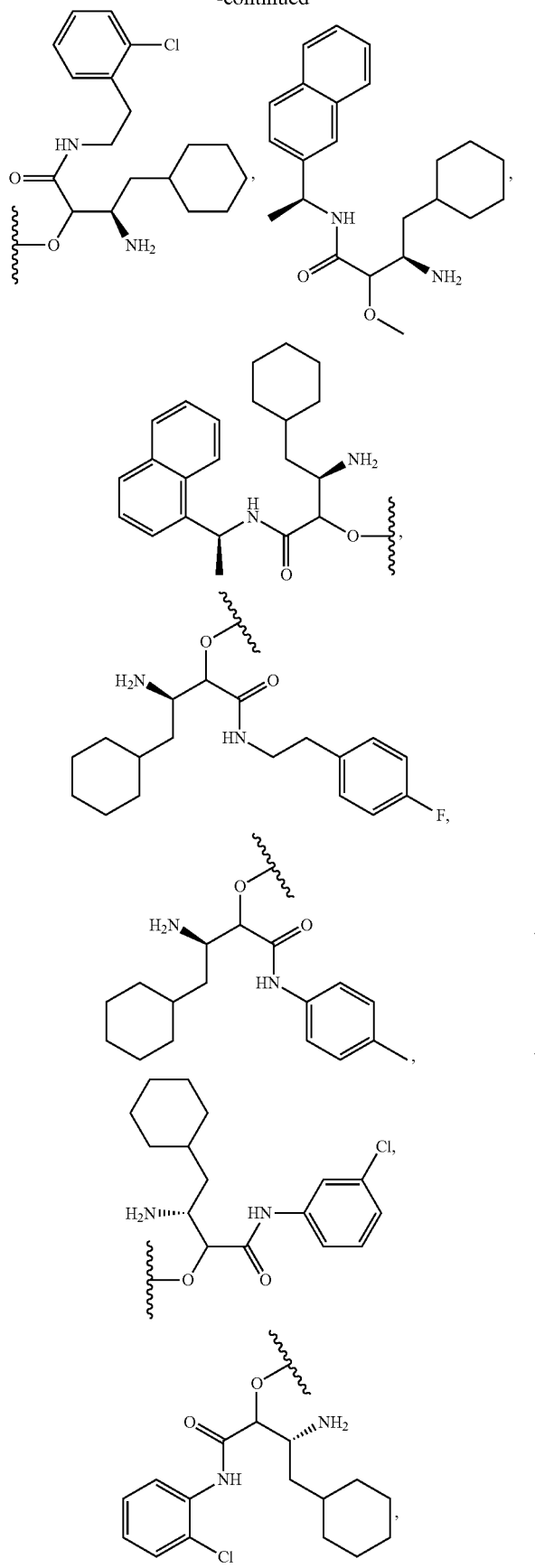
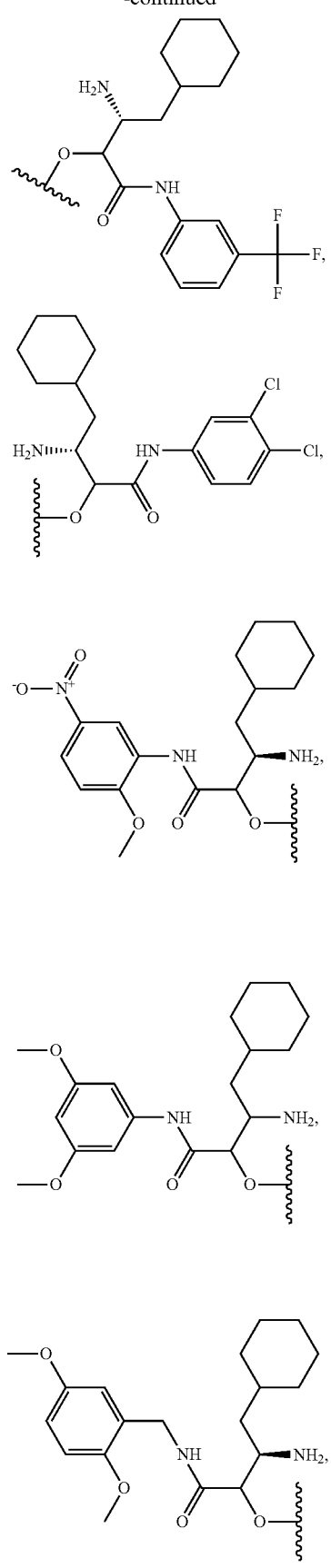

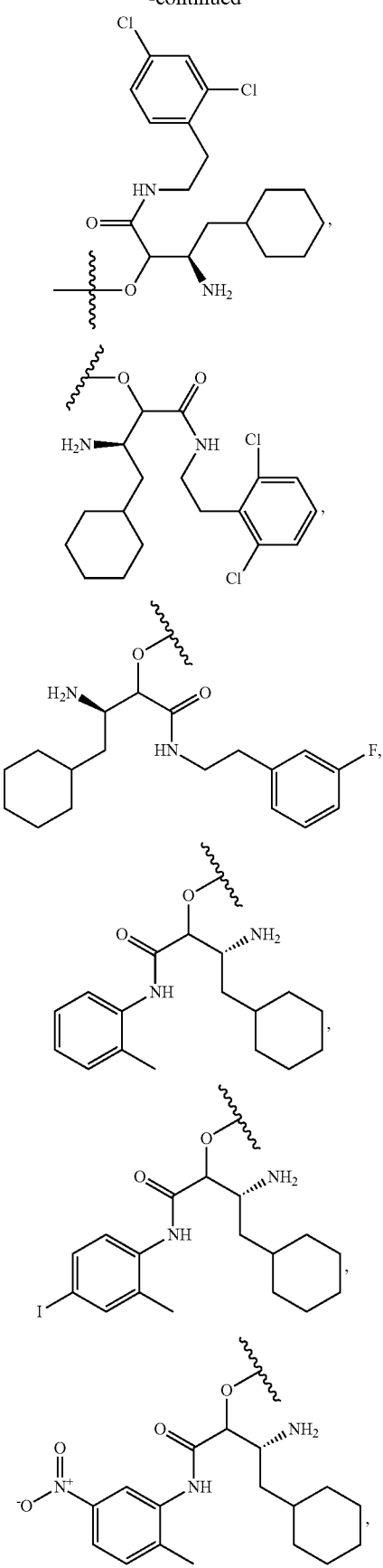
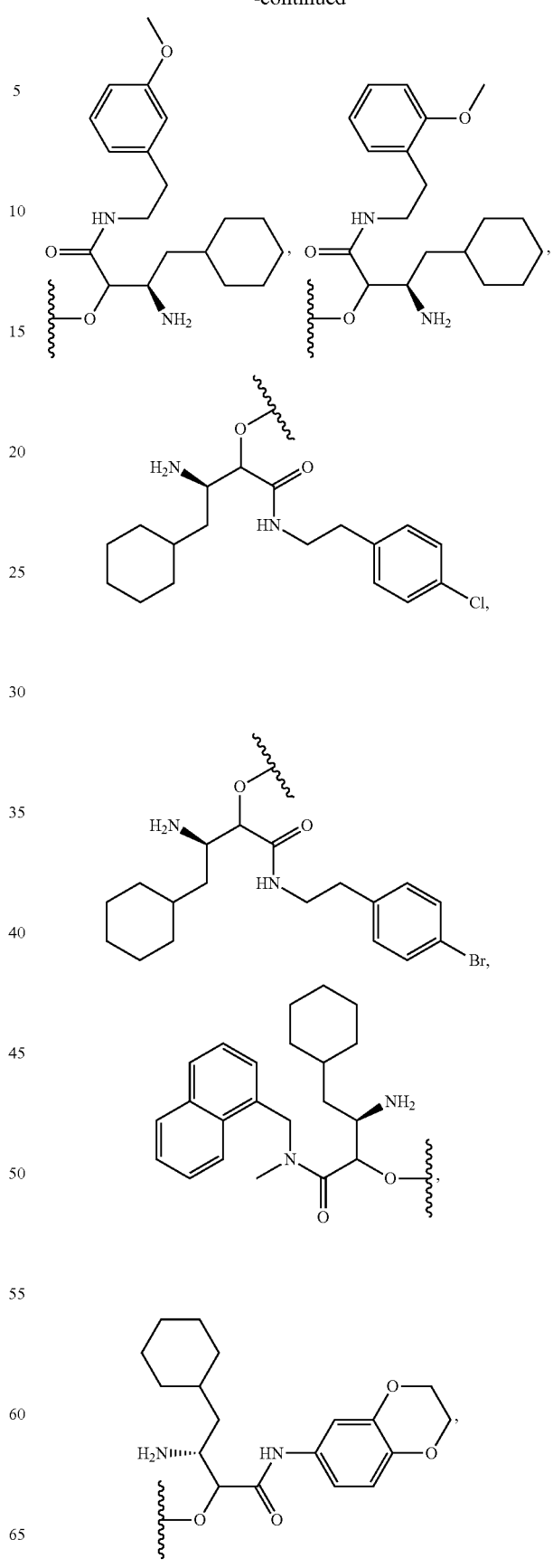

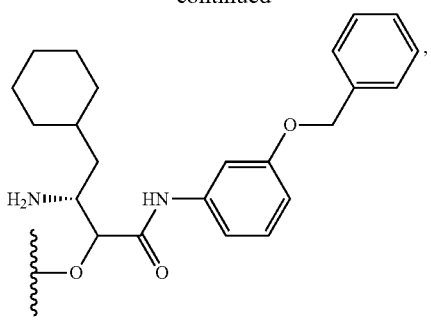
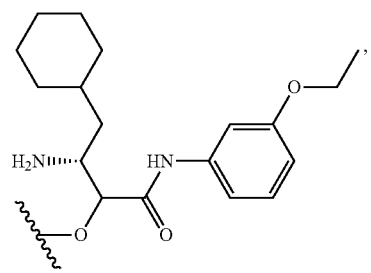
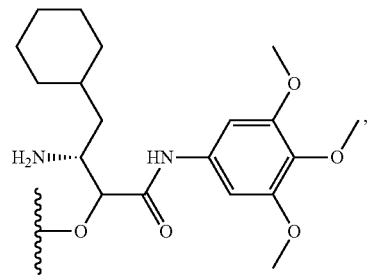
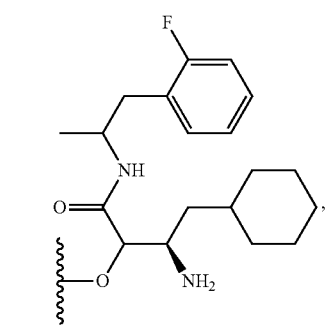
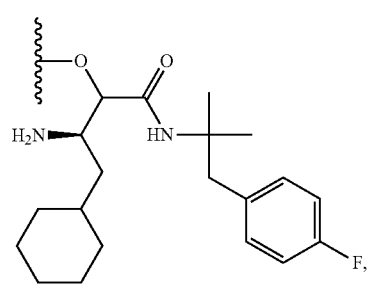
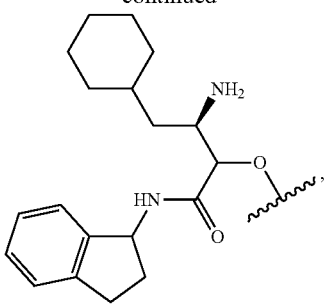
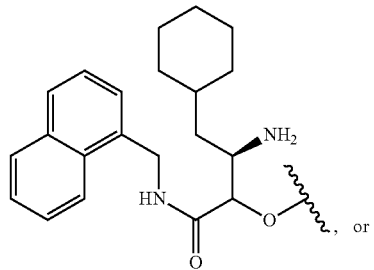
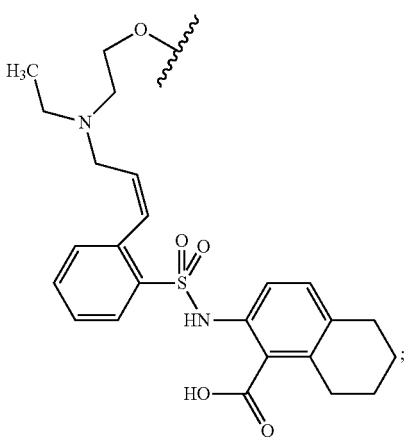
wherein $R_2$ is —OH or methoxy; and $R_3$ is H, —OH or methoxy.
In certain aspects, W is
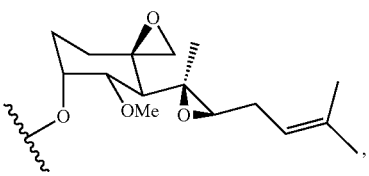
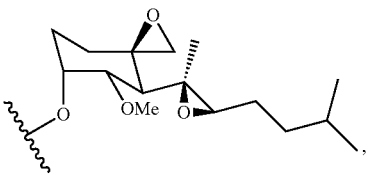
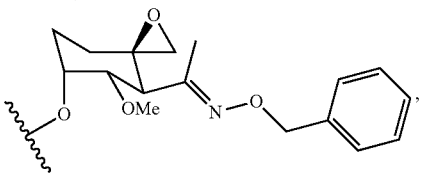

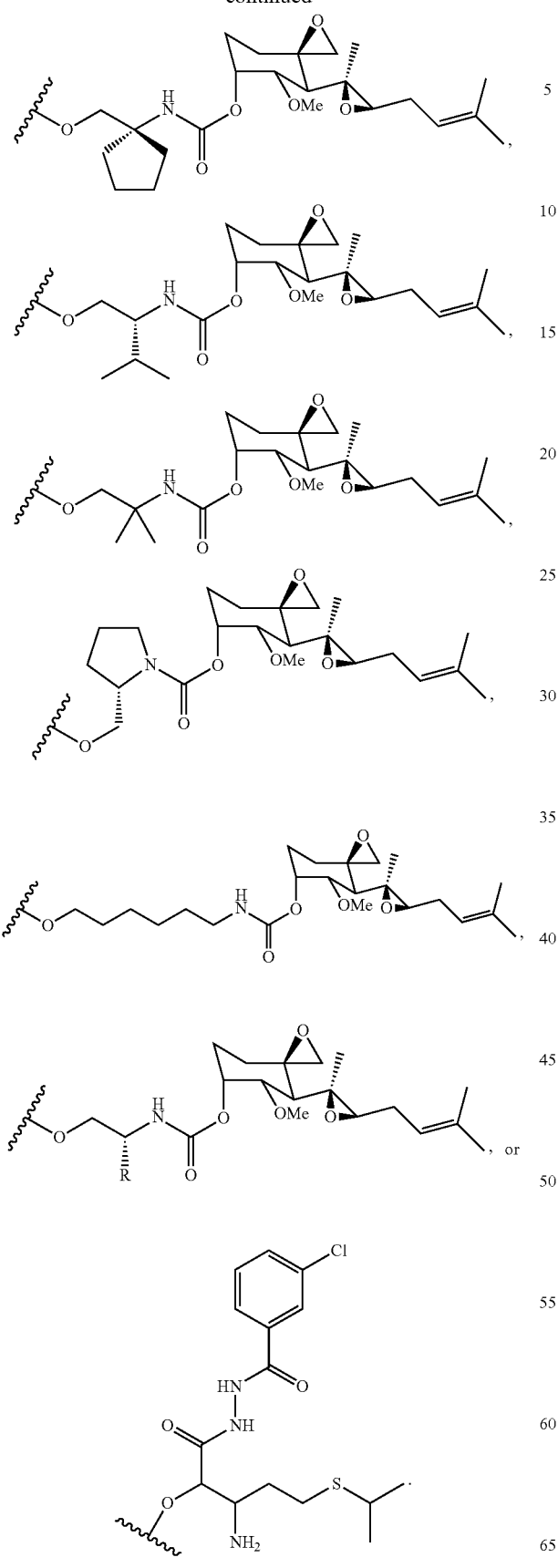
In certain aspects, W is
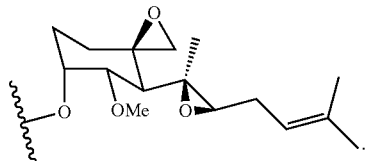
In certain aspects, -Q-X—Y— is
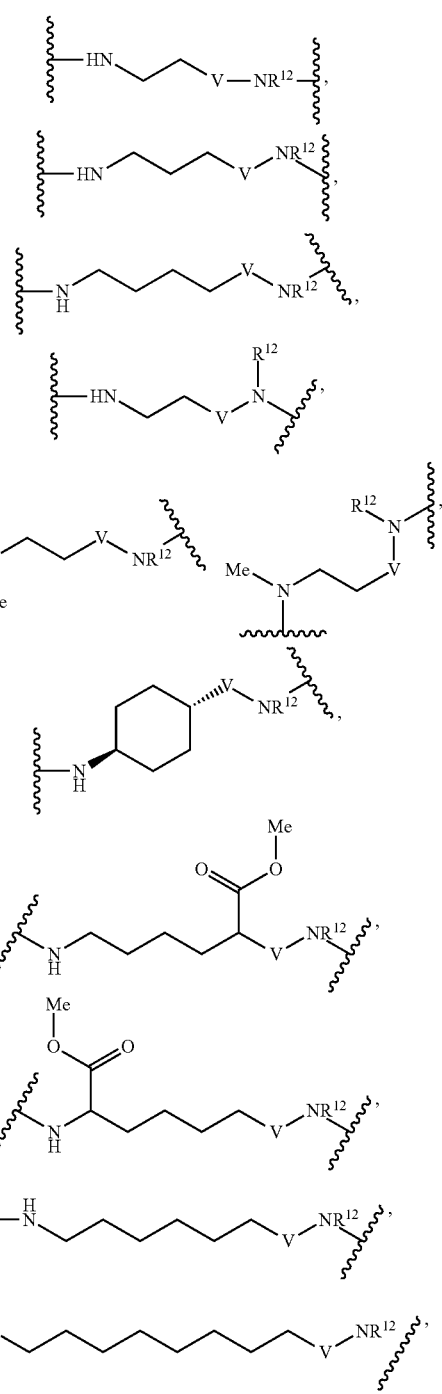

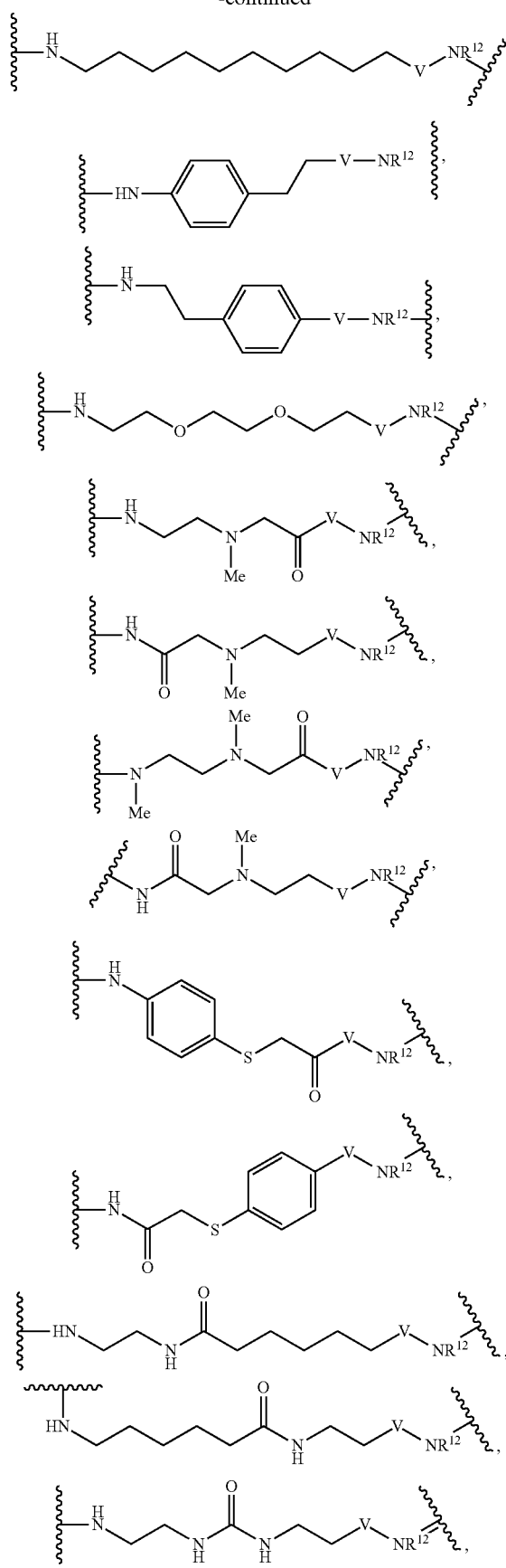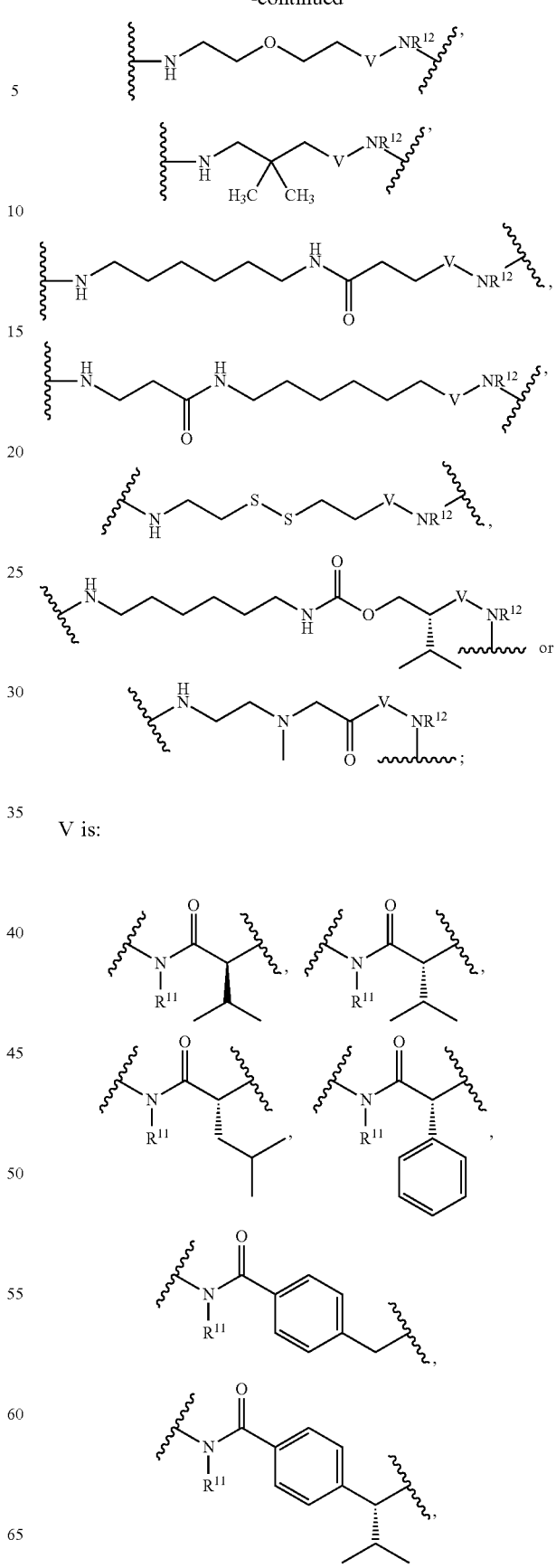
V is:

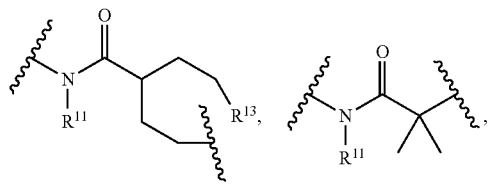

or a bond; $R^{12}$ is H or Me; or $R^{12}$ taken together with $R^{14}$ forms a piperidine ring; $R^{11}$ is H or Me; and $R^{13}$ taken together with $R^{12}$ forms a piperidine ring.

In certain aspects, Z is $H_2N$-$AA_5$-$AA_6$-C(O)—; $AA_5$ is leucine and $AA_6$ is glycine; Q-X—Y is

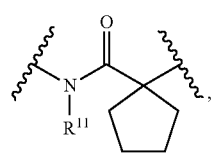

and W is

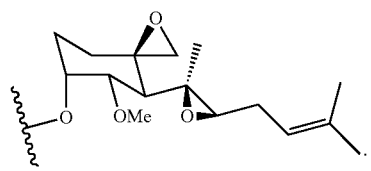

In certain aspects, Z is $H_2N$-$AA_5$-$AA_6$-C(O)—; $AA_5$ is valine and $AA_6$ is glycine; Q-X—Y is

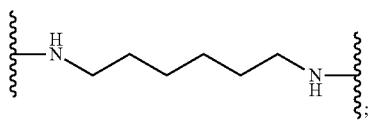 [SMILES: *NCCCCCCN*]

and W is

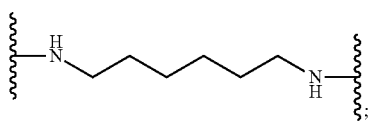 [SMILES: *NCCCCCCN*]

In certain aspects, Z is $H_2N$-$AA_5$-$AA_6$-C(O)—; $AA_5$ is phenylalanine and $AA_6$ is glycine; Q-X—Y is

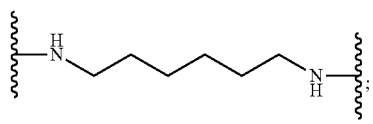 [SMILES: *NCCCCCCN*]

and W is

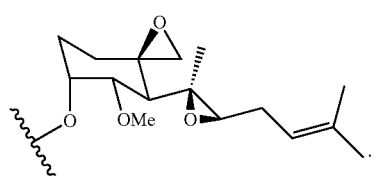

In certain aspects, Z is $H_2N$-$AA_5$-$AA_6$-C(O)—; $AA_5$ is glycine and $AA_6$ is glycine; Q-X—Y is

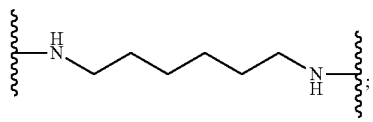 [SMILES: *NCCCCCCN*]

and W is

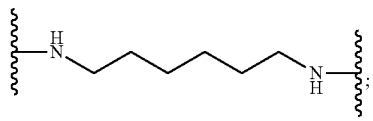 [SMILES: *NCCCCCCN*]

In certain aspects, Z is $H_2N$-$AA_3$-$AA_4$-$AA_5$-$AA_6$-C(O)—; $AA_5$ is leucine and each of $AA_3$, $AA_4$, or $AA_6$ is glycine; Q-X—Y is

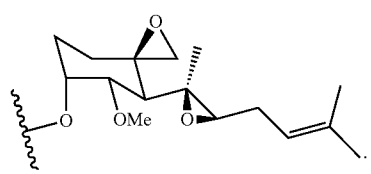

and W is

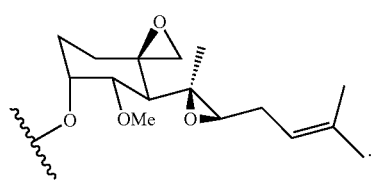

In certain aspects, Z is $H_2N$-$AA_3$-$AA_4$-$AA_5$-$AA_6$-C(O)—; $AA_5$ is valine and each of $AA_3$, $AA_4$, or $AA_6$ is glycine; Q-X—Y is

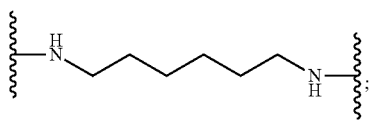 [SMILES: *NCCCCCCN*]

and W is

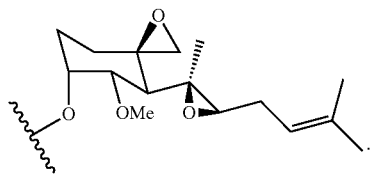

In certain aspects, Z is H$_2$N-AA$_3$-AA$_4$-AA$_5$-AA$_6$-C(O)—; AA$_5$ is phenylalanine and each of AA$_3$, AA$_4$, or AA$_6$ is glycine; Q-X—Y is

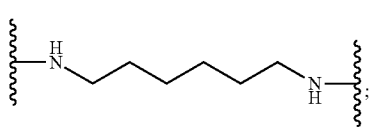 [SMILES: *NCCCCCCN*]

and W is

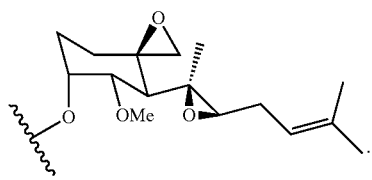

In certain aspects, Z is H$_2$N-AA$_3$-AA$_4$-AA$_5$-AA$_6$-C(O)—; AA$_3$ is glycine, AA$_4$ is phenylalanine, AA$_5$ is leucine and AA$_6$ is glycine; Q-X—Y is

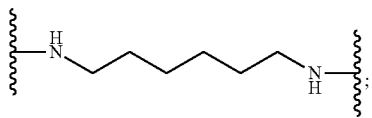 [SMILES: *NCCCCCCN*]

and W is

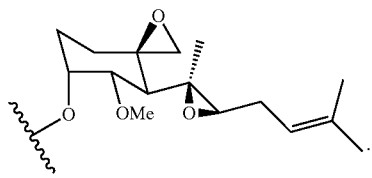

In certain aspects, Z is H$_2$N-AA$_3$-AA$_4$-AA$_5$-AA$_6$-C(O)—; each of AA$_3$, AA$_4$, AA$_5$ and AA$_6$ is glycine; Q-X—Y is

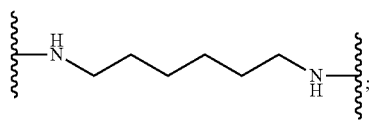 [SMILES: *NCCCCCCN*]

and W is

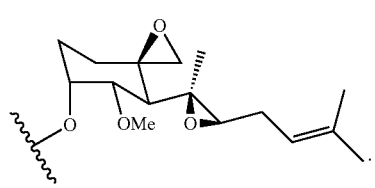

In certain aspects, Z is H$_2$N-AA$_6$-C(O)—; AA$_6$ is glycine; Q-X—Y is

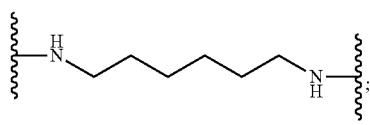 [SMILES: *NCCCCCCN*]

and W is

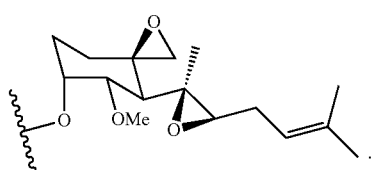

In certain aspects, Z is H; Q-X—Y is

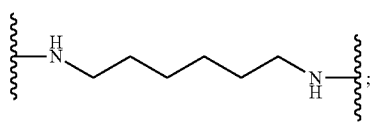 [SMILES: *NCCCCCCN*]

and W is

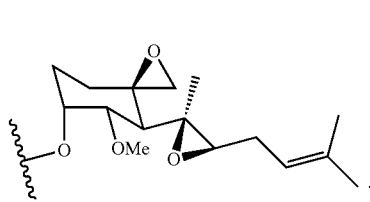

In certain aspects, Z is H$_2$N-AA$_5$-AA$_6$-C(O)—; AA$_5$ is leucine and AA$_6$ is glycine; Q-X—Y is

77

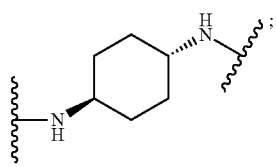 [SMILES: *N[C@H]1CC[C@H](N*)CC1]

and W is

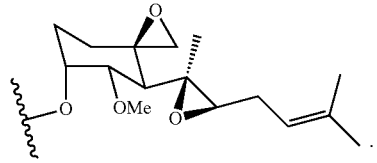

In certain aspects, Z is H$_2$N-AA$_5$-AA$_6$-C(O)—; AA$_5$ is valine and AA$_6$ is glycine; Q-X—Y is

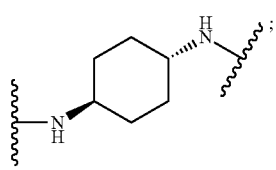 [SMILES: *N[C@H]1CC[C@H](N*)CC1]

and W is

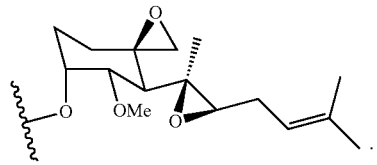

In certain aspects, Z is H$_2$N-AA$_5$-AA$_6$-C(O)—; AA$_5$ is phenylalanine and AA$_6$ is glycine; Q-X—Y is

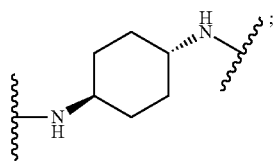 [SMILES: *N[C@H]1CC[C@H](N*)CC1]

and W is

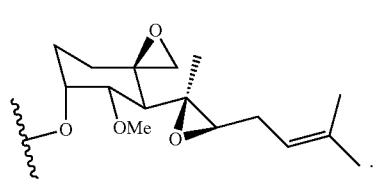

In certain aspects, Z is H$_2$N-AA$_5$-AA$_6$-C(O)—; AA$_5$ is glycine and AA$_6$ is glycine; Q-X—Y is

78

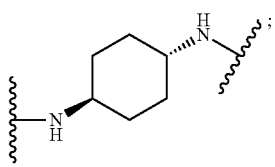 [SMILES: *N[C@H]1CC[C@H](N*)CC1]

and W is

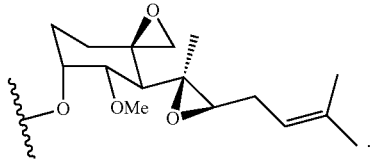

In certain aspects, Z is H$_2$N-AA$_3$-AA$_4$-AA$_5$-AA$_6$-C(O)—; AA$_5$ is leucine and each of AA$_3$, AA$_4$, or AA$_6$ is glycine; Q-X—Y is

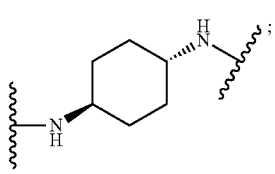 [SMILES: *N[C@H]1CC[C@H](N*)CC1]

and W is

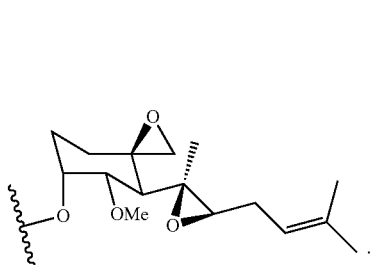

In certain aspects, Z is H$_2$N-AA$_3$-AA$_4$-AA$_5$-AA$_6$-C(O)—; AA$_5$ is valine and each of AA$_3$, AA$_4$, or AA$_6$ is glycine; Q-X—Y is

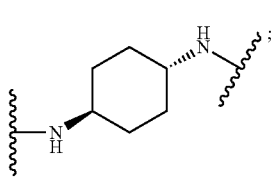 [SMILES: *N[C@H]1CC[C@H](N*)CC1]

and W is

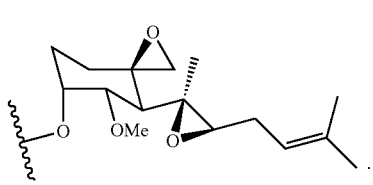

In certain aspects, Z is H$_2$N-AA$_3$-AA$_4$-AA$_5$-AA$_6$-C(O)—; AA$_5$ is phenylalanine and each of AA$_3$, AA$_4$, or AA$_6$ is glycine; Q-X—Y is

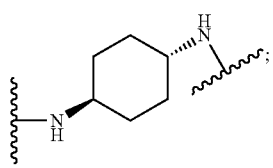 [SMILES: *N[C@H]1CC[C@H](N*)CC1]

and W is

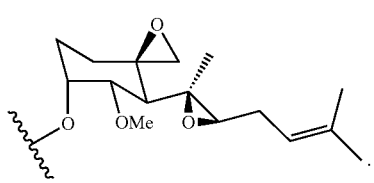

In certain aspects, Z is H$_2$N-AA$_3$-AA$_4$-AA$_5$-AA$_6$-C(O)—; AA$_3$ is glycine, AA$_4$ is phenylalanine, AA$_5$ is leucine and AA$_6$ is glycine; Q-X—Y is

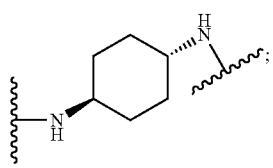 [SMILES: *N[C@H]1CC[C@H](N*)CC1]

and W is

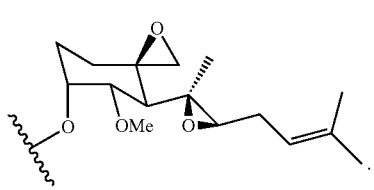

In certain aspects, Z is H$_2$N-AA$_3$-AA$_4$-AA$_5$-AA$_6$-C(O)—; each of AA$_3$, AA$_4$, AA$_5$ and AA$_6$ is glycine; Q-X—Y is

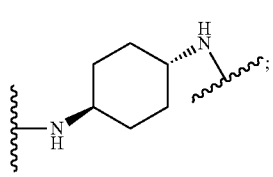 [SMILES: *N[C@H]1CC[C@H](N*)CC1]

and W is

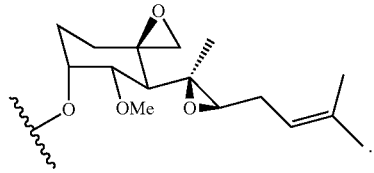

In certain aspects, Z is H$_2$N-AA$_6$-C(O)—; AA$_6$ is glycine; Q-X—Y is

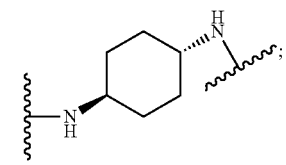 [SMILES: *N[C@H]1CC[C@H](N*)CC1]

and W is

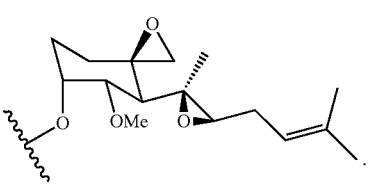

In certain aspects, Z is H; Q-X—Y is

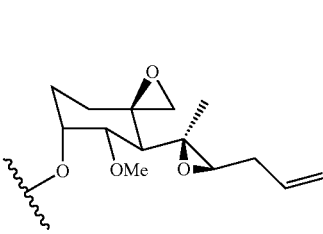

and W is

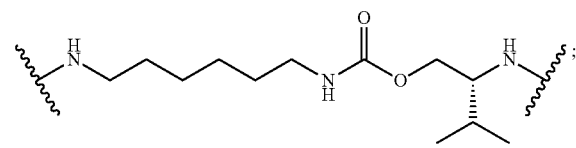 [SMILES: *NCCCCCCNC(=O)OC[C@H](N*)C(C)C]

In certain aspects, Z is H$_2$N-AA$_5$-AA$_6$-C(O)—; AA$_5$ is leucine and AA$_6$ is glycine; Q-X—Y is and W is

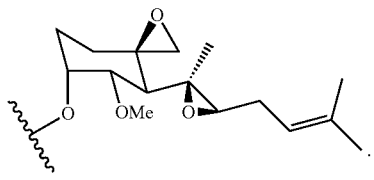

In certain aspects, Z is H₂N-AA₅-AA₆-C(O)—; AA₅ is valine and AA₆ is glycine; Q-X—Y is

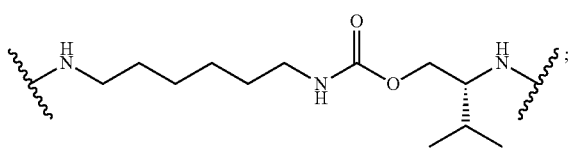 [SMILES: *NCCCCCCNC(=O)OC[C@H](N*)C(C)C]

and W is

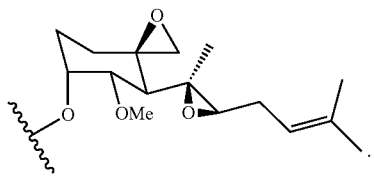

In certain aspects, Z is H₂N-AA₅-AA₆-C(O)—; AA₅ is phenylalanine and AA₆ is glycine; Q-X—Y is

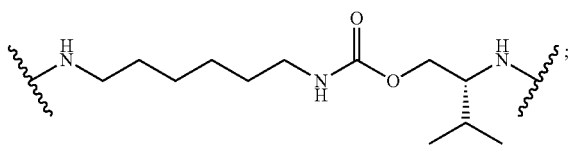 [SMILES: *NCCCCCCNC(=O)OC[C@H](N*)C(C)C]

and W is

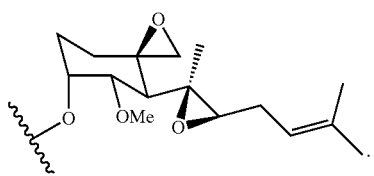

In certain aspects, Z is H₂N-AA₅-AA₆-C(O)—; AA₅ is glycine and AA₆ is glycine; Q-X—Y is

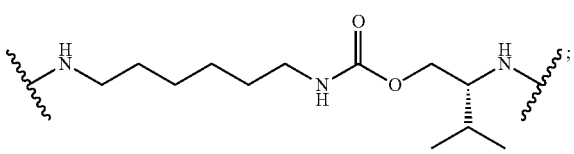 [SMILES: *NCCCCCCNC(=O)OC[C@H](N*)C(C)C]

and W is

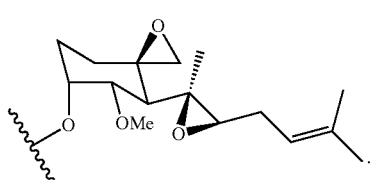

In certain aspects, Z is H₂N-AA₃-AA₄-AA₅-AA₆-C(O)—; AA₅ is leucine and each of AA₃, AA₄, or AA₆ is glycine; Q-X—Y is

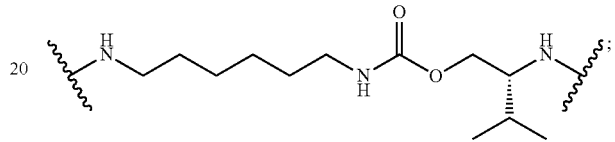

and W is

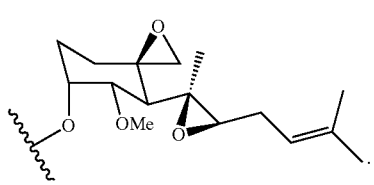

In certain aspects, Z is H₂N-AA₃-AA₄-AA₅-AA₆-C(O)—; AA₅ is valine and each of AA₃, AA₄, or AA₆ is glycine; Q-X—Y is

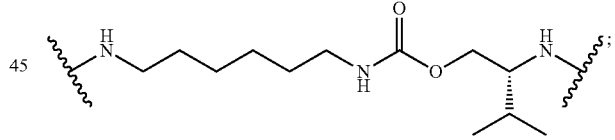

and W is

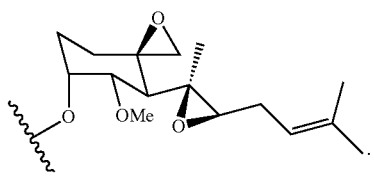

In certain aspects, Z is H₂N-AA₃-AA₄-AA₅-AA₆-C(O)—; AA₅ is phenylalanine and each of AA₃, AA₄, or AA₆ is glycine; Q-X—Y is

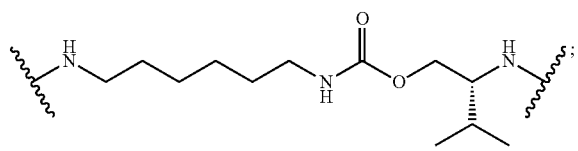 [SMILES: *NCCCCCCNC(=O)OC[C@H](N*)C(C)C]

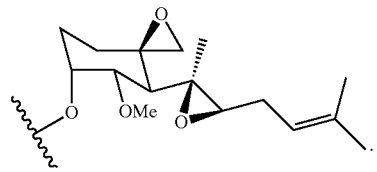

In certain aspects, Z is H$_2$N-AA$_3$-AA$_4$-AA$_5$-AA$_6$-C(O)—; AA$_3$ is glycine, AA$_4$ is phenylalanine, AA$_5$ is leucine and AA$_6$ is glycine; Q-X—Y is

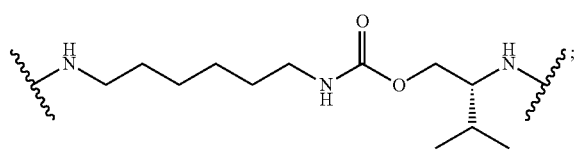 [SMILES: *NCCCCCCNC(=O)OC[C@H](N*)C(C)C]

and W is

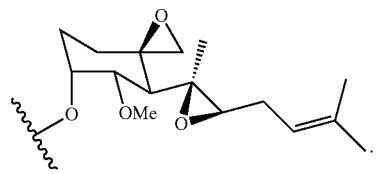

In certain aspects, Z is H$_2$N-AA$_3$-AA$_4$-AA$_5$-AA$_6$-C(O)—; each of AA$_3$, AA$_4$, AA$_5$ and AA$_6$ is glycine; Q-X—Y is

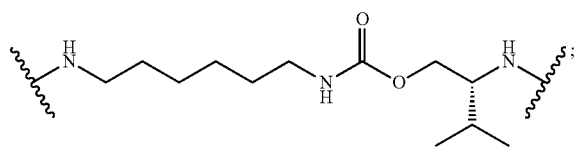 [SMILES: *NCCCCCCNC(=O)OC[C@H](N*)C(C)C]

and W is

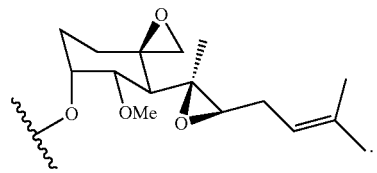

In certain aspects, Z is H$_2$N-AA$_6$-C(O)—; AA$_6$ is glycine; Q-X—Y is

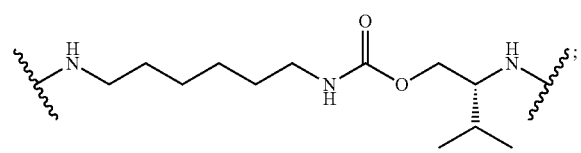 [SMILES: *NCCCCCCNC(=O)OC[C@H](N*)C(C)C]

and W is

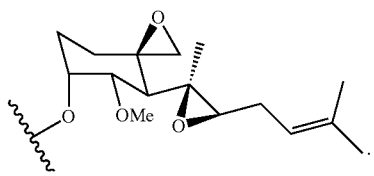

In certain aspects, Z is H; Q-X—Y is

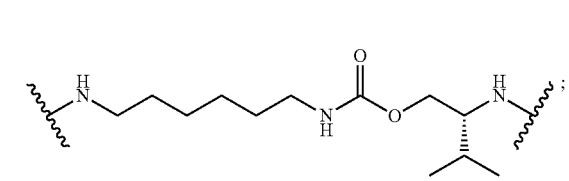 [SMILES: *NCCCCCCNC(=O)OC[C@H](N*)C(C)C]

and W is

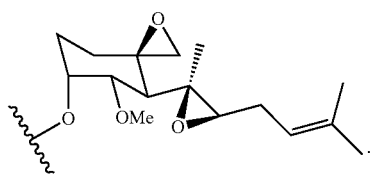

In certain aspects, Z is H$_2$N-AA$_5$-AA$_6$-C(O)—; AA$_5$ is leucine and AA$_6$ is glycine; Q-X—Y is

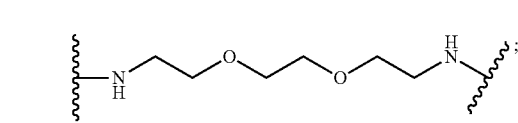 [SMILES: *NCCOCCOCCN*]

and W is

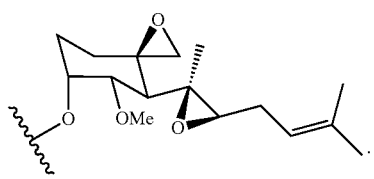

In certain aspects, Z is H$_2$N-AA$_5$-AA$_6$-C(O)—; AA$_5$ is valine and AA$_6$ is glycine; Q-X—Y is

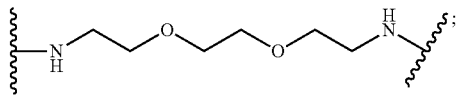 [SMILES: *NCCOCCOCCN*]

and W is

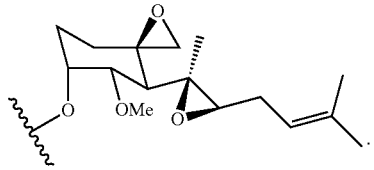

In certain aspects, Z is H$_2$N-AA$_5$-AA$_6$-C(O)—; AA$_5$ is phenylalanine and AA$_6$ is glycine; Q-X—Y is

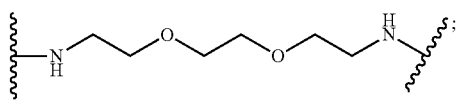 [SMILES: *NCCOCCOCCN*]

and W is

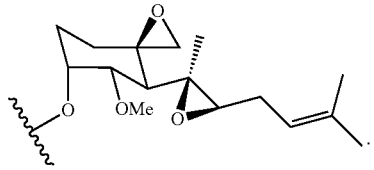

In certain aspects, Z is H$_2$N-AA$_5$-AA$_6$-C(O)—; AA$_5$ is glycine and AA$_6$ is glycine; Q-X—Y is

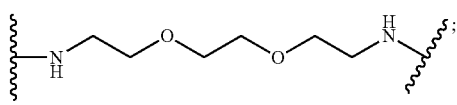 [SMILES: *NCCOCCOCCN*]

and W is

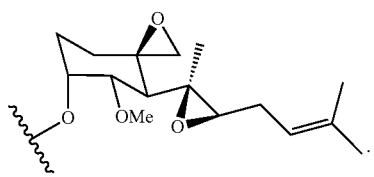

In certain aspects, Z is H$_2$N-AA$_3$-AA$_4$-AA$_5$-AA$_6$-C(O)—; AA$_5$ is leucine and each of AA$_3$, AA$_4$, or AA$_6$ is glycine; Q-X—Y is

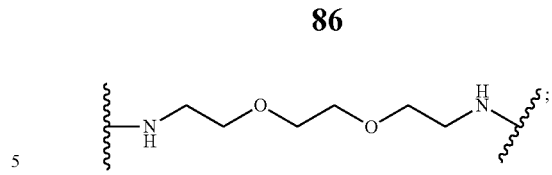

and W is

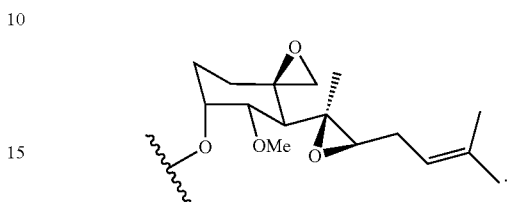

In certain aspects, Z is H$_2$N-AA$_3$-AA$_4$-AA$_5$-AA$_6$-C(O)—; AA$_5$ is valine and each of AA$_3$, AA$_4$, or AA$_6$ is glycine; Q-X—Y is

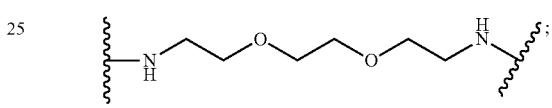

and W is

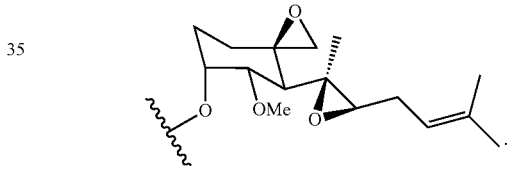

In certain aspects, Z is H$_2$N-AA$_3$-AA$_4$-AA$_5$-AA$_6$-C(O)—; AA$_5$ is phenylalanine and each of AA$_3$, AA$_4$, or AA$_6$ is glycine; Q-X—Y is

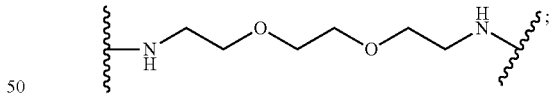

and W is

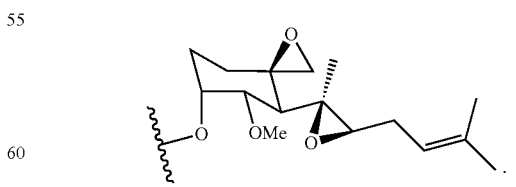

In certain aspects, Z is H$_2$N-AA$_3$-AA$_4$-AA$_5$-AA$_6$-C(O)—; AA$_3$ is glycine, AA$_4$ is phenylalanine, AA$_5$ is leucine and AA$_6$ is glycine; Q-X—Y is

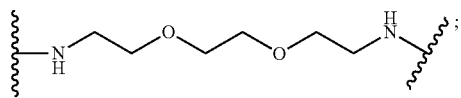 [SMILES: *NCCOCCOCCN*]
and W is
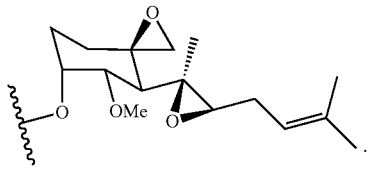
In certain aspects, Z is H$_2$N-AA$_3$-AA$_4$-AA$_5$-AA$_6$-C(O)—; each of AA$_3$, AA$_4$, AA$_5$ and AA$_6$ is glycine; Q-X—Y is
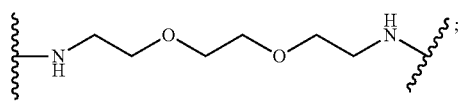 [SMILES: *NCCOCCOCCN*]
and W is
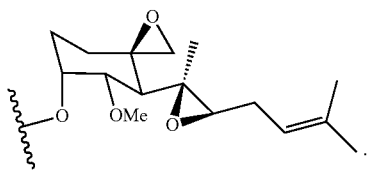
In certain aspects, Z is H$_2$N-AA$_6$-C(O)—; AA$_6$ is glycine; Q-X—Y is
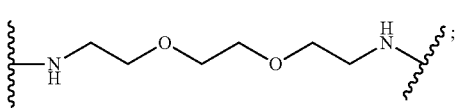 [SMILES: *NCCOCCOCCN*]
and W is
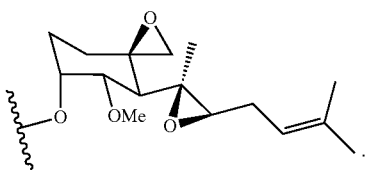
In certain aspects, Z is H; Q-X—Y is
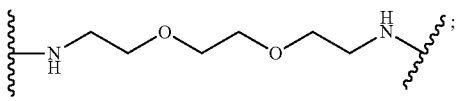
and W is
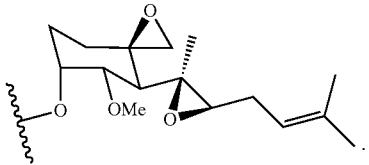
Other active moieties that may be modified to be used in conjugates of the disclosure include the following structures:
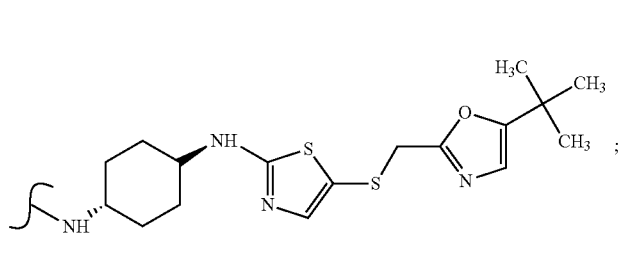
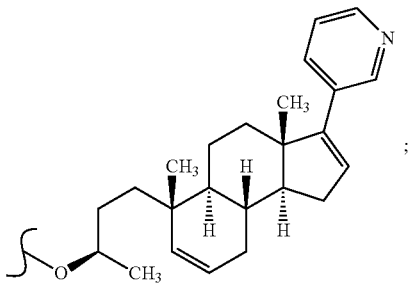
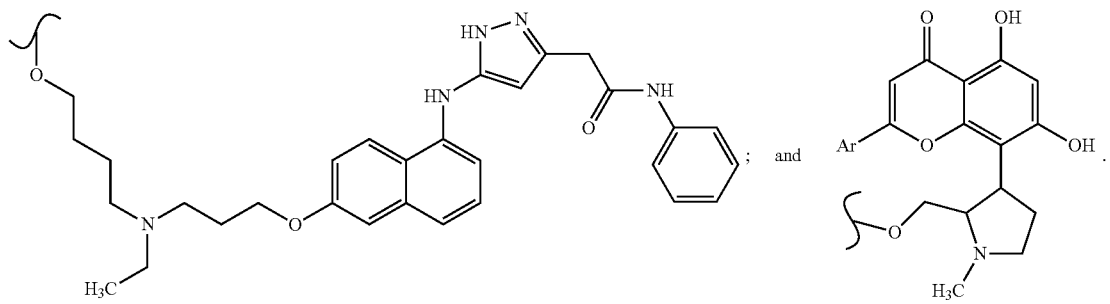
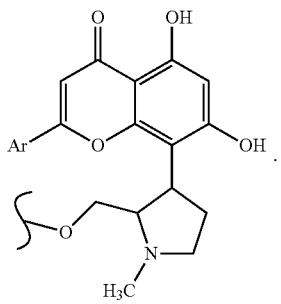

In certain aspects, the active moiety is an anti-tumor compound. In other aspects, the active moiety is a molecule that inhibits methionine aminopeptidase-2 (MetAP2), such as fumagillin, fumagillol, or an analog, derivative, salt or ester thereof. MetAP2 is a co-translational enzyme responsible for cleaving the initiator methionine off nascent polypeptides. It has several exclusive substrates that tend to be up-regulated under conditions of cellular stress, hypoxia and when cells are dividing. Fumagillin is a natural product derived from the biomass of the fungus *Aspergillus Fumigatus* Fresenius. Fumagillin and its derivatives are known to inhibit the aminopeptidase activity of MetAP2. Further exemplary MetAP2 inhibitors have been described in U.S. Pat. No. 6,242,494 to Craig et al, U.S. Pat. No. 6,063,812 to Hong et al., U.S. Pat. No. 6,887,863 to Craig et al., U.S. Pat. No. 7,030,262 to BaMaung et al., U.S. Pat. No. 7,491,718 to Comess et al., each of which is incorporated by reference in its entirety. Additional exemplary MetAP2 inhibitors have been described in Wang et al. "Correlation of tumor growth suppression and methionine aminopeptidase-2 activity blockade using an orally active inhibitor," *PNAS* 105(6) 1838-1843 (2008); Lee at al. "Design, Synthesis, and Antiangiogenic Effects of a Series of Potent Novel Fumagillin Analogues," *Chem. Pharm. Bull.* 55(7) 1024-1029 (2007); Jeong et al. "Total synthesis and antiangiogenic activity of cyclopentane analogues of fumagillol," *Bioorganic and Medicinal Chemistry Letters* 15, 3580-3583 (2005); Arico-Muendel et al. "Carbamate Analogues of Fumagillin as Potent, Targeted Inhibitors of Methionine Aminopeptidase-2," *J. Med. Chem.* 52, 8047-8056 (2009); and International Publication No. WO 2010/003475 to Heinrich et al.

Fumagillin is a small molecule which has been used as an antimicrobial and antiprotozoal agent. Its physiochemical properties and method of production are well known (See U.S. Pat. No. 2,803,586 and Turner, J. R. et al., The Stereochemistry of Fumagillin, Proc. Natl. Acad. Sci. 48, 733-735 (1962)). The fermentation product, fumagillin, may be hydrolyzed to yield the alcohol fumagillol which in turn may be converted into various derivatives including carbamoylfumagillol, MW 325. The synthesis and preparation of carbamoylfumagillol and some small molecule derivatives are described in U.S. Pat. No. 5,166,172.

Fumagillin and related compounds are believed to exert their biological effects through the inhibition of MetAP2. This enzyme removes N-terminal methionine from nascent cellular proteins. (See Tucker, L. A., et al. "Ectopic Expression of Methionine Aminopeptidase-2 Causes Cell Transformation and Stimulates Proliferation", Oncogene 27, 3967 (2008).)

Carbamoylfumagillol and derivatives as well as other inhibitors of MetAP2 have shown therapeutic benefits in preclinical and clinical studies. These compounds inhibit cell proliferation and angiogenesis as described in U.S. Pat. No. 5,166,172. Fumagillin analogs or derivatives, such as CKD-732 and PI-2458, are well studied in various systems as described in detail in Bernier et al., "Fumagillin class inhibitors of methionine aminopeptidase-2" *Drugs of the Future* 30(5): 497-508, 2005.

The anti-obesity effects of fumagillin and its analogs are well-known. Rupnick et al. "Adipose tissue mass can be regulated through the vasculature" PNAS 99, 10730-10735, 2002 describes weight loss in ob/ob mice with daily doses of TNP-470 ranging from 2.5 mg/kg to 10 mg/kg. Brakenhielm describes prevention of obesity at TNP-470 doses of 15 or 20 mg/kg every other day, "The Angiogenesis Inhibitor, TNP-470, Prevents Diet-Induced and Genetic Obesity in Mice" *Circulation Research* 94: 1579-1588, 2004. Kim, et al., in the "Assessment of the anti-obesity effects of the TNP-470 analog, CKD-732" J Molecular Endocrinology 38, 455-465, 2007 describe weight loss in C57BL/6J mice and SD rats at doses of 5 mg/kg/day. Lijnen et al. "Fumagillin reduces adipose tissue formation in murine models of nutritionally induced obesity" Obesity 12, 2241-2246, 2010 describes oral delivery of 1 mg/kg fumagillin daily resulting in weight loss in C57BL/6 mice.

One of these derivatives, chloroacetylcarbamoylfumagillol (TNP-470) has been extensively studied. (See H Mann-Steinberg, et al., "TNP-470: The Resurrection of the First Synthetic Angiogenesis Inhibitor", Chapter 35 in Folkman and Figg, Angiogenesis: An Integrative Approach from Science to Medicine, Springer N.Y. (2008).) TNP-470 has shown activity against many cancers including lung cancer, cervical cancer, ovarian cancer, breast cancer and colon cancer. Because of dose-limiting neurotoxicity, TNP-470 has been tested using multiple dosing regimens, but these attempts to limit its toxicity have been unsuccessful. Thus, TNP-470 has been found to be too toxic for human use. TNP-470 has a short half-life and requires extended intravenous administration for therapeutic use. A metabolite of TNP-470, carbamoylfumagillol has a half-life of 12 minutes in man. (See Herbst et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", *Journal of Clinical Oncology* 20(22) 4440-4447 (2002). In addition, fumagillin and its derivatives are hydrophobic and difficult to formulate.

Despite the known usefulness of fumagillin derivatives, they have not been used successfully as treatments because of the failure to overcome the problems of the low water solubility, short half-life values, and neurotoxic side-effects of these compounds. TNP-470 in combination with paclitaxel was determined to have an MTD of 60 mg/m2 dosed three times per week based on the previously observed dose limiting neuropsychiatric toxicities Herbst et al., "Safety and pharmacokinetic effects of TNP-470, an angiogenesis inhibitor, combined with paclitaxel in patients with solid tumors: evidence for activity in non-small-cell lung Cancer" Journal of Clinical Oncology 20, 4440-4447, 2002. Similarly Shin et al. "A Phase 1 pharmacokinetic and pharmacodynamics study of CKD-732, an antiangiogenic agent, in patients with refractory solid cancer" Investigational New Drugs 28, 650-658, 2010 reports that the MTD of CKD-732 was 15 mg/m2/day dosed on an every fourth day schedule due to confusion and insomnia. Accordingly, the compounds of the present disclosure are more potent, show reduced toxicity (less neurotoxic), improved water solubility, more stable, and/or have longer half-life (serum half-life) than presently known fumagillin derivatives.

The phrase "reduced toxicity" as used herein has its ordinary meaning as understood by persons of skill in the art. Merely by way of example, and by no means as a limitation on the meaning of the term, the administration of the fumagillin analog conjugate causes less side effects in open field tests with mice, as compared to the fumagillin analog alone.

The phrase "improved water solubility" has its ordinary meaning as understood by persons of skill in the art. Merely by way of example, and by no means as a limitation on the meaning of the term, the following description of the term is informative: an increased amount of a fumagillin analog will dissolve in water as a result of its covalent incorporation into a conjugate as compared to the amount of the unconjugated fumagillin analog that will dissolve in water alone.

The phrase "longer half-life" has its ordinary meaning as understood by persons of skill in the art. Merely by way of example, and by no means as a limitation on the meaning of the term, the following description of the term is informative: any appreciable increase in the length of time required to deactivate fumagillin conjugate either in vivo or in vitro as compared to the half-life of the fumagillin analog alone either in vivo or in vitro.

Without being bound by any theory, non-enzymatic actions of MetAP2 to suppress activity of extra-cellular signal regulated kinases 1 and 2 (ERK1/2) may be important as may be the binding of eukaryotic initiation factor, eIF, by MetAP2. Cellular responses to MetAP2 inhibition reflective of potential ERK-related processes may include suppression of sterol regulatory element binding protein (SREBP) activity, leading to reduced lipid and cholesterol biosynthesis. Interesting, changes in the expression patterns of hepatic and adipose tissue genes after prolonged (approximately 9 months) fumagillin exposure suggest that MetAP2 inhibition also may alter the relative abundance of factors involved in inflammation, consistent with reduced ERK-dependent cellular processes. The putative mechanism of MetAP2 inhibition leading to mobilization of adipose depot and catabolism of free fatty acids as energy source by the body is supported by changes in plasma β-hydroxybutyrate, adiponectin, leptin, and FGF21 observed in previous studies. Elevation in the levels of key catabolic hormones adiponectin and FGF21, coupled with the appearance of ketone bodies (β-hydroxybutyrate), suggest MetAP2 inhibition with the conjugated or modified fumagillin, fumagillol, or an analog, derivative, salt or ester thereof compounds of the present disclosure stimulates energy expenditure, fat utilization and lipid excretion. The reduction in leptin observed in previous studies and the studies provided herein is also consistent with a decrease in total adipose tissue and negative energy balance. It is also possible that the conjugated or modified fumagillin, fumagillol, or an analog, derivative, salt or ester thereof compounds of the present disclosure form a covalent bond with MetAP2, thereby irreversibly inhibiting and silencing existing enzyme until a newly produced pool of MetAP2 is generated in target tissues (e.g., liver and adipose tissue).

In certain aspects, the conjugated or modified fumagillin, fumagillol, or an analog, derivative, salt or ester thereof compounds of the present disclosure, for example have the following formula as shown in Table 1:

TABLE 1

| Compound No. | Chemical Structure |
|---|---|
| 5 | 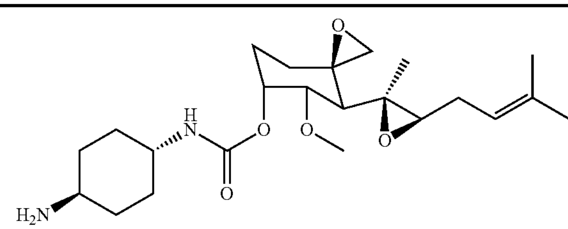 |
| 6 | 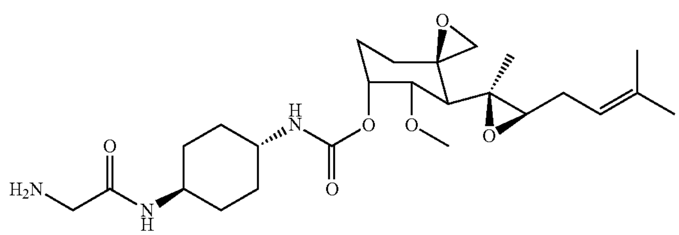 |
| 7 | 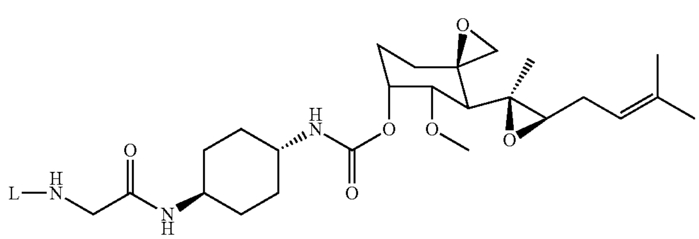 |
| 8 | 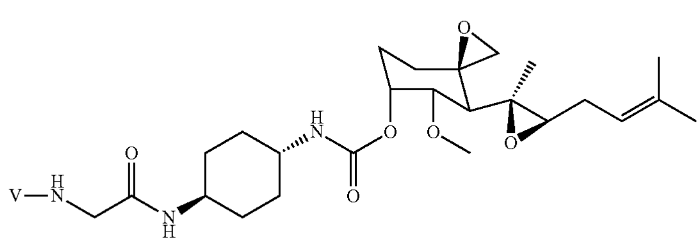 |

TABLE 1-continued
| Compound No. | Chemical Structure |
|---|---|
| 9 | 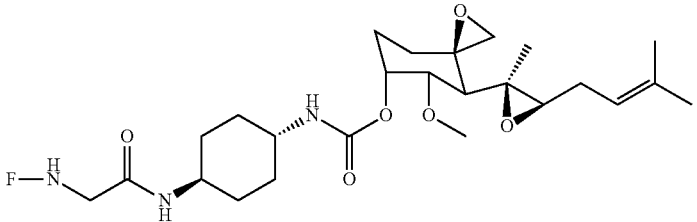 |
| 10 | 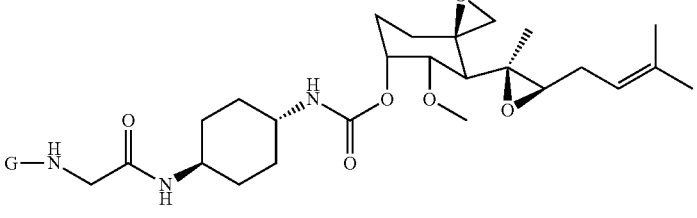 |
| 11 | 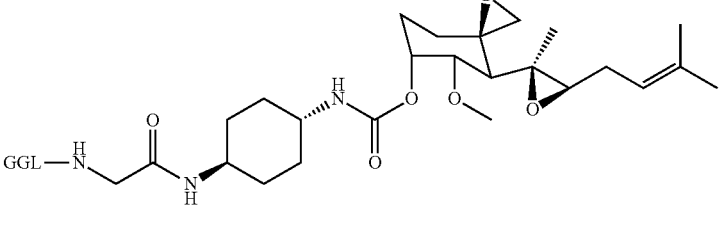 |
| 12 | 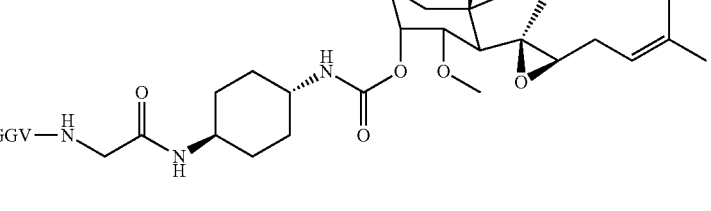 |
| 13 | 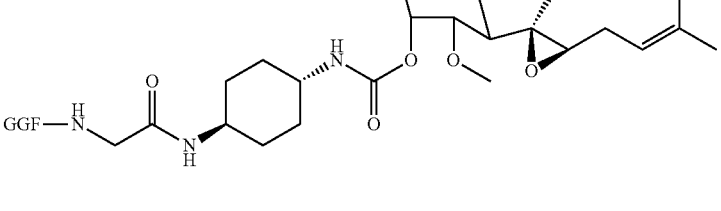 |
| 14 | 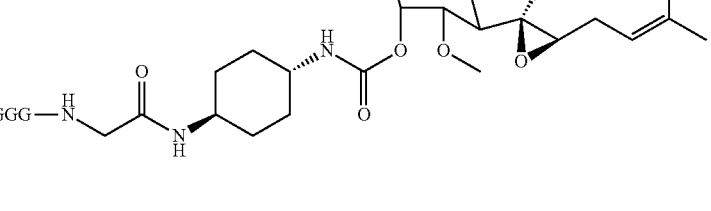 |

TABLE 1-continued
| Compound No. | Chemical Structure |
|---|---|
| 15 | 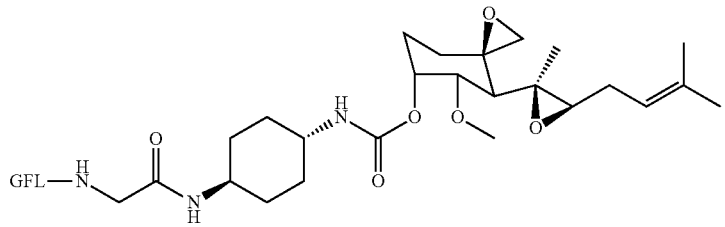 |
| 16 | 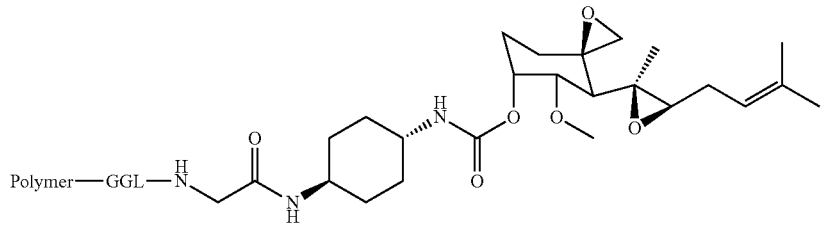 |
| 17 | 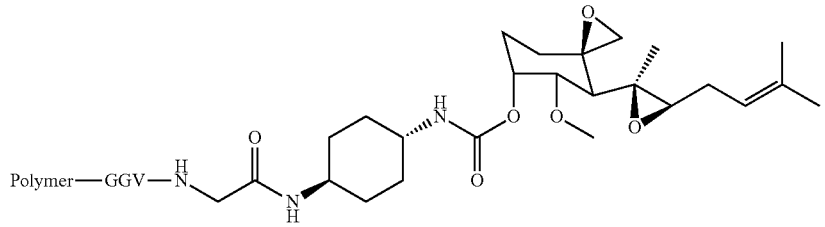 |
| 18 | 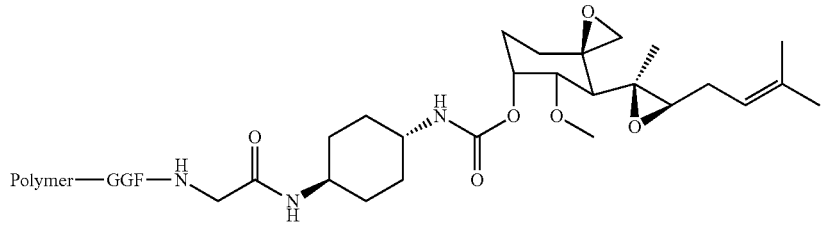 |
| 19 | 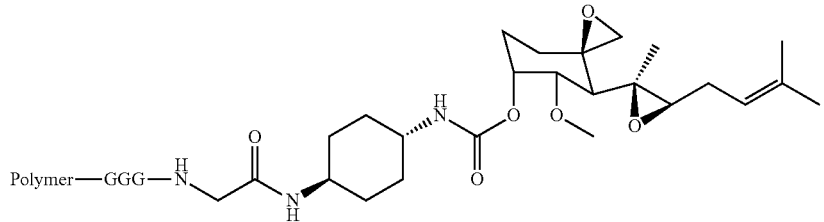 |
| 20 | 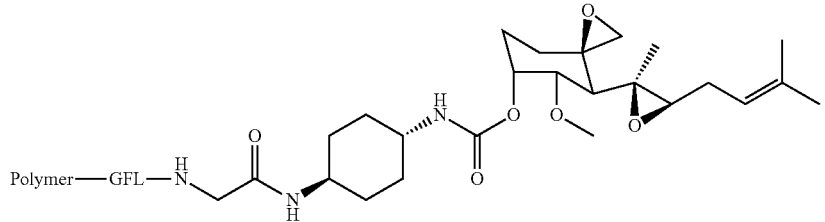 |

TABLE 1-continued

| Compound No. | Chemical Structure |
|---|---|
| 21 | ![structure] |
| 22 | ![structure] |
| 23 | ![structure] |
| 24 | ![structure] |
| 25 | ![structure] |
| 26 | ![structure] |
| 27 | ![structure] |

TABLE 1-continued

| Compound No. | Chemical Structure |
|---|---|
| 28 | GGV—NH–CH₂–C(=O)–NH–(CH₂)₆–NH–C(=O)–O–[fumagillol core] |
| 29 | GGF—NH–CH₂–C(=O)–NH–(CH₂)₆–NH–C(=O)–O–[fumagillol core] |
| 30 | GGG—NH–CH₂–C(=O)–NH–(CH₂)₆–NH–C(=O)–O–[fumagillol core] |
| 31 | GFL—NH–CH₂–C(=O)–NH–(CH₂)₆–NH–C(=O)–O–[fumagillol core] |
| 32 | Polymer—GGL—NH–CH₂–C(=O)–NH–(CH₂)₆–NH–C(=O)–O–[fumagillol core] |
| 33 | Polymer—GGV—NH–CH₂–C(=O)–NH–(CH₂)₆–NH–C(=O)–O–[fumagillol core] |
| 34 | Polymer—GGF—NH–CH₂–C(=O)–NH–(CH₂)₆–NH–C(=O)–O–[fumagillol core] |

TABLE 1-continued
| Compound No. | Chemical Structure |
|---|---|
| 35 | 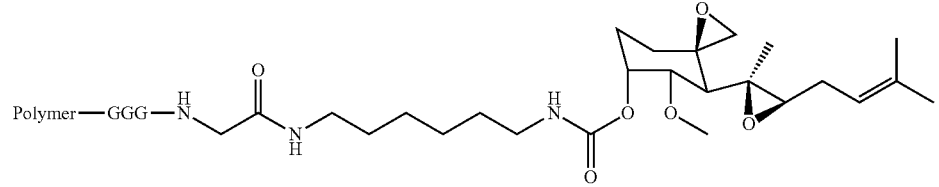 |
| 36 | 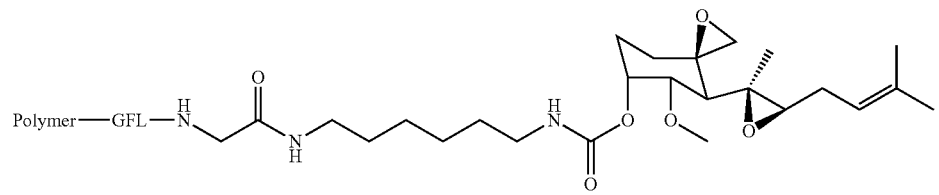 |
| 37 | 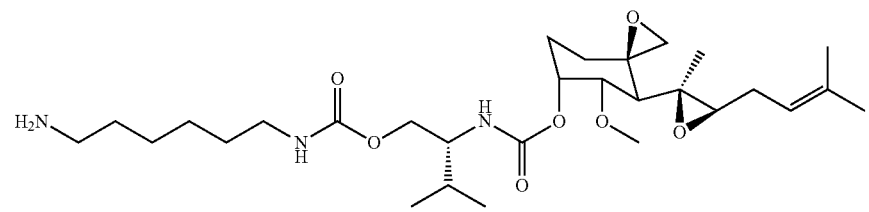 |
| 38 | 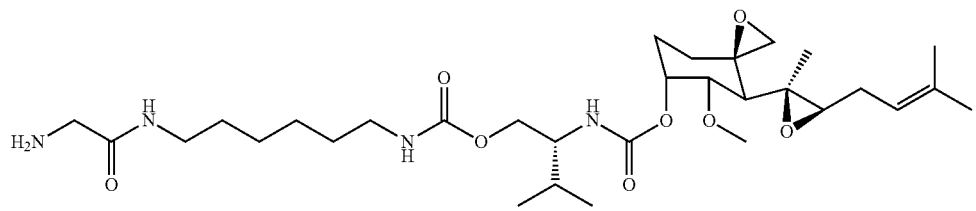 |
| 39 | 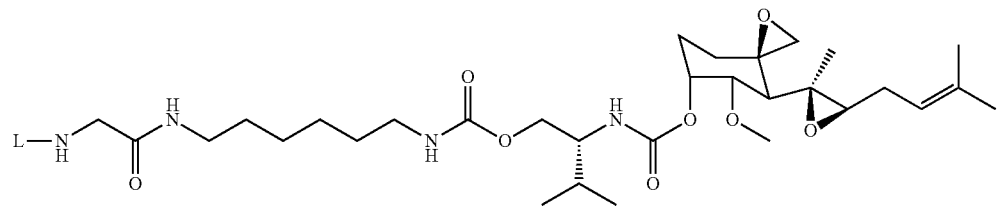 |
| 40 | 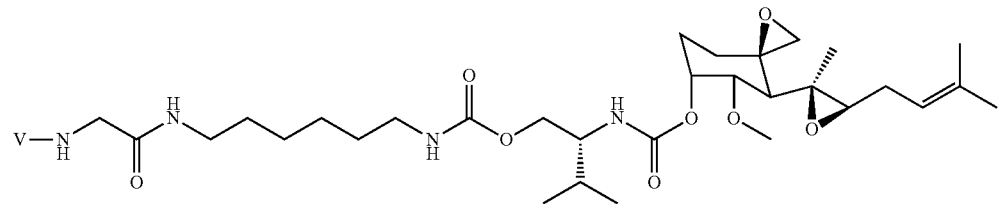 |
| 41 | 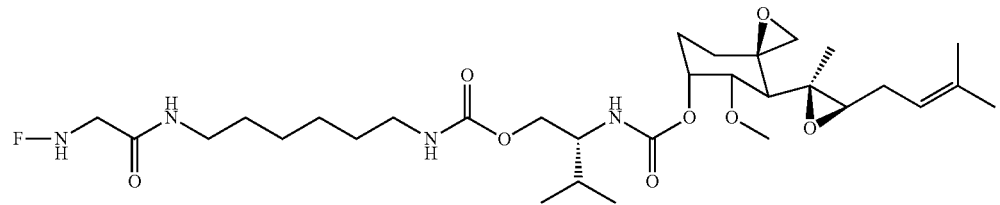 |

TABLE 1-continued
| Compound No. | Chemical Structure |
|---|---|
| 42 | 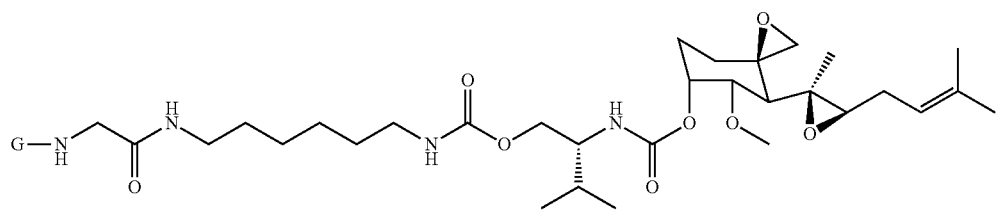 |
| 43 | 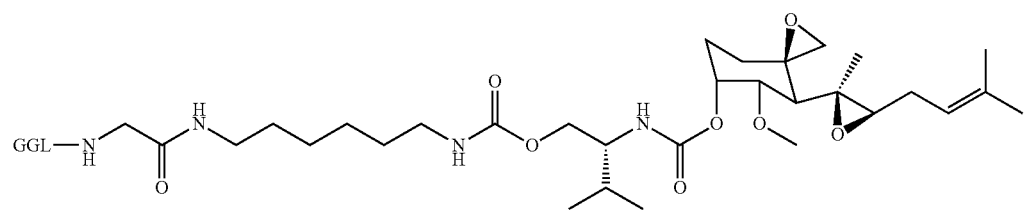 |
| 44 | 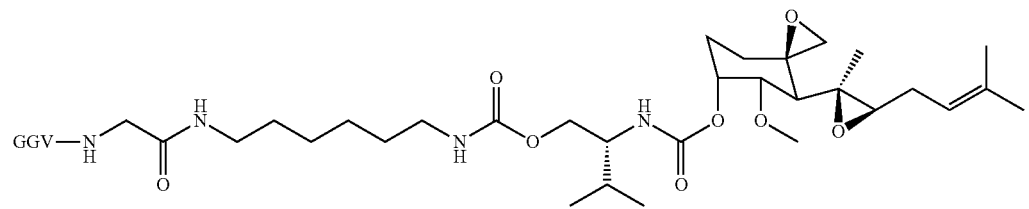 |
| 45 | 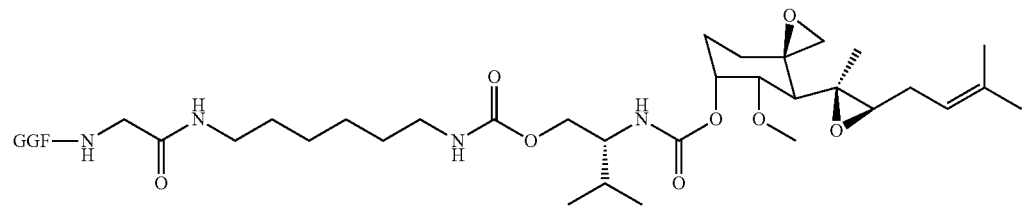 |
| 46 | 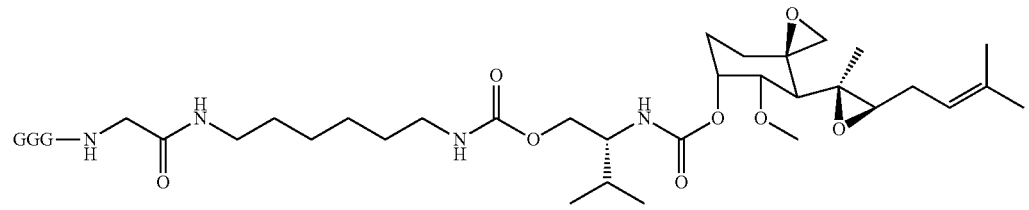 |
| 47 | 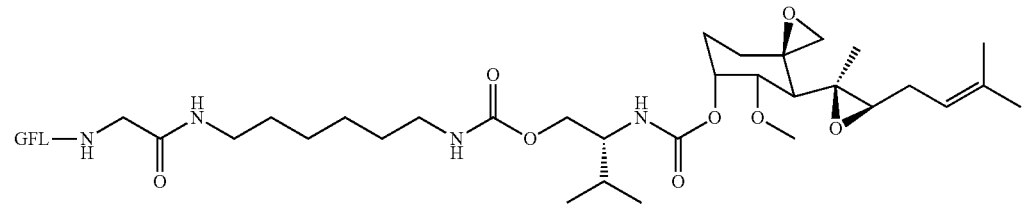 |
| 48 | 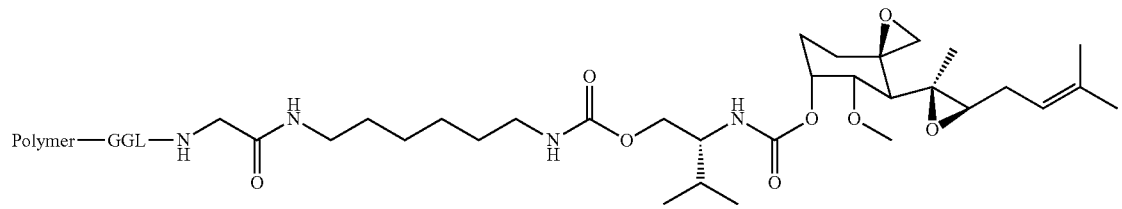 |

TABLE 1-continued
| Compound No. | Chemical Structure |
|---|---|
| 49 | 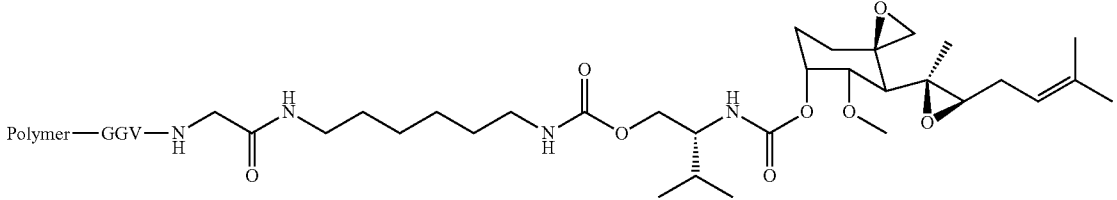 |
| 50 | 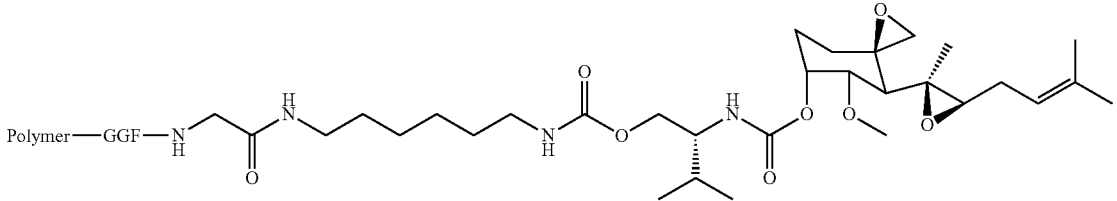 |
| 51 | 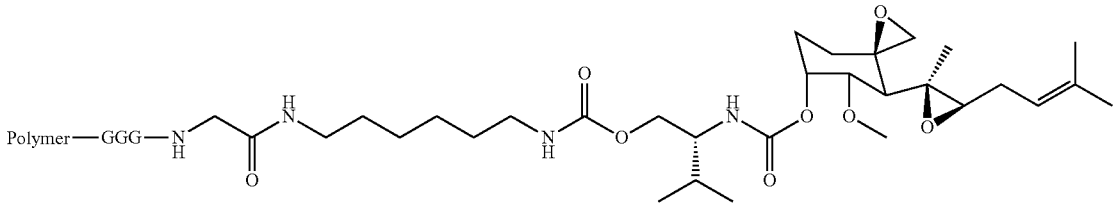 |
| 52 | 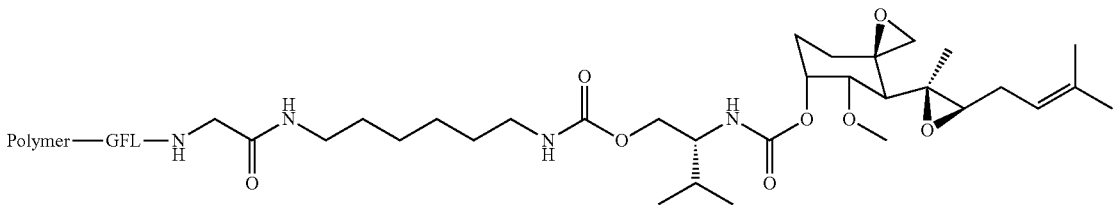 |
| 53 | 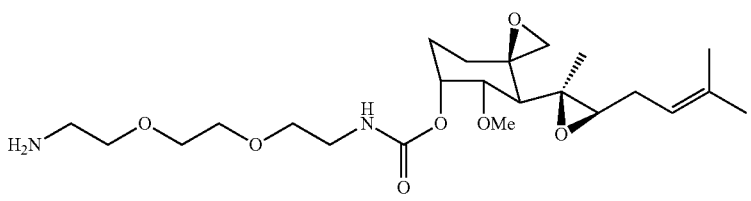 |
| 54 | 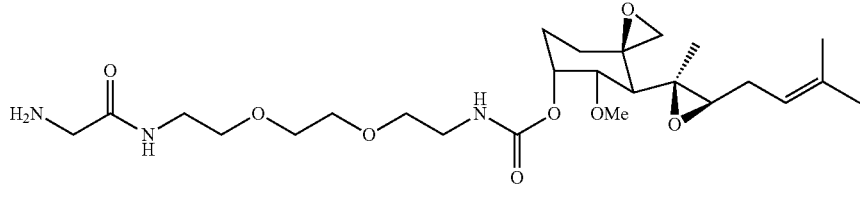 |
| 55 | 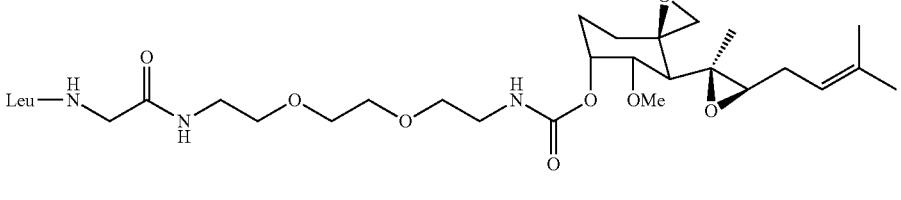 |

TABLE 1-continued

| Compound No. | Chemical Structure |
|---|---|
| 56 | Val-NH-C(O)-CH2-NH-CH2CH2-O-CH2CH2-O-CH2CH2-NH-C(O)-O-[core with OMe, epoxides, prenyl] |
| 57 | Phe-NH-C(O)-CH2-NH-CH2CH2-O-CH2CH2-O-CH2CH2-NH-C(O)-O-[core with OMe, epoxides, prenyl] |
| 58 | Gly-NH-C(O)-CH2-NH-CH2CH2-O-CH2CH2-O-CH2CH2-NH-C(O)-O-[core with OMe, epoxides, prenyl] |
| 59 | Gly-Gly-Leu-NH-C(O)-CH2-NH-CH2CH2-O-CH2CH2-O-CH2CH2-NH-C(O)-O-[core with OMe, epoxides, prenyl] |
| 60 | Gly-Gly-Val-NH-C(O)-CH2-NH-CH2CH2-O-CH2CH2-O-CH2CH2-NH-C(O)-O-[core with OMe, epoxides, prenyl] |
| 61 | Gly-Gly-Phe-NH-C(O)-CH2-NH-CH2CH2-O-CH2CH2-O-CH2CH2-NH-C(O)-O-[core with OMe, epoxides, prenyl] |
| 62 | Gly-Gly-Gly-NH-C(O)-CH2-NH-CH2CH2-O-CH2CH2-O-CH2CH2-NH-C(O)-O-[core with OMe, epoxides, prenyl] |

TABLE 1-continued
| Compound No. | Chemical Structure |
|---|---|
| 63 | 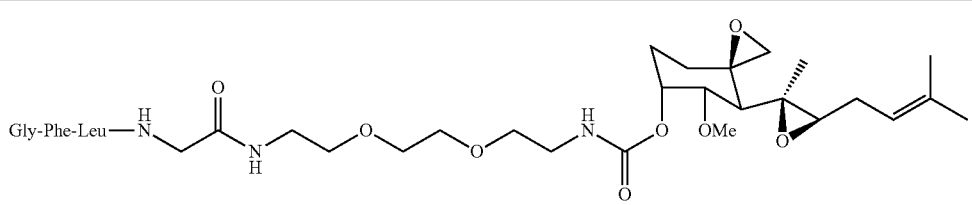 |
| 64 | 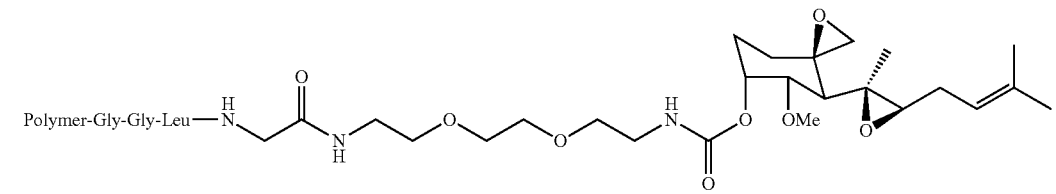 |
| 65 | 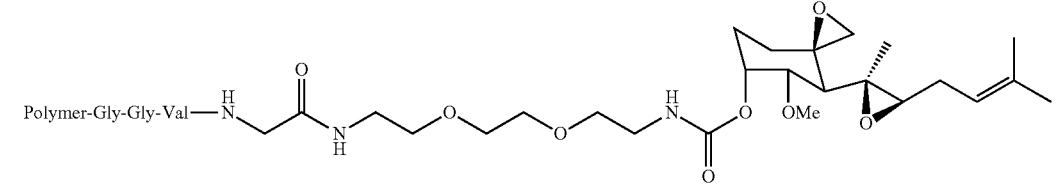 |
| 66 | 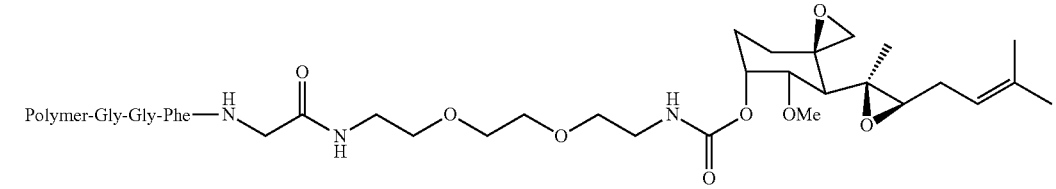 |
| 67 | 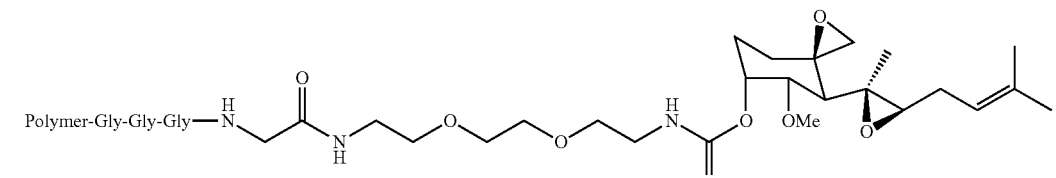 |
| 68 | 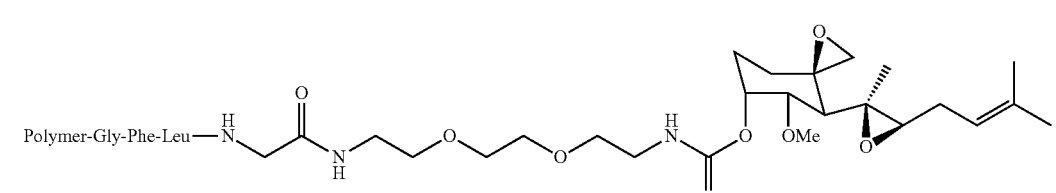 |
| 69 | 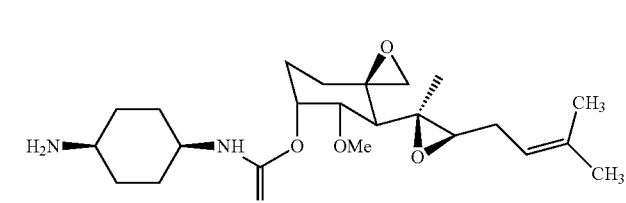 |

\* wherein Polymer has the structure of:
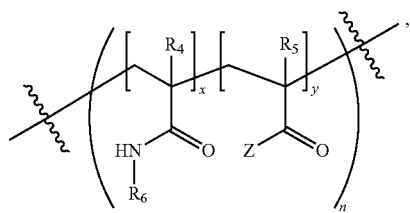
and preferably the structure of:
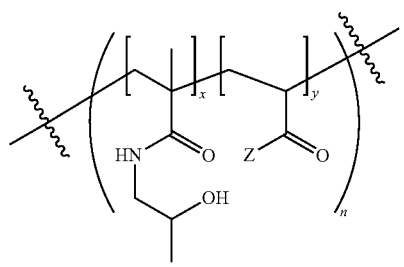
In some aspects, the compound is:
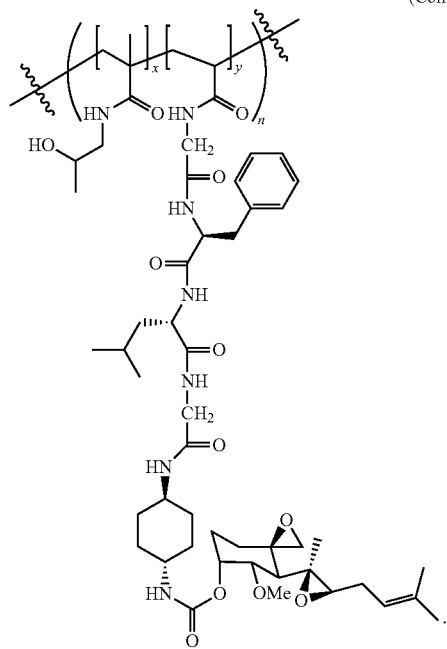
(Compound 1)
In some aspects, the compound is:
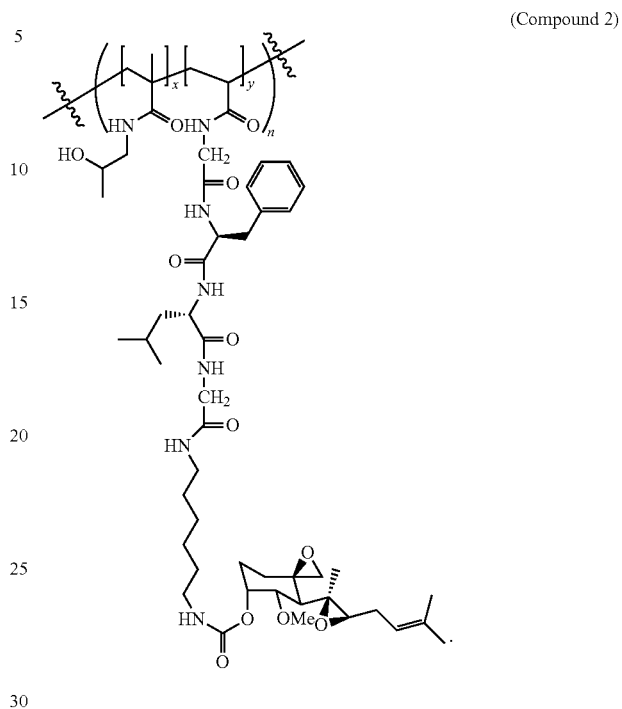
(Compound 2)
In some aspects, the compound is:
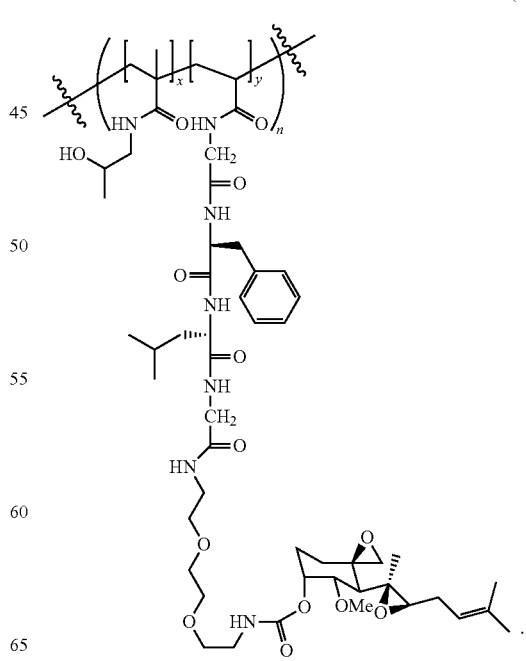
(Compound 3)

In some aspects, the compound is:

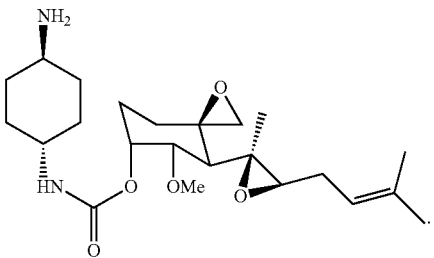

In some aspects, the compound is:

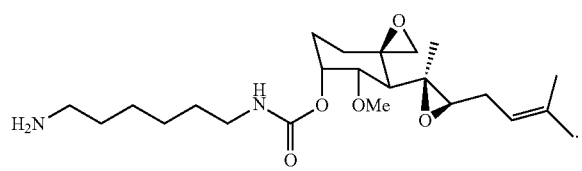

In some aspects, the compound is:

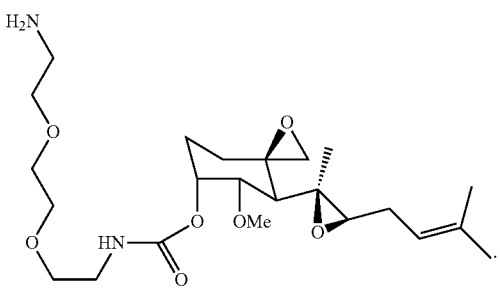

In one or more aspects, a compound for use in the present disclosure can be selected from cis-(3aRS,9bRS)-7-(benzenesulfonylamino)-1,3a,4,9b-tetrahydro-2H-furo[2,3-c]chromene-6-carboxylic acid; cis-(3aRS,9bRS)-7-[2-(3-diethylaminopropyl)-4-fluorobenzenesulfonyl-amino]-1,3a,4,9b-tetrahydro-2H-furo[2,3-c]chromene-6-carboxylic acid; cis-(3aRS,9bRS)-7-[2-(3-{pyrrolidin-1-yl}propyl)-4-fluorobenzenesulfonylamino]-1,3a,4,9b-tetrahydro-2H-furo[2,3-c]chromene-6-carboxylic acid; cis-(3aRS,9bRS)-7-[2-((Z)-3-diethylaminoprop-1-enyl)-4-fluorobenzenesulfonylamino]-1,3a,4,9b-tetrahydro-2H-furo[2,3-c]chromene-6-carboxylic acid; cis-(3aR,9bR)-7-[2-((Z)-3-diethylaminoprop-1-enyl)-4-fluoro-benzenesulfonylamino]-1,3a,4,9b-tetrahydro-2H-furo[2,3-c]chromene-6-carboxylic acid; cis-(3aS,9bS)-7-[2-((Z)-3-diethylaminoprop-1-enyl)-4-fluorobenzenesulfonylamino]-1,3a,4,9b-tetrahydro-2H-furo[2,3-c]chromene-6-carboxylic acid; 7-[2-((Z)-3-diethylaminoprop-1-enyl)-4-fluorobenzenesulfonylamino]-1,2-dihydrofuro[2,3-c]quinoline-6-carboxylic acid formate salt; 7-(benzenesulfonylamino))-1,2-dihydrofuro[2,3-c]quinoline-6-carboxylic acid formate salt; cis-(3aRS,9bRS)-7-[2-((Z)-3-diethylaminoprop-1-enyl)-4-fluorobenzenesulfonylamino]-1,2,3a,4,5,9b-hexahydrofuro[2,3-c]quinoline-6-carboxylic acid; (1 aRS,7bSR)-5-[2-((Z)-3-diethylaminoprop-1-enyl)-4-fluorobenzenesulfonylamino]-1,1a,2,7b-tetrahydrocyclopropa[c]chromene-4-carboxylic acid; (1aR,7bS)-5-[2-((Z)-3-diethylaminoprop-1-enyl)-4-fluorobenzenesulfonylamino]-1,1a,2,7b-tetrahydrocyclopropa[c]chromene-4-carboxylic acid; (1 aS,7bR)-5-[2-((Z)-3-diethylaminoprop-1-enyl)-4-fluorobenzenesulfonylamino]-1,1a,2,7b-tetrahydrocyclopropa[c]chromene-4-carboxylic acid; (1aRS,7bSR)-5-[2-((Z)-3-diethylaminoprop-1-enyl)-4-fluorobenzenesulfonylamino]-7b-methyl-1, 1a,2,7b-tetrahydrocyclopropa[c]chromene-4-carboxylic acid; (1aRS,7bSR)-5-[2-((E)-3-diethylaminoprop-1-enyl)-4-fluorobenzenesulfonylamino]-7b-methyl-1,1a,2,7b-tetrahydrocyclopropa[c]chromene-4-carboxylic acid; cis-(3aRS,9bRS)-7-[2-(4-dimethylamino-butylamino)-benzenesulfonylamino]-1,3a,4,9b-tetrahydro-2H-furo[2,3-c]chromene-6-carboxylic acid; (1 aR,7bS)-5-[2-(3-diethylaminopropyl)-4-fluorobenzenesulfonyl-amino]-1,1a,2,7b-tetrahydrocyclopropa[c]chromene-4-carboxylic acid; (1aRS,7bSR)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1aR,7bS)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1 aS,7bR)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1aRS,7bSR)-5-[2((Z)-3-ethylaminoprop-1-enyl)-4-fluorobenzenesulfonylamino]-1,1a,2,7b-tetrahydrocyclopropa-[c]chromene-4-carboxylic acid; (1aR,7bS)-5-[2((Z)-3-ethylaminoprop-1-enyl)-4-fluorobenzenesulfonylamino]-1,1a,2,7b-tetrahydrocyclopropa[c]chromene-4-carboxylic acid; (1aS,7bR)-5-[2((Z)-3-ethylaminoprop-1-enyl)-4-fluorobenzene-sulfonylamino]-1,1a,2,7b-tetrahydro-cyclopropa[c]chromene-4-carboxylic acid; (1aRS,7bSR)-5-{2[(Z)-3-(pyrrolidin-1-yl)prop-1-enyl]-4-fluorobenzenesulfonylamino}-1,1a,2,7b-tetrahydro-cyclopropa[c]chromene-4-carboxylic acid; (1aR,7bS)-5-{2[(Z)-3-(pyrrolidin-1-yl)prop-1-enyl]-4-fluorobenzenesulfonyl-amino}-1,1a,2,7b-tetrahydro-cyclopropa[c]chromene-4-carboxylic acid; (1 aS,7bR)-5-{2[(Z)-3-(pyrrolidin-1-yl)prop-1-enyl]-4-fluorobenzenesulfonylamino}-1,1a,2,7b-tetrahydro-cyclopropa[c]chromene-4-carboxylic acid; (1aRS,7bSR)-5-[2-(3-dimethylaminopropylamino)-benzenesulfonylamino]-1,1a,2,7b-tetrahydrocyclopropa[c]chromene-4-carboxylic acid; (1 aR,7bS)-5-[2-(3-dimethylaminopropylamino)benzene-sulfonylamino]-1,1a,2,7b-tetrahydrocyclopropa[c]chromene-4-carboxylic acid; (1aS,7bR)-5-[2-(3-dimethylaminopropyl-amino)benzenesulfonylamino]-1,1a,2,7b-tetrahydrocyclopropa[c]chromene-4-carboxylic acid; (1aRS,7bSR)-5-[2-(4-dimethylaminobutylamino)benzenesulfonylamino]-1,1a,2,7b-tetrahydrocyclopropa[c]chromene-4-carboxylic acid; (1aR,7bS)-5-[2-(4-dimethyl-amino-butylamino)benzenesulfonylamino]-1,1a,2,7b-tetrahydrocyclopropa[c]chromene-4-carboxylic acid; (1aS,7bR)-5-[2-(4-dimethylaminobutylamino]-1,1a,2,7b-tetrahydrocyclopropa[c]chromene-4-carboxylic acid; (1 aRS,7bSR)-5-[2-(5-dimethylamino-pentylamino)benzenesulfonylamino]-1,1a,2,7b-tetrahydrocyclopropa[c]chromene-4-carboxylic acid; (1aRS,7bSR)-5-{2[(Z)-3-(propan-2-yl)aminoprop-1-enyl]-4-fluorobenzenesulfonyl-amino}-1,1a,2,7b-tetrahydrocyclopropa[c]chromene-4-carboxylic acid; (1 aRS,7bSR)-5-{2[(Z)-3-((S)-3-hydroxypyrrolidin-1-yl)aminoprop-1-enyl]-4-fluorobenzenesulfonylamino}-1,1a,2,7b-tetrahydrocyclopropa[c]chromene-4-carboxylic acid; (1 aRS,7bSR)-5-{2[(Z)-3-((R)-3-hydroxypyrrolidin-1-yl)aminoprop-1-enyl]-4-fluorobenzene-sulfonylamino}-1,1a, 2,7b-tetrahydro-cyclopropa[c]chromene-4-carboxylic acid; (1aRS,7bSR)-5-[2((Z)-4-diethylaminobut-1-enyl)-4-fluorobenzenesulfonyl-amino]-1,1a,2,7b-tetrahydrocyclopropa[c]chromene-4-carboxylic acid; (1aR,7bS)-5-[2((Z)-4-diethylaminobut-1-enyl)-4-fluorobenzenesulfonyl-amino]-1,1a,2,7b-tetrahydrocyclopropa[c]chromene-4-carboxylic acid; (1aS,7bR)-5-[2((Z)-4-diethylaminobut-1-enyl)-4-fluorobenzenesulfonyl-amino]-1,1a,2,7b-tetrahydro-cyclopropa[c]chromene-4-carboxylic acid; (1aRS,7bSR)-5-{2-[2-(4-ethylpiperazin-1-yl)-ethyl]-4-fluorobenzenesulfonylamino}-1,1a,2,7b-tetrahydrocyclopropa[c]chromene-4-carboxylic acid; (1aRS,7bSR)-5-{2[(Z)-3-(azetidin-1-yl)prop-1-enyl]-4-fluorobenzene-sulfonylamino}-1,1a,2,7b-tetrahydro-cyclopropa[c]chromene-4-carboxylic acid; (1aRS,7bSR)-5-{2[(Z)-3-(3-hydroxy-azetidin-1-yl)prop-1-enyl]-4-fluorobenzene-sulfonylamino}-1,1a,2,7b-tetrahydrocyclopropa-[c]chromene-4-carboxylic acid; (1aRS,7bSR)-5-{2[(Z)-3-(azetidin-1-yl)propyl]-4-fluorobenzenesulfonylamino}-1,1a,2,7b-tetrahydrocyclopropa[c]chromene-4-carboxylic acid; (1aRS,7bSR)-5-[2((Z)-4-diethylaminobutyl)-4-fluorobenzenesulfonylamino]-1,1a,2,7b-tetrahydrocyclopropa[c]chromene-4-carboxylic acid; (1aRS,7bSR)-5-{2-[N-(4-dimethylaminobutyl)-N-methyl-amino]-benzenesulfonyl-amino}-1,1a,2,7b-tetrahydrocyclopropa-[c]chromene-4-carboxylic acid; (1aRS,7bSR)-5-{2-[((S)-1-ethylpyrrolidin-3-ylcarbamoyl)-methyl]-4-fluorobenzenesulfonyl-amino}-1,1a,2,7b-tetrahydrocyclopropa-[c]chromene-4-carboxylic acid; (1aRS,7bSR)-5-[2-(1-ethylazetidin-3-yl)-4-fluorobenzenesulfonylamino]-1,1a,2,7b-tetrahydro-cyclopropa[c]chromene-4-carboxylic acid; (1aRS,7bSR)-5-{2-[((R)-1-ethylpyrrolidin-3-ylcarbamoyl)methyl]-4-fluorobenzenesulfonyl-amino}-1,1a,2,7b-tetrahydro-cyclopropa[c]chromene-4-carboxylic acid; (1aRS, 7bSR)-5-{2-[2-(pyrrolidin-1-yl)-ethyl]-4-fluorobenzenesulfonylamino}-1,1a,2,7b-tetrahydrocyclopropa[c]chromene-4-carboxylic acid; (1aRS,7bSR)-5-[2-((R)-1-ethylpyrrolidin-3-ylmethyl)-4-fluorobenzenesulfonyl-amino]-1,1a,2,7b-tetrahydro-cyclopropa[c]chromene-4-carboxylic acid; (1aS,7bR)-5-[2-((R)-1-ethylpyrrolidin-3-ylmethyl)-4-fluorobenzenesulfonyl-amino]-1,1a,2,7b-tetrahydro-cyclopropa[c]chromene-4-carboxylic acid; (1aR,7bS)-5-[2-((R)-1-ethylpyrrolidin-3-ylmethyl)-4-fluorobenzenesulfonyl-amino]-1,1a,2,7b-tetrahydro-cyclopropa[c]chromene-4-carboxylic acid; (1aRS,7bSR)-5-{2-[((S)-1-ethylpyrrolidin-2-yl)carbonyl-aminomethyl]-4-fluorobenzene-sulfonylamino}-1,1a,2,7b-tetrahydrocyclopropa[c]chromene-4-carboxylic acid; (1aRS,7bSR)-5-[2-(4-dimethylaminobutyrylamino)-4-fluorobenzenesulfonyl-amino]-1,1a,2,7b-tetrahydrocyclopropa-[c]chromene-4-carboxylic acid; (1aRS,7bSR)-5-[2-((S)-1-ethyl-pyrrolidin-3-ylmethyl)-4-fluorobenzenesulfonyl-amino]-1,1a,2,7b-tetrahydrocyclopropa[c]chromene-4-carboxylic acid; (1aRS,7bSR)-5-[2-(3-dimethylaminopropylcarbamoyl)benzene-sulfonylamino]-1,1a,2,7b-tetrahydrocyclopropa[c]chromene-4-carboxylic acid; (1aRS,7bSR)-5-(2-{[N—((S)-1-ethyl-pyrrolidin-3-yl)-N-methylcarbamoyl]methyl}-4-fluoro-benzenesulfonylamino)-1,1a,2,7b-tetrahydrocyclopropa-[c]chromene-4-carboxylic acid; (1aRS,7bSR)-5-(2-{[N—((R)-1-ethyl-pyrrolidin-3-yl)-N-methylcarbamoyl]methyl}-4-fluoro-benzenesulfonylamino)-1,1a,2,7b-tetrahydrocyclopropa-[c]chromene-4-carboxylic acid; (1aRS,7bSR)-5-{2-[2-((S)-1-ethylpyrrolidin-2-yl)ethylamino]-benzenesulfonyl-amino}-1,1a,2,7b-tetrahydrocyclopropa-[c]chromene-4-carboxylic acid; (1aRS,7bSR)-5-{2-[2-((R)-1-ethylpyrrolidin-2-yl)ethylamino]-benzenesulfonyl-amino}-1,1a,2,7b-tetrahydrocyclopropa-[c]chromene-4-carboxylic acid; (1aRS,7bSR)-5-[2-(3-N,N,-diethylaminopropylamino)benzene-sulfonylamino]-1,1a,2,7b-tetrahydrocyclopropa[c]chromene-4-carboxylic acid; (1aRS,7bSR)-5-(2-{[((R)-1-ethylpyrrolidine-2-yl)carbonyl-amino]methyl}-4-fluorobenzenesulfonylamino)-1,1a,2,7b-tetrahydrocyclopropa[c]chromene-4-carboxylic acid; (1aRS,7bSR)-5-{2-[(1-ethylazetidin-3-ylmethyl)amino]benzene-sulfonylamino}-1,1a,2,7b-tetrahydrocyclopropa[c]chromene-4-carboxylic acid; (1aS,7bR)-5-[2-((Z)-3-diethylaminoprop-1-enyl)benzenesulfonylamino]-1,1a,2,7b-tetrahydrocyclopropa[c]chromene-4-carboxylic acid; (1aR,7bS)-5-[2-((Z)-3-diethylaminoprop-1-enyl)benzenesulfonylamino]-1,1a,2,7b-tetrahydrocyclopropa[c]chromene-4-carboxylic acid; (1aRS,7b SR)-5-(2-{N-[((R)-1-ethylpyrrolidine-2-yl)carbonyl]-N-methyl-aminomethyl}-4-fluorobenzenesulfonylamino)-1,1a,2,7b-tetrahydrocyclopropa[c]chromene-4-carboxylic acid; (1aRS,7bSR)-5-(2-{N-[((S)-1-ethylpyrrolidine-2-yl)carbonyl]-N-methylamino-methyl}-4-fluorobenzenesulfonylamino)-1,1a,2,7b-tetrahydrocyclopropa[c]chromene-4-carboxylic acid; (1aRS,7bSR)-5-[2-(4-dimethylaminobutylamino)-4-fluorobenzenesulfonyl-amino]-1,1a,2,7b-tetrahydrocyclopropa[c]chromene-4-carboxylic acid; (1aRS,7bSR)-5-{2-[((R)-1-ethylpyrrolidin-3-ylmethyl)amino]-benzenesulfonylamino}-1,1a,2,7b-tetrahydrocyclopropa-[c]chromene-4-carboxylic acid; (1aRS,7bSR)-5-{2-[((S)-1-ethylpyrrolidin-3-ylmethyl)amino]-benzenesulfonylamino}-1,1a,2,7b-tetrahydrocyclopropa-[c]chromene-4-carboxylic acid; (1aRS,7bSR)-5-[2-(4-ethyl-2-oxopiperazin-1-ylmethyl)-4-fluorobenzene-sulfonylamino]-1,1a,2,7b-tetrahydrocyclopropa[c]chromene-4-carboxylic acid; (1aRS,7bSR)-5-[2-(1-ethylpiperidin-4-ylmethyl)-4-fluoro-benzenesulfonylamino]-1,1a,2,7b-tetrahydrocyclopropa-[c]chromene-4-carboxylic acid; (1aRS,7bSR)-5-{2-[2-(1-ethylazetidin-3-yl)ethyl]-4-fluoro-benzenesulfonyl-amino}-1,1a,2,7b-tetrahydrocyclopropa[c]chromene-4-carboxylic acid; (1aRS,7bSR)-5-{2-[((S)-1-azabicyclo[2.2.2]oct-3-yl)amino]benzenesulfonyl-amino}-1,1a,2,7b-tetrahydrocyclopropa[c]chromene-4-carboxylic acid; (1aRS,7bSR)-5-{2-[((R)-1-azabicyclo-[2.2.2]oct-3-yl)amino]benzenesulfonyl-amino}-1,1a,2,7b-tetrahydrocyclopropa[c]chromene-4-carboxylic acid; (1aRS,7bSR)-5-(2-{[((S)-1-ethylpyrrolidine-3-carbonyl)amino]methyl}-4-fluoro-benzenesulfonylamino)-1,1a,2,7b-tetrahydrocyclopropa[c]chromene-4-carboxylic acid; (1aRS,7bSR)-5-{2-[2-((R)-1-ethylpyrrolidin-3-ylamino)ethyl]-4-fluoro-benzenesulfonylamino}-1,1a,2,7b-tetrahydrocyclopropa-[c]chromene-4-carboxylic acid; (1aRS,7bSR)-5-{2-[((R)-1-ethylpyrrolidin-3-yl)amino]-benzenesulfonylamino}-1,1a,2,7b-tetrahydrocyclopropa-[c]chromene-4-carboxylic acid; (1aRS,7bSR)-5-{2-[((S)-1-ethylpyrrolidin-3-yl)amino]-benzenesulfonylamino}-1,1a,2,7b-tetrahydrocyclopropa-[c]chromene-4-carboxylic acid; (1aRS,7bSR)-5-(2-{[((R)-1-ethylpyrrolidine-3-carbonyl)amino]-methyl})-4-fluoro-benzenesulfonylamino)-1,1a,2,7b-tetrahydro-cyclopropa[c]chromene-4-carboxylic acid; (1aRS,7bSR)-5-[2-((Z)-3-diethylamino-2-methylprop-1-enyl)-4-fluorobenzene-sulfonylamino]-1,1a,2,7b-tetrahydrocyclopropa[c]chromene-4-carboxylic acid; (1aRS,7bSR)-5-{2-[2-((R)-1-ethylpyrrolidin-3-yl)ethylamino]-benzenesulfonylamino}-1,1a,2,7b-tetrahydrocyclopropa-[c]chromene-4-carboxylic acid; (1aRS,7bSR)-5-{2-[2-((S)-1-ethylpyrrolidin-3-yl)ethylamino]-benzenesulfonyl-amino}-1,1a,2,7b-tetrahydrocyclopropa-[c]chromene-4-carboxylic acid; (1aR,7bS)-5-[2-((S)-1-ethylpyrrolidin-3-yloxymethyl)-4-fluorobenzenesulfonylamino]-1,1a,2,7b-tetrahydrocyclopropa-[c]chromene-4-carboxylic acid; (1aR,7bS)-5-[2-((R)-1-ethylpyrrolidin-3-yloxymethyl)-4-fluoro-benzenesulfonylamino]-1,1a,2,7b-tetrahydrocyclopropa-[c]chromene-4-carboxylic acid; (1aR,7bS)-5-[2-(1-ethylpiperidin-3-ylmethyl)-4-fluorobenzene-sulfonylamino]-1,1a,2,7b-tetrahydrocyclopropa[c]chromene-4-carboxylic acid; (1aR,7bS)-5-{2-[2-((R)-1-ethylpyrrolidin-2-yl)ethyl]-4-fluorobenzenesulfonyl-amino}-1,1a,2,7b-tetrahydrocyclopropa-[c]chromene-4-carboxylic acid; and pharmaceutically acceptable salts, stereoisomers, esters and prodrugs thereof.

In one or more aspects, the compound is selected from:

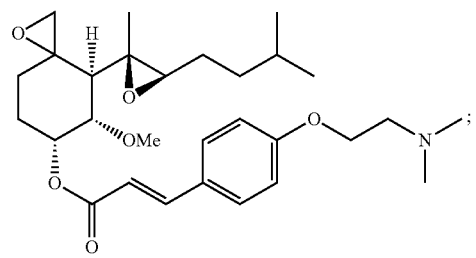

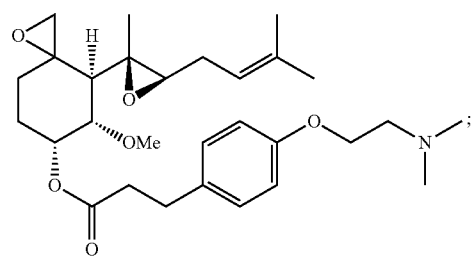

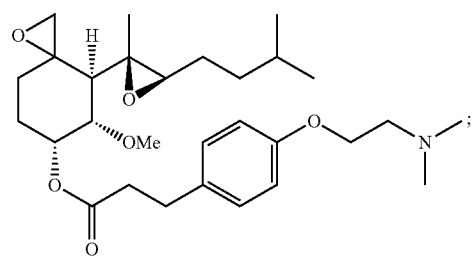

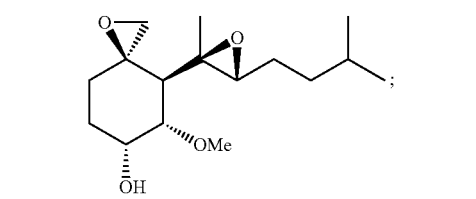

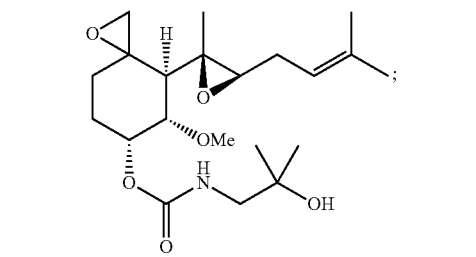

-continued

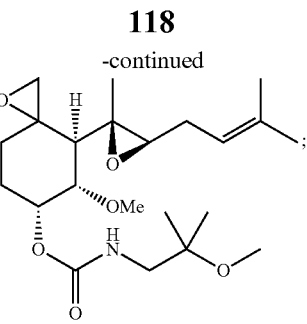

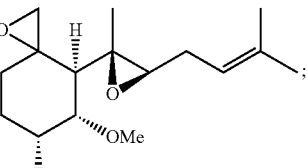

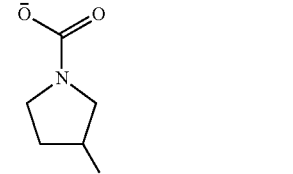

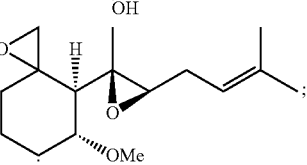

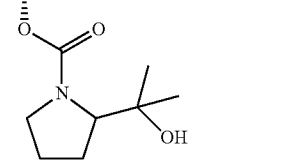

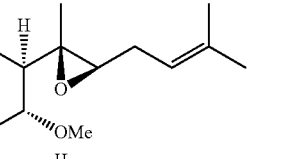

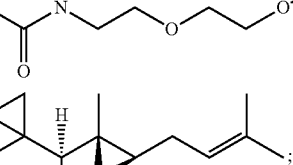

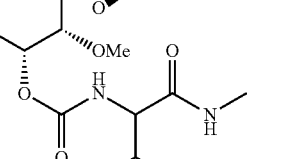

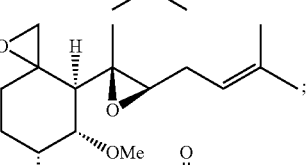

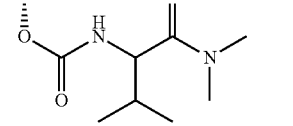

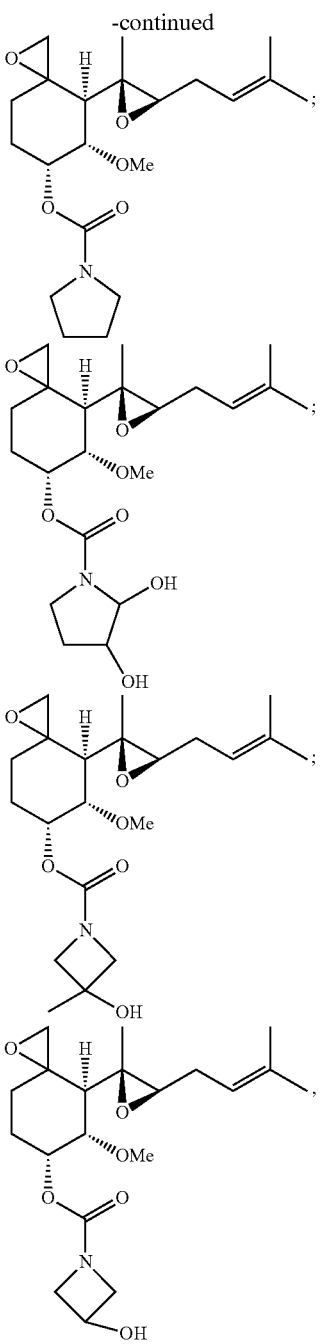

and pharmaceutically acceptable salts or stereoisomers thereof.

For purposes of this disclosure, the chemical elements are identified in accordance with the Periodic Table of the Elements, CAS version, Handbook of Chemistry and Physics, 67th Ed., 1986-87, inside cover.

The term "alkyl" refers to a fully saturated branched or unbranched carbon chain radical having the number of carbon atoms specified, or up to 30 carbon atoms if no specification is made. For example, a "lower alkyl" refers to an alkyl having from 1 to 10 carbon atoms, such as methyl, ethyl, propyl, butyl, pentyl, hexyl, heptyl, and octyl, and those which are positional isomers of these alkyls. Alkyl of 10 to 30 carbon atoms includes decyl, undecyl, dodecyl, tridecyl, tetradecyl, pentadecyl, hexadecyl, heptadecyl, octa-decyl, nonadecyl, eicosyl, heneicosyl, docosyl, tricosyl and tetracosyl. In certain aspects, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, certain cycloalkyls have from 3-10 carbon atoms in their ring structure, and may have 5, 6, or 7 carbons in the ring structure.

Unless the number of carbons is otherwise specified, "lower alkyl", as used herein, means an alkyl group, as defined above, but having from one to ten carbons, or from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, certain alkyl groups are lower alkyls. In certain aspects, a substituent designated herein as alkyl is a lower alkyl.

The term "carbocycle", as used herein, refers to an aromatic or non-aromatic ring in which each atom of the ring is carbon.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

"Alkenyl" refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the (E) configuration about the double bond(s).

The term "alkynyl" refers to hydrocarbyl radicals of the scope of alkenyl, but having one or more triple bonds in the radical.

The terms "alkoxyl" or "alkoxy" as used herein refers to an alkyl group, as defined below, having an oxygen radical attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_1$, where m and $R_1$ are described below.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF$_3$, —CN, or the like.

The term "alkylthio" refers to an alkyl group, as defined above, having a sulfur radical attached thereto. In certain aspects, the "alkylthio" moiety is represented by one of —(S)-alkyl, —(S)-alkenyl, —(S)-alkynyl, and —(S)—(CH$_2$)$_m$—R$_1$, wherein m and R$_1$ are defined below. Representative alkylthio groups include methylthio, ethylthio, and the like.

As used herein, the term "nitro" means —NO$_2$; the term "halogen" designates F, Cl, Br or I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formulae:

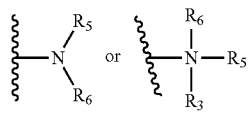

wherein R$_3$, R$_5$ and R$_6$ each independently represent a hydrogen, an alkyl, an alkenyl, —(CH$_2$)$_m$—R$_1$, or R$_3$ and R$_5$ taken together with the N atom to which they are attached complete a heterocycle having from 4 to 8 atoms in the ring structure; R$_1$ represents an alkenyl, aryl, cycloalkyl, a cycloalkenyl, a heterocyclyl or a polycyclyl; and m is zero or an integer in the range of 1 to 8. In certain aspects, only one of R$_3$ or R$_5$ can be a carbonyl, e.g., R$_3$, R$_5$ and the nitrogen together do not form an imide. In certain aspects, R$_3$ and R$_5$ (and optionally R$_6$) each independently represent a hydrogen, an alkyl, an alkenyl, or —(CH$_2$)$_m$—R$_1$. Thus, the term "alkylamine" as used herein means an amine group, as defined above, having a substituted or unsubstituted alkyl attached thereto, i.e., at least one of R$_3$ and R$_5$ is an alkyl group. In certain aspects, an amino group or an alkylamine is basic, meaning it has a pK$_a \geq 7.00$. The protonated forms of these functional groups have pK$_a$s relative to water above 7.00.

The term "carbonyl" (C(O)) is art-recognized and includes such moieties as can be represented by the general formula:

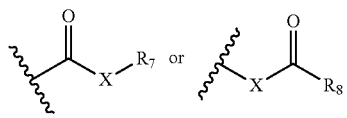

wherein X is a bond or represents an oxygen or a sulfur, and R$_7$ represents a hydrogen, an alkyl, an alkenyl, —(CH$_2$)$_m$—R$_1$ or a pharmaceutically acceptable salt, R$_8$ represents a hydrogen, an alkyl, an alkenyl or —(CH$_2$)$_m$—R$_1$, where m and R$_1$ are as defined above. Where X is an oxygen and R$_7$ or R$_8$ is not hydrogen, the formula represents an "ester". Where X is an oxygen, and R$_7$ is as defined above, the moiety is referred to herein as a carboxyl group, and particularly when R$_7$ is a hydrogen, the formula represents a "carboxylic acid". Where X is an oxygen, and R$_8$ is hydrogen, the formula represents a "formate". In general, where the oxygen atom of the above formula is replaced by sulfur, the formula represents a "thiocarbonyl" group. Where X is a sulfur and R$_7$ or R$_8$ is not hydrogen, the formula represents a "thioester" group. Where X is a sulfur and R$_7$ is hydrogen, the formula represents a "thiocarboxylic acid" group. Where X is a sulfur and R$_8$ is hydrogen, the formula represents a "thioformate" group. On the other hand, where X is a bond, and R$_7$ is not hydrogen, the above formula represents a "ketone" group. Where X is a bond, and R$_7$ is hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

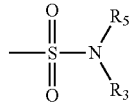

in which R$_3$ and R$_5$ are as defined above.

The term "sulfate" is art recognized and includes a moiety that can be represented by the general formula:

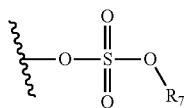

in which R$_7$ is as defined above.

The term "sulfamido" is art recognized and includes a moiety that can be represented by the general formula:

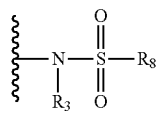

in which $R_2$ and $R_4$ are as defined above.

The term "sulfonate" is art-recognized and includes a moiety that can be represented by the general formula:

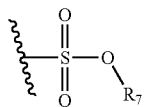

in which $R_7$ is an electron pair, hydrogen, alkyl, cycloalkyl, or aryl.

The terms "sulfoxido" or "sulfinyl", as used herein, refers to a moiety that can be represented by the general formula:

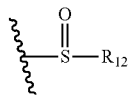

in which $R_{12}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The term "amino acid" is intended to embrace all compounds, whether natural or synthetic, which include both an amino functionality and an acid functionality, including amino acid analogs and derivatives. In certain aspects, the amino acids contemplated in the present disclosure are those naturally occurring amino acids found in proteins, or the naturally occurring anabolic or catabolic products of such amino acids, which contain amino and carboxyl groups. Naturally occurring amino acids are identified throughout by the conventional three-letter and/or one-letter abbreviations, corresponding to the trivial name of the amino acid, in accordance with the following list. The abbreviations are accepted in the peptide art and are recommended by the IUPAC-IUB commission in biochemical nomenclature.

By the term "amino acid residue" is meant an amino acid. In general the abbreviations used herein for designating the naturally occurring amino acids are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group.

The term "amino acid side chain" is that part of an amino acid residue exclusive of the backbone, as defined by K. D. Kopple, "Peptides and Amino Acids", W. A. Benjamin Inc., New York and Amsterdam, 1966, pages 2 and 33; examples of such side chains of the common amino acids are —$CH_2CH_2SCH_3$ (the side chain of methionine), —$CH_2$(CH$_3$)—$CH_2CH_3$ (the side chain of isoleucine), —$CH_2CH$(CH$_3$)$_2$ (the side chain of leucine) or H-(the side chain of glycine). These side chains are pendant from the backbone Ca carbon.

The term "peptide," as used herein, refers to a sequence of amino acid residues linked together by peptide bonds or by modified peptide bonds. The term "peptide" is intended to encompass peptide analogs, peptide derivatives, peptidomimetics and peptide variants. The term "peptide" is understood to include peptides of any length. Peptide sequences set out herein are written according to the generally accepted convention whereby the N-terminal amino acid is on the left, and the C-terminal amino acid is on the right (e.g., $H_2N$-$AA_1$-$AA_2$-$AA_3$-$AA_4$-$AA_5$-$AA_6$-$CO_2H$).

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, the racemic mixtures thereof, and other mixtures thereof, as falling within the scope of the disclosure. Additional asymmetric carbon atoms may be present in a substituent such as an alkyl group. All such isomers, as well as mixtures thereof, are intended to be included in this disclosure. Any representation of a particular isomer is merely exemplary (e.g., the exemplification of a trans-isomer, also encompasses a cis-isomer).

If, for instance, a particular enantiomer of a compound of the present disclosure is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present disclosure. Furthermore, so-called metabolite which is produced by degradation of the present compound in vivo is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this disclosure include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The synthetic processes of the disclosure can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, 5$^{th}$ edition, John Wiley & Sons: New York, 2001; and Greene, T. W., Wuts, P. G. M., *Protective Groups in Organic Synthesis*, 3$^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present disclosure.

In particular, the compounds of the present disclosure, and their synthesis, are further described in PCT Publication Nos. WO 2011/150022 and WO 2011/150088 and U.S. Pat. Nos. 9,173,956, 9,320,805, and 9,433,600. Each of these publications is incorporated by reference in their entireties for all purposes.

The present disclosure also provides pharmaceutical compositions comprising a compound of the present disclosure, or pharmaceutically acceptable salts, solvates, diastereomers, and polymorphs thereof, and a pharmaceutically acceptable carrier or excipient.

A "pharmaceutical composition" is a formulation containing the compounds of the present disclosure in a form suitable for administration to a subject. In one aspect, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one aspect, the active compound is mixed under sterile conditions with a pharmaceutically acceptable carrier, and with any preservatives, buffers or propellants that are required.

As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this disclosure. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions. In certain aspects, the pharmaceutical composition comprises DMSO.

The term "pharmaceutically acceptable salts" refers to the relatively non-toxic, inorganic and organic acid addition salts of the compound(s). These salts can be prepared in situ during the final isolation and purification of the compound (s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (See, for example, Berge et al. (1977) "Pharmaceutical Salts", *J. Pharm. Sci.* 66:1-19)

The phrase "pharmaceutically acceptable" is employed herein to refer to those ligands, materials, compositions, and/or dosage forms which are, within the scope of sound medical judgment, suitable for use in contact with the tissues of human beings and animals, substantially non-pyrogenic, without excessive toxicity, irritation, allergic response, or other problem or complication, commensurate with a reasonable benefit/risk ratio.

As used herein, the term "metabolite" means a product of metabolism of the compound of present disclosure, or pharmaceutically acceptable salts, solvates, diastereomers, and polymorphs thereof, that exhibits a similar activity in vivo to the compound of present disclosure, or pharmaceutically acceptable salts, solvates, diastereomers, and polymorphs thereof.

As used herein, the term "prodrug" means the compound of present disclosure, or pharmaceutically acceptable salts, solvates, diastereomers, and polymorphs thereof covalently linked to one or more pro-moieties, such as an amino acid moiety or other water solubilizing moiety. The compound of present disclosure, or pharmaceutically acceptable salts, solvates, diastereomers, and polymorphs thereof may be released from the pro-moiety via hydrolytic, oxidative, and/or enzymatic release mechanisms. In an aspect, a prodrug composition of the present disclosure exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate within R4, may be selected based on solubility, stability, bioavailability, and/or in vivo delivery or uptake. Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the disclosure, and the like, See Bundegaard, H., *Design of Prodrugs*, p 1-92, Elesevier, New York-Oxford (1985).

The compounds of the present disclosure, or pharmaceutically acceptable salts, esters, solvates, diastereomers, polymorphs, or pro-drugs thereof (or pharmaceutical compositions thereof) can be administered by any means known in the art. For example, the compounds or compositions of the present disclosure are administered orally, nasally, transdermally, topically, pulmonary, inhalationally, buccally, sublingually, intraperintoneally, subcutaneously, intramuscularly, intravenously, rectally, intrapleurally, intrathecally and parenterally. Administration can be systemic, e.g., intravenous administration, or localized. In certain aspects, the route of administration may be intravenous, intramuscular, subcutaneous, intradermal, intraperitoneal, intrathecal, intrapleural, intrauterine, rectal, vaginal, topical, and the like. In certain aspects, the compound is administered subcutaneously.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the disclosure can be administered to a subject in many of the well-known methods currently used for chemotherapeutic treatment. For example, for treatment of cancers, a compound of the disclosure may be injected directly into tumors, injected into the blood stream or body cavities, injected subcutaneously, or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

In one aspect, the compounds of the present disclosure, or pharmaceutically acceptable salts, esters, solvates, diastereomers, polymorphs, or pro-drugs thereof, are administered in a suitable dosage form or formulation prepared by combining a therapeutically effective amount (e.g., an efficacious level sufficient to achieve the desired therapeutic effect) of the compounds of the present disclosure, or pharmaceutically acceptable salts, esters, solvates, diastereomers, polymorphs, or pro-drugs thereof (as an active ingredient) with standard pharmaceutical carriers or diluents according to conventional procedures (i.e., by producing a pharmaceutical composition of the disclosure). These procedures may involve mixing, granulating, and compressing or dissolving the ingredients as appropriate to attain the desired preparation.

Parenteral dosage forms may be prepared by any means known in the art. For example, sterile injectable aqueous or oleaginous suspensions may be formulated according to the known art using suitable dispersing or wetting agents and suspending agents.

Oral dosage forms, such as capsules, tablets, pills, powders, and granules, may be prepared using any suitable process known to the art. For example, the compounds of the present disclosure may be mixed with enteric materials and compressed into tablets. Alternatively, formulations of the disclosure are incorporated into chewable tablets, crushable tablets, tablets that dissolve rapidly within the mouth, or mouth wash.

For pulmonary (e.g., intrabronchial) administration, the compounds of the present disclosure can be formulated with conventional excipients to prepare an inhalable composition in the form of a fine powder or atomizable liquid. For ocular administration, the compounds of the present disclosure can be formulated with conventional excipients, for example, in the form of eye drops or an ocular implant. Among excipients useful in eye drops are viscosifying or gelling agents, to minimize loss by lacrimation through improved retention in the eye.

Liquid dosage forms for oral or other administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Commercially available nebulizers for liquid formulations, including jet nebulizers and ultrasonic nebulizers are useful for administration. Liquid formulations can be directly nebulized and lyophilized powder can be nebulized after reconstitution. Alternatively, the compounds of the present disclosure can be aerosolized using a fluorocarbon formulation and a metered dose inhaler, or inhaled as a lyophilized and milled powder.

Dosage forms for topical or transdermal administration of an inventive pharmaceutical composition may include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration are achieved with aqueous drops, a mist, an emulsion, or a cream.

Transdermal patches may have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compositions for rectal or vaginal administration may be suppositories which can be prepared by mixing the compounds of the present disclosure with suitable non-irritating excipients or carriers such as cocoa butter, polyethylene glycol or a suppository wax which are solid at ambient temperature but liquid at body temperature and therefore melt in the rectum or vaginal cavity and release the active agent(s). Alternatively, contemplated formulations can be administered by release from a lumen of an endoscope after the endoscope has been inserted into a rectum of a subject.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

EXAMPLES

Examples are provided below to further illustrate different features of the present disclosure. The examples also illustrate useful methodology for practicing the disclosure. These examples do not limit the claimed disclosure.

Example 1—In Vivo Testing B16F10 Melanoma/DIO Mice—Body Weight, Tumor Growth, Adipose Tissue Mass and White Blood Cell Count An in vivo study was undertaken to establish a syngeneic mouse model to demonstrate that diet-induced obesity accelerates tumor growth. The study was to demonstrate the efficacy of compounds of the disclosure in this obesity-fueled, metabolically-driven, tumor model. In particular to demonstrate efficacy against tumors in obese animals and demonstrate an effect in corresponding lean animals. The study would compare weight changes in both obese and lean animal groups; measure biologic changes in hematology parameters; and compare conjugate molecules of the present disclosure against related small molecules for efficacy.

C57BL/6 male mice were ad libitum fed TD.06414 a high fat diet (HFD) composed of 60% Kcal from fat (DIO) for 12-14 weeks, until average body weight of the obese mice was >40 g. Age-matched C57B1/6 male mice were maintained on a normal rodent diet (10% fat, low-fat diet, LFD) for 12-14 weeks. The study was initiated by injecting $2 \times 10^5$ B16F10 melanoma cells into the flank of both lean and obese animals.

The mice were treated with 5% mannitol/water (vehicle control), Compound 1 or Compound 4 once tumors had reached >100 mm$^3$. Treatment was via subcutaneous, intrascapular injection at 5 ml/kg every four days (compound 1) or every 2 days (compound 4) over a 17 day period at the doses and on the schedule shown in Table 2.

TABLE 2

| | Treatment | Dose (mg/kg) | N/group | Dose Route/frequency |
|---|---|---|---|---|
| DIO (HFD) | Vehicle Control | Mannitol/water | 10 | SC/Q4D days 1, 5, 9, 13, 17 |
| | Compound 1 | 8 | 10 | SC/Q4D days 1, 5, 9, 13, 17 |
| | Compound 1 | 24 | 10 | SC/Q4D days 1, 5, 9, 13, 17 |
| | Compound 4 | 2 | 10 | SC/Q2D days 1, 3, 5, 7, 9, 11, 13, 15, 17 |
| Lean (LFD) | Vehicle Control | Mannitol/water | 10 | SC/Q4D days 1, 5, 9, 13, 17 |
| | Compound 1 | 8 | 10 | SC/Q4D days 1, 5, 9, 13, 17 |
| | Compound 1 | 24 | 10 | SC/Q4D days 1, 5, 9, 13, 17 |
| | Compound 4 | 2 | 10 | SC/Q2D days 1, 3, 5, 7, 9, 11, 13, 15, 17 |

Compound 4 is CKD-732 (also known as beloranib and ZGN-433). Compound 4 was previously shown to be efficacious in eliciting weight loss in DIO mice when dosed at 1 mg/kg (Hughes T E., et al "*ZGN*-201 (*ZGN*), *a methionine aminopeptidase 2 (MetAP2) inhibitor, durably eliminates*

*excess body fat in obese mice through regulation of fat metabolism and food intake.*" European Association for the Study of Diabetes; Sep. 20-24, 2010; Stockholm, Sweden. Presentation 244.). Compound 4 as referred to herein is the hemitartrate salt of the following structure:

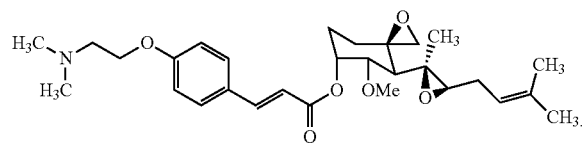

Figure 1B:
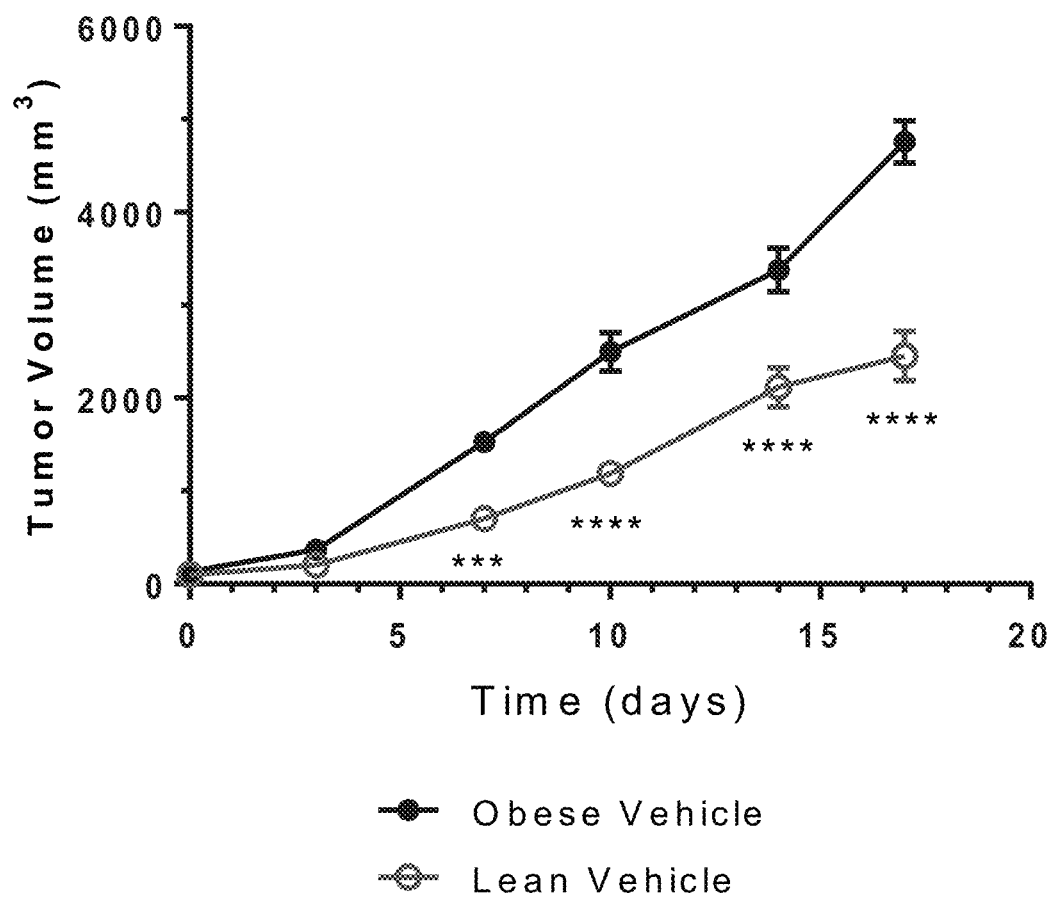
FIG. 1B is a graph showing tumor growth in mice on a high-fat diet compared to a low-fat diet.

FIG. 1A shows baseline body weight in obese and lean mice bearing B16F10 melanoma. FIG. 1B shows B16F10 melanoma tumor growth in obese and lean mice over time. The data were analyzed using two-way ANOVA with multiple comparisons, *$p<0.005$ and **$p<0.0001$. The results of FIG. 1A demonstrate that the mean body weight of the obese cohorts was significantly different from mean body weight of lean cohorts, prior to study initiation, and that there were no significant differences in body weight within the obese or lean cohorts. The results of FIG. 1B demonstrate that tumors grew significantly faster and achieved a significantly larger size in animals made obese by consuming a high-fat diet (DIO mice) compared to age-matched animals that consumed a low-fat diet (lean mice).

Figure 2A:
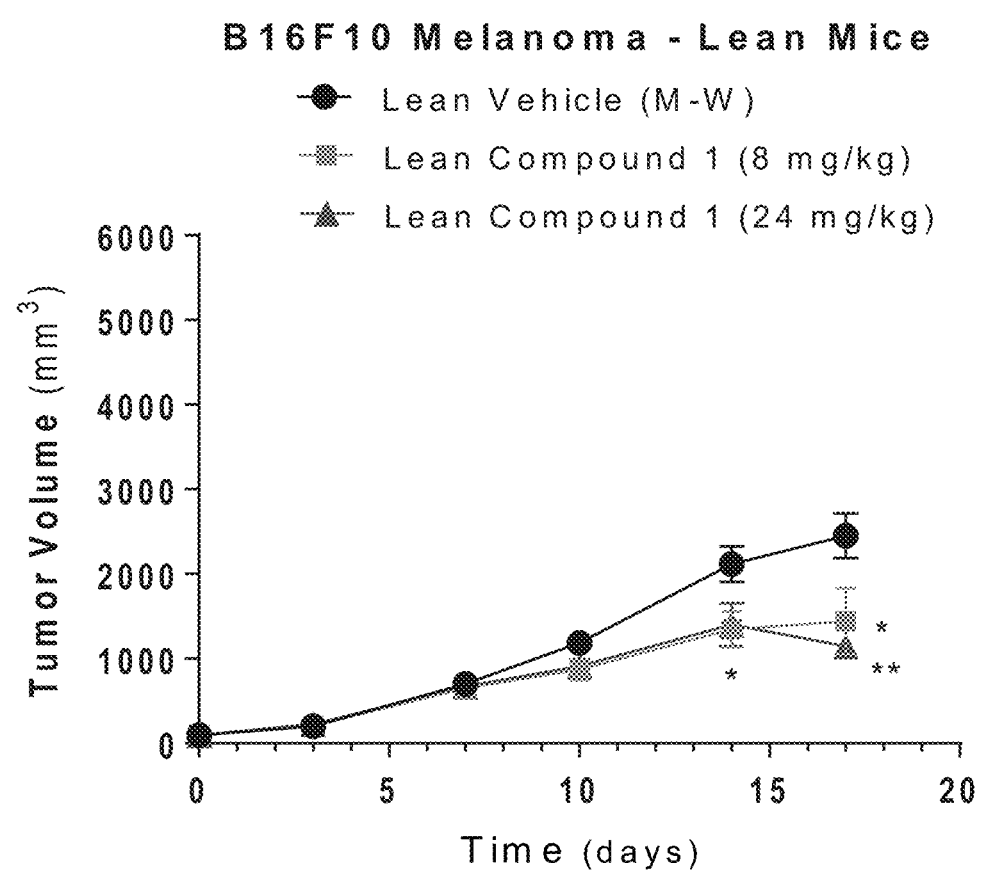
FIG. 2A is a graph showing tumor inhibition in lean mice following administration of compounds of the present disclosure.
Figure 2B:
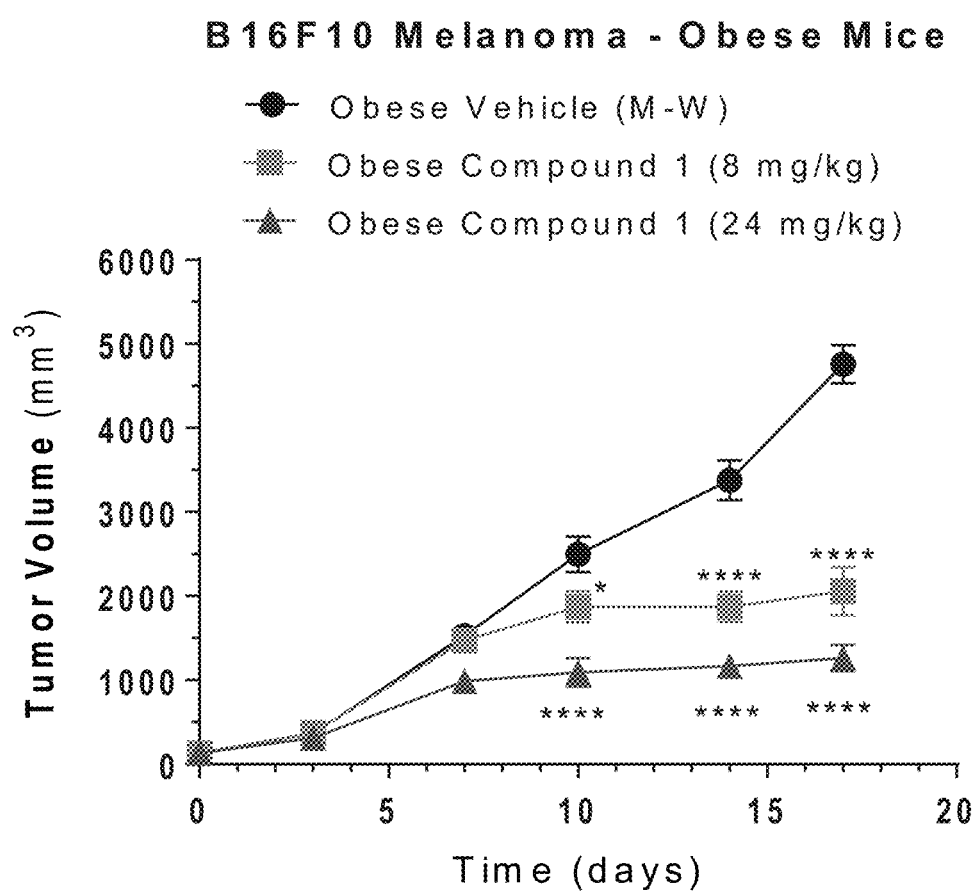
FIG. 2B is a graph showing tumor inhibition in obese mice following administration of compounds of the present disclosure.
Figure 2C:
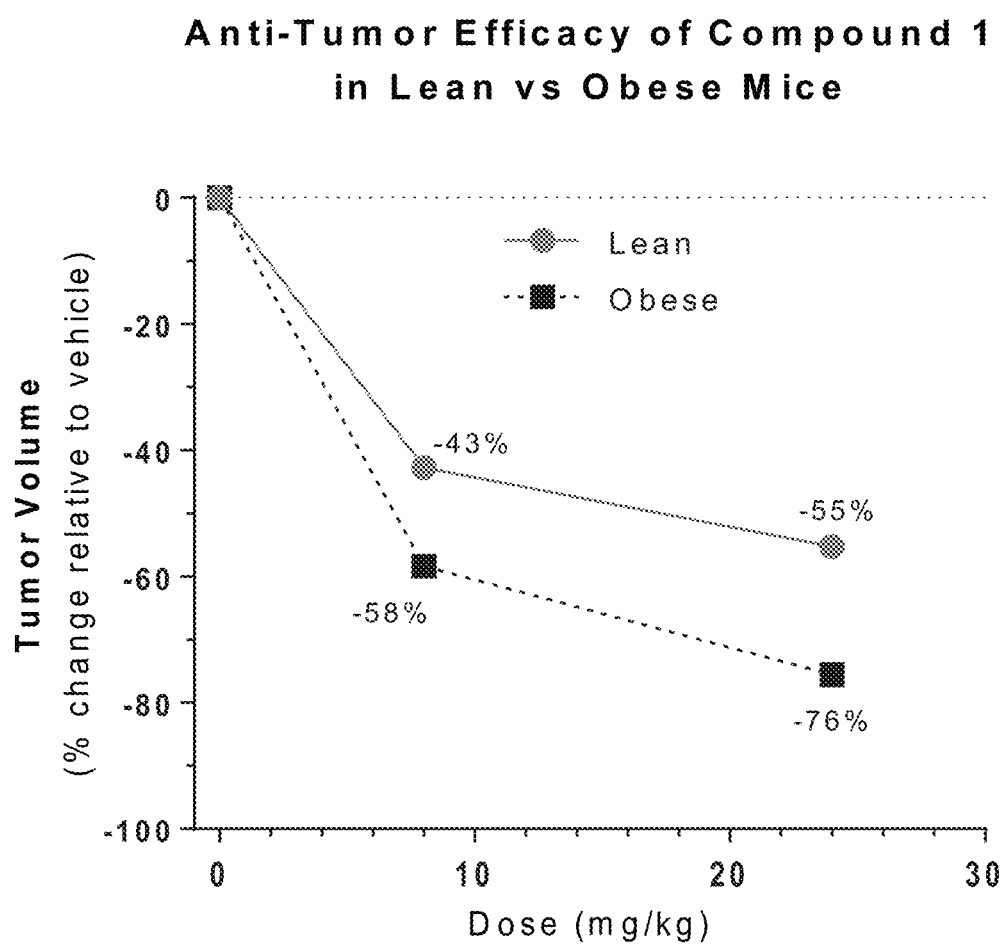
FIG. 2C is a graph showing the percentage of tumor inhibition relative to vehicle in lean mice versus obese mice following administration of compounds of the present disclosure.

FIG. 2A shows B16F10 melanoma tumor growth in lean mice following treatment with vehicle or 8 mg/kg or 24 mg/kg of compound 1 of the present disclosure. FIG. 2B shows B16F10 melanoma tumor growth in obese mice following treatment with vehicle or 8 mg/kg or 24 mg/kg of compound 1 of the present disclosure. The data were analyzed using two-way ANOVA with multiple comparisons, *$p<0.05$, $p<0.01$, *$p<0.005$ and ****$p<0.0001$. The results of FIGS. 2A and 2B demonstrate that compound 1 inhibited tumor growth in both lean and obese animals in a dose-dependent manner. However, in FIG. 2C the magnitude of inhibition was greater in obese animals (58% and 76% reduction of tumor volume in obese mice after 8 and 24 mg/kg of Compound 1, respectively) compared to lean mice (43% and 55% reduction of tumor volume after 8 and 24 mg/kg of Compound 1, respectively).

Figure 3A:
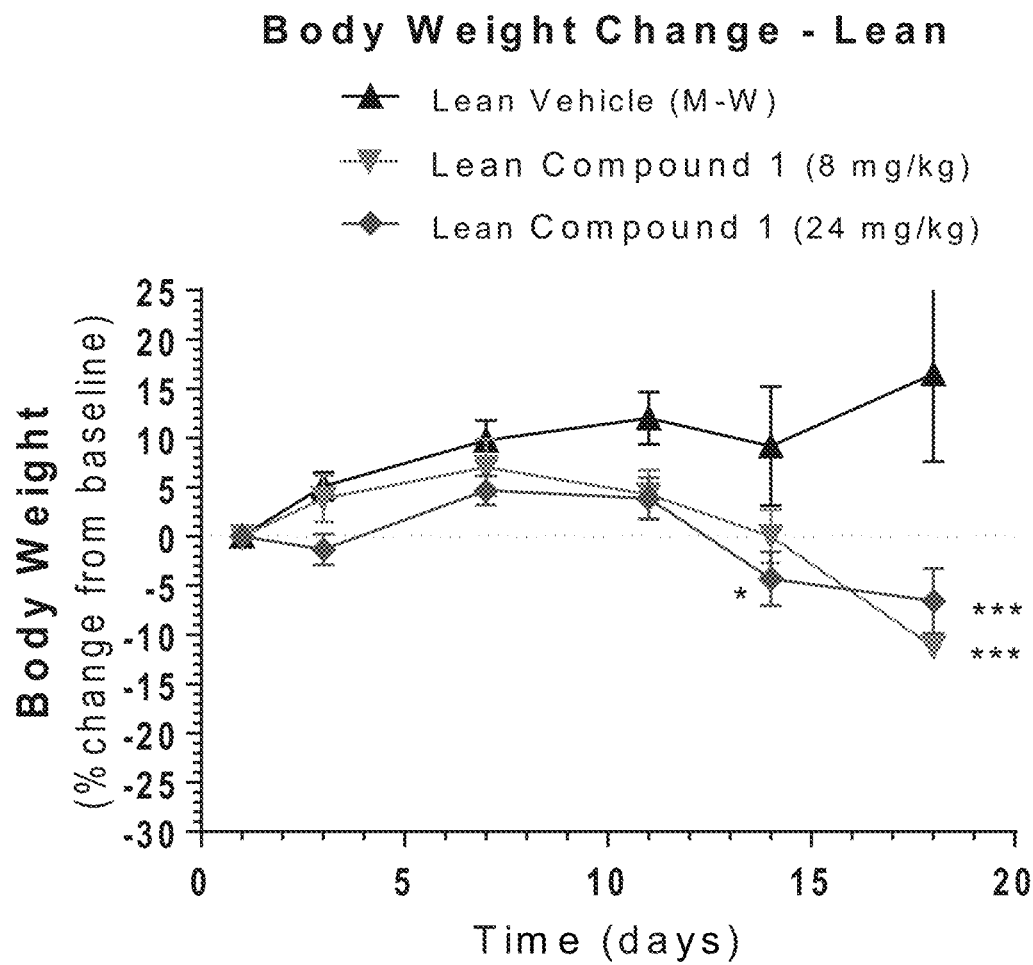
FIG. 3A is a graph showing reduction in body weight of lean mice following administration of compounds of the present disclosure.
Figure 3B:
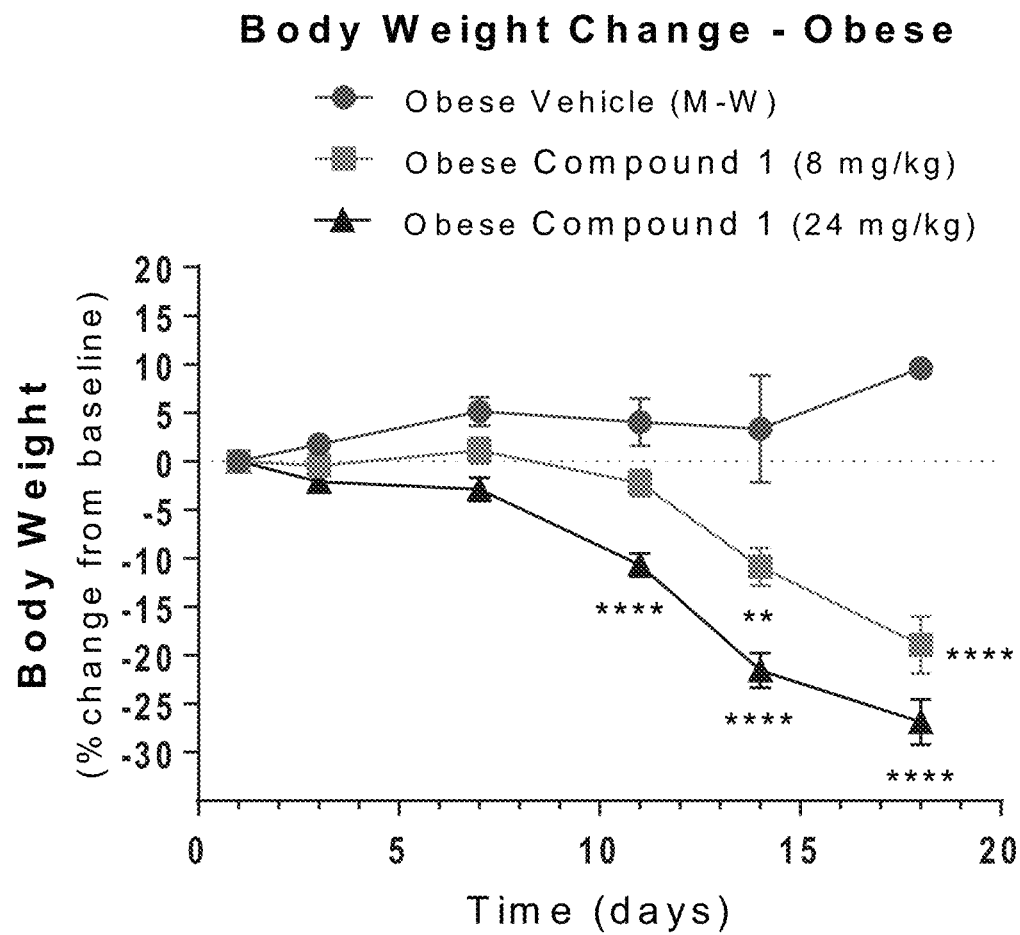
FIG. 3B is a graph showing reduction in body weight of obese mice following administration of compounds of the present disclosure.

FIG. 3A shows body weight in lean mice bearing B16F10 melanomas following treatment with vehicle or 8 mg/kg or 24 mg/kg of compound 1 of the present disclosure. FIG. 3B shows body weight in obese mice bearing B16F10 melanomas mice following treatment with vehicle or 8 mg/kg or 24 mg/kg of compound 1 of the present disclosure. The data were analyzed using two-way ANOVA with multiple comparisons, *$p<0.05$, $p<0.01$, *$p<0.005$ and ****$p<0.0001$. The results of FIGS. 3A and 3B demonstrate that compound 1 reduced body weight in both lean and obese mice. However, the magnitude of weight loss was greater in obese animals (−19% and −27% change in body weight (relative to baseline) in obese mice in response to 8 and 24 mg/kg of Compound 1, respectively) compared to lean mice (−11% and −7% change in body weight (relative to baseline) in response to 8 and 24 mg/kg of Compound 1, respectively).

Figure 4:
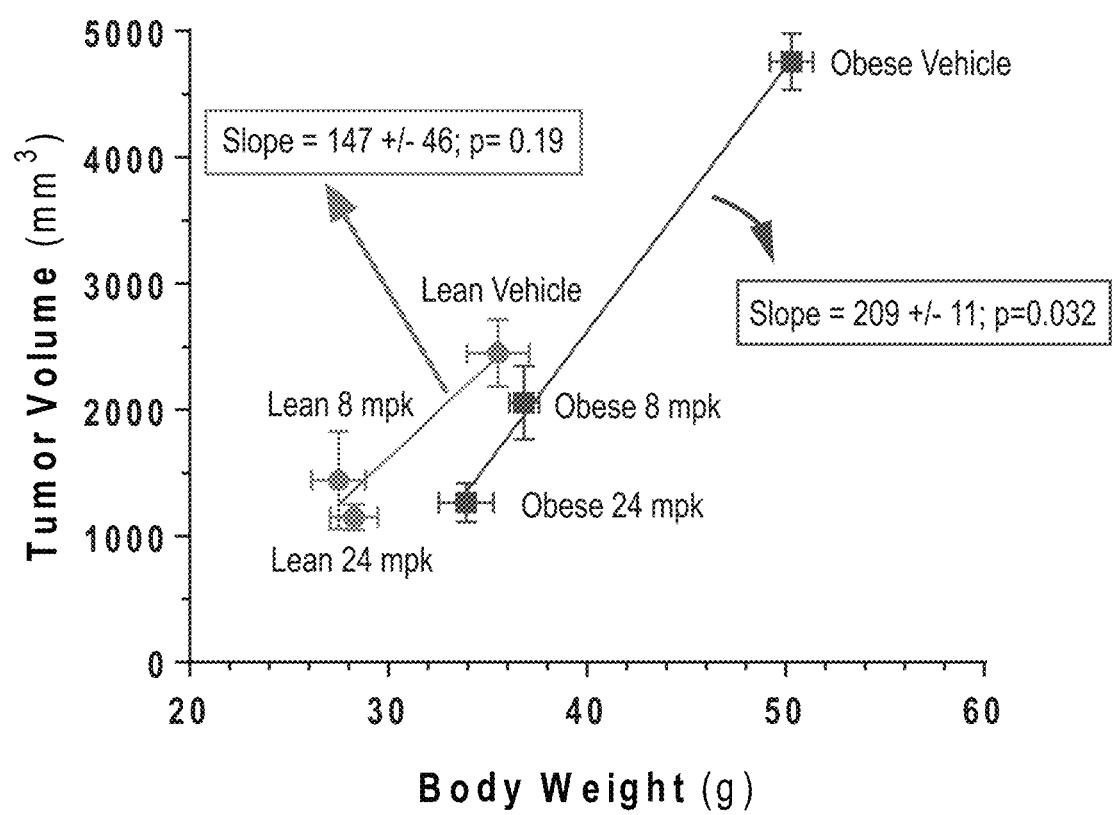
FIG. 4 is a graph showing the relationship between body weight and tumor size in lean mice and obese mice following administration of compounds of the present disclosure.

FIG. 4 shows the relationship between body weight and tumor size in vehicle- and Compound 1-treated DIO and lean mice. The results of FIG. 4 demonstrate that the effect of compound 1 to decrease tumor size relates to its ability to reduce body weight. This effect was more robust (based on magnitude of change in both parameters, as well as the greater slope of the regression line for obese mice) and was more tightly correlated in obese compared to lean mice (based on p-value from linear regression analysis).

Figure 5:
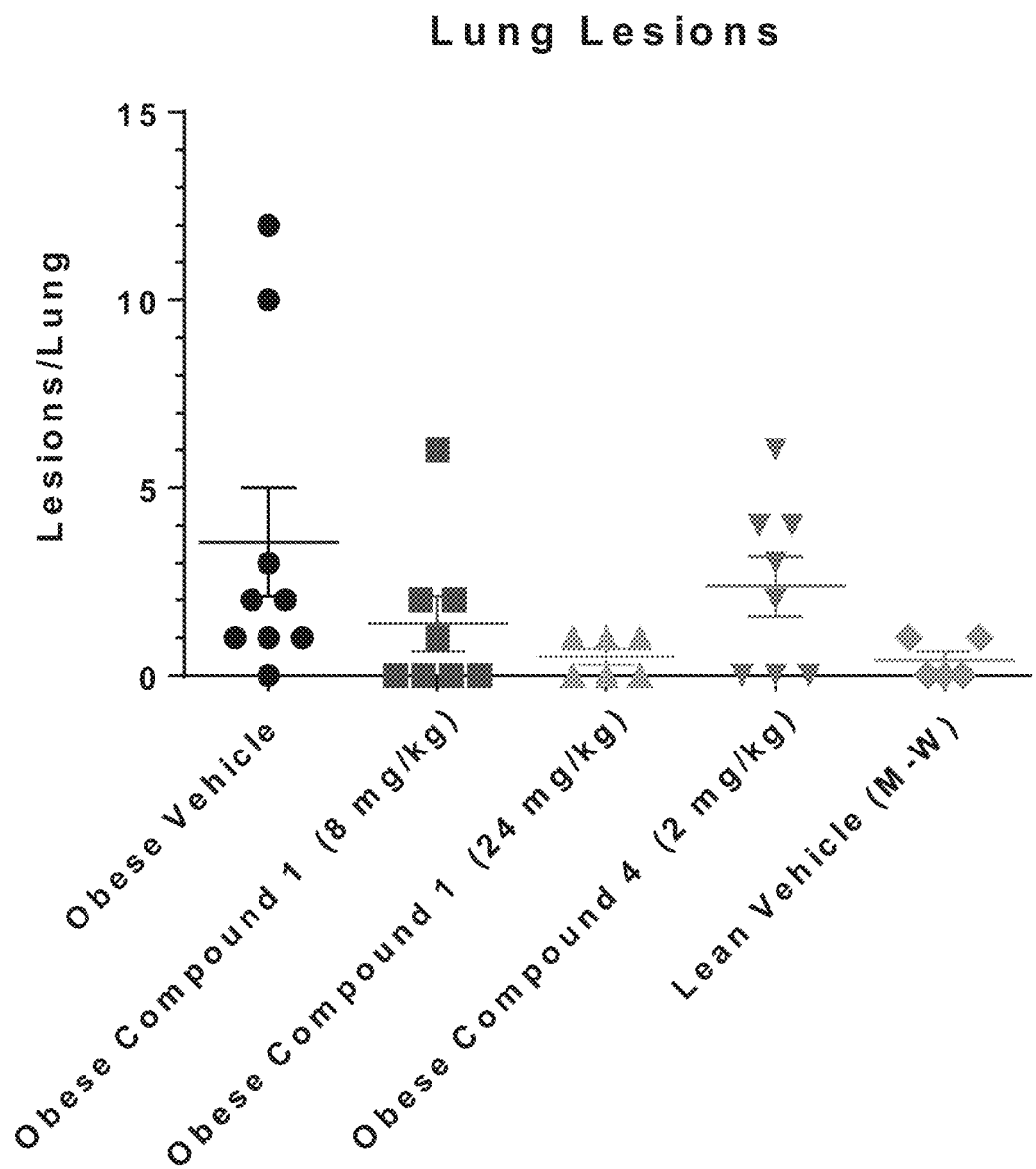
FIG. 5 is a graph showing a reduction in the number of lung metastases in lean mice and obese mice following administration of compounds of the present disclosure.

FIG. 5 shows the mean (+/−SEM) number of metastatic lung lesions in obese and lean B16F10 melanoma/DIO mice following treatment with vehicle or 8 mg/kg or 24 mg/kg of compound 1 of the present disclosure or 2 mg/kg of another MetAP2 inhibitor (Compound 4). The results of FIG. 5 demonstrate that obese mice have numerically more metastases to the lungs compared to lean animals (3.6+/−1.4 lesions/mouse versus 0.4+/−0.24 lesions/mouse in obese compared to lean mice, respectively; not statistically different). The results also show that compound 1 reduced the number of lung metastases in obese mice in a dose-dependent manner (1.38+/−0.73 lesions/mouse and 0.5+/−0.22 lesions/mouse after 8 and 24 mg/kg respectively), although the differences were not statistically significant. The other MetAP2 inhibitor (Compound 4) had a small effect on the number of lung metastases in obese mice (2.4+/−0.8 lesions/mouse). No differences were seen in lung metastases between the groups of lean mice (data not shown).

Table 3 shows adipose tissue mass in obese mice bearing B16F10 melanoma following treatment with vehicle or 8 mg/kg or 24 mg/kg of compound 1 of the present disclosure or another MetAP2 inhibitor (Compound 4) The data were analyzed using one-way ANOVA with multiple comparisons, *$p<0.05$, $p<0.01$, *$p<0.005$ and ****$p<0.0001$. The results of Table 3 demonstrate that obese, tumor-bearing mice have significantly greater adipose tissue mass compared to lean, tumor-bearing animals. They also show that compound 1 reduced body fat in obese animals (the results were statistically significant only in epididymal adipose tissue). Note that adipose tissue mass in the control, vehicle-treated animals is 2-5 times lower than in non-tumor-bearing DIO mice (not shown)

Table 3 also shows adipose tissue mass in lean mice bearing B16F10 melanoma following treatment with vehicle or 8 mg/kg or 24 mg/kg of compound 1 of the present disclosure or another MetAP2 inhibitor (Compound 4). The data were analyzed using one-way ANOVA with multiple comparisons, *$p<0.05$, $p<0.01$, *$p<0.005$ and ****$p<0.0001$. The results of Table 3 demonstrate that none of the adipose tissue depots in lean mice were affected by treatment with compound 1.

TABLE 3

| Treatment Group | | Tissue Weight (g) | SEM | P Value (One-way ANOVA with multiple comparisons) |
|---|---|---|---|---|
| Obese Mice | | | | |
| Epididymal Fat | Vehicle | 0.779 | 0.107 | |
| | Compound 1 (8 mg/kg) | 0.464 | 0.071 | <0.05 |
| | Compound 1 (24 mg/kg) | 0.335 | 0.053 | <0.01 |
| | Compound 4 (2 mg/kg) | 0.424 | 0.034 | <0.01 |

TABLE 3-continued

|  | Treatment Group | Tissue Weight (g) | SEM | P Value (One-way ANOVA with multiple comparisons) |
|---|---|---|---|---|
| Retroperitoneal Fat | Vehicle | 0.242 | 0.045 |  |
|  | Compound 1 (8 mg/kg) | 0.161 | 0.022 | NS |
|  | Compound 1 (24 mg/kg) | 0.103 | 0.018 | NS |
|  | Compound 4 (2 mg/kg) | 0.142 | 0.019 | NS |
| Inguinal Fat | Vehicle | 0.713 | 0.118 |  |
|  | Compound 1 (8 mg/kg) | 0.596 | 0.061 | NS |
|  | Compound 1 (24 mg/kg) | 0.417 | 0.057 | NS |
|  | Compound 4 (2 mg/kg) | 0.416 | 0.056 | <0.05 |
| Lean Mice |  |  |  |  |
| Epididymal Fat | Vehicle | 0.134 | 0.041 |  |
|  | Compound 1 (8 mg/kg) | 0.133 | 0.024 | NS |
|  | Compound 1 (24 mg/kg) | 0.110 | 0.024 | NS |
|  | Compound 4 (2 mg/kg) | 0.134 | 0.041 | <0.01 |
| Retroperitoneal Fat | Vehicle | 0.056 | 0.025 |  |
|  | Compound 1 (8 mg/kg) | 0.039 | 0.012 | NS |
|  | Compound 1 (24 mg/kg) | 0.064 | 0.017 | NS |
|  | Compound 4 (2 mg/kg) | 0.029 | 0.017 | NS |
| Inguinal Fat | Vehicle | 0.128 | 0.029 |  |
|  | Compound 1 (8 mg/kg) | 0.129 | 0.025 | NS |
|  | Compound 1 (24 mg/kg) | 0.212 | 0.063 | NS |
|  | Compound 4 (2 mg/kg) | 0.208 | 0.107 | NS |

Figure 6A:
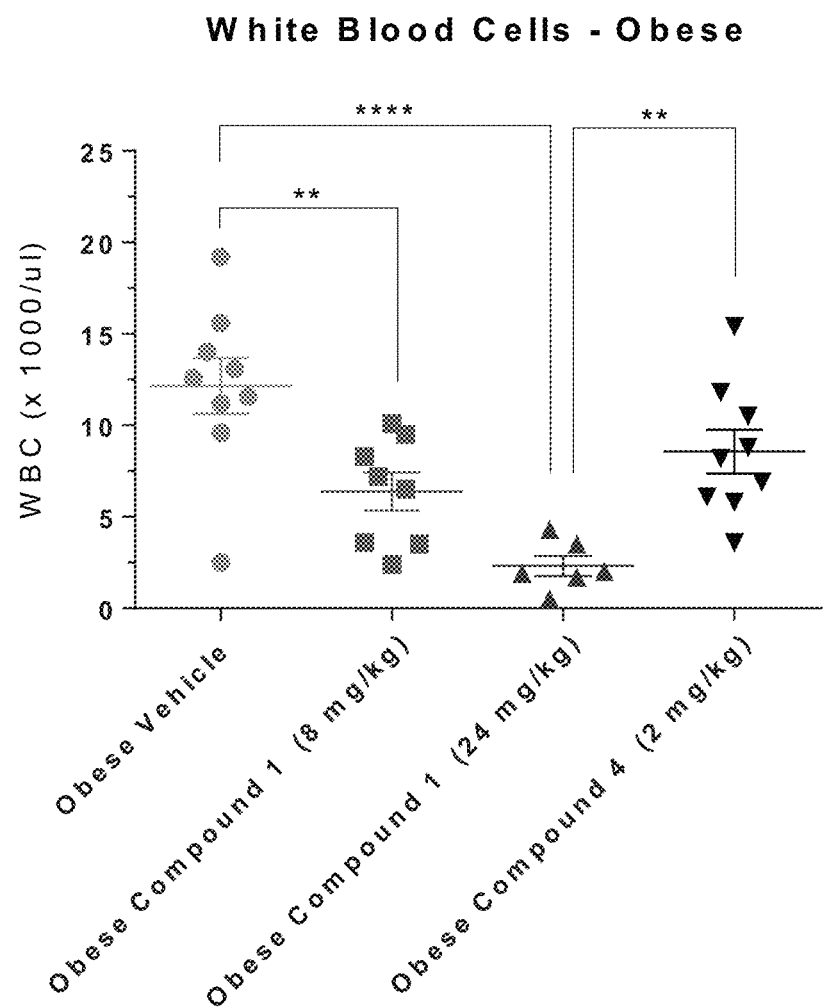
FIG. 6A is a graph showing a reduction in white blood cells in obese tumor-bearing mice following administration of compounds of the present disclosure.
Figure 6B:
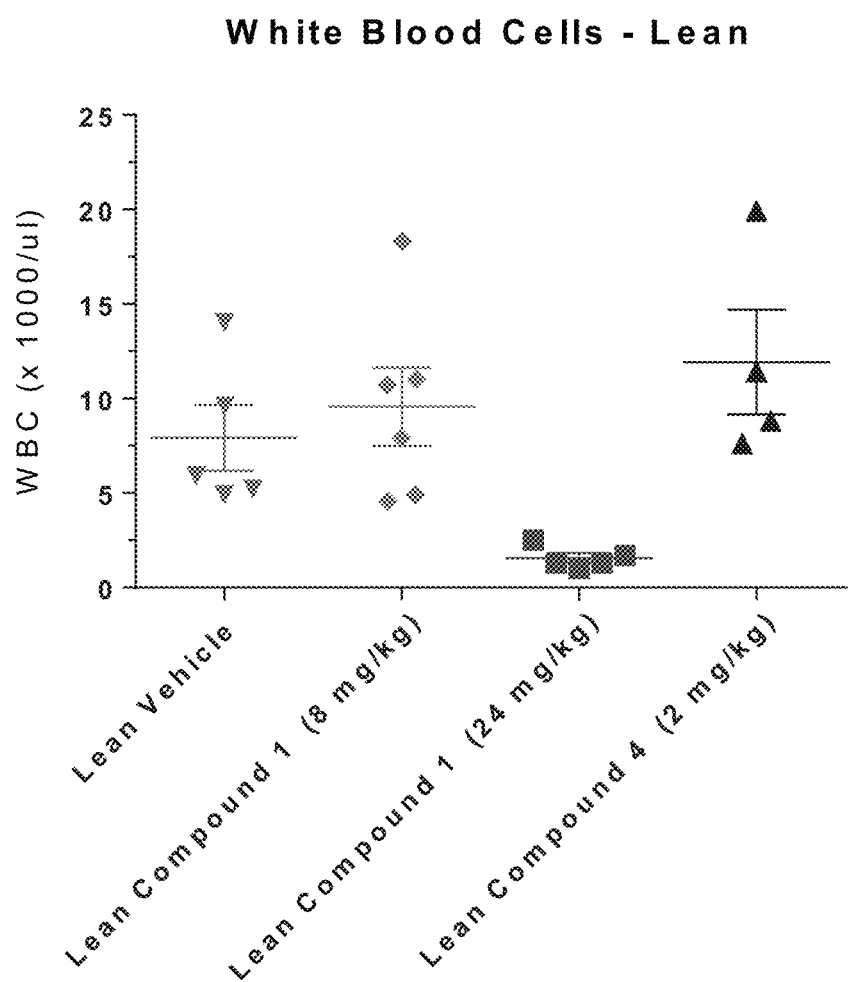
FIG. 6B is a graph showing a change in white blood cells in lean tumor-bearing mice following administration of compounds of the present disclosure.

FIG. 6 shows white blood cell count in obese and lean B16F10 melanoma/DIO mice following treatment with vehicle or 8 mg/kg or 24 mg/kg of compound 1 of the present disclosure or another MetAP2 inhibitor (Compound 4). The data were analyzed using one-way ANOVA with multiple comparisons, $*p<0.05$, $p<0.01$, $*p<0.005$ and $****p<0.0001$. The results of FIG. 6 demonstrate that obese mice exhibit leukocytosis (elevated levels of circulating white blood cells (WBCs)), and that compound 1 reduces WBCs. FIG. 6 also demonstrates that obese mice exhibited greater sensitivity to the effect on WBCs since there was a significant effect in response to 8 mg/kg of compound 1 in obese mice but not in lean mice.

Figure 7:
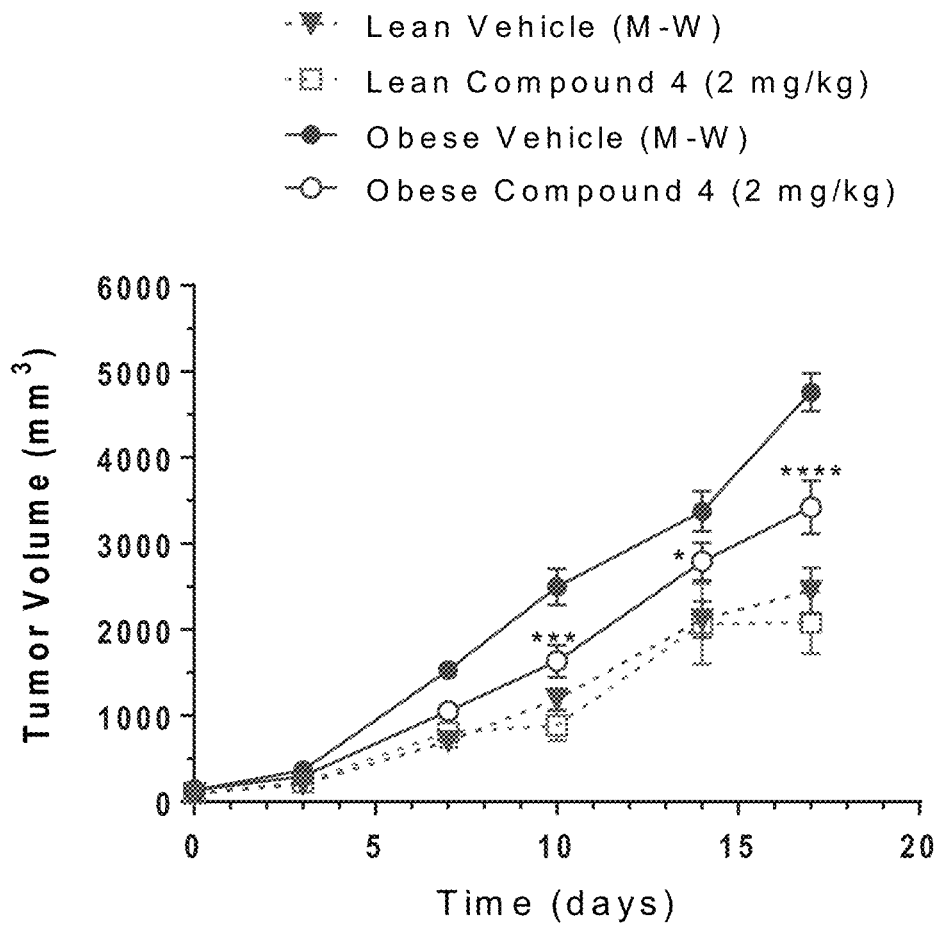
FIG. 7 is a graph showing tumor growth inhibition in lean and obese tumor-bearing mice following administration of another MetAP2 inhibitor.

FIG. 7 shows B16F10 melanoma tumor growth in obese and lean mice following treatment with vehicle or 2 mg/kg of an un-conjugated small molecule MetAP2 inhibitor (compound 4). The results of FIG. 7 demonstrate that compound 4 significantly inhibited the growth of tumors in obese mice (by 28%), although the magnitude of the effect was smaller than what was observed with compound 1 (57% reduction at 8 mg/kg). In contrast to what was observed with compound 1, compound 4 had no effect on tumor growth in lean mice.

To directly compare the amount of active MetAP2 inhibitor delivered by Compound 1 at 8 mg/kg versus Compound 4 at 2 mg/kg one must account for the quantity of active in Compound 1, which is approximately 20% by weight, or 1.6 mg/kg of active delivered in a dose of 8 mg/kg. Additionally the dosing frequency of Compound 1 was every four days; half as often as Compound 4. Therefore the dose of active MetAP2 inhibitor delivered to the mice from Compound 1 was approximately 2.5 times lower than the active MetAP2 inhibitor delivered from the Compound 4 (on a mg/kg basis for each dose). However to compare the total amount of active MetAP2 inhibitor delivered over the period of the study (17 days) the difference in dosing frequency must also be taken into account (Compound 4 was dosed every two days versus every 4 days for Compound 1). In total, nine doses of Compound 4 were given versus 5 doses of Compound 1, which means that 2.25 times more active MetAP2 inhibitor was delivered with Compound 4 versus Compound 1. Despite the greater amount of active MetAP2 delivered with Compound 4, its efficacy was lower than Compound 1, highlighting the superior and unexpected benefits provided by the compounds of the instant disclosure.

Figure 8:
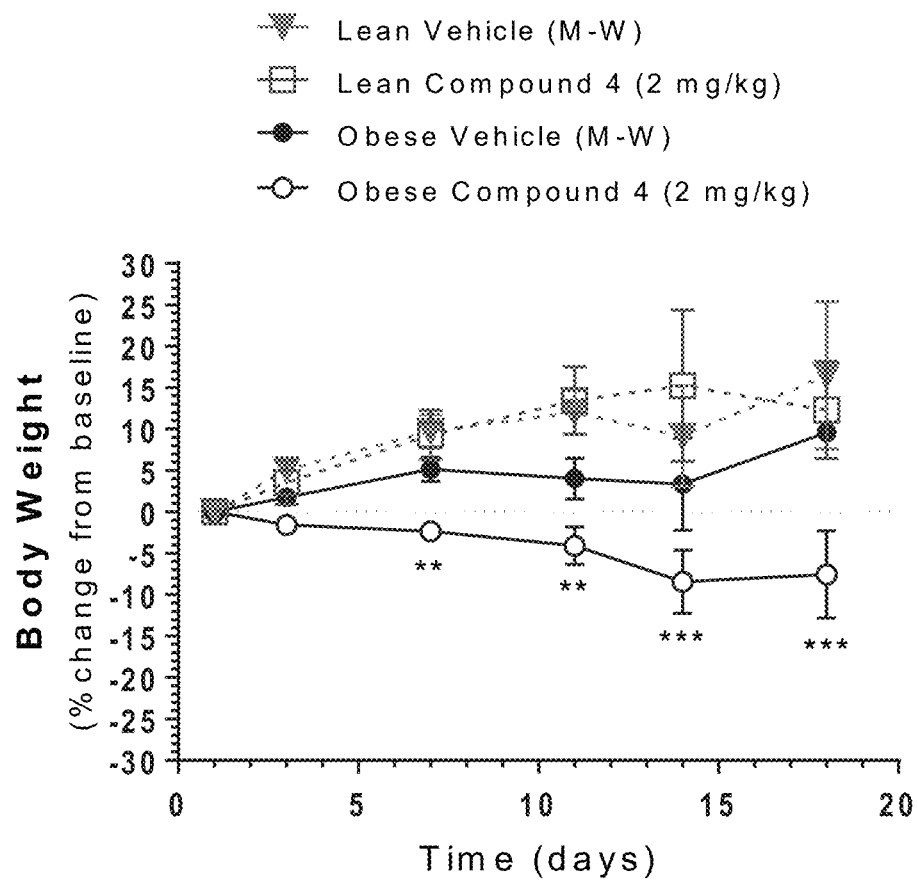
FIG. 8 is a graph showing decreased body weight in lean and obese tumor-bearing mice following administration of compounds of the present disclosure when compared to another MetAP2 inhibitor.

FIG. 8 shows body weight of tumor-bearing obese and lean mice following treatment with vehicle or 2 mg/kg of another small molecule MetAP2 inhibitor (compound 4). The results of FIG. 8 demonstrate that compound 4 significantly decreased body weight in obese mice (−7.9% after 2 mg/kg), although the magnitude of the effect was smaller than what was observed with Compound 1 (−18.9% after 8 mg/kg) despite the greater amount of compound 4 delivered over the course of the study (as discussed above). In contrast to what was observed with compound 1, compound 4 had no effect on body weight in lean mice.

Example 2—In Vivo Testing DIO Mice—Leptin and Adiponectin

Leptin is an adipocyte-derived hormone that was discovered based upon its ability to inhibit caloric intake by signaling through receptors located on neurons within the hypothalamus of the central nervous system (CNS). Genetic deletion of leptin in mice and humans causes severe obesity, which is reversed following exogenous delivery of recombinant leptin. The circulating levels of leptin are positively correlated with the mass of adipose tissue in the host, and elevated levels of leptin observed in obese animals and humans. Unlike normal weight animals and humans, obese animals and humans do not sense their endogenously elevated levels of leptin and are resistant to its anorectic, anti-obesity effects. Given the prolonged and persistent time course of obesity development, peripheral tissues and organs are exposed to elevated levels of leptin over many years. Since leptin is now recognized to regulate a number of biological processes outside of the CNS (e.g., immune function, angiogenesis, vascular endothelial homeostasis, stem cell renewal) adverse consequences of exposure to abnormally high levels of leptin are now being recognized. In particular leptin has been shown to activate survival pathways in cancer stem cells (e.g., Oct4) and thus is a likely contributor to recurrence of cancer (Feldman et al, PNAS, 2012, 109(3), 829-834). Additionally, preclinical models of tumor development have shown that leptin, derived from human adipose stromal cells can directly increase cancer cell proliferation, as well as contribute to metastatic disease. Importantly the effect of ASC-derived leptin is significantly greater when the ASCs are isolated from obese human donors, as opposed to lean human donors (Strong et al. *Breast Can. Res.*, 2015, 17:112). Therefore leptin has been suggested as a component of the mechanistic link between obesity and cancer (Park et al, *Nat Rev Endocrinol.* 2014, 10(8): 455-465).

Another endpoint of interest in both metabolic disease and now (from both a mechanistic as well as prognostic standpoint) in cancer, is the adipocyte-derived hormone adiponectin. This protein is released from adipocytes into the circulation where it acts on liver and muscle tissue to elicit beneficial responses by enhancing the action of insulin. More recently adiponectin has been shown to directly regulate pathways that control malignant potential (cell proliferation, adhesion, invasion and colony formation), regulate metabolic (AMPK/S6), inflammatory (STAT3/VEGF) and cell cycle (p21/p27/p53/cyclins) in both mouse MCA38 and human HT29, HCT116 and LoVo colon cancer cell lines in a LKB1-dependent manner, suggesting that adiponectin may be protective in colorectal cancer (Moon et al, Gut, 2013, 2(4):561-70). A recent clinical study showed that adiponectin may be protective against the recurrence of cancer since increased levels positively correlated with disease-free survival in breast cancer (Duggan et al, J Clin Oncol, 2011, 29(1):32-9). Given the potential role of the two hormones leptin and adiponectin in metabolic disease and cancer, plasma levels of leptin and adiponectin were measured (using an ELISA) in samples obtained from in vivo studies of obese animals after dosing compound 1 in obese and lean mice bearing syngeneic B16F10 melanomas, or obese mice without tumors.

Male C57BL/6 mice were ad libitum fed TD.06414 a high fat diet (HFD) composed of 60% Kcal from fat (DIO) for 16 weeks, until average body weight was >40 g.

The mice were treated with 5% mannitol in water (vehicle control) and Compound 1. Treatment was via subcutaneous injection at 5 ml/kg every four days (q4d) with compound 1 injected at either 2.0 mg/kg or 6.0 mg/kg.

Figure 9A:
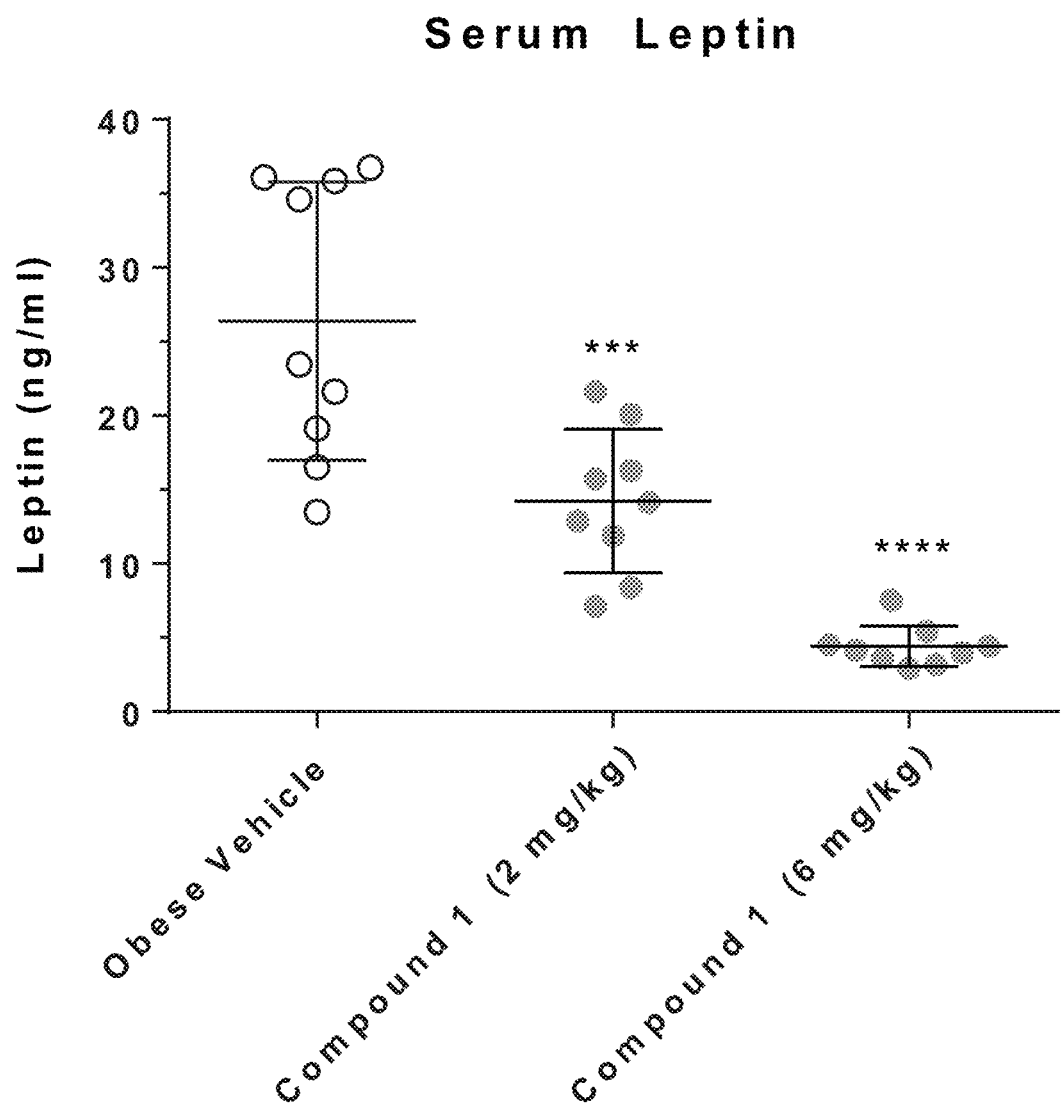
FIG. 9A is a graph showing a reduction in serum leptin in obese non-tumor-bearing mice following administration of compounds of the present disclosure.
Figure 9B:
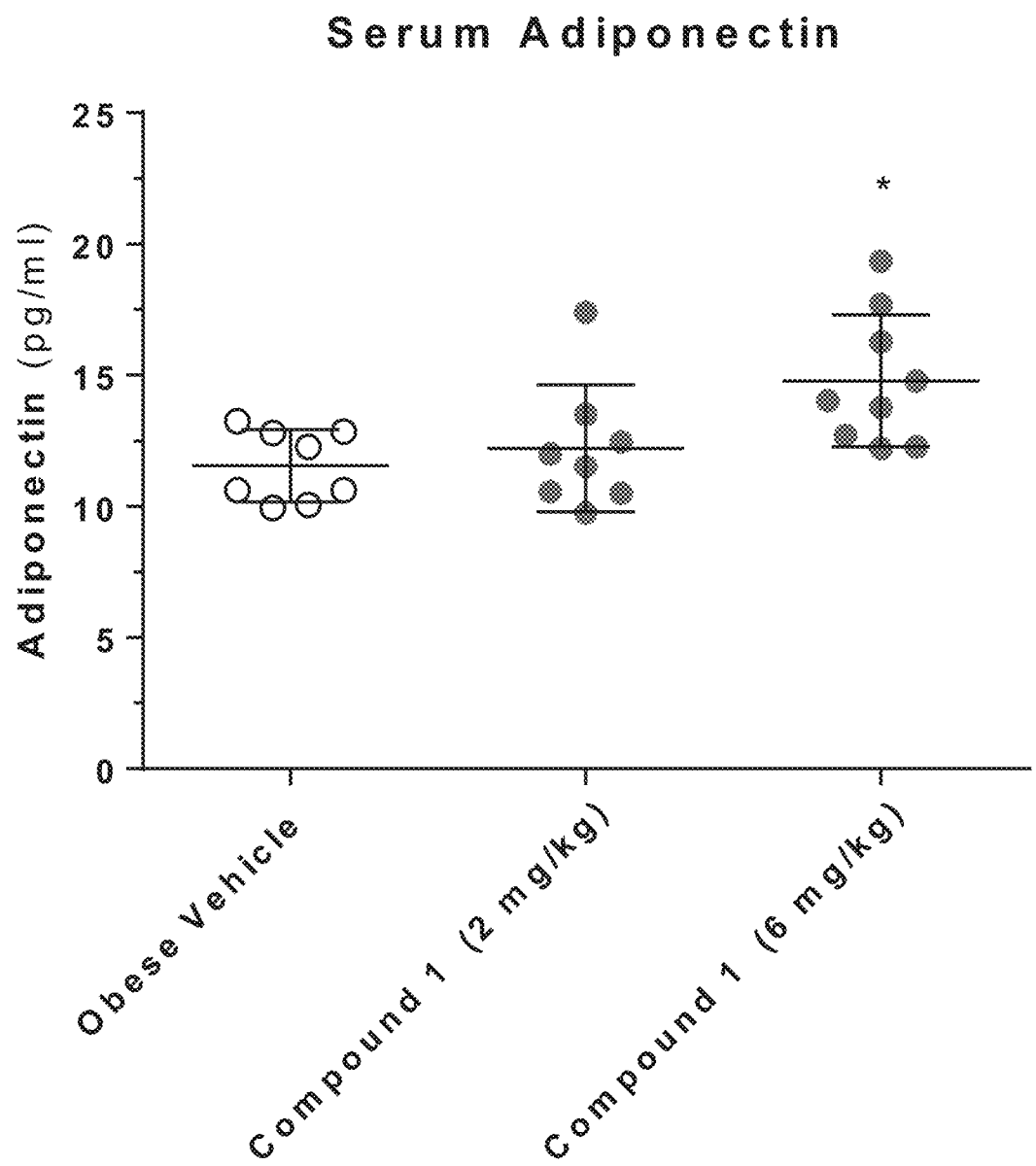
FIG. 9B is a graph showing an increase in serum adiponectin in obese non-tumor-bearing mice following administration of compounds of the present disclosure.

FIG. 9A shows the levels of serum leptin in obese DIO mice following treatment with vehicle or 2 mg/kg or 6 mg/kg of compound 1 of the present disclosure. FIG. 9B shows serum adiponectin in obese DIO mice following treatment with vehicle or 2 mg/kg or 6 mg/kg of compound 1 of the present disclosure. The data were analyzed using one-way ANOVA with multiple comparisons, *p<0.05, p<0.01, *p<0.005 and ****p<0.0001. The results in FIG. 9A and FIG. 9B demonstrate that compound 1 reduces serum leptin levels and increases serum adiponectin at each dose tested. In particular, compound 1 has a significant effect at decreasing serum leptin levels.

Figure 9C:
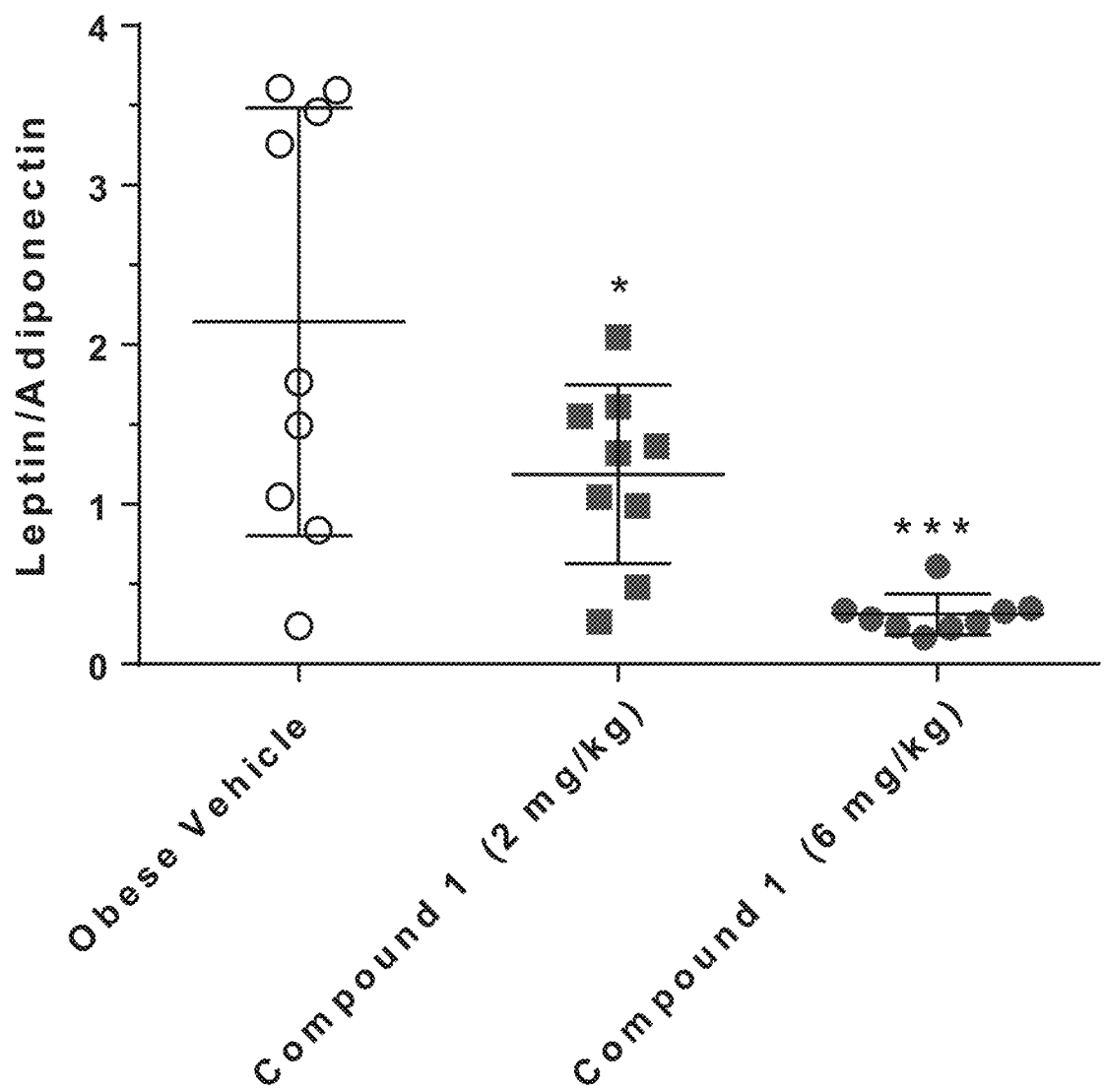
FIG. 9C is a graph showing the ratio of leptin to adiponectin levels in obese non-tumor-bearing mice following administration of compounds of the present disclosure.

FIG. 9C shows the ratio of serum leptin:adiponectin from obese DIO mice following treatment with vehicle or 2 mg/kg or 6 mg/kg of compound 1 of the present disclosure. The data were analyzed using one-way ANOVA with multiple comparisons, *p<0.05, p<0.01, *p<0.005 and ****p<0.0001. The results in FIG. 9C show a reduction in the leptin:adiponectin ratio at each dose tested. In particular, compound 1 has a significant effect at decreasing leptin:adiponectin serum levels at the 6 mg/kg dose.

Figure 9D:
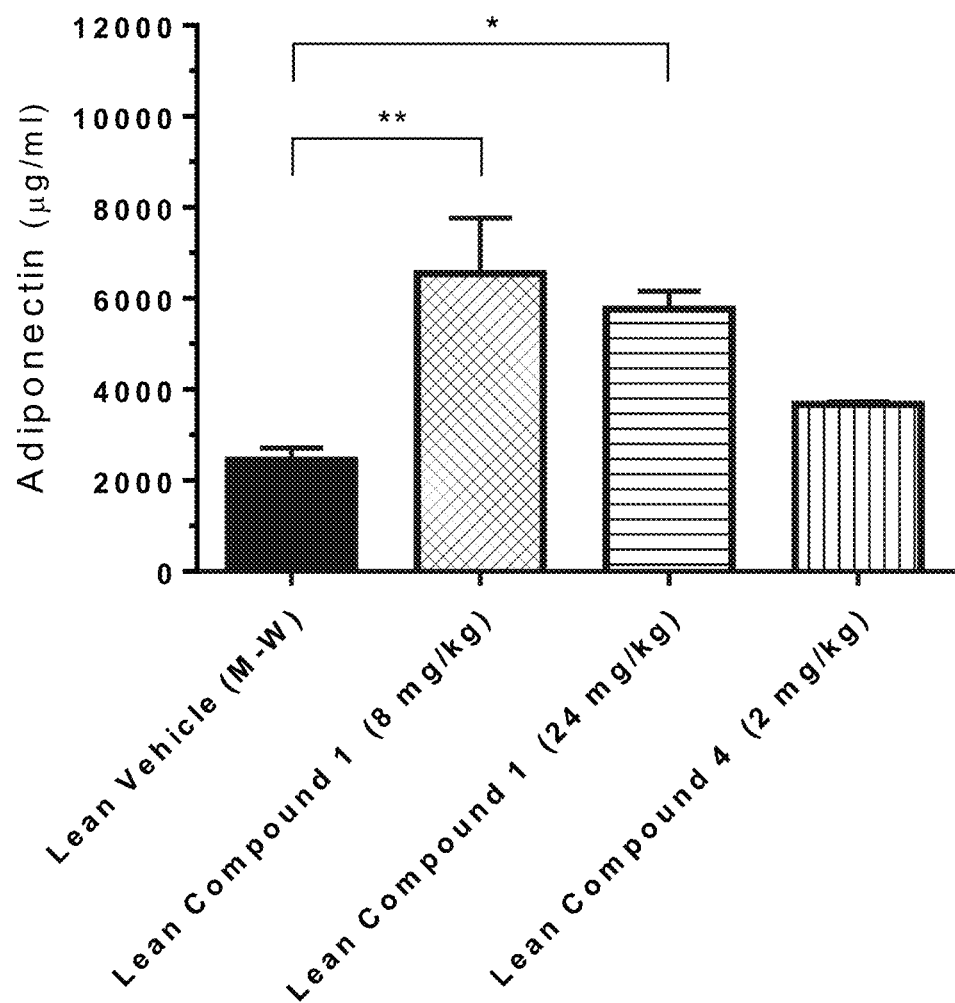
FIG. 9D is a graph showing serum adiponectin levels in lean tumor-bearing mice following administration of compounds of the present disclosure when compared to another MetAP2 inhibitor.
Figure 9E:
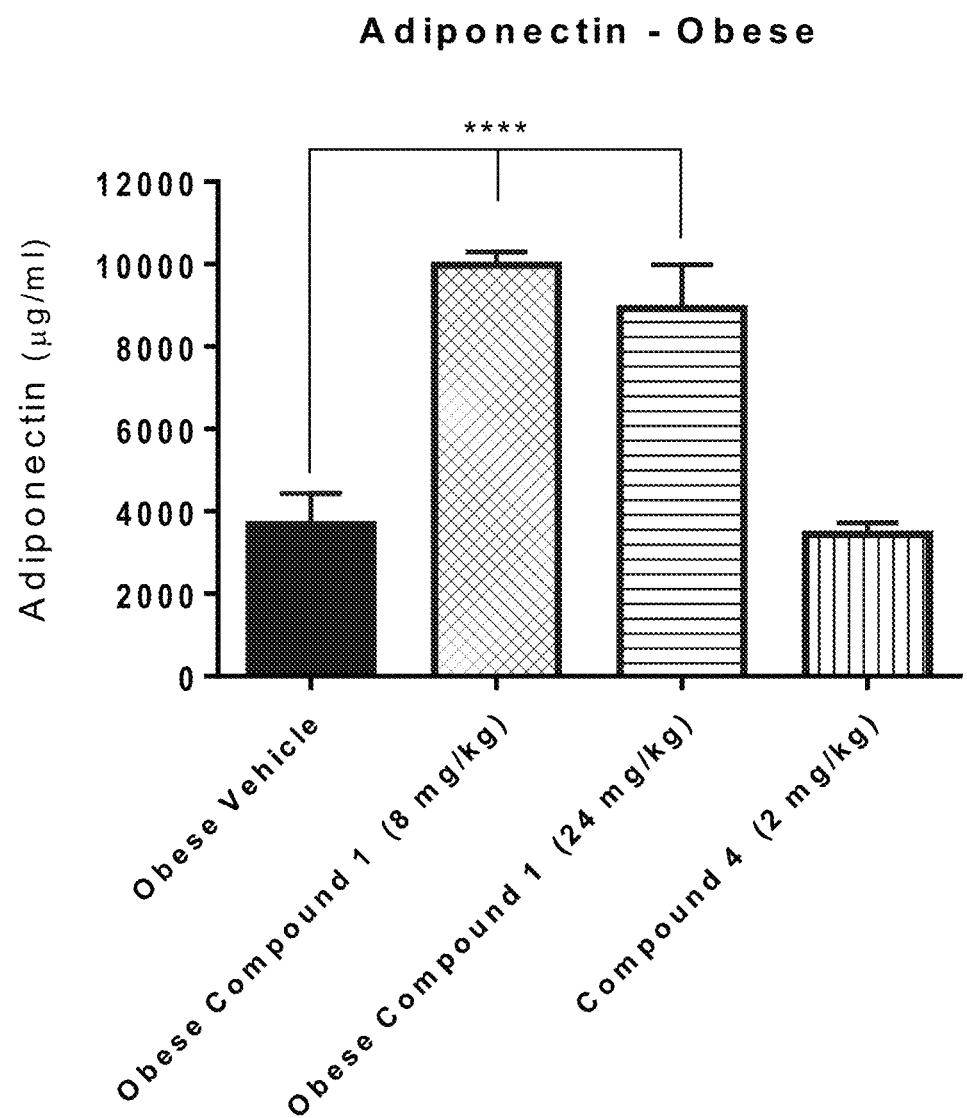
FIG. 9E is a graph showing serum adiponectin levels in obese tumor-bearing mice following administration of compounds of the present disclosure when compared to another MetAP2 inhibitor.

FIG. 9D shows the levels of serum adiponectin in lean mice bearing B16F10 melanomas following treatment with vehicle, 8 mg/kg or 24 mg/kg of compound 1 or 2 mg/kg of compound 4. FIG. 9E shows the levels of serum adiponectin in obese DIO mice bearing B16F10 melanoma following treatment with vehicle, 8 mg/kg or 24 mg/kg of compound 1 or 2 mg/kg of compound 4. The data show a one-way ANOVA with multiple comparisons, *p<0.05, p<0.01, *p<0.005 and ****p<0.0001. The results in FIG. 9D and FIG. 9E demonstrate that compound 1 significantly increases serum adiponectin levels in both lean and obese, tumor-bearing mice. In contrast, compound 2 had no effect on serum adiponectin levels in either lean or obese tumor-bearing mice.

Example 3—In Vivo Testing E0771 Mammary Tumor/DIO Mice—Tumor Growth, Body Weight Female mice were surgically ovariectomized then fed a high fat diet (60% fat) for 14 weeks, to induce obesity and metabolic dysfunction or a low-fat diet (10% fat). Subsequently mammary gland tumors were induced by injecting syngeneic E0771 cells into the fourth mammary gland (50,000/mouse). When tumors became palpable, Compound 1 (at 24 mg/kg) or vehicle (5% mannitol/water) were dosed subcutaneously every four days for a total of four doses.

Figure 10A:
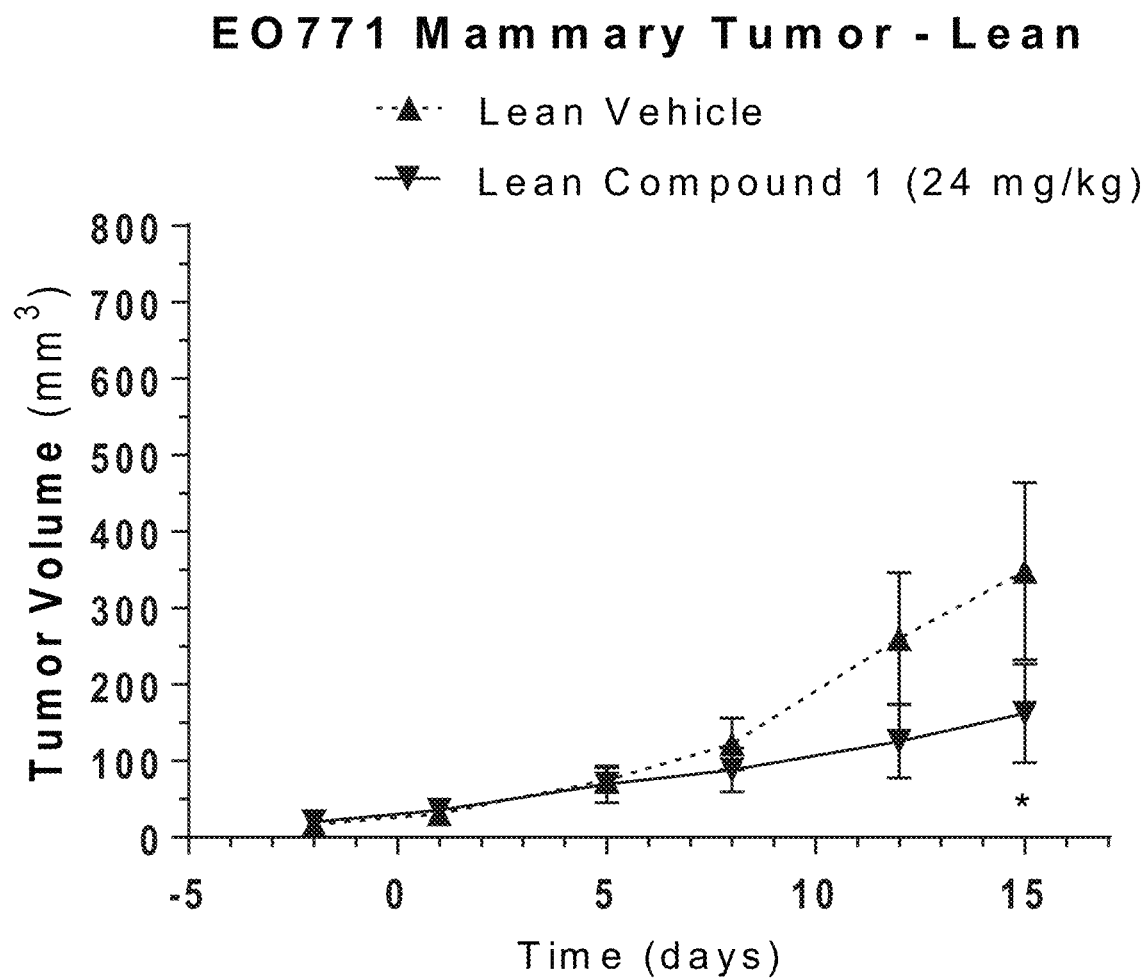
FIG. 10A is a graph showing reduced tumor growth in lean mammary tumor-bearing mice following administration of compounds of the present disclosure.
Figure 10B:
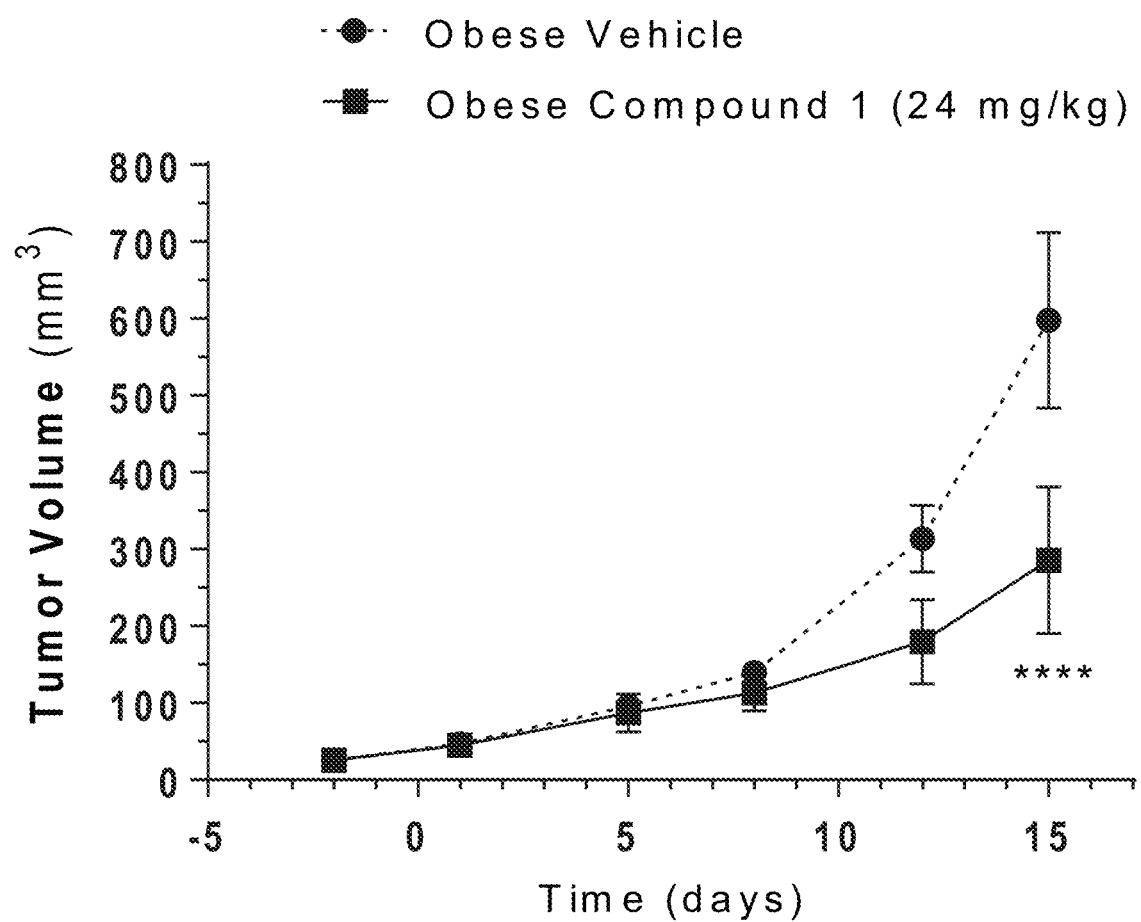
FIG. 10B is a graph showing reduced tumor growth in obese mammary tumor-bearing mice following administration of compounds of the present disclosure.

FIG. 10A shows tumor growth in lean E0771 Mammary Tumor/DIO mice following treatment with vehicle or 24 mg/kg of compound 1 of the present disclosure. FIG. 10B shows tumor growth in obese E0771 Mammary Tumor/DIO mice following treatment with vehicle or 24 mg/kg of compound 1 of the present disclosure. The data were analyzed using two-way ANOVA with multiple comparisons, *p<0.05, p<0.01, *p<0.005 and ****p<0.0001. The results of FIGS. 10A and 10B demonstrate that EO771 tumors in obese female mice were 71% larger on day 15 than in lean female mice. The results also show that compound 1 reduced tumor growth in both lean and obese female mice, with a similar magnitude of effect on tumor size (52% reduction in obese mice compared to 53% reduction in lean mice).

Figure 11A:
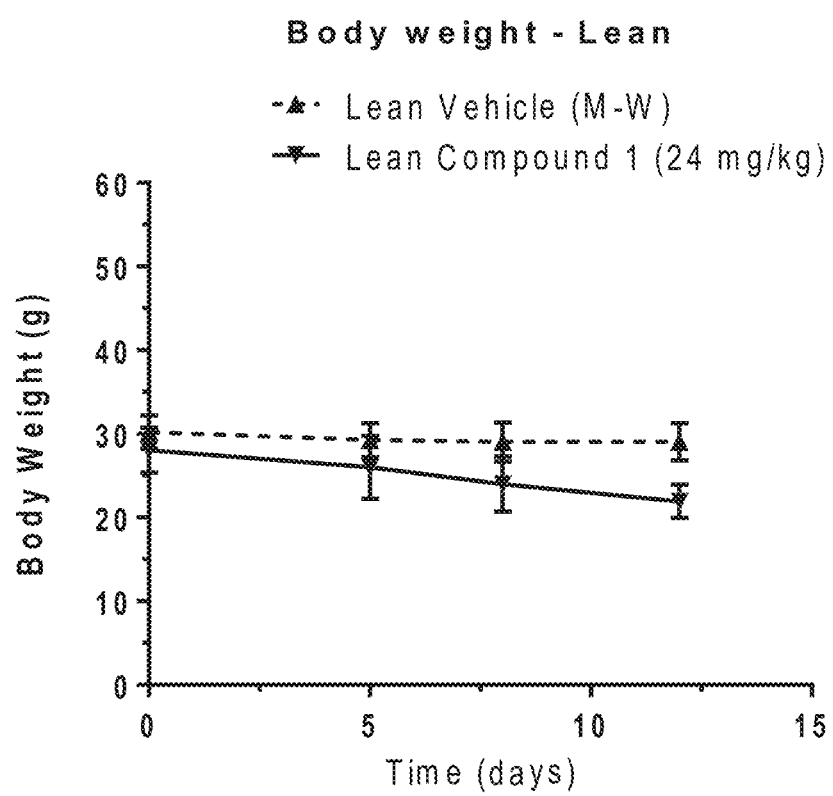
FIG. 11A is a graph showing reduced body weight in lean mammary tumor-bearing mice following administration of compounds of the present disclosure.
Figure 11B:
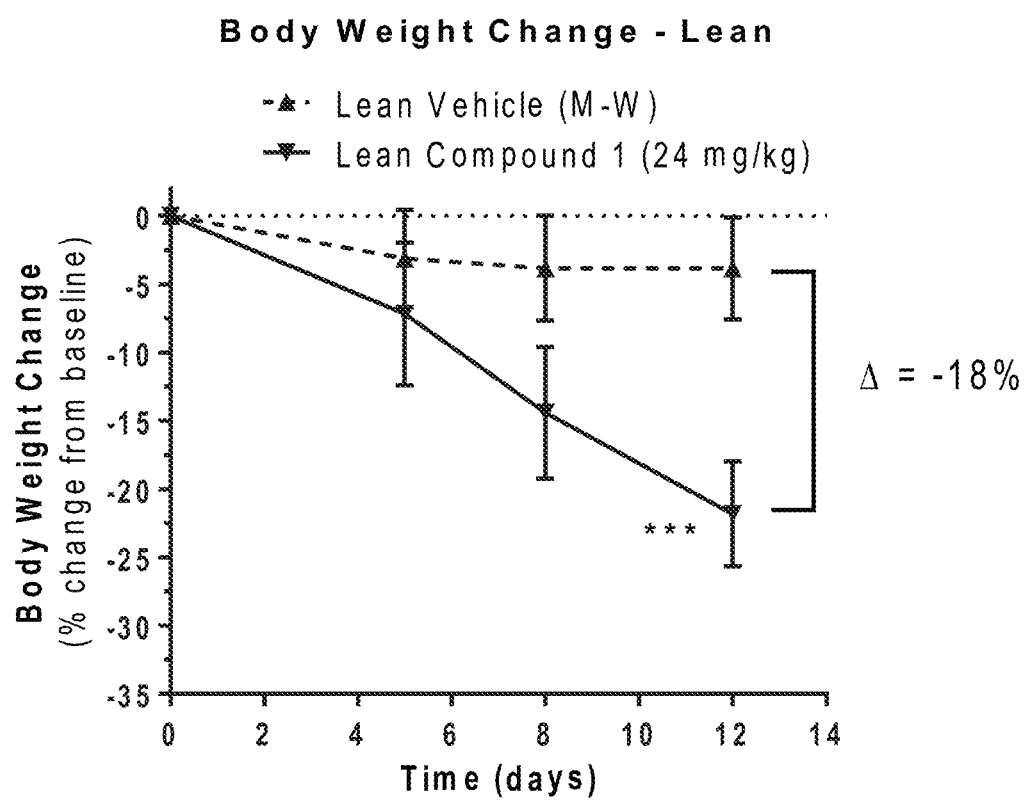
FIG. 11B is a graph showing body weight change relative to baseline in lean mammary tumor-bearing mice following administration of compounds of the present disclosure.
Figure 11C:
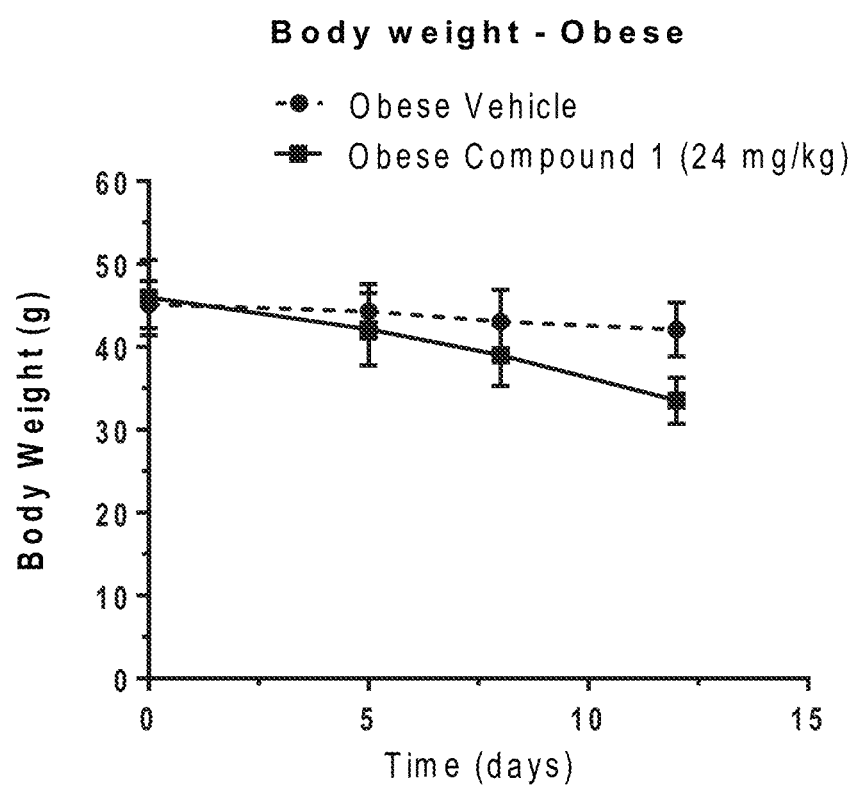
FIG. 11C is a graph showing reduced body weight in obese mammary tumor-bearing mice following administration of compounds of the present disclosure.
Figure 11D:
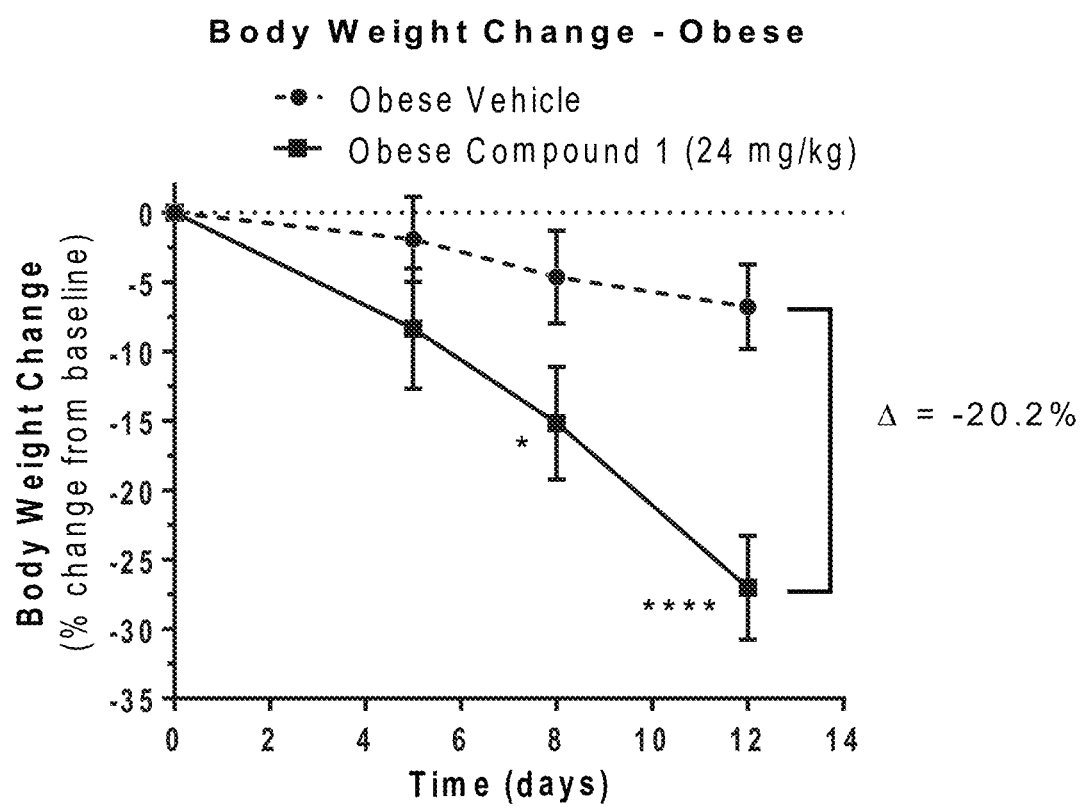
FIG. 11D is a graph showing body weight change relative to baseline in obese mammary tumor-bearing mice following administration of compounds of the present disclosure.

FIG. 11A shows body weight in lean EO771 Mammary Tumor mice following treatment with vehicle or 24 mg/kg of compound 1 of the present disclosure. FIG. 16B shows body weight change relative to baseline in lean EO771 Mammary Tumor mice following treatment with vehicle or 24 mg/kg of compound 1 of the present disclosure. FIG. 11C shows body weight in obese EO771 Mammary Tumor mice following treatment with vehicle or 24 mg/kg of compound 1 of the present disclosure. FIG. 1D shows body weight change in obese EO771 Mammary Tumor mice following treatment with vehicle or 24 mg/kg of compound 1 of the present disclosure. The data were analyzed using two-way ANOVA with multiple comparisons, *p<0.05, p<0.01, *p<0.005 and ****p<0.0001. The results of FIG. 11A-11D demonstrate that compound 1, dosed at 24 mg/kg every four days, reduced body weight in both lean and obese female mice bearing mammary gland tumors, with a similar magnitude of effect (18% reduction in lean mice and 21% reduction in obese mice, respectively).

Table 4 shows that compound 1 significantly decreased the mass of adipose tissue (three depots—parametrial, retroperitoneal and inguinal—measured at necropsy) in obese mice, after treatment every other day for two weeks. Similar effects of Compound 1, though less significant, were observed in lean mice.

TABLE 4

| | Treatment Group | Tissue Weight (g) | SEM | P Value (One-way ANOVA with multiple comparisons) |
|---|---|---|---|---|
| Obese Female Mice | | | | |
| Parametrial Fat | Vehicle | 1.845 | 0.163 | |
| | Compound 1 (24 mg/kg) | 1.175 | 0.100 | <0.005 |
| Retroperitoneal Fat | Vehicle | 0.986 | 0.081 | |
| | Compound 1 (24 mg/kg) | 0.489 | 0.054 | <0.001 |
| Inguinal Fat | Vehicle | 2.413 | 0.205 | |
| | Compound 1 (24 mg/kg) | 1.211 | 0.085 | <0.001 |
| Lean Mice | | | | |
| Parametrial Fat | Vehicle | 1.015 | 0.138 | |
| | Compound 1 (24 mg/kg) | 0.453 | 0.047 | <0.01 |
| Retroperitoneal Fat | Vehicle | 0.393 | 0.043 | |
| | Compound 1 (24 mg/kg) | 0.173 | 0.035 | <0.05 |
| Inguinal Fat | Vehicle | 0.855 | 0.162 | |
| | Compound 1 (24 mg/kg) | 0.480 | 0.073 | NS |

Example 4—Phase 1 Dose Escalation Study of Compound 1 to Assess the Safety and Tolerability in Patients with Advanced Refractory or Late-Stage Solid Tumors—Study Design The phase 1 clinical trial of compound 1 has several objectives.

The primary objectives are:
To determine the safety and tolerability of COMPOUND 1 in patients with advanced refractory or late-stage solid tumors.
To determine the maximum tolerated dose (MTD) of COMPOUND 1 in patients with advanced refractory or late-stage solid tumors.
To determine the recommended Phase 2 dose (RP2D) of COMPOUND 1 in patients with advanced refractory or late-stage solid tumors.

The secondary objectives are:
To evaluate the pharmacokinetic (PK) profile of compound 5, the active moiety of COMPOUND 1 and metabolites in patients with advanced refractory or late-stage solid tumors.
To document evidence of anti-tumor activity of COMPOUND 1 in patients with advanced refractory or late-stage solid tumors.

Exploratory objectives include:
To evaluate the effects of COMPOUND 1 by biomarker analysis, and by PET scan imaging (where clinically relevant and approved by the Investigator and Medical Monitor) in patients with advanced refractory or late-stage solid tumors.
To evaluate the pharmacodynamic (PD) effects of COMPOUND 1 by MetAP2 analysis, and by DCE MRI imaging (where clinically relevant and approved by the Investigator and Medical Monitor) in patients with advanced refractory or late-stage solid tumors.
To document the effects of COMPOUND 1 on metabolic parameters in patients with advanced refractory or late-stage solid tumors.
To evaluate muscle and fat tissue volumes in the body by MRI or CT imaging in selected patients.

Study Description

This is a Phase 1 dose escalation study to assess the safety and tolerability of subcutaneously administered COMPOUND 1 in patients with advanced refractory or late-stage solid tumors. An accelerated titration dose escalation design will be used with one patient per dose level until that patient has a Grade 2 toxicity deemed by the Investigator as possibly, probably, or definitely related to study drug in their first cycle of treatment. A cycle is 28 days, consisting of a total of 4-weekly treatments and includes the pre-dose safety testing prior to initiating the next treatment cycle. Once a Grade 2 toxicity deemed at least possibly related to study drug is observed in a patient's first cycle of treatment, the accelerated phase of the study will end and the non-accelerated phase (3+3 dose escalation design) will begin. A minimum of three evaluable patients will be accrued at the dose that triggered the switch to the non-accelerated design and at each subsequent dose level until a dose limiting toxicity (DLT) is found.

During the accelerated titration dose escalation design phase the Sponsor, Medical Monitor, and Safety Review Committee (SRC) may decide to switch to the 3+3 non-accelerated dose escalation phase prior to the observance of any Grade 2 toxicity deemed at least possibly related to study drug in the patient's first cycle of treatment.

In the 3+3 non-accelerated phase, if one of the three patients has a DLT (as defined below), the cohort will be expanded to a maximum of six patients. If only one of the six patients has a DLT, dose escalation will continue. If two patients have a DLT, dose escalation will stop, regardless of the number of patients that have been treated in this cohort (e.g., if patients 1 and 4 have DLTs then patients 5 and 6 would not be treated). The dose at which two of six patients have a DLT will be considered at least one dose level above the MTD. The next lower dose will be fully evaluated by treating a total of six patients. If two or more patients have DLTs at this lower dose level, de-escalation will continue until a dose level is identified at which none or one of six patients has a DLT. This dose will be identified as the MTD.

Once the MTD has been determined, up to six more patients, for a total of up to 12 patients may be treated at this dose level to further characterize treatment emergent adverse events (TEAEs).

Patients who experience a Grade 3 or greater toxicity that is deemed by the Investigator to be possibly, probably, or definitely related to the administration of COMPOUND 1, can have their next dose withheld for up to 14 days (the day that the dose is due being considered Day 1 of the dose delay), and when the patient's toxicity has returned to a Grade 1 or to the patient's pre-event baseline, the treatment can be resumed at the same dose level. Patients that have their dose withheld longer than 14 days, will be discontinued from the study. Dose delays for up to two weeks from the scheduled Day 1 start of treatment may be considered for the patient's clinical concerns, which may be deemed not related to the study drug, upon agreement between the Investigator, Medical Monitor and the patient.

During the study, the SRC may decide if additional dose groups should be opened. New dose groups either above or below the highest dose used can be added with the approval of the Investigator(s), Medical Monitor and SRC.

Intra-patient dose escalation to the next higher cohort will be considered for those patients who have not demonstrated a Grade 2 toxicity deemed at least possibly related to study drug, in their first cycle and have successfully completed their Tumor Burden Assessment after Cycle 2. This type of dose escalation will only be allowed once a patient in the next higher dose cohort has successfully completed their Cycle 1 safety assessment by not demonstrating a Grade 2 toxicity event that is deemed at least possibly related to study drug. The decision to dose escalate will be made in a discussion between the Investigator, Medical Monitor and Sponsor, taking in account the patient's permission. If a patient escalates to the next higher dose level at Cycle 4, 5, or 7 and beyond, additional plasma PK samples will be collected according to a defined schedule.

Patients will be allowed to continue treatment:
if there is a clinical response, or
if they have stable disease as assessed on imaging studies following C2, C4, C6 and every three cycles subsequently, or
if the Investigator and Medical Monitor agree that the patient is receiving benefit from the treatment.

Each patient will be dosed once weekly for 4 weeks (days 1, 8, 15, and 22) and includes a safety follow-up prior to initiation of the next treatment cycle. Patients will go through 2 cycles prior to disease assessment by RECIST 1.1 criteria. Below are the following dose levels that will be used:

| Dose cohort | Proposed dose level (mg/m$^2$) |
| --- | --- |
| 1 | 1.7 |
| 2 | 3.4 |
| 3 | 6.0 |
| 4 | 8.5 |
| 5 | 11.9$^a$ |
| 6 | 15.3 |
| 7 | 20.4$^b$ |
| 8 | 27.0 |
| 9 | 36.0 |
| 10 | 49.0 |
| 11+ | Additional cohorts |

$^a$NOAEL in dog was 0.4 ng/ml COMPOUND 5 (Cmax)/20.7 h * ng/ml (AUC) after a dose of 0.5 mg/kg (10 mg/m$^2$) COMPOUND 1
$^b$NOAEL in rat was 1.5 ng/ml COMPOUND 5 (Cmax)/23.3 h * ng/ml (AUC) after a dose of 3 mg/kg (18 mg/m$^2$) COMPOUND 1

The Common Terminology Criteria for Adverse Events (CTCAE) v4.02 will be used to determine toxicity.

A DLT is defined as any of the following adverse events that are clinically significant and are deemed by the Investigator to be possibly, probably, or definitely related to the administration of COMPOUND 1 that persist(s) despite maximal medical support:
any Grade 3 or greater non-hematological toxicity; lasting seven (7) days, or
any Grade 3 or greater nausea, diarrhea, and/or vomiting lasting three (3) days, provided the patient received maximal medical intervention and/or prophylactic anti-emetic therapy; or
any Grade 3 or greater hematologic toxicity; lasting three (3) days, or
any Grade 3 or greater febrile neutropenia.

Study Population: Approximately 30 patients

Study Drug Administration: COMPOUND 1 will be administered by subcutaneous injection on days, 1, 8, 15, and 22 of each cycle, and includes a safety follow-up prior to initiation of the next treatment cycle.

Inclusion Criteria:

The patient has the ability to provide written, informed consent, to understand the requirements of the study, and agree to abide by the requirements of the study.

Male or female ≥21 to ≤85 years of age.

Patients with histologically or cytologically confirmed advanced, refractory, late-stage solid tumors who have progressed on standard therapy or for whom no effective anti-cancer therapy is available.

Patients with at least one site of radiographically measurable disease of ≥1 cm in the largest dimension by traditional computerized tomography (CT) scanning technique (per RECIST 1.1 criteria); or if, in the Investigator's opinion, evaluable disease can be reliably and consistently followed, the patient may be eligible upon approval by the Medical Monitor.

Eastern Cooperative Oncology Group (ECOG) status ≤1.
Life expectancy ≥3 months.

Women of childbearing potential must not be breastfeeding or lactating and must have a negative serum pregnancy test within 72 hours of starting the study. If the female partner is not menopausal or is not surgically sterile, then women and men study patients must be willing to use double barrier birth control methods such as condom or occlusive cap (e.g., diaphragm or cervical/vault caps) plus spermicidal agent (e.g., foam, gel, film, cream, suppository) throughout the duration of their participation in the study, including a 90 day period after their last treatment.

Laboratory data as specified below:
Hematology: ANC>1500 cells/mm$^3$, platelet count>100,000 cells/mm$^3$ and hemoglobin>9 g/dL.
Urinalysis: No clinically significant abnormalities.
Coagulation: INR and PTT within normal limits.
HIV-positive patients are eligible provided the following criteria are met: CD4 count ≥100/mm$^3$, undetectable viral load within the past 3 months, receiving a stable antiretroviral regimen for ≥4 weeks before study entry.

Patients eligible for imaging study scans must be able to lie flat for up to 45 minutes.

Exclusion Criteria

Patients that have undergone organ transplant surgery.

Patients with known primary brain malignancy, brain metastases or active CNS pathology.

Patients with known history of Hepatitis A, B, or C that are on active anti-viral therapy.

Patients on anticoagulation medication; however, standard dose ASA, anti-platelet agents, are allowed as approved in advance by Medical Monitor.

Patients with a history of gastric bypass surgery or banding procedure.

Patients requiring insulin for control of diabetes. Subjects taking insulin secretagogues that act in a non-glucose dependent manner—sulfonylureas such as glyburide and any in this class.

Patients on greater than physiological replacement equivalent corticosteroids; e.g., prednisone 5 mg, dexamethasone 0.75 mg, hydrocortisone 20 mg, betamethasone 0.6 mg, methylprednisolone 4 mg, cortisone 25 mg, etc., per day. Nasal, inhaled, and topical corticosteroids are permitted.

Patients with uncontrolled or refractory hypertension: systolic>180 or diastolic>110, or hypotension: systolic<90 or diastolic<50 despite medical treatment.

Patients for whom the resting 12-lead electrocardiogram obtained during screening shows QTc (Bazett's correction) ≥470 ms or that have congenital prolonged QT syndrome. Isolated right bundle branch block (RBBB) and incomplete right bundle branch block (IRBBB) and left anterior hemiblock (LAH) are acceptable. Any uncontrolled cardiac arrhythmia (patients with rate-controlled atrial fibrillation are not excluded unless on chronic anti-coagulation as per Exclusion Criterion #4).

Renal: serum creatinine>1.5× upper limit of normal (ULN), or calculated creatinine clearance<50 mL/min/1.73 m$^2$ for patients with creatinine levels above institutional normal.

Hepatic: Total bilirubin≥1.5×ULN; alanine aminotransferase (ALT) or aspartate aminotransferase (AST)≥2.5× ULN. For patients with known liver metastases or liver neoplasms, then ALT or AST≤5.0×ULN is allowed.

Participation in any other trial of an investigational agent within 30 days prior to first dose of study drug.

Previous Therapies:
treatment with the following medications≤4 weeks or 5 half-lives, whichever is shorter, prior to first dose of study drug:
any treatment with cytotoxic or cytostatic chemotherapy, monoclonal antibody therapy, radiation therapy, molecular targeted therapy, hormonal agents, TKIs (tyrosine kinase inhibitors), angiogenesis and VEGF inhibitors.
major surgery≤4 weeks prior to study first dose of study drug.
any radio-immunotherapy≤12 weeks prior to first dose of study drug.

Any other concurrent condition or social situation, which in the opinion of the Investigator, would preclude participation in this study or interfere with the patient's study compliance.

Any serious medical condition, laboratory abnormality, or psychiatric illness that would prevent the patient from following study procedure or places the patient at unacceptable risk if s/he were to participate in the study or confounds the ability to interpret data from the study.

Patients with a known history of hypersensitivity to any of the test materials or related compounds.

Patients requiring chronic, concomitant treatment of strong cytochrome P450, family 3, subfamily A, polypeptide 4 (CYP3A4/5) inducers (e.g., dexamethasone, phenytoin, carbamazepine, rifampin, rifabutin, rifapentine, phenobarbital, and St. John's Wort) given that the biologically active small molecule moiety of COMPOUND 1, COMPOUND 5, is a CYP3A 4 & 5 substrate.

Patients who have had radiotherapy≤4 weeks prior to starting study drug, or ≤2 weeks prior to starting study drug in the case of localized radiotherapy (e.g. for analgesic purpose or for lytic lesions at risk of fracture), or who have not recovered from radiotherapy toxicities.

Prior use of prescription or non-prescription orexigenics (appetite stimulants), (i.e., megestrol acetate, mirtazapine, dronabinol, anabolic steroids) within 2 months of first dose of study drug.

Study Assessments

Below is a summary of the requirements and tests needed prior to enrollment and that will be performed during a patient's participation in this Phase 1 study.

Screening Period (up to 14 days prior to Day 1)
Signed informed consent
Medical history
Physical examination (all body systems); may defer rectal and genital exam if not clinically indicated
Height and weight
ECOG Performance Status
Vital signs (temperature, blood pressure, pulse and respiratory rate)
Concomitant medication assessment
12-lead electrocardiogram (triplicate)
Serum Pregnancy test (for nonsterile women of childbearing potential)
Hematology
Clinical chemistry, coagulation, lipid, and urinalysis (microscopic examination if positive on dipstick)
Assessment of tumor burden by radiologic evaluations using RECIST 1.1 criteria (CT scans can be used if captured no more than 30 Days prior to Treatment Day 1)
PET and DCE MRI Scan as clinically indicated, and approved by the Investigator and Medical Monitor
MRI or CT scan for selected patients approved by the Investigator and Medical Monitor for body composition analysis, see Imaging Manual
Record any available clinically accepted assay results for protein biomarkers relevant to the patient's specific tumor type (e.g., PSA, CA-125, AFP, CEA, beta-hCG, CA19-9, etc.)

Treatment Period (Pre-dose testing with the exception of PK, PD, biomarkers and retains can be performed within 72 hours prior to treatment)

Medical history
Weight (every treatment day pre-dose for study drug calculation—weight from the previous visit may be used for study drug dosing calculations)
Questions on eating habits, diet, and physical activity
ECOG Performance Status (Pre-dose Day 1 of each cycle)
Vital signs (temperature, blood pressure, pulse and respiratory rate)
Concomitant medication assessment
12-lead electrocardiogram (triplicate).
Local tolerance of subcutaneous treatment injection site(s)
Serum pregnancy test for female patients with childbearing potential (Pre-dose Day 1)
Hematology
Clinical chemistry, coagulation, lipid, and urinalysis (microscopic examination if positive on dipstick)
Blood sample collection for PK and PD analysis
Blood sample collection for exploratory biomarkers and retains
PET and DCE MRI scans as clinically indicated, and approved by the Investigator and Medical Monitor, see Imaging Manual
MRI or CT scan for selected patients approved by the Investigator and Medical Monitor for body composition analysis, see Imaging Manual
Tumor burden assessment using RECIST 1.1 conducted every other cycle (i.e. at end of Cycles 2, 4, and 6). After Cycle 6 is completed, tumor burden assessment will be performed every 3 Cycles. If a stable or positive response is noted, a follow-up (4 weeks) confirmatory radiographic assessment will be performed Record any available clinically accepted assay results for protein biomarkers relevant to the patient's specific tumor type (e.g., PSA, CA-125, AFP, CEA, beta-hCG, CA19-9, etc.)

Review of adverse events (includes symptom review)

End-of-Treatment (EOT) Assessments (The EOT visit will be scheduled as soon as possible after the investigator decides that the study drug treatment is no longer an option or after the patient withdraws from the study)

Weight
Questions on diet, eating habits, and physical activity
ECOG Performance Status
Vital signs (temperature, blood pressure, pulse and respiratory rate)
Concomitant medication assessment
12-lead electrocardiogram (triplicate)
Local tolerance of the subcutaneous treatment injection site(s)
Hematology
Clinical chemistry, coagulation, lipid, and urinalysis (microscopic examination)
Blood sample collection for PK and PD analysis
Blood sample collection for exploratory biomarkers and retains
Tumor burden assessment using RECIST 1.1 will be done
Record any available clinically accepted assay results for protein biomarkers relevant to the patient's specific tumor type (e.g., PSA, CA-125, AFP, CEA, beta-hCG, CA19-9, etc.)
Review of adverse events (includes symptom review)

End-of-Study (EOS) Assessments (The EOS is 30-days after the EOT (±3 days) visit)

Physical exam
Height and Weight
Questions on diet, eating habits, and physical activity
ECOG Performance Status
Vital signs (temperature, blood pressure, pulse and respiratory rate)
Concomitant medication assessment
12-lead electrocardiogram (triplicate)
Local tolerance of the subcutaneous treatment injection site(s)
Serum Pregnancy test (for nonsterile women of childbearing potential)
Hematology
Clinical chemistry, coagulation, lipid, and urinalysis (microscopic examination)
Blood sample collection for PK and PD analysis
Blood sample collection for exploratory biomarkers and retains
Tumor burden assessment using RECIST 1.1 will be done
Record any available clinically accepted assay results for protein biomarkers relevant to the patient's specific tumor type (e.g., PSA, CA-125, AFP, CEA, beta-hCG, CA19-9, etc.)
Review of adverse events Study Endpoints
Safety Endpoints
Incidence, grade and duration of AEs
Global and local tolerability assessments
Laboratory assessments
Physical examinations, vital signs and ECG parameters
Pharmacokinetic and Tumor Burden Endpoints
PK profile from dose 1 until patient is no longer taking drug
Change in disease status, Overall response rate (CR+PR) and disease control rate (CR+PR+SD)

Exploratory Endpoints
PET and DCE MRI assessments
PD (MetAP2) profile from dose 1 until the patient is no longer taking study drug
MRI or CT assessments of change in body composition
Biomarker assessments (TNF-α, IL-6, MCP-1, IGF-1, hsCRP, leptin, insulin, SHBG (for selected patients), VEGF, bFGF, and adiponectin) from dose 1 until patient is no longer taking study drug
Metabolic assessments (glucose, total cholesterol, LDL, HDL, free fatty acids, lipids, triglycerides, and VLDL) and eating and dietary assessments from dose 1 until patient is no longer taking study drug Statistical Analysis Given the small patient sampling size in this Phase 1 trial, descriptive statistics will be utilized for all safety, efficacy, and pharmacokinetic parameters. Categorical variables will be summarized by frequency distributions (number and percentages of patients), continuous variables will be summarized by mean, standard deviation, median, minimum, maximum, and time-to-event variables will be summarized using Kaplan-Meier methods and figures for the estimated median time.

Frequencies of patients experiencing at least one AE will be displayed by body system and preferred term according to MedDRA terminology. Detailed information collected for each AE will include: description of the event, duration, whether the AE was serious, severity, relationship to study drug, action taken, clinical outcome, and whether or not it was a DLT. Severity of the AEs will be graded according to the CTCAE v4.02. AEs classified as dose limiting will be listed.

Summary tables will present the number of patients (per dose group) observed with AEs and corresponding percentages. The denominator used to calculate incidence percentages consists of patients receiving at least one dose of COMPOUND 1 for each dose group. Within each table, the AEs will be categorized by MedDRA body system and preferred term. Additional subcategories will be based on event severity and relationship to study drug.

Adverse events resulting in discontinuation of treatment or withdrawal from the study, serious adverse events, and deaths on-study will be tabulated. All DLTs will be reported and the MTD identified.

Vital signs and ECGs will be summarized using descriptive statistics. Summary tables will be prepared to examine the distribution of laboratory measures over time. Shift tables may be provided to examine the distribution of laboratory toxicities. In addition, patient listings will be presented for adverse events, vital signs, clinical laboratory tests, physical examinations, and ECGs (pre- and post-treatment).

Example 5—Phase 1 Studies—Metabolic Dysfunction

Metabolic dysfunction, defined as elevated levels of hormones such as insulin, leptin, IGF-1 or low level of a hormone such as adiponectin or an elevated leptin:adiponectin ratio, is typically associated with obesity (defined as having a body mass index>30 kg/m2). Obesity most often results from over-nutrition and sedentary lifestyle, which over time leads to increased nutrient storage as triglyceride within adipose tissue. In this scenario adipocytes within adipose tissue undergo hypertrophy as more triglyceride is deposited and obesity develops, but these cells eventually reach a critical size beyond which they cannot expand.

Hypertrophic adipocytes exhibit enhanced leptin secretion (which leads to increased levels of circulating leptin, in proportion to adipose tissue mass) and reduced secretion of adiponectin (which leads to lower levels of circulating adiponectin, indicative of metabolic dysfunction).

Additionally hypertrophic adipocytes create local hypoxia, which causes cellular stress, cell death and concomitant infiltration of immune cells (macrophages and lymphocytes) to ingest excess triglyceride and cellular debris. Subsequent events include sustained inflammation within adipose tissue, proliferation of adipose stem cells contributing to adipocyte hyperplasia, increased angiogenesis all of which contribute to development of metabolic dysfunction.

These events occurs principally in visceral (abdominal) adipose tissue as opposed to subcutaneous adipose tissue, and the association of visceral adipose tissue mass (but to a lesser degree, subcutaneous adipose tissue) with metabolic dysfunction is well known. However, because measurement of BMI does not capture adipose tissue distribution within the body or take into account muscle mass, hyper-adiposity and pathological disturbances in adipose tissue that lead to metabolic dysfunction as defined above, can all occur in patients with BMI in the normal (e.g., 20-25 kg/m2) or overweight (e.g., 25-30 kg/m2) categories. In order to determine whether or not a patient has metabolic dysfunction, BMI is not accurate for the reasons stated above, and more accurate tests would involve measuring the levels of circulating hormones such as insulin, leptin, adiponectin and IGF-1.

In the instant study, circulating hormones such as insulin, leptin, adiponectin and IGF-1 were measured in cancer patients (in the fasted state), and the response to once-weekly subcutaneous dosing of Compound 1, using a range of doses. It is noted that patients with carcinoid, colorectal, cervical, endometrial and breast cancer exhibited baseline levels of such hormones indicating varying degrees of metabolic dysfunction. Furthermore, the directionality of changes in the level of these hormones following weekly administration of Compound 1 indicates improvement of metabolic dysfunction.

Figure 12A:
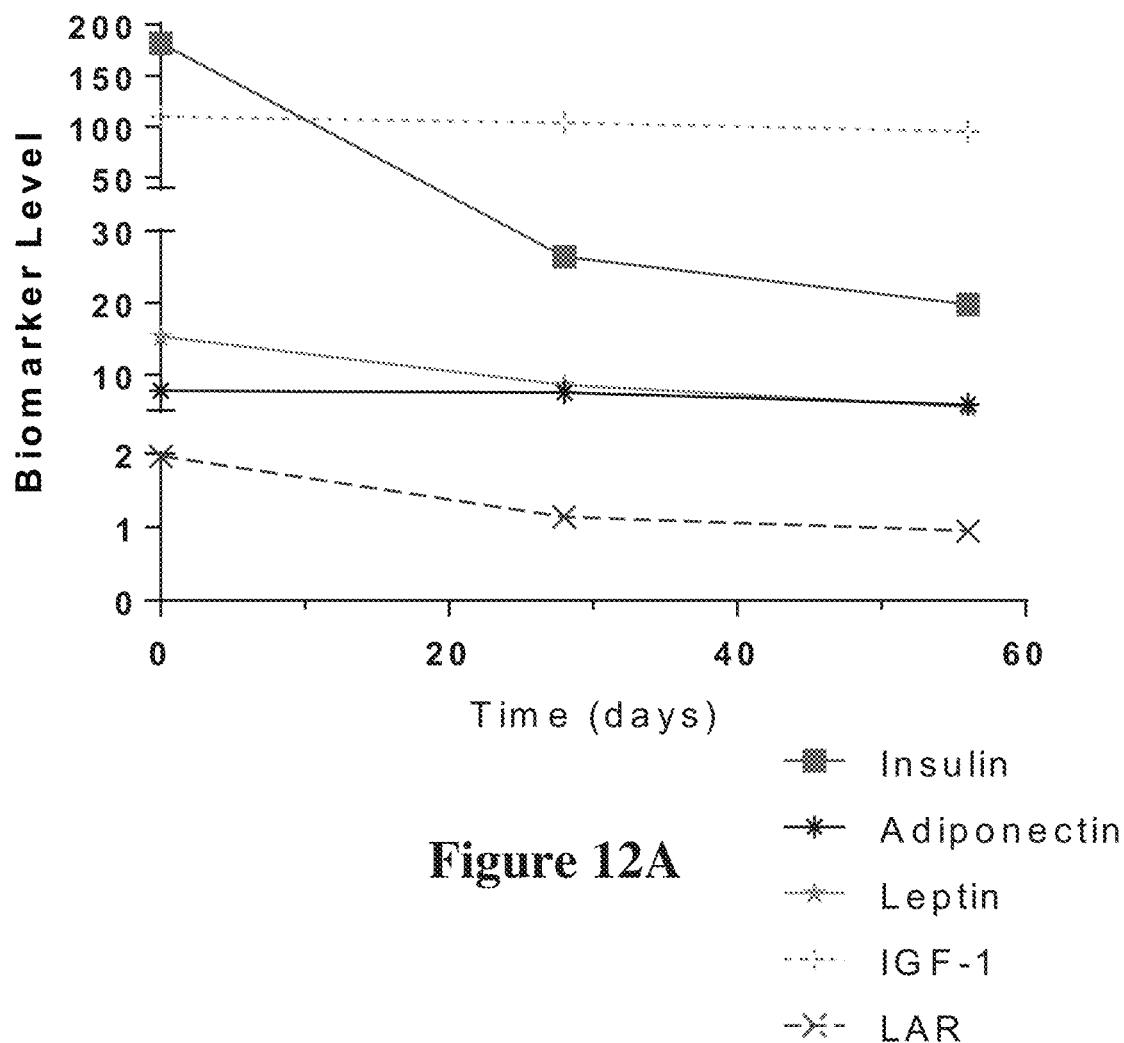
FIG. 12A is a graph showing absolute values of various metabolic biomarkers in the serum of a patient with carcinoid tumors following administration of compounds of the present disclosure.
Figure 12B:
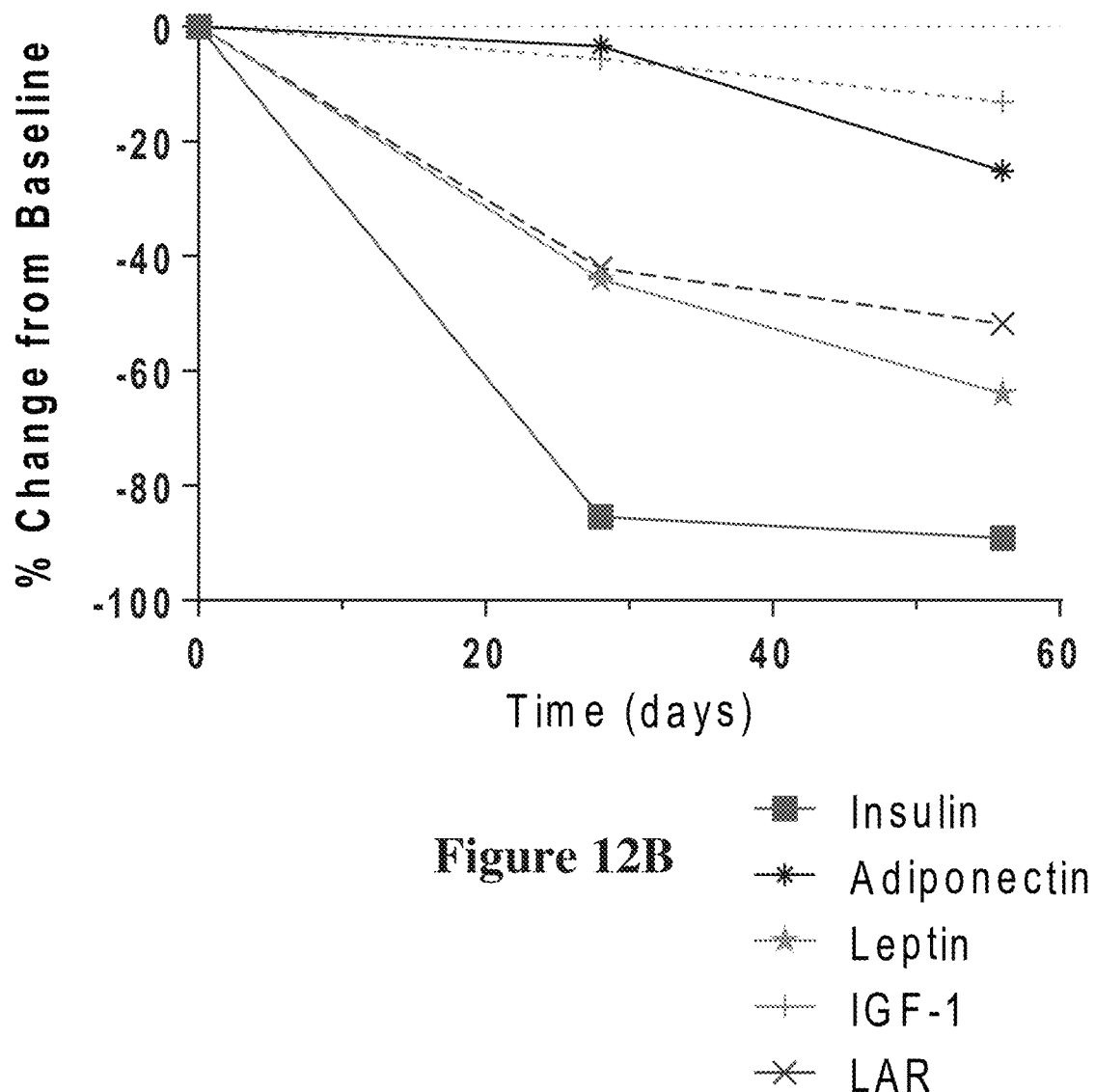
FIG. 12B is a graph showing the percentage change relative to baseline of various metabolic biomarkers in the serum of a patient with carcinoid tumors following administration of compounds of the present disclosure.

FIG. 12 shows circulating levels of metabolic biomarkers insulin, adiponectin, leptin, IGF-1 and the leptin:adiponectin ration (LAR) both at baseline and after once weekly dosing of Compound 1 to a male patient with carcinoid tumors and a BMI of 24.5 kg/m2 (e.g., normal). FIG. 12A shows absolute values of the metabolic biomarkers and FIG. 12B shows % change relative to baseline over time. The results in FIGS. 12A and 12B demonstrate that the level of fasting insulin at baseline was abnormally high but declined by 89% (relative to baseline) after four weekly doses of Compound 1. In addition leptin levels as well as the leptin:adiponectin ratio (LAR) all decreased, indicating improvement in metabolic function following administration of Compound 1.

Figure 13A:
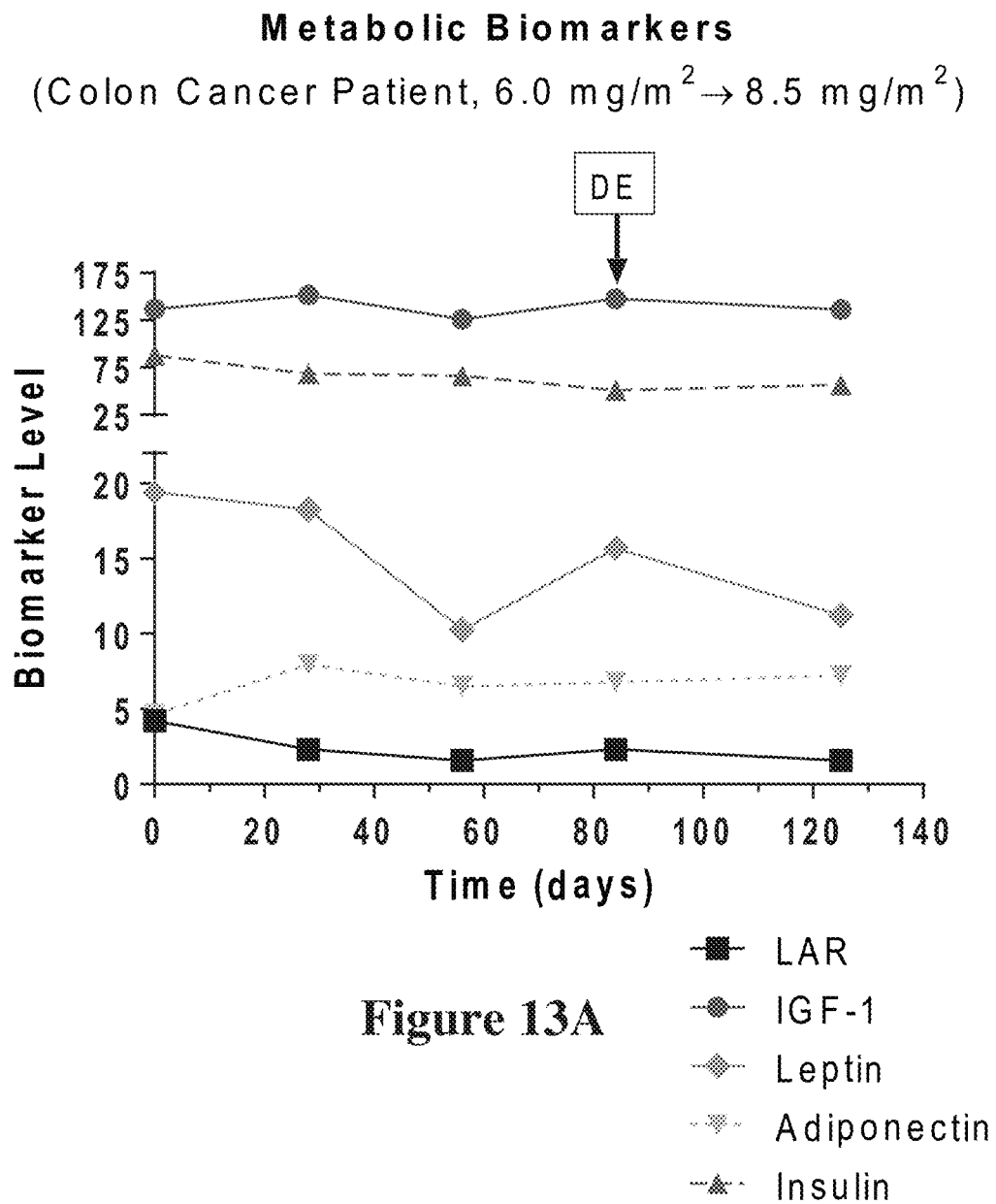
FIG. 13A is a graph showing absolute values of various metabolic biomarkers in the serum of a patient with colon cancer following administration of compounds of the present disclosure.
Figure 13B:
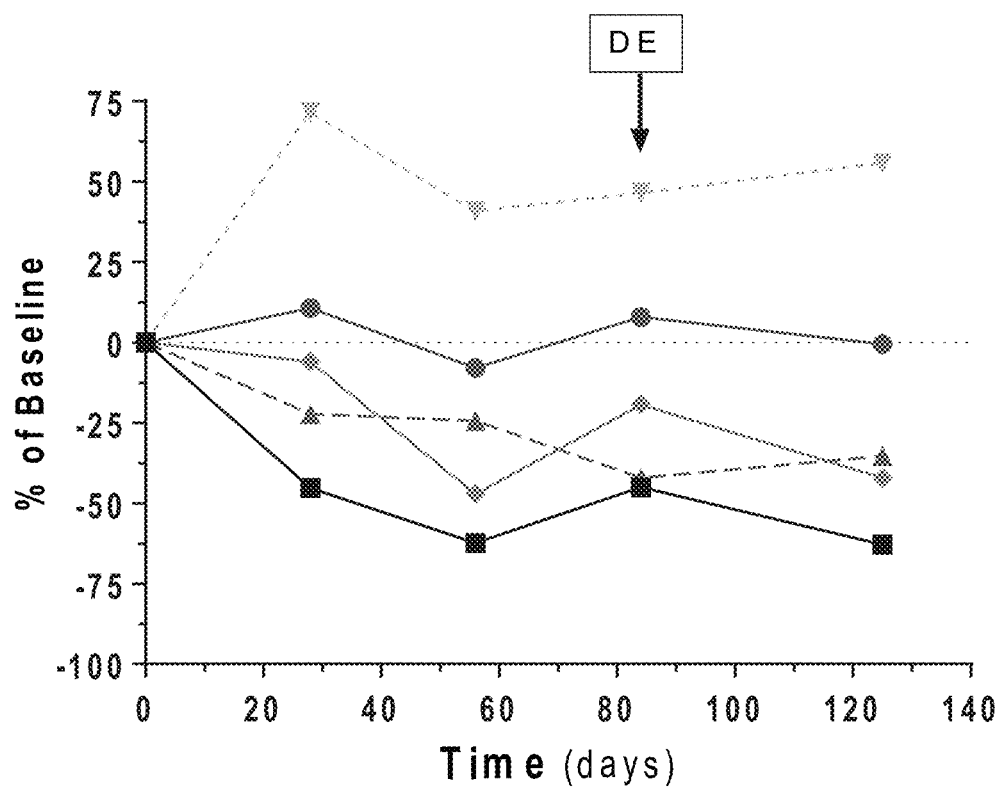
FIG. 13B is a graph showing the percentage change relative to baseline of various metabolic biomarkers in the serum of a patient with colon cancer following administration of compounds of the present disclosure.

In another example shown in FIG. 13, a female patient with colon cancer (BMI=23.5, or normal) was administered Compound 1 once-weekly at 6 mg/m² for 12 weeks followed by dose escalation (DE) to 8.5 mg/m² for an additional six weeks. FIG. 13A shows absolute values of the metabolic biomarkers and FIG. 18B shows % change over time. The results in FIGS. 13A and 13B demonstrate that leptin declined from baseline while adiponectin increased over the same time such that the LAR declined by 62% from an elevated value of 4.7 at baseline, indicating improvements in metabolic dysfunction following administration of Compound 1.

Figure 14A:
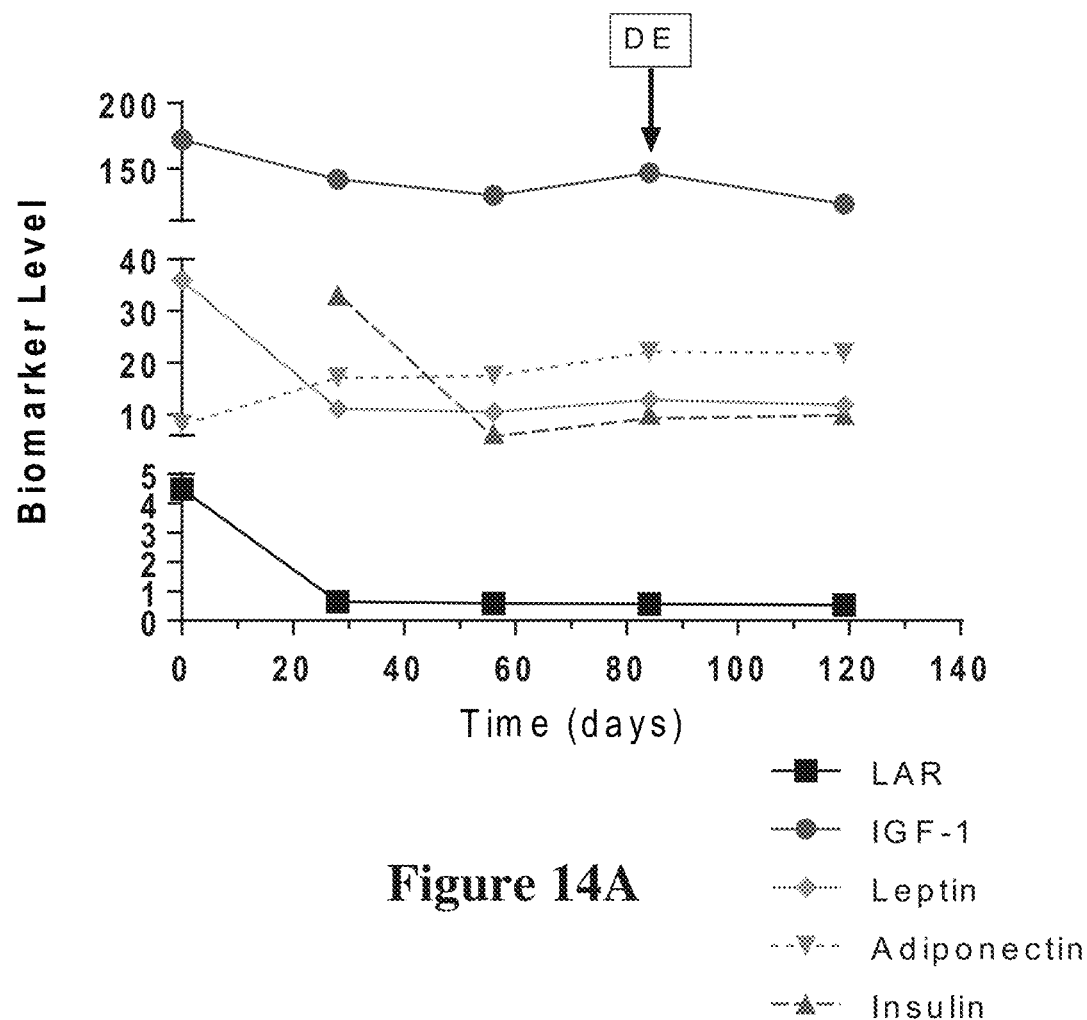
FIG. 14A is a graph showing absolute values of various metabolic biomarkers in the serum of a patient with endometrial cancer following administration of compounds of the present disclosure.
Figure 14B:
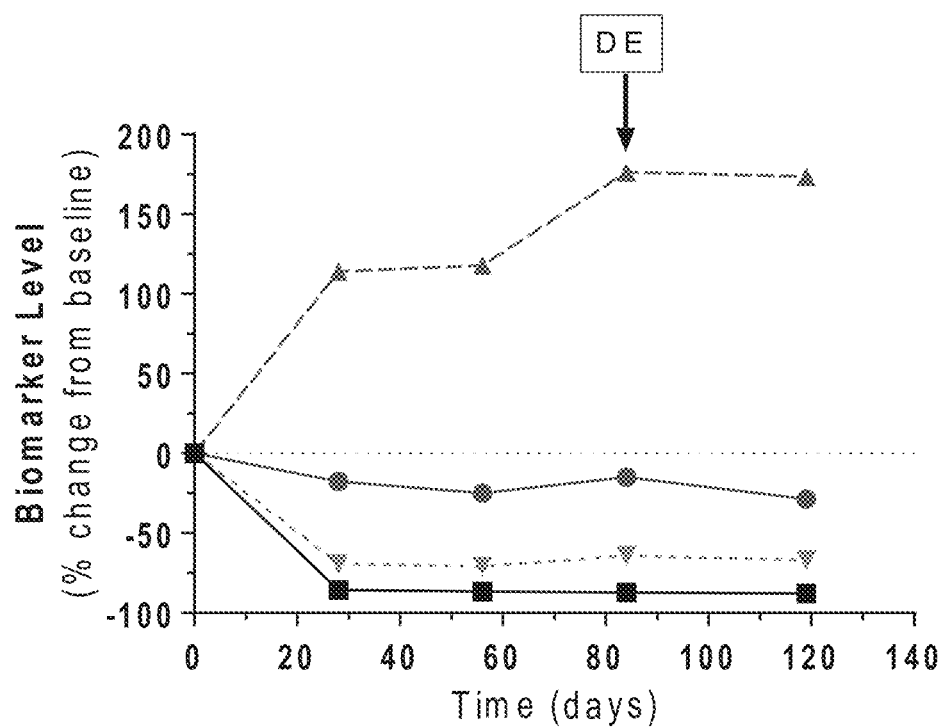
FIG. 14B is a graph showing the percentage change relative to baseline of various metabolic biomarkers in the serum of a patient with endometrial cancer following administration of compounds of the present disclosure.

In another example shown in FIG. 14, a female patient with endometrial cancer (BMI=25.1, or overweight) was administered Compound 1 once-weekly at 8.5 mg/m² for 12 weeks followed by dose-escalation (DE) to 11.9 mg/m² for an additional five weeks. FIG. 14A shows absolute values of the metabolic biomarkers and FIG. 14B shows % change over time. The results in FIGS. 14A and 14B demonstrate that leptin declined from baseline while adiponectin increased over the same time such that the LAR declined by 85% from an elevated value of 4.5 at baseline, indicating improvements in metabolic dysfunction following administration of Compound 1. Insulin data was not available at baseline, so % change from baseline was not calculated, but insulin did decrease by 80% from the period beginning 4 weeks after initiating dosing (when data for insulin first became available) to 8 weeks after initiating dosing.

Figure 15A:
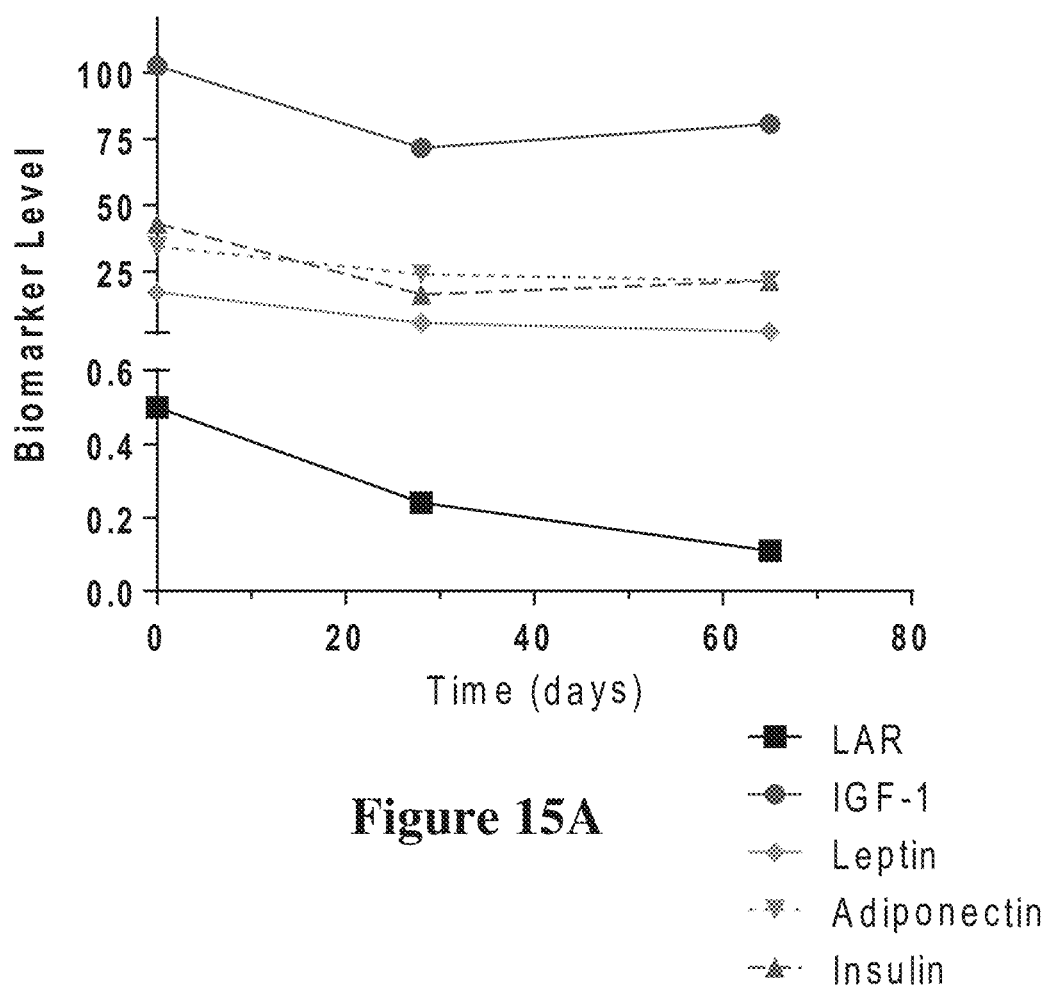
FIG. 15A is a graph showing absolute values of various metabolic biomarkers in the serum of a patient with cervical cancer following administration of compounds of the present disclosure.
Figure 15B:
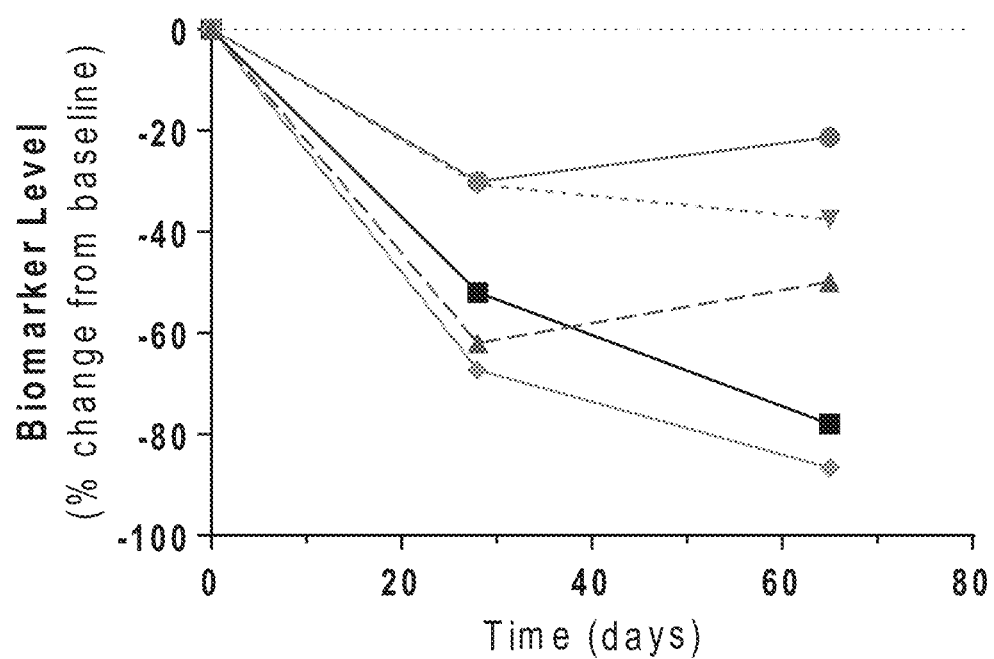
FIG. 15B is a graph showing the percentage change relative to baseline of various metabolic biomarkers in the serum of a patient with cervical cancer following administration of compounds of the present disclosure.

In another example shown in FIG. 15, a female patient with cervical cancer (BMI=22.5, or normal) was administered Compound 1 once-weekly at 11.9 mg/m² for 8 weeks. FIG. 15A shows absolute values of the metabolic biomarkers and FIG. 15B shows % change over time. The results in FIGS. 15A and 15B demonstrate that leptin declined by 88% from baseline and the LAR declined by 78% from baseline, indicating improvements in metabolic dysfunction after 8 weeks of dosing with Compound 1. Insulin decreased by 50% from baseline to 8 weeks post-dosing, also indicating improvements in metabolic dysfunction following administration of Compound 1.

Figure 16A:
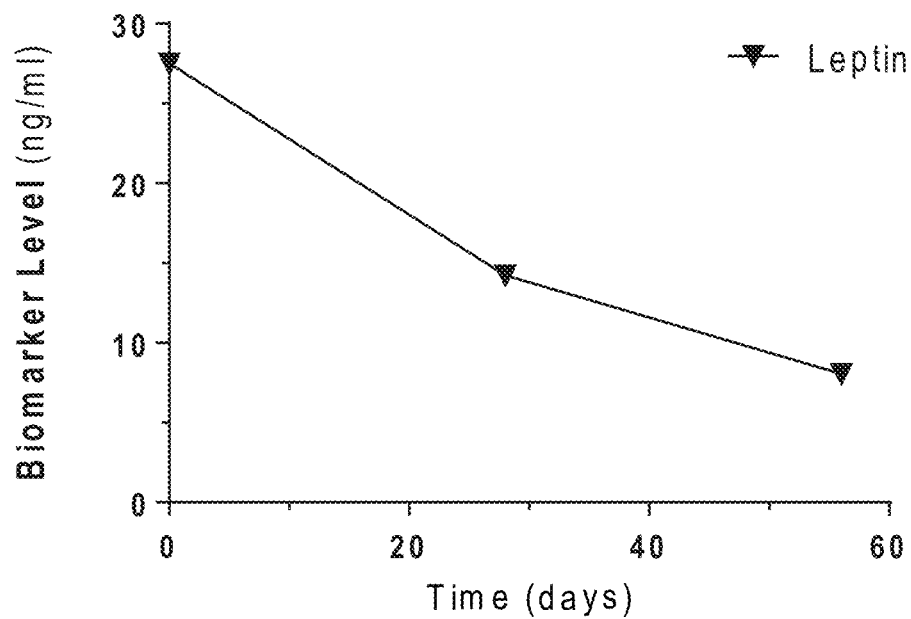
FIG. 16A is a graph showing absolute values of leptin in the serum of a patient with hormone receptor-positive breast cancer following administration of compounds of the present disclosure.
Figure 16B:
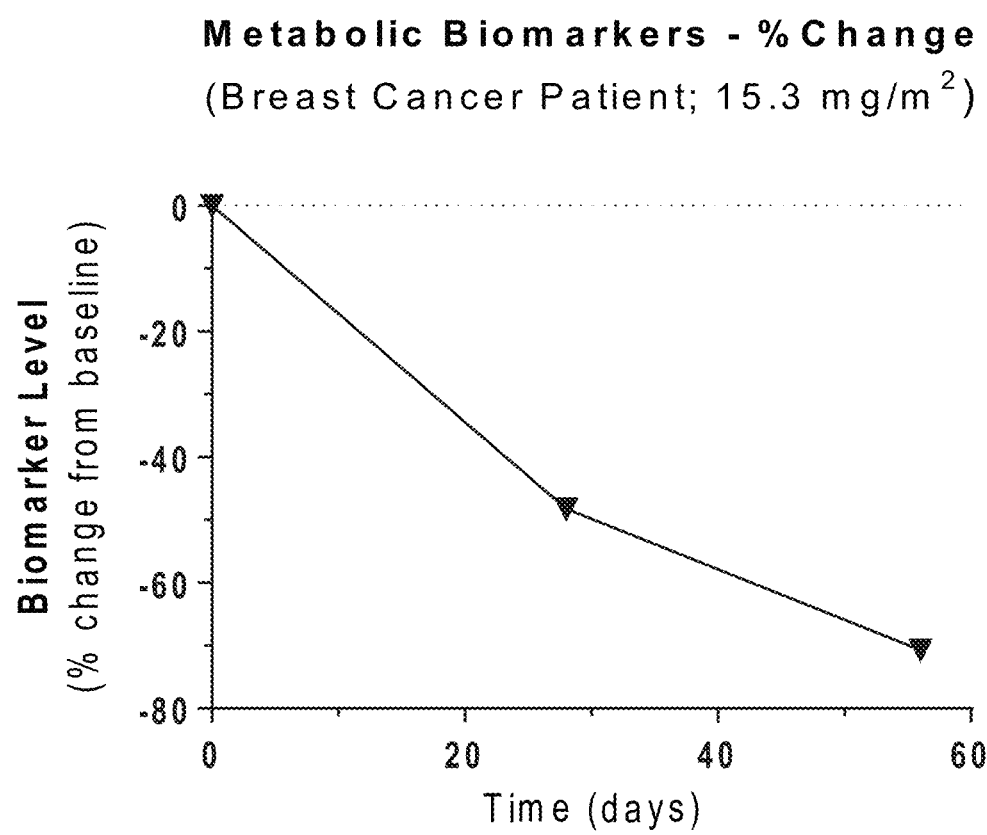
FIG. 16B is a graph showing the percentage change relative to baseline of leptin in the serum of a patient with hormone receptor-positive breast cancer following administration of compounds of the present disclosure.

In another example shown in FIG. 16, a female patient with hormone receptor-positive breast cancer (BMI=27.5, or overweight) was administered Compound 1 once-weekly at 15.3 mg/m² for 8 weeks. FIG. 16A shows absolute values of the metabolic biomarkers and FIG. 16B shows % change over time. The results in FIGS. 16A and 16B demonstrate that leptin declined by 70% from baseline indicating an improvement in metabolic dysfunction after 8 weeks of dosing with Compound 1.

What we claim:

1. A method for treating, or ameliorating at least one symptom of, cancer in a subject in need thereof comprising administering at therapeutically effective amount of at least one polymer conjugate, wherein the polymer conjugate comprises the Formula

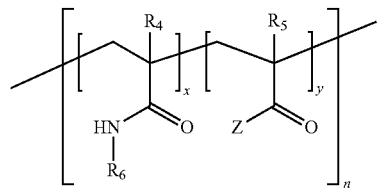

wherein, independently for each occurrence,
$R_4$ is H or $C_1$-$C_6$ alkyl;
$R_5$ is H or $C_1$-$C_6$ alkyl;
$R_6$ is $C_2$-$C_6$ hydroxyalkyl;
Z is NH-$AA_1$-$AA_2$-$AA_3$-$AA_4$-$AA_5$-$AA_6$-C(O)-L or NH-$AA_1$-$AA_2$-$AA_3$-$AA_4$-$AA_5$-$AA_6$-C(O)-Q-X—Y—C(O)—W;
$AA_1$ is glycine, alanine, or $H_2N(CH_2)mCO_2H$, wherein m is 2, 3, 4 or 5;
$AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

$AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

$AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

$AA_5$ is a bond, or glycine, valine, tyrosine, tryptophan, phenylalanine, methionine, leucine, isoleucine, or asparagine;

$AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5;

L is —OH, —O-succinimide, —O-sulfosuccinimide, alkoxy, aryloxy, acyloxy, aroyloxy, alkoxycarbonyloxy, aryloxycarbonyloxy, —$NH_2$, —$NH(C_2$-$C_6$ hydroxyalkyl), halide or perfluoroalkyloxy;

Q is NR, O, or S;

X is M-$(C(R)_2)_p$-M-J-M-$(C(R)_2)_p$-M-V;

M is a bond, or C(O);

J is a bond, or $((CH_2)_qQ)_r$, $C_5$-$C_8$ cycloalkyl, aryl, heteroaryl, NR, O, or S;

Y is NR, O, or S;

R is H or alkyl;

V is a bond or

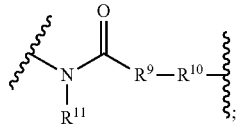
;

$R^9$ is alkyl, aryl, aralkyl, or a bond; or $R^9$ taken together with Y forms a heterocyclic ring;

$R^{10}$ is amido or a bond;

$R^{11}$ is H or alkyl;

W is a Methionine aminopeptidase 2 (MetAP2) inhibitor moiety or alkyl;

x is in the range of 1 to about 450;

y is in the range of 1 to about 30;

n is in the range of 1 to about 100;

p is 0 to 20;

q is 2 or 3;

r is 1, 2, 3, 4, 5, or 6;

or a pharmaceutically acceptable salt, prodrug or analog thereof, wherein the cancer is post-menopausal HR+/Her2− breast cancer, esophageal carcinoma, esophageal adenocarcinoma, cancer of the tongue, colorectal adenocarcinoma, gastro-intestinal stromal tumor (GIST), cervical cancer, endometrial cancer, ovarian cancer, pancreatic cancer, gall bladder cancer, cholangiocarcinoma, liver cancer, clear-cell renal cancer, melanoma, multiple myeloma, thyroid cancer or combinations thereof, wherein the subject has excessive visceral adiposity, elevated leptin levels, depressed adiponectin levels, a high leptin-to-adiponectin ratio, elevated fasting insulin levels, elevated fasting insulin levels accompanied by chronic inflammation, insulin resistance or any combination thereof, and wherein the cancer is treated.

2. The method of claim 1, wherein Z is represented by a formula selected from the group consisting of

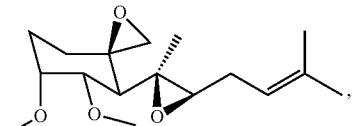

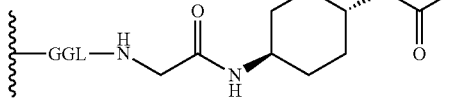

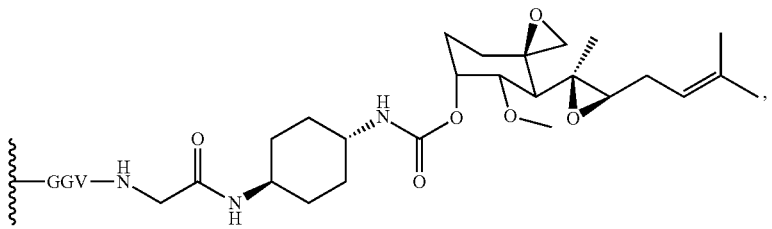

-continued
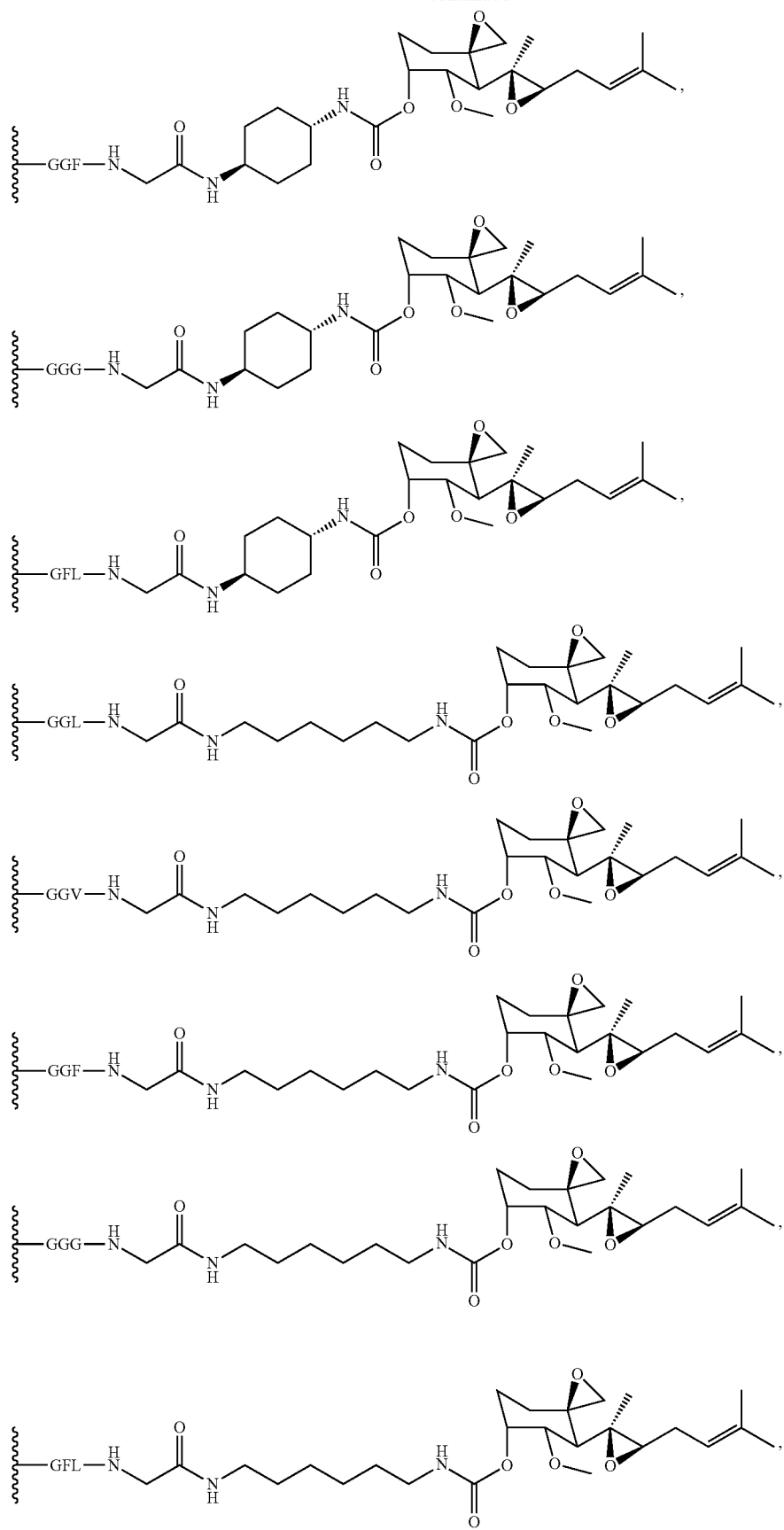

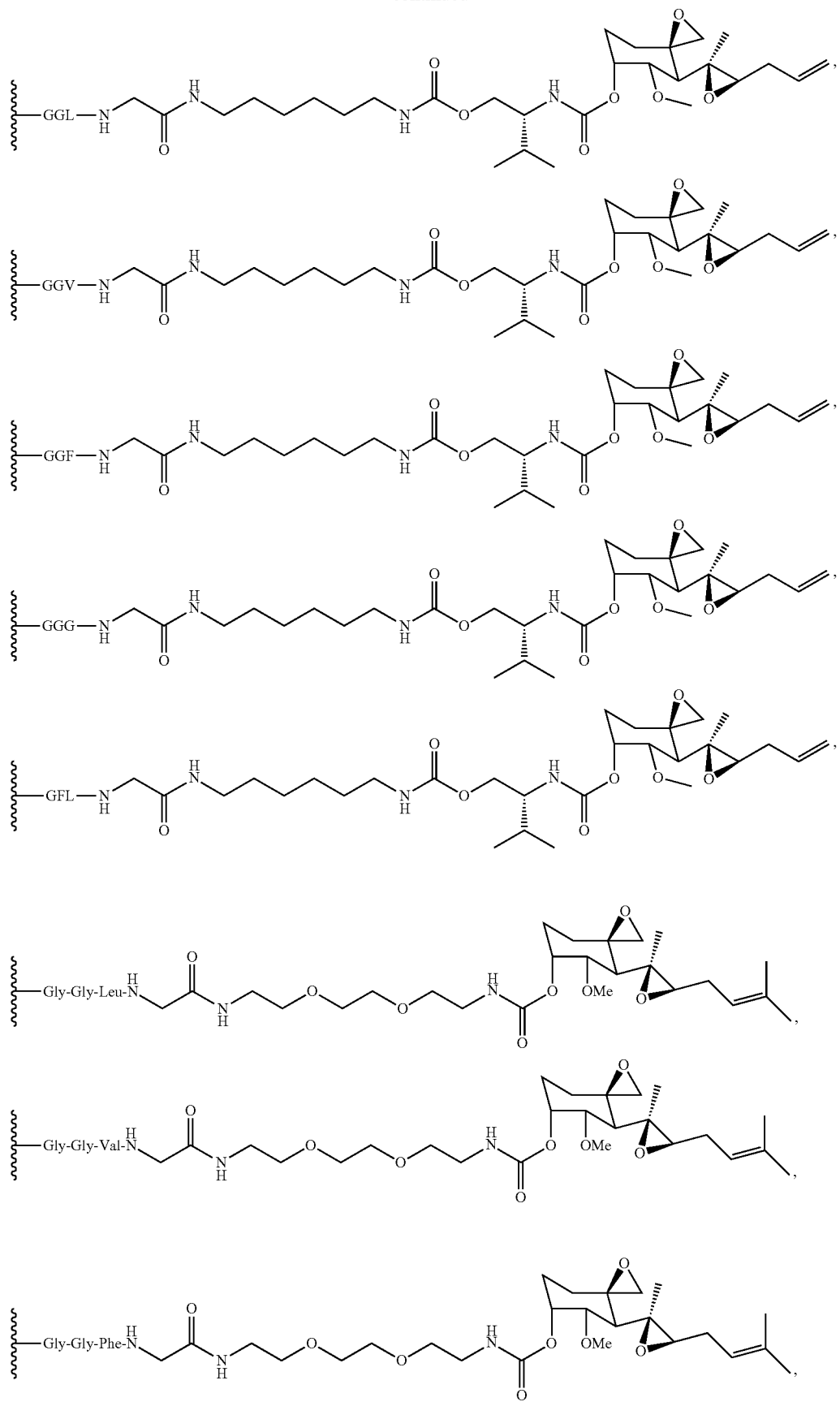

-continued
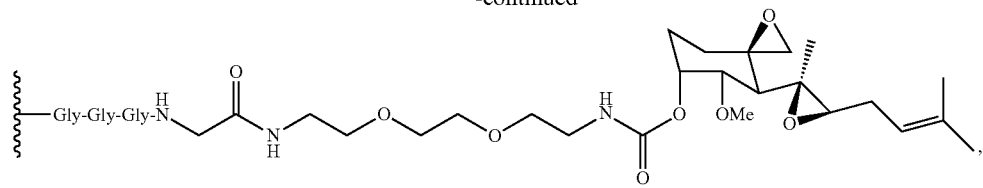
,
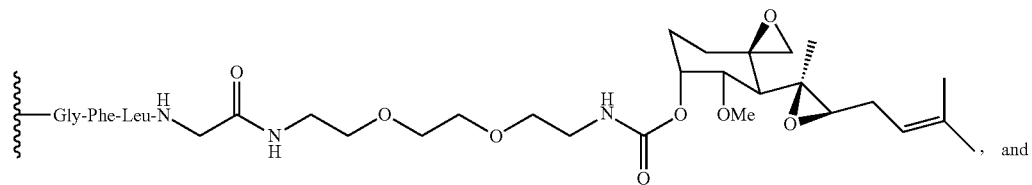
, and
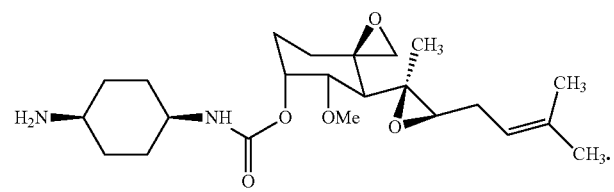
3. The method of claim 1, wherein the at least one polymer conjugate, or a pharmaceutically acceptable salt, prodrug or analog thereof, comprises the Formula
-continued
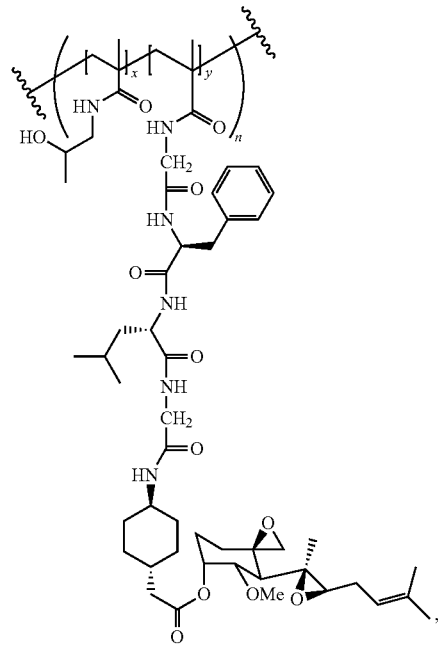
,
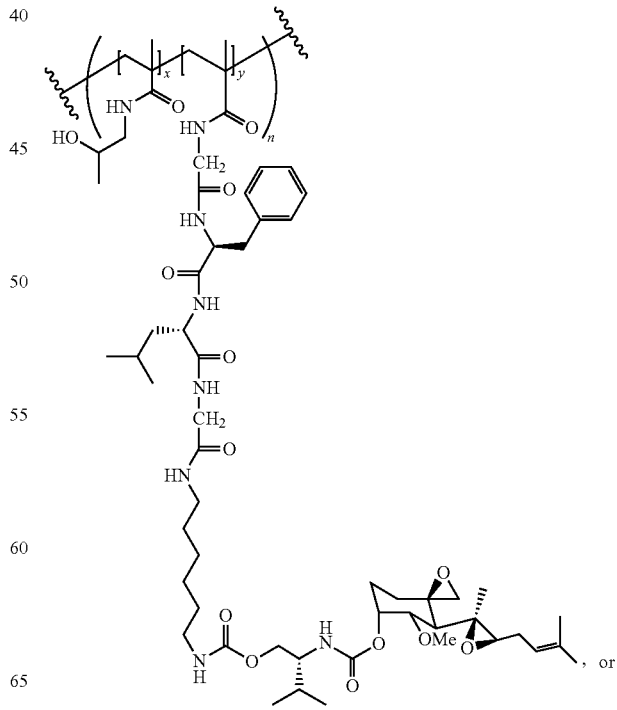
, or 157
-continued

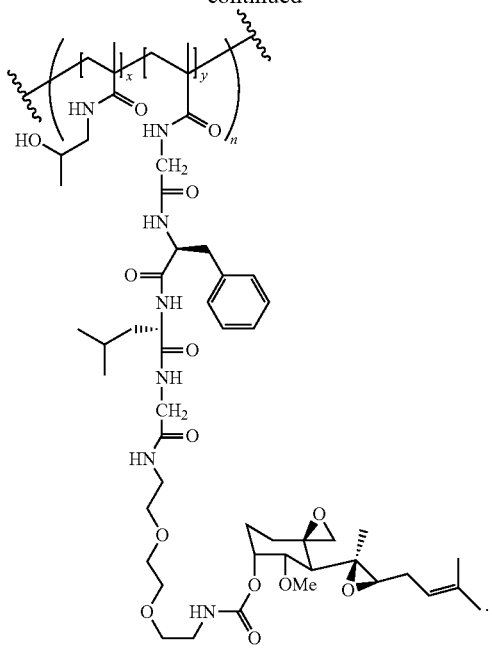

4. The method of claim 1, wherein $R_4$ is methyl.
5. The method of claim 1, wherein $R_5$ is methyl.
6. The method of claim 1, wherein $R_6$ is 2-hydroxypropyl.
7. The method of claim 1, wherein Z is —NH-AA$_6$-C(O)-Q-X—Y—C(O)—W.
8. The method of claim 7, wherein AA$_6$ is glycine.
9. The method of claim 1, wherein Z is —NH-AA$_5$-AA$_6$-C(O)-Q-X—Y—C(O)—W.
10. The method of claim 9, wherein AA$_5$ is leucine and AA$_6$ is glycine.
11. The method of claim 9, wherein AA$_5$ is valine and AA$_6$ is glycine.
12. The method of claim 9, wherein AA$_5$ is phenylalanine and AA$_6$ is glycine.
13. The method of claim 9, wherein AA$_5$ is glycine and AA$_6$ is glycine.
14. The method of claim 1, wherein Z is —NH-AA$_3$-AA$_4$-AA$_5$-AA$_6$-C(O)-Q-X—Y—C(O)—W.
15. The method of claim 14, wherein AA$_5$ is leucine and each of AA$_3$, AA$_4$, or AA$_6$ is glycine.
16. The method of claim 14, wherein AA$_5$ is valine and each of AA$_3$, AA$_4$, or AA$_6$ is glycine.
17. The method of claim 14, wherein AA$_5$ is phenylalanine and each of AA$_3$, AA$_4$, or AA$_6$ is glycine.
18. The method of claim 14, wherein AA$_3$ is glycine, AA$_4$ is phenylalanine, AA$_5$ is leucine and AA$_6$ is glycine.
19. The method of claim 14, wherein each of AA$_3$, AA$_4$, AA$_5$ and AA$_6$ is glycine.
20. The method of claim 1, wherein -Q-X-Y is

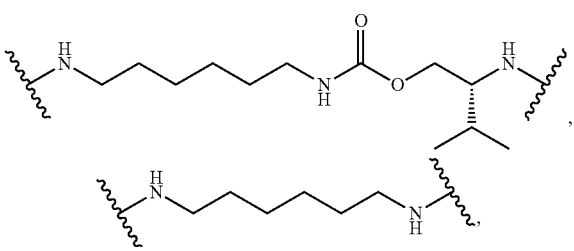

158
-continued

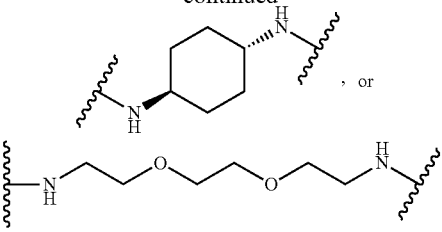
, or

21. The method of claim 1, wherein W is

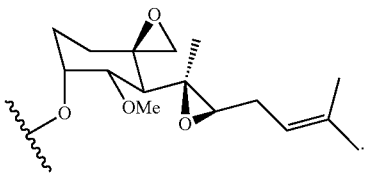

22. The method of claim 1, wherein the ratio of x toy is in the range of about 30:1 to about 3:1.
23. The method of claim 1, wherein the ratio of x to y is about 11:1.
24. The method of claim 1, wherein administration of the therapeutically effective amount of the at least one polymer conjugate increases adiponectin, decreases leptin, decreases fasting insulin, decreases the leptin-to-adiponectin ratio or combinations thereof in said subject.
25. The method of claim 1, wherein said therapeutically effective amount is from about 0.0001 mg/kg of body weight per day to about 5 mg/kg of body weight per day.
26. The method of claim 1, wherein said therapeutically effective amount is from or about 0.001 mg/kg of body weight per day to about 0.1 mg/kg of body weight per day.
27. The method of claim 1, wherein said polymer conjugate is administered from about 1 to about 5 times per week.
28. The method of claim 1, wherein said polymer conjugate is administered in a q4d dosing schedule.
29. The method of claim 1, wherein said polymer conjugate is administered in a q7d dosing schedule.
30. The method of claim 1, wherein said subject is treated for at least about six months.
31. The method of claim 1, wherein said subject is treated for at least about one year.
32. The method of claim 1, wherein said compound polymer conjugate is administered parenterally.
33. The method of claim 1, wherein said polymer conjugate is administered subcutaneously.
34. The method of claim 1, further comprising administering a second active agent.
35. The method of claim 1, wherein said compound is provided as a pharmaceutical composition comprising said polymer conjugate and a pharmaceutically acceptable carrier.
36. The method of claim 1, wherein said polymer conjugate is administered once every two weeks.
37. The method of claim 1, wherein said subject is treated for at least about one month.
38. The method of claim 1, wherein the cancer is hormone receptor-positive breast cancer.

* * * * *